United States Patent
Bobrowicz et al.

(10) Patent No.: US 10,883,997 B2
(45) Date of Patent: Jan. 5, 2021

(54) POLYSPECIFICITY REAGENTS, METHODS FOR THEIR PREPARATION AND USE

(71) Applicant: Adimab, LLC, Lebanon, NH (US)

(72) Inventors: Piotr Bobrowicz, Lebanon, NH (US); Amber D. Hanna, Lebanon, NH (US); Jerry M. Thomas, Lebanon, NH (US)

(73) Assignee: Adimab, LLC, Lebanon, NH (US)

( * ) Notice: Subject to any disclaimer, the term of this patent is extended or adjusted under 35 U.S.C. 154(b) by 80 days.

(21) Appl. No.: 16/196,940

(22) Filed: Nov. 20, 2018

(65) Prior Publication Data
US 2019/0079098 A1 Mar. 14, 2019

Related U.S. Application Data

(62) Division of application No. 14/787,760, filed as application No. PCT/US2014/035958 on Apr. 29, 2014, now Pat. No. 10,156,574.

(60) Provisional application No. 61/817,072, filed on Apr. 29, 2013.

(51) Int. Cl.
*C40B 30/04* (2006.01)
*G01N 33/68* (2006.01)
*C12N 15/10* (2006.01)

(52) U.S. Cl.
CPC ..... *G01N 33/6845* (2013.01); *C12N 15/1037* (2013.01); *C12N 15/1058* (2013.01); *G01N 33/68* (2013.01); *C40B 30/04* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| 10,156,574 B2 | 12/2018 | Bobrowicz et al. |
| 2002/0098524 A1 | 7/2002 | Murray et al. |
| 2004/0038307 A1 | 2/2004 | Lee et al. |
| 2007/0059755 A1 | 3/2007 | Janssen et al. |
| 2009/0074749 A1 | 3/2009 | Chtourou et al. |
| 2010/0184606 A1 | 7/2010 | Janssen et al. |
| 2011/0076752 A1 | 3/2011 | Wu et al. |
| 2014/0323315 A1 | 10/2014 | Bobrowicz et al. |
| 2016/0077105 A1 | 3/2016 | Bobrowicz et al. |

FOREIGN PATENT DOCUMENTS

| WO | WO-99/36569 A1 | 7/1999 |
| WO | WO-2001/079479 A2 | 10/2001 |
| WO | WO-2005/072112 A2 | 8/2005 |
| WO | WO-2005/073375 A1 | 8/2005 |
| WO | WO-2009/080370 A1 | 7/2009 |
| WO | WO-2010/059981 A2 | 5/2010 |

(Continued)

OTHER PUBLICATIONS

Di Niro, R. et al., Rapid interactome profiling by massive sequencing, Nucleic Acids Research, 38(9)(e110): 10 pages (2010).

(Continued)

*Primary Examiner* — Christian C Boesen
(74) *Attorney, Agent, or Firm* — Choate, Hall & Stewart LLP; Brenda Herschbach Jarrell; Meaghan E. Bychowski

(57) ABSTRACT

The present invention relates, inter alia, to polyspecificity reagents, methods of making the same, and methods of using the same in, inter alia, the selection, screening, enrichment, and identification of non-polyspecific, and thus developable, polypeptides.

13 Claims, 31 Drawing Sheets

Specification includes a Sequence Listing.

(56) References Cited

FOREIGN PATENT DOCUMENTS

| WO | WO-2011/009058 A2 | 1/2011 |
|---|---|---|
| WO | WO-2011/139369 A1 | 11/2011 |
| WO | WO-2013/007740 A1 | 1/2013 |

OTHER PUBLICATIONS

Frese, K. et al., An automated immunoassay for early specificity profiling of antibodies, MAbs, 5(2): 279-287 (2013).

International Search Report for PCT/US2014/035958, 3 pages (dated Sep. 26, 2014).

Matthews, D.J. and Wells, J.A., Substrate phage: selection of protease substrates by monovalent phage display, Science, 260(5111):1113-7 (1993).

Peipp, M. et al., An improved procedure for the generation of recombinant single-chain Fv antibody fragments reacting with human CD13 on intact cells, Journal of Immunological Methods, 251:161-176 (2001).

Sepp, A. et al., Microbead display by in vitro compartmentalisation: selection for binding using flow cytometry, FEBS Letters, 532: 455-458 (2002).

Sharon, J. et al., Recombinant Polyclonal Antibody Libraries, Combinatorial Chemistry & High Throughput Screening, 3:185-196 (2000).

Siegel, D. et al., Isolation of cell surface-specific human monoclonal antibodies using phage display and magentically-activated cell sorting: applications in immunohematology, Journal of Immunological Methods, 206:73-85 (1997).

Written Opinion for PCT/US2014/035958, 20 pages (dated Sep. 26, 2014).

Wu, W. et al., Antibody Array Analysis with Label-based Detection and Resolution of Protein Size, Molecular & Cellular Proteomics, 8(2): 245-257 (2008).

Yang, S.Q. and Craik, C.S., Engineering Bidentate Macromolecular Inhibitors for Trypsin and Urokinase-type Plasminogen Activator, J. Mol. Biol., 279:1001-1011 (1998).

Figure 3

Comparison sets of antibodies

C: 24 clinical antibodies

U: 158 randomly chosen antibodies expressed from uninterrogated naïve host cell library P: 48 preferred library-derived output antibodies D: 116 unpreferred library-derived output antibodies representing wide quality distribution Many unpreferred library-derived output antibodies (D) display unattractive CIC profiles relative to C, U, and P antibodies

SEQUENCE LISTING

```
<160> NUMBER OF SEQ ID NOS: 36

<210> SEQ ID NO 1
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 'Gly Ser'
      repeating units

<400> SEQUENCE: 1

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser Gly Ser Gly Ser
    50                  55                  60

Gly Ser Gly Ser Gly Ser Gly Ser Gly Ser Gly Ser Gly Ser Gly Ser
65                  70                  75                  80

Gly Ser Gly Ser Gly Ser Gly Ser Gly Ser Gly Ser Gly Ser Gly Ser
            85                  90                  95

Gly Ser Gly Ser Gly Ser Gly Ser Gly Ser Gly Ser Gly Ser Gly Ser
            100                 105                 110
```

```
Gly Ser Gly Ser Gly Ser Gly Ser Gly Ser Gly Ser
        115                 120                 125

Gly Ser Gly Ser Gly Ser Gly Ser Gly Ser Gly Ser
    130                 135                 140

Gly Ser Gly Ser Gly Ser
145                 150

<210> SEQ ID NO 2
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 'Gly Gly Ser'
      repeating units

<400> SEQUENCE: 2

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125

Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
                165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
        195                 200                 205

Gly Ser Gly Gly Ser Gly Gly Ser Gly Gly Ser Gly Gly Ser Gly Gly
    210                 215                 220

Ser
225

<210> SEQ ID NO 3
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MISC_FEATURE
<222> LOCATION: (1)..(300)
<223> OTHER INFORMATION: This sequence may encompass 1-75 'Gly Gly Gly
      Ser' repeating units

<400> SEQUENCE: 3

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
            85                  90                  95

Gly Gly Gly Ser Gly Gly Gly Ser Gly Gly Gly Ser Gly Gly Gly Ser
        100                 105                 110

Gly Gly Gly Ser Gly Gly Gly Ser Gly Gly Gly Ser Gly Gly Gly Ser
    115                 120                 125

Gly Gly Gly Ser Gly Gly Gly Ser Gly Gly Gly Ser Gly Gly Gly Ser
130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
            165                 170                 175

Gly Gly Gly Ser Gly Gly Gly Ser Gly Gly Gly Ser Gly Gly Gly Ser
        180                 185                 190

Gly Gly Gly Ser Gly Gly Gly Ser Gly Gly Gly Ser Gly Gly Gly Ser
    195                 200                 205

Gly Gly Gly Ser Gly Gly Gly Ser Gly Gly Gly Ser Gly Gly Gly Ser
210                 215                 220

Gly Gly Gly Ser Gly Gly Gly Ser Gly Gly Gly Ser Gly Gly Gly Ser
225                 230                 235                 240

Gly Gly Gly Ser Gly Gly Gly Ser Gly Gly Gly Ser Gly Gly Gly Ser
            245                 250                 255

Gly Gly Gly Ser Gly Gly Gly Ser Gly Gly Gly Ser Gly Gly Gly Ser
        260                 265                 270

Gly Gly Gly Ser Gly Gly Gly Ser Gly Gly Gly Ser Gly Gly Gly Ser
    275                 280                 285

Gly Gly Gly Ser Gly Gly Gly Ser Gly Gly Gly Ser
290                 295                 300

<210> SEQ ID NO 4
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Gly Gly Gly
      Gly Ser' repeating units
```

<400> SEQUENCE: 4

```
Gly Gly Gly Gly Ser Gly Gly Gly Ser Gly Gly Gly Ser Gly
  1               5                  10                 15
Gly Gly Gly Ser Gly Gly Gly Ser Gly Gly Gly Ser Gly Gly
                 20                  25                 30
Gly Gly Ser Gly Gly Gly Ser Gly Gly Gly Ser Gly Gly Gly
             35                  40                 45
Gly Ser Gly Gly Gly Gly Ser Gly Gly Gly Ser Gly Gly Gly
         50                  55              60
Ser Gly Gly Gly Ser Gly Gly Gly Ser Gly Gly Gly Gly Ser
 65                  70                  75             80
Gly Gly Gly Gly Ser Gly Gly Gly Ser Gly Gly Gly Ser Gly
                 85                  90                 95
Gly Gly Gly Ser Gly Gly Gly Ser Gly Gly Gly Ser Gly Gly
                100                 105                110
Gly Gly Ser Gly Gly Gly Ser Gly Gly Gly Ser Gly Gly Gly
            115                 120                125
Gly Ser Gly Gly Gly Ser Gly Gly Gly Ser Gly Gly Gly Gly
        130                 135                 140
Ser Gly Gly Gly Gly Ser Gly Gly Gly Ser Gly Gly Gly Ser
145                 150                 155                160
Gly Gly Gly Gly Ser Gly Gly Gly Ser Gly Gly Gly Ser Gly
                165                 170                175
Gly Gly Gly Ser Gly Gly Gly Ser Gly Gly Gly Ser Gly Gly
                180                 185                190
Gly Gly Ser Gly Gly Gly Ser Gly Gly Gly Ser Gly Gly Gly
            195                 200                 205
Gly Ser Gly Gly Gly Ser Gly Gly Gly Ser Gly Gly Gly Gly
        210                 215                 220
Ser Gly Gly Gly Ser Gly Gly Gly Ser Gly Gly Gly Gly Ser
225                 230                 235                240
Gly Gly Gly Gly Ser Gly Gly Gly Ser Gly Gly Gly Ser Gly
                245                 250                255
Gly Gly Gly Ser Gly Gly Gly Ser Gly Gly Gly Ser Gly Gly
                260                 265                270
Gly Gly Ser Gly Gly Gly Ser Gly Gly Gly Ser Gly Gly Gly
            275                 280                 285
Gly Ser Gly Gly Gly Ser Gly Gly Gly Ser Gly Gly Gly Gly
        290                 295                 300
Ser Gly Gly Gly Gly Ser Gly Gly Gly Ser Gly Gly Gly Ser
305                 310                 315                320
Gly Gly Gly Gly Ser Gly Gly Gly Gly Ser Gly Gly Gly Ser Gly
                325                 330                 335
Gly Gly Gly Ser Gly Gly Gly Ser Gly Gly Gly Ser Gly Gly
            340                 345                 350
Gly Gly Ser Gly Gly Gly Gly Ser Gly Gly Gly Ser Gly Gly Gly
            355                 360                 365
Gly Ser Gly Gly Gly Gly Ser
        370                 375
```

<210> SEQ ID NO 5
<211> LENGTH: 675
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(675)
<223> OTHER INFORMATION: This sequence may encompass 1-75 'Gly Gly Gly
      Gly Ser Gly Gly Gly Gly' repeating units

<400> SEQUENCE: 5

Gly Gly Gly Gly Ser Gly Gly Gly Gly Gly Gly Gly Ser Gly Gly
1               5                   10                  15

Gly Gly Gly Gly Gly Gly Ser Gly Gly Gly Gly Gly Gly Gly Ser
                20                  25                  30

Gly Gly Gly Gly Gly Gly Gly Ser Gly Gly Gly Gly Gly Gly Gly
            35                  40                  45

Gly Ser Gly Gly Gly Gly Gly Gly Gly Ser Gly Gly Gly Gly Gly
        50                  55                  60

Gly Gly Gly Ser Gly Gly Gly Gly Gly Gly Gly Ser Gly Gly Gly
65                  70                  75                  80

Gly Gly Gly Gly Gly Ser Gly Gly Gly Gly Gly Gly Gly Ser Gly
                85                  90                  95

Gly Gly Gly Gly Gly Gly Ser Gly Gly Gly Gly Gly Gly Gly Gly
                100                 105                 110

Ser Gly Gly Gly Gly Gly Gly Gly Ser Gly Gly Gly Gly Gly Gly
        115                 120                 125

Gly Gly Ser Gly Gly Gly Gly Gly Gly Gly Ser Gly Gly Gly Gly
    130                 135                 140

Gly Gly Gly Gly Ser Gly Gly Gly Gly Gly Gly Gly Ser Gly Gly
145                 150                 155                 160

Gly Gly Gly Gly Gly Gly Ser Gly Gly Gly Gly Gly Gly Gly Ser
                165                 170                 175

Gly Gly Gly Gly Gly Gly Gly Ser Gly Gly Gly Gly Gly Gly Gly
                180                 185                 190

Gly Ser Gly Gly Gly Gly Gly Gly Gly Ser Gly Gly Gly Gly Gly
        195                 200                 205

Gly Gly Gly Ser Gly Gly Gly Gly Gly Gly Gly Ser Gly Gly Gly
    210                 215                 220

Gly Gly Gly Gly Gly Ser Gly Gly Gly Gly Gly Gly Gly Ser Gly
225                 230                 235                 240

Gly Gly Gly Gly Gly Gly Ser Gly Gly Gly Gly Gly Gly Gly Gly
                245                 250                 255

Ser Gly Gly Gly Gly Gly Gly Gly Ser Gly Gly Gly Gly Gly Gly
        260                 265                 270

Gly Gly Ser Gly Gly Gly Gly Gly Gly Gly Ser Gly Gly Gly Gly
    275                 280                 285

Gly Gly Gly Gly Ser Gly Gly Gly Gly Gly Gly Gly Ser Gly Gly
    290                 295                 300

Gly Gly Gly Gly Gly Gly Ser Gly Gly Gly Gly Gly Gly Gly Ser
305                 310                 315                 320

Gly Gly Gly Gly Gly Gly Gly Ser Gly Gly Gly Gly Gly Gly Gly
                325                 330                 335

Gly Ser Gly Gly Gly Gly Gly Gly Gly Ser Gly Gly Gly Gly Gly
        340                 345                 350

Gly Gly Gly Ser Gly Gly Gly Gly Gly Gly Gly Ser Gly Gly Gly
    355                 360                 365
```

```
Gly Gly Gly Gly Gly Ser Gly Gly Gly Gly Gly Gly Ser Gly
        370                 375                 380

Gly Gly Gly Gly Gly Gly Ser Gly Gly Gly Gly Gly Gly Gly
385                 390                 395                 400

Ser Gly Gly Gly Gly Gly Gly Gly Ser Gly Gly Gly Gly Gly
            405                 410                 415

Gly Gly Ser Gly Gly Gly Gly Gly Gly Ser Gly Gly Gly Gly
            420                 425                 430

Gly Gly Gly Gly Ser Gly Gly Gly Gly Gly Gly Ser Gly Gly
            435                 440                 445

Gly Gly Gly Gly Gly Ser Gly Gly Gly Gly Gly Gly Gly Ser
450                 455                 460

Gly Gly Gly Gly Gly Gly Ser Gly Gly Gly Gly Gly Gly
465                 470                 475             480

Gly Ser Gly Gly Gly Gly Gly Gly Ser Gly Gly Gly Gly Gly
            485                 490                 495

Gly Gly Gly Ser Gly Gly Gly Gly Gly Gly Ser Gly Gly Gly
            500                 505                 510

Gly Gly Gly Gly Gly Ser Gly Gly Gly Gly Gly Gly Ser Gly
            515                 520                 525

Gly Gly Gly Gly Gly Gly Ser Gly Gly Gly Gly Gly Gly Gly
            530                 535                 540

Ser Gly Gly Gly Gly Gly Gly Gly Ser Gly Gly Gly Gly Gly
545                 550                 555                 560

Gly Gly Ser Gly Gly Gly Gly Gly Gly Ser Gly Gly Gly Gly
            565                 570                 575

Gly Gly Gly Gly Ser Gly Gly Gly Gly Gly Gly Ser Gly Gly
            580                 585                 590

Gly Gly Gly Gly Gly Ser Gly Gly Gly Gly Gly Gly Gly Ser
            595                 600                 605

Gly Gly Gly Gly Gly Gly Gly Ser Gly Gly Gly Gly Gly Gly
            610                 615                 620

Gly Ser Gly Gly Gly Gly Gly Gly Ser Gly Gly Gly Gly Gly
625                 630                 635                 640

Gly Gly Gly Ser Gly Gly Gly Gly Gly Gly Ser Gly Gly Gly
            645                 650                 655

Gly Gly Gly Gly Gly Ser Gly Gly Gly Gly Gly Gly Ser Gly
            660                 665                 670

Gly Gly Gly
        675

<210> SEQ ID NO 6
<211> LENGTH: 1050
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1050)
<223> OTHER INFORMATION: This sequence may encompass 1-75 'Gly Gly Gly
      Gly Ser Gly Gly Gly Gly Ser Gly Gly Gly Gly' repeating units

<400> SEQUENCE: 6

Gly Gly Gly Gly Ser Gly Gly Gly Gly Ser Gly Gly Gly Gly Gly
1               5                   10                  15
```

-continued

Gly Gly Ser Gly Gly Gly Ser Gly Gly Gly Gly Gly Gly
         20              25              30

Ser Gly Gly Gly Gly Ser Gly Gly Gly Gly Gly Ser Gly
         35              40              45

Gly Gly Gly Ser Gly Gly Gly Gly Gly Gly Ser Gly Gly
         50              55              60

Gly Ser Gly Gly Gly Gly Gly Gly Ser Gly Gly Gly Ser
65              70              75              80

Gly Gly Gly Gly Gly Gly Gly Ser Gly Gly Gly Ser Gly
             85              90              95

Gly Gly Gly Gly Gly Ser Gly Gly Gly Ser Gly Gly Gly
         100             105             110

Gly Gly Gly Gly Ser Gly Gly Gly Ser Gly Gly Gly Gly
         115             120             125

Gly Gly Ser Gly Gly Gly Ser Gly Gly Gly Gly Gly Gly
         130             135             140

Ser Gly Gly Gly Gly Ser Gly Gly Gly Gly Gly Ser Gly
145             150             155             160

Gly Gly Gly Ser Gly Gly Gly Gly Gly Gly Ser Gly Gly
             165             170             175

Gly Ser Gly Gly Gly Gly Gly Gly Ser Gly Gly Gly Ser
         180             185             190

Gly Gly Gly Gly Gly Gly Gly Ser Gly Gly Gly Ser Gly
         195             200             205

Gly Gly Gly Gly Gly Ser Gly Gly Gly Ser Gly Gly Gly
         210             215             220

Gly Gly Gly Gly Ser Gly Gly Gly Ser Gly Gly Gly Gly
225             230             235             240

Gly Gly Ser Gly Gly Gly Ser Gly Gly Gly Gly Gly Gly
             245             250             255

Ser Gly Gly Gly Gly Ser Gly Gly Gly Gly Gly Ser Gly
         260             265             270

Gly Gly Gly Ser Gly Gly Gly Gly Gly Gly Ser Gly Gly
         275             280             285

Gly Ser Gly Gly Gly Gly Gly Gly Ser Gly Gly Gly Ser
         290             295             300

Gly Gly Gly Gly Gly Gly Gly Ser Gly Gly Gly Ser Gly
305             310             315             320

Gly Gly Gly Gly Gly Ser Gly Gly Gly Ser Gly Gly Gly
             325             330             335

Gly Gly Gly Gly Ser Gly Gly Gly Ser Gly Gly Gly Gly
         340             345             350

Gly Gly Ser Gly Gly Gly Ser Gly Gly Gly Gly Gly Gly
         355             360             365

Ser Gly Gly Gly Gly Ser Gly Gly Gly Gly Gly Ser Gly
         370             375             380

Gly Gly Gly Ser Gly Gly Gly Gly Gly Gly Ser Gly Gly
385             390             395             400

Gly Ser Gly Gly Gly Gly Gly Gly Ser Gly Gly Gly Ser
             405             410             415

Gly Gly Gly Gly Gly Gly Gly Ser Gly Gly Gly Ser Gly Gly
             420             425             430

Gly Gly Gly Gly Gly Ser Gly Gly Gly Ser Gly Gly Gly
            435                 440                 445

Gly Gly Gly Gly Ser Gly Gly Ser Gly Gly Gly Gly Gly
            450                 455                 460

Gly Gly Ser Gly Gly Gly Ser Gly Gly Gly Gly Gly Gly
465                 470                 475                 480

Ser Gly Gly Gly Ser Gly Gly Gly Gly Gly Gly Ser Gly
                    485                 490                 495

Gly Gly Gly Ser Gly Gly Gly Gly Gly Gly Ser Gly Gly
                500                 505                 510

Gly Ser Gly Gly Gly Gly Gly Gly Ser Gly Gly Gly Ser
        515                 520                 525

Gly Gly Gly Gly Gly Gly Gly Ser Gly Gly Gly Ser Gly Gly
    530                 535                 540

Gly Gly Gly Gly Gly Ser Gly Gly Gly Ser Gly Gly Gly
545                 550                 555                 560

Gly Gly Gly Gly Ser Gly Gly Gly Ser Gly Gly Gly Gly
                565                 570                 575

Gly Gly Ser Gly Gly Gly Ser Gly Gly Gly Gly Gly Gly
            580                 585                 590

Ser Gly Gly Gly Ser Gly Gly Gly Gly Gly Gly Ser Gly
                    595                 600                 605

Gly Gly Gly Ser Gly Gly Gly Gly Gly Gly Ser Gly Gly
                610                 615                 620

Gly Ser Gly Gly Gly Gly Gly Gly Ser Gly Gly Gly Ser
625                 630                 635                 640

Gly Gly Gly Gly Gly Gly Gly Ser Gly Gly Gly Ser Gly Gly
                    645                 650                 655

Gly Gly Gly Gly Gly Ser Gly Gly Gly Ser Gly Gly Gly
                660                 665                 670

Gly Gly Gly Gly Ser Gly Gly Gly Ser Gly Gly Gly Gly
            675                 680                 685

Gly Gly Ser Gly Gly Gly Ser Gly Gly Gly Gly Gly Gly
            690                 695                 700

Ser Gly Gly Gly Ser Gly Gly Gly Gly Gly Gly Ser Gly
705                 710                 715                 720

Gly Gly Gly Ser Gly Gly Gly Gly Gly Gly Ser Gly Gly
                725                 730                 735

Gly Ser Gly Gly Gly Gly Gly Gly Ser Gly Gly Gly Ser
        740                 745                 750

Gly Gly Gly Gly Gly Gly Gly Ser Gly Gly Gly Ser Gly Gly
    755                 760                 765

Gly Gly Gly Gly Gly Ser Gly Gly Gly Ser Gly Gly Gly
770                 775                 780

Gly Gly Gly Gly Ser Gly Gly Gly Ser Gly Gly Gly Gly
785                 790                 795                 800

Gly Gly Ser Gly Gly Gly Gly Ser Gly Gly Gly Gly Gly Gly
                805                 810                 815

Ser Gly Gly Gly Ser Gly Gly Gly Gly Gly Gly Ser Gly
                    820                 825                 830

Gly Gly Gly Ser Gly Gly Gly Gly Gly Gly Ser Gly Gly
                835                 840                 845

Gly Ser Gly Gly Gly Gly Gly Gly Gly Gly Ser Gly Gly Gly Gly Ser

-continued

```
                850                 855                 860
Gly Gly Gly Gly Gly Gly Gly Ser Gly Gly Ser Gly Gly
865                 870                 875                 880

Gly Gly Gly Gly Gly Gly Ser Gly Gly Gly Ser Gly Gly Gly
                885                 890                 895

Gly Gly Gly Gly Ser Gly Gly Gly Gly Ser Gly Gly Gly Gly
                900                 905                 910

Gly Gly Ser Gly Gly Gly Ser Gly Gly Gly Gly Gly Gly
        915                 920                 925

Ser Gly Gly Gly Gly Ser Gly Gly Gly Gly Gly Gly Ser Gly
        930                 935                 940

Gly Gly Gly Ser Gly Gly Gly Gly Gly Gly Ser Gly Gly Gly
945                 950                 955                 960

Gly Ser Gly Gly Gly Gly Gly Gly Ser Gly Gly Gly Ser
        965                 970                 975

Gly Gly Gly Gly Gly Gly Ser Gly Gly Gly Ser Gly Gly
                980                 985                 990

Gly Gly Gly Gly Gly Gly Ser Gly Gly Gly Ser Gly Gly Gly
        995                 1000                1005

Gly Gly  Gly Gly Ser Gly Gly  Gly Gly Ser Gly Gly  Gly Gly Gly
        1010                1015                1020

Gly Gly  Gly Ser Gly Gly Gly  Gly Ser Gly Gly Gly  Gly Gly Gly
        1025                1030                1035

Gly Gly  Ser Gly Gly Gly Gly  Ser Gly Gly Gly Gly
        1040                1045                1050
```

<210> SEQ ID NO 7
<211> LENGTH: 1425
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MISC_FEATURE
<222> LOCATION: (1)..(1425)
<223> OTHER INFORMATION: This sequence may encompass 1-75 'Gly Gly Gly
    Gly Ser Gly Gly Gly Gly Ser Gly Gly Gly Gly Ser Gly Gly Gly Gly'
    repeating units

<400> SEQUENCE: 7

```
Gly Gly Gly Gly Ser Gly Gly Gly Ser Gly Gly Gly Ser Gly
1               5                   10                  15

Gly Gly Gly Gly Gly Gly Ser Gly Gly Gly Ser Gly Gly Gly
                20                  25                  30

Gly Ser Gly Gly Gly Gly Gly Gly Ser Gly Gly Gly Gly Ser
        35                  40                  45

Gly Gly Gly Gly Ser Gly Gly Gly Gly Gly Gly Ser Gly Gly
        50                  55                  60

Gly Gly Ser Gly Gly Gly Ser Gly Gly Gly Gly Gly Gly Gly
65                  70                  75                  80

Ser Gly Gly Gly Gly Ser Gly Gly Gly Gly Ser Gly Gly Gly
                85                  90                  95

Gly Gly Gly Ser Gly Gly Gly Gly Ser Gly Gly Gly Ser Gly Gly
        100                 105                 110

Gly Gly Gly Gly Gly Gly Ser Gly Gly Gly Ser Gly Gly Gly Gly
        115                 120                 125
```

-continued

Ser Gly Gly Gly Gly Gly Gly Ser Gly Gly Gly Ser Gly
130                 135             140

Gly Gly Gly Ser Gly Gly Gly Gly Gly Gly Ser Gly Gly
145             150                 155             160

Gly Ser Gly Gly Gly Ser Gly Gly Gly Gly Gly Gly Ser
        165             170                 175

Gly Gly Gly Gly Ser Gly Gly Gly Ser Gly Gly Gly Gly
            180             185                 190

Gly Gly Ser Gly Gly Gly Gly Ser Gly Gly Gly Ser Gly
        195                 200             205

Gly Gly Gly Gly Gly Ser Gly Gly Gly Ser Gly Gly Gly Ser
210                     215             220

Gly Gly Gly Gly Gly Gly Gly Ser Gly Gly Gly Ser Gly Gly
225                 230                 235             240

Gly Gly Ser Gly Gly Gly Gly Gly Gly Ser Gly Gly Gly
        245                 250                 255

Ser Gly Gly Gly Gly Ser Gly Gly Gly Gly Gly Gly Ser Gly
        260             265                 270

Gly Gly Gly Ser Gly Gly Gly Ser Gly Gly Gly Gly Gly
        275                 280             285

Gly Ser Gly Gly Gly Gly Ser Gly Gly Gly Ser Gly Gly Gly
        290                 295             300

Gly Gly Gly Gly Ser Gly Gly Gly Gly Ser Gly Gly Gly Ser Gly
305                 310                 315                 320

Gly Gly Gly Gly Gly Gly Ser Gly Gly Gly Ser Gly Gly
                325                 330                 335

Gly Ser Gly Gly Gly Gly Gly Gly Gly Ser Gly Gly Gly Ser
        340                 345                 350

Gly Gly Gly Ser Gly Gly Gly Gly Gly Gly Ser Gly Gly
        355                 360                 365

Gly Gly Ser Gly Gly Gly Ser Gly Gly Gly Gly Gly Gly Gly
        370                 375                 380

Ser Gly Gly Gly Ser Gly Gly Gly Ser Gly Gly Gly Gly
385                 390                 395                 400

Gly Gly Gly Ser Gly Gly Gly Ser Gly Gly Gly Ser Gly Gly
                405                 410                 415

Gly Gly Gly Gly Gly Ser Gly Gly Gly Ser Gly Gly Gly
                420                 425                 430

Ser Gly Gly Gly Gly Gly Gly Gly Ser Gly Gly Gly Ser Gly
435                             440                 445

Gly Gly Gly Ser Gly Gly Gly Gly Gly Gly Gly Ser Gly Gly
450                 455                 460

Gly Ser Gly Gly Gly Gly Ser Gly Gly Gly Gly Gly Gly Ser
465                 470                 475                 480

Gly Gly Gly Gly Ser Gly Gly Gly Gly Ser Gly Gly Gly Gly
                485                 490                 495

Gly Gly Ser Gly Gly Gly Gly Ser Gly Gly Gly Ser Gly Gly
            500                 505                 510

Gly Gly Gly Gly Gly Ser Gly Gly Gly Ser Gly Gly Gly Ser
                515                 520                 525

Gly Gly Gly Gly Gly Gly Gly Ser Gly Gly Gly Ser Gly Gly
530                             535                 540

Gly Gly Ser Gly Gly Gly Gly Gly Gly Gly Gly Ser Gly Gly Gly Gly

```
                545                 550                 555                 560
Ser Gly Gly Gly Gly Ser Gly Gly Gly Gly Gly Gly Gly Ser Gly
                565                 570                 575
Gly Gly Gly Ser Gly Gly Gly Ser Gly Gly Gly Gly Gly Gly
            580                 585                 590
Gly Ser Gly Gly Gly Gly Ser Gly Gly Gly Gly Ser Gly Gly Gly
            595                 600                 605
Gly Gly Gly Gly Ser Gly Gly Gly Ser Gly Gly Gly Ser Gly
            610                 615                 620
Gly Gly Gly Gly Gly Gly Ser Gly Gly Gly Ser Gly Gly Gly
625                 630                 635                 640
Gly Ser Gly Gly Gly Gly Gly Gly Gly Ser Gly Gly Gly Ser
            645                 650                 655
Gly Gly Gly Gly Ser Gly Gly Gly Gly Gly Gly Ser Gly Gly
            660                 665                 670
Gly Gly Ser Gly Gly Gly Ser Gly Gly Gly Gly Gly Gly
            675                 680                 685
Ser Gly Gly Gly Gly Ser Gly Gly Gly Ser Gly Gly Gly Gly
            690                 695                 700
Gly Gly Gly Ser Gly Gly Gly Ser Gly Gly Gly Ser Gly Gly
705                 710                 715                 720
Gly Gly Gly Gly Gly Ser Gly Gly Gly Ser Gly Gly Gly Gly
                725                 730                 735
Ser Gly Gly Gly Gly Gly Gly Gly Ser Gly Gly Gly Gly Ser Gly
                740                 745                 750
Gly Gly Gly Ser Gly Gly Gly Gly Gly Gly Gly Ser Gly Gly Gly
            755                 760                 765
Gly Ser Gly Gly Gly Gly Ser Gly Gly Gly Gly Gly Gly Gly Ser
            770                 775                 780
Gly Gly Gly Gly Ser Gly Gly Gly Gly Ser Gly Gly Gly Gly Gly
785                 790                 795                 800
Gly Gly Ser Gly Gly Gly Gly Ser Gly Gly Gly Ser Gly Gly Gly
                805                 810                 815
Gly Gly Gly Gly Gly Ser Gly Gly Gly Gly Ser Gly Gly Gly Ser
                820                 825                 830
Gly Gly Gly Gly Gly Gly Gly Gly Ser Gly Gly Gly Ser Gly Gly
            835                 840                 845
Gly Gly Ser Gly Gly Gly Gly Gly Gly Ser Gly Gly Gly Gly
            850                 855                 860
Ser Gly Gly Gly Gly Ser Gly Gly Gly Gly Gly Gly Gly Ser Gly
865                 870                 875                 880
Gly Gly Gly Ser Gly Gly Gly Gly Ser Gly Gly Gly Gly Gly Gly
                885                 890                 895
Gly Ser Gly Gly Gly Gly Ser Gly Gly Gly Gly Ser Gly Gly Gly Gly
                900                 905                 910
Gly Gly Gly Gly Ser Gly Gly Gly Gly Gly Gly Ser Gly Gly Gly
            915                 920                 925
Gly Gly Gly Gly Gly Gly Gly Ser Gly Gly Gly Gly Ser Gly Gly
            930                 935                 940
Gly Ser Gly Gly Gly Gly Gly Gly Gly Ser Gly Gly Gly Gly Ser
945                 950                 955                 960
Gly Gly Gly Gly Ser Gly Gly Gly Gly Gly Gly Gly Ser Gly Gly
                965                 970                 975
```

```
Gly Gly Ser Gly Gly Gly Ser Gly Gly Gly Gly Gly Gly Gly
            980             985             990

Ser Gly Gly Gly Gly Ser Gly Gly Gly Gly Ser Gly Gly Gly Gly Gly
        995             1000            1005

Gly Gly Gly Ser Gly Gly Gly Gly Ser Gly Gly Gly Gly Ser Gly
        1010            1015            1020

Gly Gly Gly Gly Gly Gly Ser Gly Gly Gly Ser Gly Gly
        1025            1030            1035

Gly Gly Ser Gly Gly Gly Gly Gly Gly Gly Ser Gly Gly Gly
        1040            1045            1050

Gly Ser Gly Gly Gly Gly Ser Gly Gly Gly Gly Gly Gly Gly
        1055            1060            1065

Ser Gly Gly Gly Gly Ser Gly Gly Gly Ser Gly Gly Gly Gly
        1070            1075            1080

Gly Gly Gly Gly Ser Gly Gly Gly Gly Ser Gly Gly Gly Ser
        1085            1090            1095

Gly Gly Gly Gly Gly Gly Gly Ser Gly Gly Gly Gly Ser Gly
        1100            1105            1110

Gly Gly Gly Ser Gly Gly Gly Gly Gly Gly Gly Ser Gly Gly
        1115            1120            1125

Gly Gly Ser Gly Gly Gly Gly Ser Gly Gly Gly Gly Gly Gly
        1130            1135            1140

Gly Ser Gly Gly Gly Gly Ser Gly Gly Gly Gly Ser Gly Gly Gly
        1145            1150            1155

Gly Gly Gly Gly Gly Ser Gly Gly Gly Gly Ser Gly Gly Gly Gly
        1160            1165            1170

Ser Gly Gly Gly Gly Gly Gly Gly Ser Gly Gly Gly Gly Ser
        1175            1180            1185

Gly Gly Gly Gly Ser Gly Gly Gly Gly Gly Gly Gly Ser Gly
        1190            1195            1200

Gly Gly Gly Ser Gly Gly Gly Gly Ser Gly Gly Gly Gly Gly
        1205            1210            1215

Gly Gly Ser Gly Gly Gly Gly Ser Gly Gly Gly Gly Ser Gly Gly
        1220            1225            1230

Gly Gly Gly Gly Gly Gly Ser Gly Gly Gly Gly Ser Gly Gly Gly
        1235            1240            1245

Gly Ser Gly Gly Gly Gly Gly Gly Gly Gly Ser Gly Gly Gly Gly
        1250            1255            1260

Ser Gly Gly Gly Gly Ser Gly Gly Gly Gly Gly Gly Gly Gly Ser
        1265            1270            1275

Gly Gly Gly Gly Ser Gly Gly Gly Gly Ser Gly Gly Gly Gly Gly
        1280            1285            1290

Gly Gly Gly Ser Gly Gly Gly Gly Ser Gly Gly Gly Gly Ser Gly
        1295            1300            1305

Gly Gly Gly Gly Gly Gly Ser Gly Gly Gly Gly Ser Gly Gly
        1310            1315            1320

Gly Gly Ser Gly Gly Gly Gly Gly Gly Gly Gly Ser Gly Gly Gly
        1325            1330            1335

Gly Ser Gly Gly Gly Gly Ser Gly Gly Gly Gly Gly Gly Gly Gly
        1340            1345            1350

Ser Gly Gly Gly Gly Ser Gly Gly Gly Gly Ser Gly Gly Gly Gly
        1355            1360            1365
```

```
Gly Gly  Gly Gly Ser Gly Gly  Gly Gly Ser Gly  Gly Gly Ser
    1370            1375            1380

Gly Gly  Gly Gly Gly Gly Gly  Gly Ser Gly Gly  Gly Gly Ser Gly
    1385            1390            1395

Gly Gly  Gly Ser Gly Gly Gly  Gly Gly Gly Gly  Ser Gly Gly
    1400            1405            1410

Gly Gly  Ser Gly Gly Gly Gly  Ser Gly Gly Gly Gly
    1415            1420            1425

<210> SEQ ID NO 8
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1800)
<223> OTHER INFORMATION: This sequence may encompass 1-75 'Gly Gly Gly
      Gly Ser Gly Gly Gly Gly Ser Gly Gly Gly Gly Ser Gly Gly Gly Gly
      Ser Gly Gly Gly Gly' repeating units

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Gly Gly Gly Ser Gly Gly Gly
            20                  25                  30

Gly Ser Gly Gly Gly Ser Gly Gly Gly Gly Ser Gly Gly Gly
        35                  40                  45

Gly Gly Gly Gly Ser Gly Gly Gly Gly Ser Gly Gly Gly Ser Gly
    50                  55                  60

Gly Gly Gly Ser Gly Gly Gly Gly Gly Gly Ser Gly Gly Gly Gly
65                  70                  75                  80

Gly Ser Gly Gly Gly Ser Gly Gly Gly Gly Ser Gly Gly Gly Gly
        85                  90                  95

Gly Gly Gly Gly Ser Gly Gly Gly Gly Ser Gly Gly Gly Gly Ser Gly
            100                 105                 110

Gly Gly Gly Ser Gly Gly Gly Gly Gly Gly Gly Ser Gly Gly Gly
        115                 120                 125

Gly Ser Gly Gly Gly Ser Gly Gly Gly Gly Ser Gly Gly Gly Gly
    130                 135                 140

Gly Gly Gly Gly Ser Gly Gly Gly Gly Ser Gly Gly Gly Ser Gly
145                 150                 155                 160

Gly Gly Gly Ser Gly Gly Gly Gly Gly Gly Gly Ser Gly Gly Gly
            165                 170                 175

Gly Ser Gly Gly Gly Gly Ser Gly Gly Gly Ser Gly Gly Gly Gly
        180                 185                 190

Gly Gly Gly Gly Ser Gly Gly Gly Gly Ser Gly Gly Gly Gly Ser Gly
            195                 200                 205

Gly Gly Gly Ser Gly Gly Gly Gly Gly Gly Gly Ser Gly Gly Gly Gly
        210                 215                 220

Gly Ser Gly Gly Gly Gly Ser Gly Gly Gly Ser Gly Gly Gly Gly
225                 230                 235                 240

Gly Gly Gly Gly Ser Gly Gly Gly Gly Ser Gly Gly Gly Gly Ser Gly
            245                 250                 255

Gly Gly Gly Ser Gly Gly Gly Gly Gly Gly Gly Ser Gly Gly Gly
            260                 265                 270
```

```
Gly Ser Gly Gly Gly Ser Gly Gly Gly Ser Gly Gly Gly
    275                 280             285
Gly Gly Gly Gly Ser Gly Gly Gly Ser Gly Gly Gly Ser Gly
        290             295             300
Gly Gly Gly Ser Gly Gly Gly Gly Gly Gly Ser Gly Gly Gly
305             310              315                 320
Gly Ser Gly Gly Gly Ser Gly Gly Gly Ser Gly Gly Gly Gly
        325             330             335
Gly Gly Gly Gly Ser Gly Gly Gly Ser Gly Gly Gly Ser Gly
            340             345             350
Gly Gly Gly Ser Gly Gly Gly Gly Gly Gly Ser Gly Gly Gly
        355             360             365
Gly Ser Gly Gly Gly Ser Gly Gly Gly Ser Gly Gly Gly Gly
        370             375             380
Gly Gly Gly Gly Ser Gly Gly Gly Ser Gly Gly Gly Ser Gly
385             390             395                 400
Gly Gly Gly Ser Gly Gly Gly Gly Gly Gly Ser Gly Gly Gly
            405             410             415
Gly Ser Gly Gly Gly Ser Gly Gly Gly Ser Gly Gly Gly Gly
        420             425             430
Gly Gly Gly Gly Ser Gly Gly Gly Ser Gly Gly Gly Ser Gly
        435             440             445
Gly Gly Gly Ser Gly Gly Gly Gly Gly Gly Ser Gly Gly Gly
        450             455             460
Gly Ser Gly Gly Gly Ser Gly Gly Gly Ser Gly Gly Gly Gly
465             470             475                 480
Gly Gly Gly Gly Ser Gly Gly Gly Ser Gly Gly Gly Ser Gly
            485             490             495
Gly Gly Gly Ser Gly Gly Gly Gly Gly Gly Ser Gly Gly Gly
        500             505             510
Gly Ser Gly Gly Gly Ser Gly Gly Gly Ser Gly Gly Gly Gly
        515             520             525
Gly Gly Gly Gly Ser Gly Gly Gly Ser Gly Gly Gly Ser Gly
        530             535             540
Gly Gly Gly Ser Gly Gly Gly Gly Gly Gly Ser Gly Gly Gly
545             550             555                 560
Gly Ser Gly Gly Gly Gly Ser Gly Gly Gly Ser Gly Gly Gly
            565             570             575
Gly Gly Gly Gly Ser Gly Gly Gly Ser Gly Gly Gly Ser Gly
        580             585             590
Gly Gly Gly Ser Gly Gly Gly Gly Gly Gly Ser Gly Gly Gly
        595             600             605
Gly Ser Gly Gly Gly Gly Ser Gly Gly Gly Ser Gly Gly Gly
        610             615             620
Gly Gly Gly Gly Ser Gly Gly Gly Gly Ser Gly Gly Gly Ser Gly
625             630             635                 640
Gly Gly Gly Ser Gly Gly Gly Gly Gly Gly Ser Gly Gly Gly
            645             650             655
Gly Ser Gly Gly Gly Gly Ser Gly Gly Gly Ser Gly Gly Gly
        660             665             670
Gly Gly Gly Gly Ser Gly Gly Gly Gly Ser Gly Gly Gly Ser Gly
        675             680             685
```

Gly Gly Gly Ser Gly Gly Gly Gly Gly Ser Gly Gly Gly
    690             695             700
Gly Ser Gly Gly Gly Ser Gly Gly Gly Ser Gly Gly Gly Gly
705             710             715             720
Gly Gly Gly Gly Ser Gly Gly Gly Gly Ser Gly Gly Gly Ser Gly
            725             730             735
Gly Gly Gly Ser Gly Gly Gly Gly Gly Gly Ser Gly Gly Gly
        740             745             750
Gly Ser Gly Gly Gly Gly Ser Gly Gly Gly Ser Gly Gly Gly
        755             760             765
Gly Gly Gly Gly Ser Gly Gly Gly Ser Gly Gly Gly Ser Gly
    770             775             780
Gly Gly Gly Ser Gly Gly Gly Gly Gly Gly Ser Gly Gly Gly
785             790             795             800
Gly Ser Gly Gly Gly Gly Ser Gly Gly Gly Ser Gly Gly Gly
        805             810             815
Gly Gly Gly Gly Ser Gly Gly Gly Gly Ser Gly Gly Gly Ser Gly
            820             825             830
Gly Gly Gly Ser Gly Gly Gly Gly Gly Gly Ser Gly Gly Gly
        835             840             845
Gly Ser Gly Gly Gly Gly Ser Gly Gly Gly Ser Gly Gly Gly Gly
    850             855             860
Gly Gly Gly Gly Ser Gly Gly Gly Gly Ser Gly Gly Gly Ser Gly
865             870             875             880
Gly Gly Gly Ser Gly Gly Gly Gly Gly Gly Ser Gly Gly Gly
        885             890             895
Gly Ser Gly Gly Gly Ser Gly Gly Gly Ser Gly Gly Gly Gly
        900             905             910
Gly Gly Gly Ser Gly Gly Gly Gly Ser Gly Gly Gly Ser Gly
    915             920             925
Gly Gly Gly Ser Gly Gly Gly Gly Gly Gly Ser Gly Gly Gly
    930             935             940
Gly Ser Gly Gly Gly Gly Ser Gly Gly Gly Ser Gly Gly Gly Gly
945             950             955             960
Gly Gly Gly Gly Ser Gly Gly Gly Ser Gly Gly Gly Ser Gly
            965             970             975
Gly Gly Gly Ser Gly Gly Gly Gly Gly Gly Gly Ser Gly Gly Gly
        980             985             990
Gly Ser Gly Gly Gly Gly Ser Gly Gly Gly Ser Gly Gly Gly Gly
        995             1000            1005
Gly Gly Gly Gly Ser Gly Gly Gly Gly Ser Gly Gly Gly Ser
    1010            1015            1020
Gly Gly Gly Gly Ser Gly Gly Gly Gly Gly Gly Gly Ser Gly
    1025            1030            1035
Gly Gly Gly Ser Gly Gly Gly Ser Gly Gly Gly Gly Ser Gly
    1040            1045            1050
Gly Gly Gly Gly Gly Gly Ser Gly Gly Gly Gly Ser Gly Gly
    1055            1060            1065
Gly Gly Ser Gly Gly Gly Gly Ser Gly Gly Gly Gly Gly Gly
    1070            1075            1080
Gly Ser Gly Gly Gly Gly Ser Gly Gly Gly Gly Ser Gly Gly Gly
    1085            1090            1095
Gly Ser Gly Gly Gly Gly Gly Gly Gly Gly Ser Gly Gly Gly Gly

```
            1100                1105                1110

Ser  Gly  Gly  Gly  Gly  Ser  Gly  Gly  Gly  Ser  Gly  Gly  Gly
    1115                1120                1125

Gly  Gly  Gly  Gly  Ser  Gly  Gly  Gly  Gly  Ser  Gly  Gly  Gly  Ser
    1130                1135                1140

Gly  Gly  Gly  Gly  Ser  Gly  Gly  Gly  Gly  Gly  Gly  Gly  Ser  Gly
    1145                1150                1155

Gly  Gly  Gly  Ser  Gly  Gly  Gly  Ser  Gly  Gly  Gly  Ser  Gly
    1160                1165                1170

Gly  Gly  Gly  Gly  Gly  Gly  Ser  Gly  Gly  Gly  Ser  Gly  Gly
    1175                1180                1185

Gly  Gly  Ser  Gly  Gly  Gly  Gly  Ser  Gly  Gly  Gly  Gly  Gly  Gly
    1190                1195                1200

Gly  Ser  Gly  Gly  Gly  Gly  Ser  Gly  Gly  Gly  Gly  Ser  Gly  Gly
    1205                1210                1215

Gly  Ser  Gly  Gly  Gly  Gly  Gly  Gly  Gly  Ser  Gly  Gly  Gly  Gly
    1220                1225                1230

Ser  Gly  Gly  Gly  Ser  Gly  Gly  Gly  Ser  Gly  Gly  Gly  Gly
    1235                1240                1245

Gly  Gly  Gly  Gly  Ser  Gly  Gly  Gly  Gly  Ser  Gly  Gly  Gly  Ser
    1250                1255                1260

Gly  Gly  Gly  Gly  Ser  Gly  Gly  Gly  Gly  Gly  Gly  Ser  Gly
    1265                1270                1275

Gly  Gly  Gly  Ser  Gly  Gly  Gly  Ser  Gly  Gly  Gly  Ser  Gly
    1280                1285                1290

Gly  Gly  Gly  Gly  Gly  Gly  Gly  Ser  Gly  Gly  Gly  Ser  Gly  Gly
    1295                1300                1305

Gly  Gly  Ser  Gly  Gly  Gly  Gly  Ser  Gly  Gly  Gly  Gly  Gly  Gly
    1310                1315                1320

Gly  Ser  Gly  Gly  Gly  Gly  Ser  Gly  Gly  Gly  Gly  Ser  Gly  Gly
    1325                1330                1335

Gly  Ser  Gly  Gly  Gly  Gly  Gly  Gly  Gly  Ser  Gly  Gly  Gly  Gly
    1340                1345                1350

Ser  Gly  Gly  Gly  Gly  Ser  Gly  Gly  Gly  Ser  Gly  Gly  Gly  Gly
    1355                1360                1365

Gly  Gly  Gly  Gly  Ser  Gly  Gly  Gly  Gly  Ser  Gly  Gly  Gly  Ser
    1370                1375                1380

Gly  Gly  Gly  Gly  Ser  Gly  Gly  Gly  Gly  Gly  Gly  Gly  Ser  Gly
    1385                1390                1395

Gly  Gly  Gly  Ser  Gly  Gly  Gly  Gly  Ser  Gly  Gly  Gly  Ser  Gly
    1400                1405                1410

Gly  Gly  Gly  Gly  Gly  Gly  Gly  Ser  Gly  Gly  Gly  Gly  Ser  Gly  Gly
    1415                1420                1425

Gly  Gly  Ser  Gly  Gly  Gly  Gly  Ser  Gly  Gly  Gly  Gly  Gly  Gly
    1430                1435                1440

Gly  Ser  Gly  Gly  Gly  Gly  Ser  Gly  Gly  Gly  Gly  Ser  Gly  Gly
    1445                1450                1455

Gly  Ser  Gly  Gly  Gly  Gly  Gly  Gly  Gly  Ser  Gly  Gly  Gly  Gly
    1460                1465                1470

Ser  Gly  Gly  Gly  Gly  Ser  Gly  Gly  Gly  Ser  Gly  Gly  Gly  Gly
    1475                1480                1485

Gly  Gly  Gly  Gly  Ser  Gly  Gly  Gly  Gly  Ser  Gly  Gly  Gly  Ser
    1490                1495                1500
```

Gly Gly Gly Gly Ser Gly Gly Gly Gly Ser Gly Gly
        1505                1510                1515

Gly Gly Gly Ser Gly Gly Gly Ser Gly Gly Gly Ser Gly
        1520                1525                1530

Gly Gly Gly Gly Gly Gly Ser Gly Gly Gly Ser Gly Gly
        1535                1540                1545

Gly Gly Ser Gly Gly Gly Ser Gly Gly Gly Gly Gly Gly
        1550                1555                1560

Gly Ser Gly Gly Gly Gly Ser Gly Gly Gly Ser Gly Gly
        1565                1570                1575

Gly Ser Gly Gly Gly Gly Gly Gly Gly Ser Gly Gly Gly
        1580                1585                1590

Ser Gly Gly Gly Gly Ser Gly Gly Gly Ser Gly Gly Gly
        1595                1600                1605

Gly Gly Gly Gly Ser Gly Gly Gly Gly Ser Gly Gly Ser
        1610                1615                1620

Gly Gly Gly Gly Ser Gly Gly Gly Gly Gly Gly Ser Gly
        1625                1630                1635

Gly Gly Gly Ser Gly Gly Gly Ser Gly Gly Gly Ser Gly
        1640                1645                1650

Gly Gly Gly Gly Gly Gly Ser Gly Gly Gly Ser Gly Gly
        1655                1660                1665

Gly Gly Ser Gly Gly Gly Gly Ser Gly Gly Gly Gly Gly Gly
        1670                1675                1680

Gly Ser Gly Gly Gly Gly Ser Gly Gly Gly Ser Gly Gly Gly
        1685                1690                1695

Gly Ser Gly Gly Gly Gly Gly Gly Gly Ser Gly Gly Gly Gly
        1700                1705                1710

Ser Gly Gly Gly Gly Ser Gly Gly Gly Ser Gly Gly Gly Gly
        1715                1720                1725

Gly Gly Gly Gly Ser Gly Gly Gly Gly Ser Gly Gly Gly Ser
        1730                1735                1740

Gly Gly Gly Gly Ser Gly Gly Gly Gly Gly Gly Gly Ser Gly
        1745                1750                1755

Gly Gly Gly Ser Gly Gly Gly Ser Gly Gly Gly Gly Ser Gly
        1760                1765                1770

Gly Gly Gly Gly Gly Gly Ser Gly Gly Gly Gly Ser Gly Gly
        1775                1780                1785

Gly Gly Ser Gly Gly Gly Gly Ser Gly Gly Gly Gly
        1790                1795                1800

<210> SEQ ID NO 9
<211> LENGTH: 2175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2175)
<223> OTHER INFORMATION: This sequence may encompass 1-75 'Gly Gly Gly
      Gly Ser Gly Gly Gly Gly Ser Gly Gly Gly Ser Gly Gly Gly Gly
      Ser Gly Gly Gly Gly Ser Gly Gly Gly Gly' repeating units

<400> SEQUENCE: 9

Gly Gly Gly Gly Ser Gly Gly Gly Gly Ser Gly Gly Gly Gly Ser Gly

-continued

```
1               5                   10                  15
Gly Gly Gly Ser Gly Gly Gly Gly Ser Gly Gly Gly Gly Gly
                20                  25                  30
Gly Ser Gly Gly Gly Ser Gly Gly Gly Ser Gly Gly Gly Gly
                35                  40                  45
Ser Gly Gly Gly Gly Ser Gly Gly Gly Gly Gly Gly Ser Gly
                50                  55                  60
Gly Gly Ser Gly Gly Gly Ser Gly Gly Gly Gly Ser Gly Gly
65                  70                  75                  80
Gly Gly Ser Gly Gly Gly Gly Gly Ser Gly Gly Gly Gly Gly
                85                  90                  95
Ser Gly Gly Gly Gly Ser Gly Gly Gly Ser Gly Gly Gly Ser
                100                 105                 110
Gly Gly Gly Gly Gly Gly Gly Ser Gly Gly Gly Ser Gly Gly
                115                 120                 125
Gly Gly Ser Gly Gly Gly Ser Gly Gly Gly Ser Gly Gly Gly
                130                 135                 140
Gly Gly Gly Gly Gly Ser Gly Gly Gly Gly Ser Gly Gly Gly Ser
145                 150                 155                 160
Gly Gly Gly Gly Ser Gly Gly Gly Ser Gly Gly Gly Gly Gly
                165                 170                 175
Gly Gly Ser Gly Gly Gly Gly Ser Gly Gly Gly Ser Gly Gly Gly
                180                 185                 190
Gly Ser Gly Gly Gly Ser Gly Gly Gly Gly Gly Gly Gly Ser
                195                 200                 205
Gly Gly Gly Ser Gly Gly Gly Ser Gly Gly Gly Gly Ser Gly
                210                 215                 220
Gly Gly Gly Ser Gly Gly Gly Gly Gly Gly Ser Gly Gly Gly
225                 230                 235                 240
Gly Ser Gly Gly Gly Ser Gly Gly Gly Gly Ser Gly Gly Gly Gly
                245                 250                 255
Ser Gly Gly Gly Gly Gly Gly Gly Ser Gly Gly Gly Gly Ser Gly
                260                 265                 270
Gly Gly Ser Gly Gly Gly Gly Gly Gly Gly Gly Ser Gly Gly
                275                 280                 285
Gly Gly Gly Gly Gly Ser Gly Gly Gly Ser Gly Gly Gly Gly
                290                 295                 300
Ser Gly Gly Gly Gly Ser Gly Gly Gly Gly Ser Gly Gly Gly Gly
305                 310                 315                 320
Gly Gly Gly Ser Gly Gly Gly Gly Ser Gly Gly Gly Ser Gly Gly
                325                 330                 335
Gly Gly Ser Gly Gly Gly Gly Ser Gly Gly Gly Gly Gly Gly
                340                 345                 350
Ser Gly Gly Gly Gly Ser Gly Gly Gly Gly Ser Gly Gly Gly Ser
                355                 360                 365
Gly Gly Gly Gly Ser Gly Gly Gly Gly Gly Gly Gly Ser Gly Gly
                370                 375                 380
Gly Gly Ser Gly Gly Gly Gly Ser Gly Gly Gly Gly Ser Gly Gly Gly
385                 390                 395                 400
Gly Ser Gly Gly Gly Gly Gly Gly Gly Ser Gly Gly Gly Gly Ser
                405                 410                 415
Gly Gly Gly Gly Ser Gly Gly Gly Gly Ser Gly Gly Gly Ser Gly
                420                 425                 430
```

```
Gly Gly Gly Gly Gly Gly Ser Gly Gly Gly Ser Gly Gly
            435                 440             445

Gly Ser Gly Gly Gly Ser Gly Gly Gly Ser Gly Gly Gly
        450             455             460

Gly Gly Gly Gly Ser Gly Gly Gly Ser Gly Gly Gly Ser Gly
465                 470             475             480

Gly Gly Gly Ser Gly Gly Gly Ser Gly Gly Gly Gly Gly
            485             490             495

Gly Ser Gly Gly Gly Gly Ser Gly Gly Gly Ser Gly Gly Gly
        500             505             510

Ser Gly Gly Gly Gly Ser Gly Gly Gly Gly Gly Gly Ser Gly
        515             520             525

Gly Gly Gly Ser Gly Gly Gly Ser Gly Gly Gly Ser Gly Gly
            530             535             540

Gly Gly Ser Gly Gly Gly Gly Gly Gly Ser Gly Gly Gly Gly
545             550             555                 560

Ser Gly Gly Gly Gly Ser Gly Gly Gly Gly Ser Gly Gly Ser
            565             570             575

Gly Gly Gly Gly Gly Gly Gly Ser Gly Gly Gly Ser Gly Gly
            580             585             590

Gly Gly Ser Gly Gly Gly Gly Ser Gly Gly Gly Ser Gly Gly
            595             600             605

Gly Gly Gly Gly Ser Gly Gly Gly Ser Gly Gly Gly Gly Ser
            610             615             620

Gly Gly Gly Gly Ser Gly Gly Gly Ser Gly Gly Gly Gly Gly
625             630             635                 640

Gly Gly Ser Gly Gly Gly Gly Ser Gly Gly Gly Ser Gly Gly
            645             650             655

Gly Ser Gly Gly Gly Gly Ser Gly Gly Gly Gly Gly Gly Ser
        660             665             670

Gly Gly Gly Gly Ser Gly Gly Gly Gly Ser Gly Gly Ser Gly
            675             680             685

Gly Gly Gly Ser Gly Gly Gly Gly Gly Gly Gly Ser Gly Gly
            690             695             700

Gly Ser Gly Gly Gly Gly Ser Gly Gly Gly Ser Gly Gly Gly
705             710             715                 720

Ser Gly Gly Gly Gly Gly Gly Gly Ser Gly Gly Gly Ser Gly
            725             730             735

Gly Gly Gly Ser Gly Gly Gly Gly Ser Gly Gly Gly Ser Gly Gly
            740             745             750

Gly Gly Gly Gly Gly Ser Gly Gly Gly Gly Ser Gly Gly Gly
            755             760             765

Ser Gly Gly Gly Gly Ser Gly Gly Gly Ser Gly Gly Gly Gly
            770             775             780

Gly Gly Gly Ser Gly Gly Gly Ser Gly Gly Gly Ser Gly Gly
            785             790             795             800

Gly Gly Ser Gly Gly Gly Gly Ser Gly Gly Gly Gly Gly Gly
            805             810             815

Ser Gly Gly Gly Gly Ser Gly Gly Gly Ser Gly Gly Gly Ser
            820             825             830

Gly Gly Gly Gly Ser Gly Gly Gly Gly Gly Gly Ser Gly Gly
            835             840             845
```

Gly Gly Ser Gly Gly Gly Ser Gly Gly Gly Ser Gly Gly Gly
            850                 855                 860

Gly Ser Gly Gly Gly Gly Gly Gly Ser Gly Gly Gly Ser
865                 870                 875             880

Gly Gly Gly Gly Ser Gly Gly Gly Gly Ser Gly Gly Gly Ser Gly
                885                 890                 895

Gly Gly Gly Gly Gly Gly Gly Ser Gly Gly Gly Gly Ser Gly Gly Gly
            900                 905                 910

Gly Ser Gly Gly Gly Ser Gly Gly Gly Ser Gly Gly Gly
            915                 920                 925

Gly Gly Gly Gly Ser Gly Gly Gly Ser Gly Gly Gly Ser Gly
            930                 935                 940

Gly Gly Gly Ser Gly Gly Gly Ser Gly Gly Gly Gly Gly
945                 950                 955             960

Gly Ser Gly Gly Gly Ser Gly Gly Gly Ser Gly Gly Gly
                965                 970                 975

Ser Gly Gly Gly Gly Ser Gly Gly Gly Gly Gly Gly Ser Gly
            980                 985                 990

Gly Gly Gly Ser Gly Gly Gly Gly Ser Gly Gly Gly Gly Ser Gly Gly
            995                 1000                1005

Gly Gly Ser Gly Gly Gly Gly Gly Gly Gly Ser Gly Gly Gly
            1010                1015                1020

Gly Ser Gly Gly Gly Gly Ser Gly Gly Gly Gly Ser Gly Gly Gly
            1025                1030                1035

Gly Ser Gly Gly Gly Gly Gly Gly Gly Ser Gly Gly Gly Gly
            1040                1045                1050

Ser Gly Gly Gly Gly Ser Gly Gly Gly Ser Gly Gly Gly Gly
            1055                1060                1065

Ser Gly Gly Gly Gly Gly Gly Gly Ser Gly Gly Gly Ser
            1070                1075                1080

Gly Gly Gly Gly Ser Gly Gly Gly Gly Ser Gly Gly Gly Ser
            1085                1090                1095

Gly Gly Gly Gly Gly Gly Gly Ser Gly Gly Gly Gly Ser Gly
            1100                1105                1110

Gly Gly Gly Ser Gly Gly Gly Gly Ser Gly Gly Gly Gly Ser Gly
            1115                1120                1125

Gly Gly Gly Gly Gly Gly Gly Ser Gly Gly Gly Gly Ser Gly Gly
            1130                1135                1140

Gly Gly Ser Gly Gly Gly Gly Ser Gly Gly Gly Gly Ser Gly Gly
            1145                1150                1155

Gly Gly Gly Gly Gly Gly Ser Gly Gly Gly Gly Ser Gly Gly Gly
            1160                1165                1170

Gly Ser Gly Gly Gly Gly Ser Gly Gly Gly Gly Ser Gly Gly Gly
            1175                1180                1185

Gly Gly Gly Gly Gly Ser Gly Gly Gly Gly Ser Gly Gly Gly
            1190                1195                1200

Ser Gly Gly Gly Gly Ser Gly Gly Gly Gly Ser Gly Gly Gly Gly
            1205                1210                1215

Gly Gly Gly Gly Ser Gly Gly Gly Gly Gly Ser Gly Gly Gly Ser
            1220                1225                1230

Gly Gly Gly Gly Ser Gly Gly Gly Gly Ser Gly Gly Gly Gly
            1235                1240                1245

Gly Gly Gly Ser Gly Gly Gly Gly Ser Gly Gly Gly Gly Ser Gly

```
                    1250                1255                1260
Gly Gly Gly Ser Gly Gly Gly Ser Gly Gly Gly Gly Gly
        1265                1270                1275
Gly Gly Ser Gly Gly Gly Gly Ser Gly Gly Gly Ser Gly Gly
    1280                1285                1290
Gly Gly Ser Gly Gly Gly Gly Ser Gly Gly Gly Gly Gly Gly
    1295                1300                1305
Gly Ser Gly Gly Gly Gly Ser Gly Gly Gly Gly Ser Gly Gly Gly
    1310                1315                1320
Gly Ser Gly Gly Gly Gly Ser Gly Gly Gly Gly Gly Gly Gly
    1325                1330                1335
Ser Gly Gly Gly Gly Ser Gly Gly Gly Gly Ser Gly Gly Gly Gly
    1340                1345                1350
Ser Gly Gly Gly Gly Ser Gly Gly Gly Gly Gly Gly Gly Ser
    1355                1360                1365
Gly Gly Gly Gly Ser Gly Gly Gly Gly Ser Gly Gly Gly Gly Ser
    1370                1375                1380
Gly Gly Gly Gly Ser Gly Gly Gly Gly Gly Gly Gly Ser Gly
    1385                1390                1395
Gly Gly Gly Ser Gly Gly Gly Gly Ser Gly Gly Gly Gly Ser Gly
    1400                1405                1410
Gly Gly Gly Ser Gly Gly Gly Gly Gly Gly Gly Ser Gly Gly
    1415                1420                1425
Gly Gly Ser Gly Gly Gly Gly Ser Gly Gly Gly Gly Ser Gly Gly
    1430                1435                1440
Gly Gly Ser Gly Gly Gly Gly Gly Gly Gly Ser Gly Gly Gly
    1445                1450                1455
Gly Ser Gly Gly Gly Gly Ser Gly Gly Gly Gly Ser Gly Gly Gly
    1460                1465                1470
Gly Ser Gly Gly Gly Gly Gly Gly Gly Ser Gly Gly Gly Gly
    1475                1480                1485
Ser Gly Gly Gly Gly Ser Gly Gly Gly Gly Ser Gly Gly Gly Gly
    1490                1495                1500
Ser Gly Gly Gly Gly Gly Gly Gly Ser Gly Gly Gly Gly Ser
    1505                1510                1515
Gly Gly Gly Gly Ser Gly Gly Gly Gly Ser Gly Gly Gly Gly Ser
    1520                1525                1530
Gly Gly Gly Gly Gly Gly Gly Ser Gly Gly Gly Gly Ser Gly
    1535                1540                1545
Gly Gly Gly Ser Gly Gly Gly Ser Gly Gly Gly Gly Ser Gly
    1550                1555                1560
Gly Gly Gly Gly Gly Gly Ser Gly Gly Gly Gly Ser Gly Gly
    1565                1570                1575
Gly Gly Ser Gly Gly Gly Gly Ser Gly Gly Gly Gly Ser Gly Gly
    1580                1585                1590
Gly Gly Gly Gly Gly Ser Gly Gly Gly Gly Ser Gly Gly Gly
    1595                1600                1605
Gly Ser Gly Gly Gly Gly Ser Gly Gly Gly Gly Ser Gly Gly Gly
    1610                1615                1620
Gly Gly Gly Gly Gly Ser Gly Gly Gly Gly Ser Gly Gly Gly
    1625                1630                1635
Ser Gly Gly Gly Gly Ser Gly Gly Gly Gly Ser Gly Gly Gly Gly
    1640                1645                1650
```

Gly Gly Gly Gly Ser Gly Gly Gly Gly Ser Gly Gly Gly Ser
    1655                1660                1665

Gly Gly Gly Gly Ser Gly Gly Gly Gly Ser Gly Gly Gly Gly
    1670                1675                1680

Gly Gly Gly Ser Gly Gly Gly Gly Ser Gly Gly Gly Gly Ser Gly
    1685                1690                1695

Gly Gly Gly Ser Gly Gly Gly Ser Gly Gly Gly Gly Gly Gly
    1700                1705                1710

Gly Gly Ser Gly Gly Gly Gly Ser Gly Gly Gly Gly Ser Gly Gly
    1715                1720                1725

Gly Gly Ser Gly Gly Gly Gly Ser Gly Gly Gly Gly Gly Gly Gly
    1730                1735                1740

Gly Ser Gly Gly Gly Gly Ser Gly Gly Gly Gly Ser Gly Gly Gly
    1745                1750                1755

Gly Ser Gly Gly Gly Gly Ser Gly Gly Gly Gly Gly Gly Gly Gly
    1760                1765                1770

Ser Gly Gly Gly Gly Ser Gly Gly Gly Gly Ser Gly Gly Gly Gly
    1775                1780                1785

Ser Gly Gly Gly Gly Ser Gly Gly Gly Gly Gly Gly Gly Gly Ser
    1790                1795                1800

Gly Gly Gly Gly Ser Gly Gly Gly Gly Ser Gly Gly Gly Gly Ser
    1805                1810                1815

Gly Gly Gly Gly Ser Gly Gly Gly Gly Gly Gly Gly Gly Ser Gly
    1820                1825                1830

Gly Gly Gly Ser Gly Gly Gly Gly Ser Gly Gly Gly Gly Ser Gly
    1835                1840                1845

Gly Gly Gly Ser Gly Gly Gly Gly Gly Gly Gly Gly Ser Gly Gly
    1850                1855                1860

Gly Gly Ser Gly Gly Gly Gly Ser Gly Gly Gly Gly Ser Gly Gly
    1865                1870                1875

Gly Gly Ser Gly Gly Gly Gly Gly Gly Gly Gly Ser Gly Gly Gly
    1880                1885                1890

Gly Ser Gly Gly Gly Gly Ser Gly Gly Gly Gly Ser Gly Gly Gly
    1895                1900                1905

Gly Ser Gly Gly Gly Gly Gly Gly Gly Gly Ser Gly Gly Gly Gly
    1910                1915                1920

Ser Gly Gly Gly Gly Ser Gly Gly Gly Gly Ser Gly Gly Gly Gly
    1925                1930                1935

Ser Gly Gly Gly Gly Gly Gly Gly Ser Gly Gly Gly Gly Gly Ser
    1940                1945                1950

Gly Gly Gly Gly Ser Gly Gly Gly Gly Ser Gly Gly Gly Gly Ser
    1955                1960                1965

Gly Gly Gly Gly Gly Gly Gly Ser Gly Gly Gly Gly Ser Gly
    1970                1975                1980

Gly Gly Gly Ser Gly Gly Gly Gly Ser Gly Gly Gly Gly Ser Gly
    1985                1990                1995

Gly Gly Gly Gly Gly Gly Ser Gly Gly Gly Gly Ser Gly Gly
    2000                2005                2010

Gly Gly Ser Gly Gly Gly Gly Ser Gly Gly Gly Gly Ser Gly Gly
    2015                2020                2025

Gly Gly Gly Gly Gly Gly Ser Gly Gly Gly Gly Ser Gly Gly Gly
    2030                2035                2040

```
Gly Ser  Gly Gly Gly Gly Ser  Gly Gly Gly Gly Ser  Gly Gly Gly
    2045              2050              2055

Gly Gly  Gly Gly Gly Ser Gly  Gly Gly Ser Gly Gly  Gly Gly Gly
    2060              2065              2070

Ser Gly  Gly Gly Gly Ser Gly  Gly Gly Gly Ser Gly  Gly Gly Gly
    2075              2080              2085

Gly Gly  Gly Gly Ser Gly Gly  Gly Gly Ser Gly Gly  Gly Gly Ser
    2090              2095              2100

Gly Gly  Gly Gly Ser Gly Gly  Gly Ser Gly Gly Gly  Gly Gly Gly
    2105              2110              2115

Gly Gly  Gly Ser Gly Gly Gly  Ser Gly Gly Gly Gly  Ser Gly Gly
    2120              2125              2130

Gly Gly  Gly Ser Gly Gly Gly  Ser Gly Gly Gly Gly  Gly Gly Gly
    2135              2140              2145

Gly Gly  Ser Gly Gly Gly Gly  Ser Gly Gly Gly Gly  Ser Gly Gly
    2150              2155              2160

Gly Gly  Ser Gly Gly Gly Gly  Ser Gly Gly Gly Gly
    2165              2170              2175

<210> SEQ ID NO 10
<211> LENGTH: 2550
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2550)
<223> OTHER INFORMATION: This sequence may encompass 1-75 'Gly Gly Gly
      Gly Ser Gly Gly Gly Gly Ser Gly Gly Gly Gly Ser Gly Gly Gly Gly
      Ser Gly Gly Gly Gly Ser Gly Gly Gly Gly Ser Gly Gly Gly
      Gly' repeating units

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Gly Ser Gly Gly Gly
            20                  25                  30

Gly Gly Gly Gly Gly Gly Ser Gly Gly Gly Ser Gly Gly Gly Gly
        35                  40                  45

Ser Gly Gly Gly Gly Ser Gly Gly Gly Gly Ser Gly Gly Gly Gly Ser
    50                  55                  60

Gly Gly Gly Gly Gly Gly Ser Gly Gly Gly Ser Gly Gly
65                  70                  75                  80

Gly Gly Ser Gly Gly Gly Ser Gly Gly Gly Ser Gly Gly Gly
            85                  90                  95

Gly Ser Gly Gly Gly Gly Gly Gly Ser Gly Gly Gly Gly Ser
        100                 105                 110

Gly Gly Gly Gly Ser Gly Gly Gly Ser Gly Gly Gly Ser Gly
        115                 120                 125

Gly Gly Gly Ser Gly Gly Gly Gly Gly Gly Ser Gly Gly Gly
        130                 135                 140

Gly Ser Gly Gly Gly Ser Gly Gly Gly Ser Gly Gly Gly Gly
145             150                 155                 160

Ser Gly Gly Gly Gly Ser Gly Gly Gly Gly Gly Gly Ser Gly
            165                 170                 175

Gly Gly Gly Ser Gly Gly Gly Gly Ser Gly Gly Gly Gly Ser Gly Gly
```

```
            180                 185                 190
Gly Gly Ser Gly Gly Gly Ser Gly Gly Gly Gly Gly Gly
        195                 200                 205
Ser Gly Gly Gly Gly Ser Gly Gly Gly Ser Gly Gly Gly Ser
    210                 215                 220
Gly Gly Gly Ser Gly Gly Gly Ser Gly Gly Gly Gly Gly
225                 230                 235                 240
Gly Gly Ser Gly Gly Gly Ser Gly Gly Gly Ser Gly Gly
            245                 250                 255
Gly Ser Gly Gly Gly Ser Gly Gly Gly Ser Gly Gly Gly
        260                 265                 270
Gly Gly Gly Gly Ser Gly Gly Gly Ser Gly Gly Gly Ser Gly
    275                 280                 285
Gly Gly Gly Ser Gly Gly Gly Ser Gly Gly Gly Ser Gly Gly
        290                 295                 300
Gly Gly Gly Gly Gly Ser Gly Gly Gly Ser Gly Gly Gly
305                 310                 315                 320
Ser Gly Gly Gly Gly Ser Gly Gly Gly Gly Ser Gly Gly Gly Ser
            325                 330                 335
Gly Gly Gly Gly Gly Gly Gly Ser Gly Gly Gly Ser Gly Gly
        340                 345                 350
Gly Gly Ser Gly Gly Gly Gly Ser Gly Gly Gly Ser Gly Gly Gly
        355                 360                 365
Gly Ser Gly Gly Gly Gly Gly Gly Ser Gly Gly Gly Ser
    370                 375                 380
Gly Gly Gly Gly Ser Gly Gly Gly Ser Gly Gly Gly Ser Gly
385                 390                 395                 400
Gly Gly Gly Ser Gly Gly Gly Gly Gly Gly Ser Gly Gly Gly
            405                 410                 415
Gly Ser Gly Gly Gly Gly Ser Gly Gly Gly Ser Gly Gly Gly
        420                 425                 430
Ser Gly Gly Gly Gly Ser Gly Gly Gly Gly Gly Gly Ser Gly
        435                 440                 445
Gly Gly Gly Ser Gly Gly Gly Ser Gly Gly Gly Ser Gly Gly
    450                 455                 460
Gly Gly Ser Gly Gly Gly Gly Ser Gly Gly Gly Gly Gly Gly
465                 470                 475                 480
Ser Gly Gly Gly Gly Ser Gly Gly Gly Gly Ser Gly Gly Gly Ser
            485                 490                 495
Gly Gly Gly Gly Ser Gly Gly Gly Ser Gly Gly Gly Gly Gly
        500                 505                 510
Gly Gly Ser Gly Gly Gly Gly Ser Gly Gly Gly Ser Gly Gly Gly
        515                 520                 525
Gly Ser Gly Gly Gly Gly Ser Gly Gly Gly Ser Gly Gly Gly Gly
        530                 535                 540
Gly Gly Gly Gly Ser Gly Gly Gly Gly Ser Gly Gly Gly Ser Gly
545                 550                 555                 560
Gly Gly Gly Ser Gly Gly Gly Ser Gly Gly Gly Ser Gly Gly
            565                 570                 575
Gly Gly Gly Gly Gly Ser Gly Gly Gly Ser Gly Gly Gly Gly
        580                 585                 590
Ser Gly Gly Gly Gly Ser Gly Gly Gly Ser Gly Gly Gly Ser
            595                 600                 605
```

-continued

Gly Gly Gly Gly Gly Gly Gly Ser Gly Gly Gly Ser Gly Gly
            610                 615                 620
Gly Gly Ser Gly Gly Gly Ser Gly Gly Gly Ser Gly Gly Gly
625                 630                 635                 640
Gly Ser Gly Gly Gly Gly Gly Gly Ser Gly Gly Gly Gly Ser
                645                 650                 655
Gly Gly Gly Gly Ser Gly Gly Gly Ser Gly Gly Gly Ser Gly
                660                 665                 670
Gly Gly Gly Ser Gly Gly Gly Gly Gly Gly Ser Gly Gly Gly
            675                 680                 685
Gly Ser Gly Gly Gly Ser Gly Gly Gly Gly Ser Gly Gly Gly
        690                 695                 700
Ser Gly Gly Gly Gly Ser Gly Gly Gly Gly Gly Gly Ser Gly
705                 710                 715                 720
Gly Gly Gly Ser Gly Gly Gly Ser Gly Gly Gly Ser Gly Gly
                725                 730                 735
Gly Gly Ser Gly Gly Gly Gly Ser Gly Gly Gly Gly Gly Gly
            740                 745                 750
Ser Gly Gly Gly Gly Ser Gly Gly Gly Gly Ser Gly Gly Ser
        755                 760                 765
Gly Gly Gly Gly Ser Gly Gly Gly Ser Gly Gly Gly Gly Gly
            770                 775                 780
Gly Gly Ser Gly Gly Gly Ser Gly Gly Gly Ser Gly Gly Gly
785                 790                 795                 800
Gly Ser Gly Gly Gly Ser Gly Gly Gly Ser Gly Gly Gly Gly
                805                 810                 815
Gly Gly Gly Gly Ser Gly Gly Gly Ser Gly Gly Gly Ser Gly
            820                 825                 830
Gly Gly Gly Ser Gly Gly Gly Ser Gly Gly Gly Ser Gly Gly
            835                 840                 845
Gly Gly Gly Gly Gly Ser Gly Gly Gly Gly Ser Gly Gly Gly
            850                 855                 860
Ser Gly Gly Gly Ser Gly Gly Gly Ser Gly Gly Gly Gly Ser
865                 870                 875                 880
Gly Gly Gly Gly Gly Gly Gly Ser Gly Gly Gly Ser Gly Gly
                885                 890                 895
Gly Gly Ser Gly Gly Gly Gly Ser Gly Gly Gly Ser Gly Gly Gly
            900                 905                 910
Gly Ser Gly Gly Gly Gly Gly Gly Gly Ser Gly Gly Gly Ser
        915                 920                 925
Gly Gly Gly Gly Ser Gly Gly Gly Ser Gly Gly Gly Ser Gly
    930                 935                 940
Gly Gly Gly Ser Gly Gly Gly Gly Gly Gly Ser Gly Gly Gly
945                 950                 955                 960
Gly Ser Gly Gly Gly Gly Ser Gly Gly Gly Ser Gly Gly Gly
                965                 970                 975
Ser Gly Gly Gly Gly Ser Gly Gly Gly Gly Gly Gly Ser Gly
            980                 985                 990
Gly Gly Gly Ser Gly Gly Gly Gly Ser Gly Gly Gly Gly Ser Gly Gly
            995                 1000                    1005
Gly Gly Ser Gly Gly Gly Gly Ser Gly Gly Gly Gly Gly Gly
        1010                1015                1020

```
Gly Ser Gly Gly Gly Gly Ser Gly Gly Gly Gly Ser Gly Gly Gly
    1025                1030                1035

Gly Ser Gly Gly Gly Gly Ser Gly Gly Gly Gly Ser Gly Gly Gly
    1040                1045                1050

Gly Gly Gly Gly Gly Ser Gly Gly Gly Gly Ser Gly Gly Gly Gly
    1055                1060                1065

Ser Gly Gly Gly Gly Ser Gly Gly Gly Gly Ser Gly Gly Gly Gly
    1070                1075                1080

Ser Gly Gly Gly Gly Gly Gly Gly Ser Gly Gly Gly Gly Gly Ser
    1085                1090                1095

Gly Gly Gly Gly Ser Gly Gly Gly Gly Ser Gly Gly Gly Gly Ser
    1100                1105                1110

Gly Gly Gly Gly Ser Gly Gly Gly Gly Gly Gly Gly Gly Ser Gly
    1115                1120                1125

Gly Gly Gly Ser Gly Gly Gly Gly Ser Gly Gly Gly Gly Ser Gly
    1130                1135                1140

Gly Gly Gly Ser Gly Gly Gly Gly Ser Gly Gly Gly Gly Gly Gly
    1145                1150                1155

Gly Gly Ser Gly Gly Gly Gly Ser Gly Gly Gly Gly Ser Gly Gly
    1160                1165                1170

Gly Gly Ser Gly Gly Gly Gly Ser Gly Gly Gly Gly Ser Gly Gly
    1175                1180                1185

Gly Gly Gly Gly Gly Gly Ser Gly Gly Gly Gly Ser Gly Gly Gly
    1190                1195                1200

Gly Ser Gly Gly Gly Gly Ser Gly Gly Gly Gly Ser Gly Gly Gly
    1205                1210                1215

Gly Ser Gly Gly Gly Gly Gly Gly Gly Ser Gly Gly Gly Gly Gly
    1220                1225                1230

Ser Gly Gly Gly Gly Ser Gly Gly Gly Gly Ser Gly Gly Gly Gly
    1235                1240                1245

Ser Gly Gly Gly Gly Ser Gly Gly Gly Gly Gly Gly Gly Gly Ser
    1250                1255                1260

Gly Gly Gly Gly Ser Gly Gly Gly Gly Ser Gly Gly Gly Gly Ser
    1265                1270                1275

Gly Gly Gly Gly Ser Gly Gly Gly Gly Ser Gly Gly Gly Gly Gly
    1280                1285                1290

Gly Gly Gly Ser Gly Gly Gly Gly Ser Gly Gly Gly Gly Ser Gly
    1295                1300                1305

Gly Gly Gly Ser Gly Gly Gly Gly Ser Gly Gly Gly Gly Ser Gly
    1310                1315                1320

Gly Gly Gly Gly Gly Gly Ser Gly Gly Gly Gly Ser Gly Gly Gly
    1325                1330                1335

Gly Gly Ser Gly Gly Gly Gly Ser Gly Gly Gly Gly Ser Gly Gly
    1340                1345                1350

Gly Gly Ser Gly Gly Gly Gly Gly Gly Gly Gly Ser Gly Gly Gly
    1355                1360                1365

Gly Ser Gly Gly Gly Gly Ser Gly Gly Gly Gly Ser Gly Gly Gly
    1370                1375                1380

Gly Ser Gly Gly Gly Gly Ser Gly Gly Gly Gly Gly Gly Gly Gly
    1385                1390                1395

Ser Gly Gly Gly Gly Ser Gly Gly Gly Gly Ser Gly Gly Gly Gly
    1400                1405                1410

Ser Gly Gly Gly Gly Ser Gly Gly Gly Gly Ser Gly Gly Gly Gly
```

```
            1415                1420                1425

Gly Gly Gly Gly Ser Gly Gly  Gly Gly Ser Gly Gly  Gly Gly Ser
    1430                1435                1440

Gly Gly Gly Gly Ser Gly Gly  Gly Gly Ser Gly Gly  Gly Gly Ser
    1445                1450                1455

Gly Gly Gly Gly Gly Gly Gly  Gly Ser Gly Gly Gly  Gly Ser Gly
    1460                1465                1470

Gly Gly Gly Ser Gly Gly Gly  Gly Ser Gly Gly Gly  Gly Ser Gly
    1475                1480                1485

Gly Gly Gly Ser Gly Gly Gly  Gly Gly Gly Gly Gly  Ser Gly Gly
    1490                1495                1500

Gly Gly Ser Gly Gly Gly Gly  Ser Gly Gly Gly Gly  Ser Gly Gly
    1505                1510                1515

Gly Gly Ser Gly Gly Gly Gly  Ser Gly Gly Gly Gly  Gly Gly Gly
    1520                1525                1530

Gly Ser Gly Gly Gly Gly Ser  Gly Gly Gly Gly Ser  Gly Gly Gly
    1535                1540                1545

Gly Ser Gly Gly Gly Gly Ser  Gly Gly Gly Gly Ser  Gly Gly Gly
    1550                1555                1560

Gly Gly Gly Gly Gly Ser Gly  Gly Gly Gly Ser Gly  Gly Gly Gly
    1565                1570                1575

Ser Gly Gly Gly Gly Ser Gly  Gly Gly Gly Ser Gly  Gly Gly Gly
    1580                1585                1590

Ser Gly Gly Gly Gly Gly Gly  Gly Gly Ser Gly Gly  Gly Gly Ser
    1595                1600                1605

Gly Gly Gly Gly Ser Gly Gly  Gly Gly Ser Gly Gly  Gly Gly Ser
    1610                1615                1620

Gly Gly Gly Gly Ser Gly Gly  Gly Gly Gly Gly Gly  Gly Ser Gly
    1625                1630                1635

Gly Gly Gly Ser Gly Gly Gly  Ser Gly Gly Gly Gly  Ser Gly Gly
    1640                1645                1650

Gly Gly Gly Ser Gly Gly Gly  Gly Ser Gly Gly Gly  Gly Gly Gly
    1655                1660                1665

Gly Gly Ser Gly Gly Gly Gly  Ser Gly Gly Gly Gly  Ser Gly Gly
    1670                1675                1680

Gly Gly Ser Gly Gly Gly Gly  Ser Gly Gly Gly Gly  Ser Gly Gly
    1685                1690                1695

Gly Gly Gly Gly Gly Gly Ser  Gly Gly Gly Gly Ser  Gly Gly Gly
    1700                1705                1710

Gly Ser Gly Gly Gly Gly Ser  Gly Gly Gly Gly Ser  Gly Gly Gly
    1715                1720                1725

Gly Ser Gly Gly Gly Gly Gly  Gly Gly Gly Ser Gly  Gly Gly Gly
    1730                1735                1740

Ser Gly Gly Gly Gly Ser Gly  Gly Gly Gly Ser Gly  Gly Gly Gly
    1745                1750                1755

Ser Gly Gly Gly Gly Ser Gly  Gly Gly Gly Gly Gly  Gly Gly Ser
    1760                1765                1770

Gly Gly Gly Gly Ser Gly Gly  Gly Gly Ser Gly Gly  Gly Gly Ser
    1775                1780                1785

Gly Gly Gly Gly Ser Gly Gly  Gly Gly Ser Gly Gly  Gly Gly Gly
    1790                1795                1800

Gly Gly Gly Ser Gly Gly Gly  Gly Ser Gly Gly Gly  Gly Ser Gly
    1805                1810                1815
```

-continued

Gly Gly     Gly Ser Gly Gly     Gly Ser Gly Gly     Gly Ser Gly
    1820            1825                1830

Gly Gly Gly Gly Gly Gly     Ser Gly Gly Gly     Ser Gly Gly
    1835            1840                1845

Gly Gly Ser Gly Gly Gly     Ser Gly Gly Gly     Ser Gly Gly
    1850            1855                1860

Gly Gly Ser Gly Gly Gly     Gly Gly Gly Ser     Gly Gly Gly
    1865            1870                1875

Gly Ser Gly Gly Gly Gly Ser     Gly Gly Gly Ser     Gly Gly Gly
    1880            1885                1890

Gly Ser Gly Gly Gly Gly Ser     Gly Gly Gly Gly     Gly Gly Gly
    1895            1900                1905

Ser Gly Gly Gly Gly Ser Gly     Gly Gly Gly Ser     Gly Gly Gly
    1910            1915                1920

Ser Gly Gly Gly Gly Ser Gly     Gly Gly Ser Gly     Gly Gly Gly
    1925            1930                1935

Gly Gly Gly Gly Ser Gly Gly     Gly Gly Ser Gly     Gly Gly Ser
    1940            1945                1950

Gly Gly Gly Gly Ser Gly Gly     Gly Gly Ser Gly     Gly Gly Ser
    1955            1960                1965

Gly Gly Gly Gly Gly Gly Gly     Ser Gly Gly Gly     Gly Ser Gly
    1970            1975                1980

Gly Gly Gly Ser Gly Gly Gly     Ser Gly Gly Gly     Gly Ser Gly
    1985            1990                1995

Gly Gly Gly Ser Gly Gly Gly     Gly Gly Gly Gly     Ser Gly Gly
    2000            2005                2010

Gly Gly Ser Gly Gly Gly Gly     Ser Gly Gly Gly     Ser Gly Gly
    2015            2020                2025

Gly Gly Ser Gly Gly Gly Gly     Ser Gly Gly Gly     Gly Gly Gly
    2030            2035                2040

Gly Ser Gly Gly Gly Gly Ser     Gly Gly Gly Ser     Gly Gly Gly
    2045            2050                2055

Gly Ser Gly Gly Gly Gly Ser     Gly Gly Gly Ser     Gly Gly Gly
    2060            2065                2070

Gly Gly Gly Gly Gly Ser Gly     Gly Gly Gly Ser     Gly Gly Gly
    2075            2080                2085

Ser Gly Gly Gly Gly Ser Gly     Gly Gly Gly Ser     Gly Gly Gly
    2090            2095                2100

Ser Gly Gly Gly Gly Gly Gly     Gly Ser Gly Gly     Gly Gly Ser
    2105            2110                2115

Gly Gly Gly Gly Ser Gly Gly     Gly Gly Ser Gly     Gly Gly Ser
    2120            2125                2130

Gly Gly Gly Gly Ser Gly Gly     Gly Gly Gly Gly     Gly Ser Gly
    2135            2140                2145

Gly Gly Gly Ser Gly Gly Gly     Gly Ser Gly Gly     Gly Ser Gly
    2150            2155                2160

Gly Gly Gly Ser Gly Gly Gly     Gly Ser Gly Gly     Gly Gly Gly
    2165            2170                2175

Gly Gly Ser Gly Gly Gly Gly     Ser Gly Gly Gly     Ser Gly Gly
    2180            2185                2190

Gly Gly Ser Gly Gly Gly Gly     Ser Gly Gly Gly     Ser Gly Gly
    2195            2200                2205

-continued

Gly Gly Gly Gly Gly Ser Gly Gly Gly Gly Ser Gly Gly Gly
    2210                2215                2220
Gly Ser Gly Gly Gly Ser Gly Gly Gly Gly Ser Gly Gly Gly
    2225                2230                2235
Gly Ser Gly Gly Gly Gly Gly Gly Gly Ser Gly Gly Gly Gly
    2240                2245                2250
Ser Gly Gly Gly Gly Ser Gly Gly Gly Ser Gly Gly Gly Gly
    2255                2260                2265
Ser Gly Gly Gly Ser Gly Gly Gly Gly Gly Gly Gly Ser
    2270                2275                2280
Gly Gly Gly Gly Ser Gly Gly Gly Gly Ser Gly Gly Gly Ser
    2285                2290                2295
Gly Gly Gly Gly Ser Gly Gly Gly Gly Ser Gly Gly Gly Gly
    2300                2305                2310
Gly Gly Gly Ser Gly Gly Gly Gly Ser Gly Gly Gly Ser Gly
    2315                2320                2325
Gly Gly Gly Ser Gly Gly Gly Gly Ser Gly Gly Gly Ser Gly
    2330                2335                2340
Gly Gly Gly Gly Gly Gly Ser Gly Gly Gly Gly Ser Gly Gly
    2345                2350                2355
Gly Gly Ser Gly Gly Gly Gly Ser Gly Gly Gly Gly Ser Gly Gly
    2360                2365                2370
Gly Gly Ser Gly Gly Gly Gly Gly Gly Gly Ser Gly Gly Gly
    2375                2380                2385
Gly Ser Gly Gly Gly Gly Ser Gly Gly Gly Ser Gly Gly Gly
    2390                2395                2400
Gly Ser Gly Gly Gly Gly Ser Gly Gly Gly Gly Gly Gly Gly
    2405                2410                2415
Ser Gly Gly Gly Gly Ser Gly Gly Gly Ser Gly Gly Gly Gly
    2420                2425                2430
Ser Gly Gly Gly Gly Ser Gly Gly Gly Ser Gly Gly Gly Gly
    2435                2440                2445
Gly Gly Gly Gly Ser Gly Gly Gly Gly Ser Gly Gly Gly Ser
    2450                2455                2460
Gly Gly Gly Gly Ser Gly Gly Gly Gly Ser Gly Gly Gly Ser
    2465                2470                2475
Gly Gly Gly Gly Gly Gly Gly Gly Ser Gly Gly Gly Ser Gly
    2480                2485                2490
Gly Gly Gly Ser Gly Gly Gly Ser Gly Gly Gly Gly Ser Gly
    2495                2500                2505
Gly Gly Gly Ser Gly Gly Gly Gly Gly Gly Gly Ser Gly Gly
    2510                2515                2520
Gly Gly Ser Gly Gly Gly Gly Ser Gly Gly Gly Gly Ser Gly Gly
    2525                2530                2535
Gly Gly Ser Gly Gly Gly Gly Ser Gly Gly Gly Gly
    2540                2545                2550

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gly Gly Gly Gly
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Lys Gly Gly Gly Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Asn Gly Ser Gly Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Cys Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Pro Asn Gly Gly
1               5

<210> SEQ ID NO 17
<211> LENGTH: 150
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 'Gly Glu'
      repeating units

<400> SEQUENCE: 17

Gly Glu Gly Glu Gly Glu Gly Glu Gly Glu Gly Glu Gly Glu Gly Glu
1               5                   10                  15

Gly Glu Gly Glu Gly Glu Gly Glu Gly Glu Gly Glu Gly Glu Gly Glu
            20                  25                  30

Gly Glu Gly Glu Gly Glu Gly Glu Gly Glu Gly Glu Gly Glu Gly Glu
        35                  40                  45

Gly Glu Gly Glu Gly Glu Gly Glu Gly Glu Gly Glu Gly Glu Gly Glu
    50                  55                  60

Gly Glu Gly Glu Gly Glu Gly Glu Gly Glu Gly Glu Gly Glu Gly Glu
65                  70                  75                  80

Gly Glu Gly Glu Gly Glu Gly Glu Gly Glu Gly Glu Gly Glu Gly Glu
                85                  90                  95

Gly Glu Gly Glu Gly Glu Gly Glu Gly Glu Gly Glu Gly Glu Gly Glu
            100                 105                 110

Gly Glu Gly Glu Gly Glu Gly Glu Gly Glu Gly Glu Gly Glu Gly Glu
        115                 120                 125

Gly Glu Gly Glu Gly Glu Gly Glu Gly Glu Gly Glu Gly Glu Gly Glu
    130                 135                 140

Gly Glu Gly Glu Gly Glu
145                 150

<210> SEQ ID NO 18
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 'Gly Gly Glu'
      repeating units

<400> SEQUENCE: 18

Gly Gly Glu Gly Gly Glu Gly Gly Glu Gly Gly Glu Gly Gly Gly
1               5                   10                  15

Gly Glu Gly Gly Glu Gly Gly Glu Gly Gly Glu Gly Gly Glu Gly
            20                  25                  30

Glu Gly Gly Glu Gly Gly Glu Gly Gly Glu Gly Gly Glu Gly Gly Glu
        35                  40                  45

Gly Gly Glu Gly Gly Glu Gly Gly Glu Gly Gly Glu Gly Gly Glu Gly
    50                  55                  60

Gly Glu Gly Gly Glu Gly Gly Glu Gly Gly Glu Gly Gly Glu Gly Gly
65                  70                  75                  80

Glu Gly Gly Glu Gly Gly Glu Gly Gly Glu Gly Gly Glu Gly Gly Glu
                85                  90                  95

Gly Gly Glu Gly Gly Glu Gly Gly Glu Gly Gly Glu Gly Gly Glu Gly
            100                 105                 110

Gly Glu Gly Gly Glu Gly Gly Glu Gly Gly Glu Gly Gly Glu Gly Gly
```

```
                    115                 120                 125
Glu Gly Gly Glu Gly Gly Gly Glu Gly Gly Gly Glu Gly Gly Glu
        130                 135                 140

Gly Gly Glu Gly Gly Glu Gly Gly Gly Glu Gly Gly Gly Glu Gly
145                 150                 155                 160

Gly Glu Gly Gly Glu Gly Gly Gly Glu Gly Gly Gly Glu Gly Gly
                165                 170                 175

Glu Gly Gly Glu Gly Gly Gly Glu Gly Gly Gly Glu Gly Gly Glu
            180                 185                 190

Gly Gly Glu Gly Gly Glu Gly Gly Gly Glu Gly Gly Gly Glu Gly
        195                 200                 205

Gly Glu Gly Gly Glu Gly Gly Gly Glu Gly Gly Gly Glu Gly Gly
    210                 215                 220

Glu
225

<210> SEQ ID NO 19
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 'Gly Gly Gly
      Glu' repeating units

<400> SEQUENCE: 19

Gly Gly Gly Glu Gly Gly Gly Glu Gly Gly Gly Glu Gly Gly Gly Glu
1               5                   10                  15

Gly Gly Gly Glu Gly Gly Gly Glu Gly Gly Gly Glu Gly Gly Gly Glu
            20                  25                  30

Gly Gly Gly Glu Gly Gly Gly Glu Gly Gly Gly Glu Gly Gly Gly Glu
        35                  40                  45

Gly Gly Gly Glu Gly Gly Gly Glu Gly Gly Gly Glu Gly Gly Gly Glu
50                  55                  60

Gly Gly Gly Glu Gly Gly Gly Glu Gly Gly Gly Glu Gly Gly Gly Glu
65                  70                  75                  80

Gly Gly Gly Glu Gly Gly Gly Glu Gly Gly Gly Glu Gly Gly Gly Glu
                85                  90                  95

Gly Gly Gly Glu Gly Gly Gly Glu Gly Gly Gly Glu Gly Gly Gly Glu
            100                 105                 110

Gly Gly Gly Glu Gly Gly Gly Glu Gly Gly Gly Glu Gly Gly Gly Glu
        115                 120                 125

Gly Gly Gly Glu Gly Gly Gly Glu Gly Gly Gly Glu Gly Gly Gly Glu
    130                 135                 140

Gly Gly Gly Glu Gly Gly Gly Glu Gly Gly Gly Glu Gly Gly Gly Glu
145                 150                 155                 160

Gly Gly Gly Glu Gly Gly Gly Glu Gly Gly Gly Glu Gly Gly Gly Glu
                165                 170                 175

Gly Gly Gly Glu Gly Gly Gly Glu Gly Gly Gly Glu Gly Gly Gly Glu
            180                 185                 190

Gly Gly Gly Glu Gly Gly Gly Glu Gly Gly Gly Glu Gly Gly Gly Glu
        195                 200                 205

Gly Gly Gly Glu Gly Gly Gly Glu Gly Gly Gly Glu Gly Gly Gly Glu
```

```
              210                 215                 220
Gly Gly Gly Glu Gly Gly Gly Glu Gly Gly Gly Glu Gly Gly Gly Glu
225                 230                 235                 240

Gly Gly Gly Glu Gly Gly Gly Glu Gly Gly Gly Glu Gly Gly Gly Glu
                245                 250                 255

Gly Gly Gly Glu Gly Gly Gly Glu Gly Gly Gly Glu Gly Gly Gly Glu
                260                 265                 270

Gly Gly Gly Glu Gly Gly Gly Glu Gly Gly Gly Glu Gly Gly Gly Glu
            275                 280                 285

Gly Gly Gly Glu Gly Gly Gly Glu Gly Gly Gly Glu
            290                 295                 300

<210> SEQ ID NO 20
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Gly Gly Gly
      Gly Glu' repeating units

<400> SEQUENCE: 20

Gly Gly Gly Gly Glu Gly Gly Gly Gly Glu Gly Gly Gly Gly Glu Gly
1               5                   10                  15

Gly Gly Gly Glu Gly Gly Gly Gly Glu Gly Gly Gly Gly Glu Gly Gly
            20                  25                  30

Gly Gly Glu Gly Gly Gly Gly Glu Gly Gly Gly Gly Glu Gly Gly Gly
        35                  40                  45

Gly Glu Gly Gly Gly Gly Glu Gly Gly Gly Gly Glu Gly Gly Gly Gly
    50                  55                  60

Glu Gly Gly Gly Gly Glu Gly Gly Gly Gly Glu Gly Gly Gly Gly Glu
65                  70                  75                  80

Gly Gly Gly Gly Glu Gly Gly Gly Gly Glu Gly Gly Gly Gly Glu Gly
                85                  90                  95

Gly Gly Gly Glu Gly Gly Gly Gly Glu Gly Gly Gly Gly Glu Gly Gly
            100                 105                 110

Gly Gly Glu Gly Gly Gly Gly Glu Gly Gly Gly Gly Glu Gly Gly Gly
        115                 120                 125

Gly Glu Gly Gly Gly Gly Glu Gly Gly Gly Gly Glu Gly Gly Gly Gly
    130                 135                 140

Glu Gly Gly Gly Gly Glu Gly Gly Gly Gly Glu Gly Gly Gly Gly Glu
145                 150                 155                 160

Gly Gly Gly Gly Glu Gly Gly Gly Gly Glu Gly Gly Gly Gly Glu Gly
                165                 170                 175

Gly Gly Gly Glu Gly Gly Gly Gly Glu Gly Gly Gly Gly Glu Gly Gly
            180                 185                 190

Gly Gly Glu Gly Gly Gly Gly Glu Gly Gly Gly Gly Glu Gly Gly Gly
        195                 200                 205

Gly Glu Gly Gly Gly Gly Glu Gly Gly Gly Gly Glu Gly Gly Gly Gly
    210                 215                 220

Glu Gly Gly Gly Gly Glu Gly Gly Gly Gly Glu Gly Gly Gly Gly Glu
225                 230                 235                 240

Gly Gly Gly Gly Glu Gly Gly Gly Gly Glu Gly Gly Gly Gly Glu Gly
```

```
                    245                 250                 255
Gly Gly Gly Glu Gly Gly Gly Gly Glu Gly Gly Gly Gly Glu Gly Gly
                260                 265                 270

Gly Gly Glu Gly Gly Gly Gly Glu Gly Gly Gly Gly Glu Gly Gly Gly
            275                 280                 285

Gly Glu Gly Gly Gly Gly Glu Gly Gly Gly Gly Glu Gly Gly Gly Gly
        290                 295                 300

Glu Gly Gly Gly Gly Glu Gly Gly Gly Gly Glu Gly Gly Gly Gly Glu
305                 310                 315                 320

Gly Gly Gly Gly Glu Gly Gly Gly Gly Glu Gly Gly Gly Gly Glu Gly
                325                 330                 335

Gly Gly Gly Glu Gly Gly Gly Gly Glu Gly Gly Gly Gly Glu Gly Gly
                340                 345                 350

Gly Gly Glu Gly Gly Gly Gly Glu Gly Gly Gly Gly Glu Gly Gly Gly
            355                 360                 365

Gly Glu Gly Gly Gly Gly Glu
        370                 375

<210> SEQ ID NO 21
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 'Gly Asp'
      repeating units

<400> SEQUENCE: 21

Gly Asp Gly Asp Gly Asp Gly Asp Gly Asp Gly Asp Gly Asp Gly Asp
1               5                   10                  15

Gly Asp Gly Asp Gly Asp Gly Asp Gly Asp Gly Asp Gly Asp Gly Asp
            20                  25                  30

Gly Asp Gly Asp Gly Asp Gly Asp Gly Asp Gly Asp Gly Asp Gly Asp
        35                  40                  45

Gly Asp Gly Asp Gly Asp Gly Asp Gly Asp Gly Asp Gly Asp Gly Asp
    50                  55                  60

Gly Asp Gly Asp Gly Asp Gly Asp Gly Asp Gly Asp Gly Asp Gly Asp
65                  70                  75                  80

Gly Asp Gly Asp Gly Asp Gly Asp Gly Asp Gly Asp Gly Asp Gly Asp
                85                  90                  95

Gly Asp Gly Asp Gly Asp Gly Asp Gly Asp Gly Asp Gly Asp Gly Asp
            100                 105                 110

Gly Asp Gly Asp Gly Asp Gly Asp Gly Asp Gly Asp Gly Asp Gly Asp
        115                 120                 125

Gly Asp Gly Asp Gly Asp Gly Asp Gly Asp Gly Asp Gly Asp Gly Asp
    130                 135                 140

Gly Asp Gly Asp Gly Asp
145                 150

<210> SEQ ID NO 22
<211> LENGTH: 225
<212> TYPE: PRT
<213> ORGANISM: Artificial Sequence
<220> FEATURE:
<223> OTHER INFORMATION: Description of Artificial Sequence: Synthetic
```

```
                        polypeptide
<220> FEATURE:
<221> NAME/KEY: MISC_FEATURE
<222> LOCATION: (1)..(225)
<223> OTHER INFORMATION: This sequence may encompass 1-75 'Gly Gly Asp'
      repeating units

<400> SEQUENCE: 22

Gly Gly Asp Gly Gly Asp Gly Gly Asp Gly Gly Asp Gly Gly Asp Gly
1               5                   10                  15

Gly Asp Gly Gly Asp Gly Gly Asp Gly Gly Asp Gly Gly Asp Gly Gly
            20                  25                  30

Asp Gly Gly Asp Gly Gly Asp Gly Gly Asp Gly Gly Asp Gly Gly Asp
        35                  40                  45

Gly Gly Asp Gly Gly Asp Gly Gly Asp Gly Gly Asp Gly Gly Asp Gly
    50                  55                  60

Gly Asp Gly Gly Asp Gly Gly Asp Gly Gly Asp Gly Gly Asp Gly Gly
65                  70                  75                  80

Asp Gly Gly Asp Gly Gly Asp Gly Gly Asp Gly Gly Asp Gly Gly Asp
                85                  90                  95

Gly Gly Asp Gly Gly Asp Gly Gly Asp Gly Gly Asp Gly Gly Asp Gly
            100                 105                 110

Gly Asp Gly Gly Asp Gly Gly Asp Gly Gly Asp Gly Gly Asp Gly Gly
        115                 120                 125

Asp Gly Gly Asp Gly Gly Asp Gly Gly Asp Gly Gly Asp Gly Gly Asp
    130                 135                 140

Gly Gly Asp Gly Gly Asp Gly Gly Asp Gly Gly Asp Gly Gly Asp Gly
145                 150                 155                 160

Gly Asp Gly Gly Asp Gly Gly Asp Gly Gly Asp Gly Gly Asp Gly Gly
                165                 170                 175

Asp Gly Gly Asp Gly Gly Asp Gly Gly Asp Gly Gly Asp Gly Gly Asp
            180                 185                 190

Gly Gly Asp Gly Gly Asp Gly Gly Asp Gly Gly Asp Gly Gly Asp Gly
        195                 200                 205

Gly Asp Gly Gly Asp Gly Gly Asp Gly Gly Asp Gly Gly Asp Gly Gly
    210                 215                 220

Asp
225

<210> SEQ ID NO 23
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 'Gly Gly Gly
      Asp' repeating units

<400> SEQUENCE: 23

Gly Gly Gly Asp Gly Gly Gly Asp Gly Gly Gly Asp Gly Gly Gly Asp
1               5                   10                  15

Gly Gly Gly Asp Gly Gly Gly Asp Gly Gly Gly Asp Gly Gly Gly Asp
            20                  25                  30

Gly Gly Gly Asp Gly Gly Gly Asp Gly Gly Gly Asp Gly Gly Gly Asp
        35                  40                  45
```

```
Gly Gly Gly Asp Gly Gly Gly Asp Gly Gly Gly Asp Gly Gly Gly Asp
    50                  55                  60
Gly Gly Gly Asp Gly Gly Gly Asp Gly Gly Gly Asp Gly Gly Gly Asp
65                  70                  75                  80
Gly Gly Gly Asp Gly Gly Gly Asp Gly Gly Gly Asp Gly Gly Gly Asp
                85                  90                  95
Gly Gly Gly Asp Gly Gly Gly Asp Gly Gly Gly Asp Gly Gly Gly Asp
            100                 105                 110
Gly Gly Gly Asp Gly Gly Gly Asp Gly Gly Gly Asp Gly Gly Gly Asp
        115                 120                 125
Gly Gly Gly Asp Gly Gly Gly Asp Gly Gly Gly Asp Gly Gly Gly Asp
    130                 135                 140
Gly Gly Gly Asp Gly Gly Gly Asp Gly Gly Gly Asp Gly Gly Gly Asp
145                 150                 155                 160
Gly Gly Gly Asp Gly Gly Gly Asp Gly Gly Gly Asp Gly Gly Gly Asp
                165                 170                 175
Gly Gly Gly Asp Gly Gly Gly Asp Gly Gly Gly Asp Gly Gly Gly Asp
            180                 185                 190
Gly Gly Gly Asp Gly Gly Gly Asp Gly Gly Gly Asp Gly Gly Gly Asp
        195                 200                 205
Gly Gly Gly Asp Gly Gly Gly Asp Gly Gly Gly Asp Gly Gly Gly Asp
    210                 215                 220
Gly Gly Gly Asp Gly Gly Gly Asp Gly Gly Gly Asp Gly Gly Gly Asp
225                 230                 235                 240
Gly Gly Gly Asp Gly Gly Gly Asp Gly Gly Gly Asp Gly Gly Gly Asp
                245                 250                 255
Gly Gly Gly Asp Gly Gly Gly Asp Gly Gly Gly Asp Gly Gly Gly Asp
            260                 265                 270
Gly Gly Gly Asp Gly Gly Gly Asp Gly Gly Gly Asp Gly Gly Gly Asp
        275                 280                 285
Gly Gly Gly Asp Gly Gly Gly Asp Gly Gly Gly Asp
    290                 295                 300

<210> SEQ ID NO 24
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Gly Gly Gly
      Gly Asp' repeating units

<400> SEQUENCE: 24

Gly Gly Gly Gly Asp Gly Gly Gly Gly Asp Gly Gly Gly Gly Asp Gly
1               5                   10                  15
Gly Gly Gly Asp Gly Gly Gly Gly Asp Gly Gly Gly Gly Asp Gly Gly
                20                  25                  30
Gly Gly Asp Gly Gly Gly Gly Asp Gly Gly Gly Gly Asp Gly Gly Gly
            35                  40                  45
Gly Asp Gly Gly Gly Gly Asp Gly Gly Gly Gly Asp Gly Gly Gly Gly
    50                  55                  60
Asp Gly Gly Gly Gly Asp Gly Gly Gly Gly Asp Gly Gly Gly Gly Asp
65                  70                  75                  80
```

```
Gly Gly Gly Gly Asp Gly Gly Gly Asp Gly Gly Gly Asp Gly
                85                  90                  95
Gly Gly Gly Asp Gly Gly Gly Asp Gly Gly Gly Asp Gly Gly
            100                 105                 110
Gly Gly Asp Gly Gly Gly Asp Gly Gly Gly Asp Gly Gly Gly
        115                 120                 125
Gly Asp Gly Gly Gly Asp Gly Gly Gly Asp Gly Gly Gly Gly
    130                 135                 140
Asp Gly Gly Gly Asp Gly Gly Gly Asp Gly Gly Gly Gly Asp
145                 150                 155                 160
Gly Gly Gly Asp Gly Gly Gly Asp Gly Gly Gly Asp Gly
                165                 170                 175
Gly Gly Gly Asp Gly Gly Gly Asp Gly Gly Gly Asp Gly Gly
            180                 185                 190
Gly Gly Asp Gly Gly Gly Asp Gly Gly Gly Asp Gly Gly Gly
        195                 200                 205
Gly Asp Gly Gly Gly Asp Gly Gly Gly Asp Gly Gly Gly Gly
    210                 215                 220
Asp Gly Gly Gly Asp Gly Gly Gly Asp Gly Gly Gly Gly Asp
225                 230                 235                 240
Gly Gly Gly Asp Gly Gly Gly Asp Gly Gly Gly Asp Gly
                245                 250                 255
Gly Gly Gly Asp Gly Gly Gly Asp Gly Gly Gly Asp Gly Gly
            260                 265                 270
Gly Gly Asp Gly Gly Gly Asp Gly Gly Gly Asp Gly Gly Gly
        275                 280                 285
Gly Asp Gly Gly Gly Asp Gly Gly Gly Asp Gly Gly Gly Gly
    290                 295                 300
Asp Gly Gly Gly Asp Gly Gly Gly Asp Gly Gly Gly Gly Asp
305                 310                 315                 320
Gly Gly Gly Gly Asp Gly Gly Gly Asp Gly Gly Gly Asp Gly
                325                 330                 335
Gly Gly Gly Asp Gly Gly Gly Asp Gly Gly Gly Asp Gly Gly
            340                 345                 350
Gly Gly Asp Gly Gly Gly Asp Gly Gly Gly Asp Gly Gly Gly
        355                 360                 365
Gly Asp Gly Gly Gly Gly Asp
    370                 375

<210> SEQ ID NO 25
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 'Gly Lys'
      repeating units

<400> SEQUENCE: 25

Gly Lys Gly Lys Gly Lys Gly Lys Gly Lys Gly Lys Gly Lys Gly Lys
1               5                   10                  15
Gly Lys Gly Lys Gly Lys Gly Lys Gly Lys Gly Lys Gly Lys Gly Lys
            20                  25                  30
```

Gly Lys Gly Lys Gly Lys Gly Lys Gly Lys Gly Lys Gly Lys Gly Lys
         35                  40                  45

Gly Lys Gly Lys Gly Lys Gly Lys Gly Lys Gly Lys Gly Lys Gly Lys
 50                  55                  60

Gly Lys Gly Lys Gly Lys Gly Lys Gly Lys Gly Lys Gly Lys Gly Lys
 65                  70                  75                  80

Gly Lys Gly Lys Gly Lys Gly Lys Gly Lys Gly Lys Gly Lys Gly Lys
             85                  90                  95

Gly Lys Gly Lys Gly Lys Gly Lys Gly Lys Gly Lys Gly Lys Gly Lys
            100                 105                 110

Gly Lys Gly Lys Gly Lys Gly Lys Gly Lys Gly Lys Gly Lys Gly Lys
            115                 120                 125

Gly Lys Gly Lys Gly Lys Gly Lys Gly Lys Gly Lys Gly Lys Gly Lys
        130                 135                 140

Gly Lys Gly Lys Gly Lys
145                 150

<210> SEQ ID NO 26
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 'Gly Gly Lys'
      repeating units

<400> SEQUENCE: 26

Gly Gly Lys Gly Gly Lys Gly Gly Lys Gly Gly Lys Gly Gly Lys Gly
1               5                  10                  15

Gly Lys Gly Gly Lys Gly Gly Lys Gly Gly Lys Gly Gly Lys Gly Gly
            20                  25                  30

Lys Gly Gly Lys Gly Gly Lys Gly Gly Lys Gly Gly Lys Gly Gly Lys
        35                  40                  45

Gly Gly Lys Gly Gly Lys Gly Gly Lys Gly Gly Lys Gly Gly Lys Gly
    50                  55                  60

Gly Lys Gly Gly Lys Gly Gly Lys Gly Gly Lys Gly Gly Lys Gly Gly
65                  70                  75                  80

Lys Gly Gly Lys Gly Gly Lys Gly Gly Lys Gly Gly Lys Gly Gly Lys
            85                  90                  95

Gly Gly Lys Gly Gly Lys Gly Gly Lys Gly Gly Lys Gly Gly Lys Gly
            100                 105                 110

Gly Lys Gly Gly Lys Gly Gly Lys Gly Gly Lys Gly Gly Lys Gly Gly
        115                 120                 125

Lys Gly Gly Lys Gly Gly Lys Gly Gly Lys Gly Gly Lys Gly Gly Lys
    130                 135                 140

Gly Gly Lys Gly Gly Lys Gly Gly Lys Gly Gly Lys Gly Gly Lys Gly
145                 150                 155                 160

Gly Lys Gly Gly Lys Gly Gly Lys Gly Gly Lys Gly Gly Lys Gly Gly
            165                 170                 175

Lys Gly Gly Lys Gly Gly Lys Gly Gly Lys Gly Gly Lys Gly Gly Lys
        180                 185                 190

Gly Gly Lys Gly Gly Lys Gly Gly Lys Gly Gly Lys Gly Gly Lys Gly
    195                 200                 205

Gly Lys Gly Gly Lys Gly Gly Lys Gly Gly Lys Gly Gly
            210                 215                 220

Lys
225

<210> SEQ ID NO 27
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 'Gly Gly Gly
      Lys' repeating units

<400> SEQUENCE: 27

Gly Gly Gly Lys Gly Gly Gly Lys Gly Gly Gly Lys Gly Gly Gly Lys
1               5                   10                  15

Gly Gly Gly Lys Gly Gly Gly Lys Gly Gly Gly Lys Gly Gly Gly Lys
                20                  25                  30

Gly Gly Gly Lys Gly Gly Gly Lys Gly Gly Gly Lys Gly Gly Gly Lys
            35                  40                  45

Gly Gly Gly Lys Gly Gly Gly Lys Gly Gly Gly Lys Gly Gly Gly Lys
        50                  55                  60

Gly Gly Gly Lys Gly Gly Gly Lys Gly Gly Gly Lys Gly Gly Gly Lys
65                  70                  75                  80

Gly Gly Gly Lys Gly Gly Gly Lys Gly Gly Gly Lys Gly Gly Gly Lys
                85                  90                  95

Gly Gly Gly Lys Gly Gly Gly Lys Gly Gly Gly Lys Gly Gly Gly Lys
            100                 105                 110

Gly Gly Gly Lys Gly Gly Gly Lys Gly Gly Gly Lys Gly Gly Gly Lys
        115                 120                 125

Gly Gly Gly Lys Gly Gly Gly Lys Gly Gly Gly Lys Gly Gly Gly Lys
    130                 135                 140

Gly Gly Gly Lys Gly Gly Gly Lys Gly Gly Gly Lys Gly Gly Gly Lys
145                 150                 155                 160

Gly Gly Gly Lys Gly Gly Gly Lys Gly Gly Gly Lys Gly Gly Gly Lys
                165                 170                 175

Gly Gly Gly Lys Gly Gly Gly Lys Gly Gly Gly Lys Gly Gly Gly Lys
            180                 185                 190

Gly Gly Gly Lys Gly Gly Gly Lys Gly Gly Gly Lys Gly Gly Gly Lys
        195                 200                 205

Gly Gly Gly Lys Gly Gly Gly Lys Gly Gly Gly Lys Gly Gly Gly Lys
    210                 215                 220

Gly Gly Gly Lys Gly Gly Gly Lys Gly Gly Gly Lys Gly Gly Gly Lys
225                 230                 235                 240

Gly Gly Gly Lys Gly Gly Gly Lys Gly Gly Gly Lys Gly Gly Gly Lys
                245                 250                 255

Gly Gly Gly Lys Gly Gly Gly Lys Gly Gly Gly Lys Gly Gly Gly Lys
            260                 265                 270

Gly Gly Gly Lys Gly Gly Gly Lys Gly Gly Gly Lys Gly Gly Gly Lys
        275                 280                 285

Gly Gly Gly Lys Gly Gly Gly Lys Gly Gly Gly Lys
    290                 295                 300

-continued

```
<210> SEQ ID NO 28
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Gly Gly Gly
      Gly Lys' repeating units

<400> SEQUENCE: 28

Gly Gly Gly Gly Lys Gly Gly Gly Gly Lys Gly Gly Gly Gly Lys Gly
1               5                   10                  15

Gly Gly Gly Lys Gly Gly Gly Gly Lys Gly Gly Gly Gly Lys Gly Gly
            20                  25                  30

Gly Gly Lys Gly Gly Gly Gly Lys Gly Gly Gly Gly Lys Gly Gly Gly
        35                  40                  45

Gly Lys Gly Gly Gly Gly Lys Gly Gly Gly Gly Lys Gly Gly Gly Gly
    50                  55                  60

Lys Gly Gly Gly Gly Lys Gly Gly Gly Gly Lys Gly Gly Gly Gly Lys
65                  70                  75                  80

Gly Gly Gly Gly Lys Gly Gly Gly Gly Lys Gly Gly Gly Gly Lys Gly
                85                  90                  95

Gly Gly Gly Lys Gly Gly Gly Gly Lys Gly Gly Gly Gly Lys Gly Gly
            100                 105                 110

Gly Gly Lys Gly Gly Gly Gly Lys Gly Gly Gly Gly Lys Gly Gly Gly
        115                 120                 125

Gly Lys Gly Gly Gly Gly Lys Gly Gly Gly Gly Lys Gly Gly Gly Gly
    130                 135                 140

Lys Gly Gly Gly Gly Lys Gly Gly Gly Gly Lys Gly Gly Gly Gly Lys
145                 150                 155                 160

Gly Gly Gly Gly Lys Gly Gly Gly Gly Lys Gly Gly Gly Gly Lys Gly
                165                 170                 175

Gly Gly Gly Lys Gly Gly Gly Gly Lys Gly Gly Gly Gly Lys Gly Gly
            180                 185                 190

Gly Gly Lys Gly Gly Gly Gly Lys Gly Gly Gly Gly Lys Gly Gly Gly
        195                 200                 205

Gly Lys Gly Gly Gly Gly Lys Gly Gly Gly Gly Lys Gly Gly Gly Gly
    210                 215                 220

Lys Gly Gly Gly Gly Lys Gly Gly Gly Gly Lys Gly Gly Gly Gly Lys
225                 230                 235                 240

Gly Gly Gly Gly Lys Gly Gly Gly Gly Lys Gly Gly Gly Gly Lys Gly
                245                 250                 255

Gly Gly Gly Lys Gly Gly Gly Gly Lys Gly Gly Gly Gly Lys Gly Gly
            260                 265                 270

Gly Gly Lys Gly Gly Gly Gly Lys Gly Gly Gly Gly Lys Gly Gly Gly
        275                 280                 285

Gly Lys Gly Gly Gly Gly Lys Gly Gly Gly Gly Lys Gly Gly Gly Gly
    290                 295                 300

Lys Gly Gly Gly Gly Lys Gly Gly Gly Gly Lys Gly Gly Gly Gly Lys
305                 310                 315                 320

Gly Gly Gly Gly Lys Gly Gly Gly Gly Lys Gly Gly Gly Gly Lys Gly
                325                 330                 335
```

-continued

```
Gly Gly Gly Lys Gly Gly Gly Lys Gly Gly Gly Lys Gly Gly
        340                 345                 350

Gly Gly Lys Gly Gly Gly Lys Gly Gly Gly Lys Gly Gly Gly
        355                 360                 365

Gly Lys Gly Gly Gly Gly Lys
        370                 375

<210> SEQ ID NO 29
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 'Gly Arg'
      repeating units

<400> SEQUENCE: 29

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg
        20                  25                  30

Gly Arg Gly Arg Gly Arg Gly Arg Gly Arg Gly Arg Gly Arg
        35                  40                  45

Gly Arg Gly Arg Gly Arg Gly Arg Gly Arg Gly Arg Gly Arg
        50                  55                  60

Gly Arg Gly Arg Gly Arg Gly Arg Gly Arg Gly Arg Gly Arg Gly Arg
65                  70                  75                  80

Gly Arg Gly Arg Gly Arg Gly Arg Gly Arg Gly Arg Gly Arg
        85                  90                  95

Gly Arg Gly Arg Gly Arg Gly Arg Gly Arg Gly Arg Gly Arg
        100                 105                 110

Gly Arg Gly Arg Gly Arg Gly Arg Gly Arg Gly Arg Gly Arg
        115                 120                 125

Gly Arg Gly Arg Gly Arg Gly Arg Gly Arg Gly Arg Gly Arg
        130                 135                 140

Gly Arg Gly Arg Gly Arg
145                 150

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 'Gly Gly Arg'
      repeating units

<400> SEQUENCE: 30

Gly Gly Arg Gly Gly Arg Gly Gly Arg Gly Gly Arg Gly Gly Arg Gly
1               5                   10                  15

Gly Arg Gly Gly Arg Gly Gly Arg Gly Gly Arg Gly Gly Arg Gly Gly
        20                  25                  30

Arg Gly Gly Arg Gly Gly Arg Gly Gly Arg Gly Gly Arg Gly Gly Arg
        35                  40                  45
```

```
Gly Gly Arg Gly Gly Arg Gly Gly Arg Gly Gly Arg Gly
            50                  55                  60

Gly Arg Gly Gly Arg Gly Gly Arg Gly Gly Arg Gly Gly
65                  70                  75                  80

Arg Gly Gly Arg Gly Gly Arg Gly Gly Arg Gly Gly Arg
                85                  90                  95

Gly Gly Arg Gly Gly Arg Gly Gly Arg Gly Gly Arg Gly
                100                 105                 110

Gly Arg Gly Gly Arg Gly Gly Arg Gly Gly Arg Gly Gly
            115                 120                 125

Arg Gly Gly Arg Gly Gly Arg Gly Gly Arg Gly Gly Arg
    130                 135                 140

Gly Gly Arg Gly Gly Arg Gly Gly Arg Gly Gly Arg Gly
145                 150                 155                 160

Gly Arg Gly Gly Arg Gly Gly Arg Gly Gly Arg Gly Gly
                165                 170                 175

Arg Gly Gly Arg Gly Gly Arg Gly Gly Arg Gly Gly Arg
                180                 185                 190

Gly Gly Arg Gly Gly Arg Gly Gly Arg Gly Gly Arg Gly
            195                 200                 205

Gly Arg Gly Gly Arg Gly Gly Arg Gly Gly Arg Gly Gly
    210                 215                 220

Arg
225

<210> SEQ ID NO 31
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 'Gly Gly Gly
      Arg' repeating units

<400> SEQUENCE: 31

Gly Gly Gly Arg Gly Gly Gly Arg Gly Gly Gly Arg Gly Gly Gly Arg
1               5                   10                  15

Gly Gly Gly Arg Gly Gly Gly Arg Gly Gly Gly Arg Gly Gly Gly Arg
            20                  25                  30

Gly Gly Gly Arg Gly Gly Gly Arg Gly Gly Gly Arg Gly Gly Gly Arg
        35                  40                  45

Gly Gly Gly Arg Gly Gly Gly Arg Gly Gly Gly Arg Gly Gly Gly Arg
    50                  55                  60

Gly Gly Gly Arg Gly Gly Gly Arg Gly Gly Gly Arg Gly Gly Gly Arg
65                  70                  75                  80

Gly Gly Gly Arg Gly Gly Gly Arg Gly Gly Gly Arg Gly Gly Gly Arg
                85                  90                  95

Gly Gly Gly Arg Gly Gly Gly Arg Gly Gly Gly Arg Gly Gly Gly Arg
            100                 105                 110

Gly Gly Gly Arg Gly Gly Gly Arg Gly Gly Gly Arg Gly Gly Gly Arg
        115                 120                 125

Gly Gly Gly Arg Gly Gly Gly Arg Gly Gly Gly Arg Gly Gly Gly Arg
    130                 135                 140
```

```
Gly Gly Gly Arg Gly Gly Gly Arg Gly Gly Gly Arg Gly Gly Gly Arg
145                 150                 155                 160

Gly Gly Gly Arg Gly Gly Gly Arg Gly Gly Gly Arg Gly Gly Gly Arg
                165                 170                 175

Gly Gly Gly Arg Gly Gly Gly Arg Gly Gly Gly Arg Gly Gly Gly Arg
            180                 185                 190

Gly Gly Gly Arg Gly Gly Gly Arg Gly Gly Gly Arg Gly Gly Gly Arg
        195                 200                 205

Gly Gly Gly Arg Gly Gly Gly Arg Gly Gly Gly Arg Gly Gly Gly Arg
    210                 215                 220

Gly Gly Gly Arg Gly Gly Gly Arg Gly Gly Gly Arg Gly Gly Gly Arg
225                 230                 235                 240

Gly Gly Gly Arg Gly Gly Gly Arg Gly Gly Gly Arg Gly Gly Gly Arg
                245                 250                 255

Gly Gly Gly Arg Gly Gly Gly Arg Gly Gly Gly Arg Gly Gly Gly Arg
            260                 265                 270

Gly Gly Gly Arg Gly Gly Gly Arg Gly Gly Gly Arg Gly Gly Gly Arg
        275                 280                 285

Gly Gly Gly Arg Gly Gly Gly Arg Gly Gly Gly Arg
    290                 295                 300

<210> SEQ ID NO 32
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Gly Gly Gly
      Gly Arg' repeating units

<400> SEQUENCE: 32

Gly Gly Gly Gly Arg Gly Gly Gly Gly Arg Gly Gly Gly Gly Arg Gly
1               5                   10                  15

Gly Gly Gly Arg Gly Gly Gly Gly Arg Gly Gly Gly Gly Arg Gly Gly
                20                  25                  30

Gly Gly Arg Gly Gly Gly Gly Arg Gly Gly Gly Gly Arg Gly Gly Gly
            35                  40                  45

Gly Arg Gly Gly Gly Gly Arg Gly Gly Gly Gly Arg Gly Gly Gly Gly
        50                  55                  60

Arg Gly Gly Gly Gly Arg Gly Gly Gly Gly Arg Gly Gly Gly Gly Arg
65                  70                  75                  80

Gly Gly Gly Gly Arg Gly Gly Gly Gly Arg Gly Gly Gly Gly Arg Gly
                85                  90                  95

Gly Gly Gly Arg Gly Gly Gly Gly Arg Gly Gly Gly Gly Arg Gly Gly
                100                 105                 110

Gly Gly Arg Gly Gly Gly Gly Arg Gly Gly Gly Gly Arg Gly Gly Gly
            115                 120                 125

Gly Arg Gly Gly Gly Gly Arg Gly Gly Gly Gly Arg Gly Gly Gly Gly
        130                 135                 140

Arg Gly Gly Gly Gly Arg Gly Gly Gly Gly Arg Gly Gly Gly Gly Arg
145                 150                 155                 160

Gly Gly Gly Gly Arg Gly Gly Gly Gly Arg Gly Gly Gly Gly Arg Gly
                165                 170                 175
```

```
Gly Gly Gly Arg Gly Gly Gly Arg Gly Gly Gly Arg Gly Gly
            180                 185                 190

Gly Gly Arg Gly Gly Gly Arg Gly Gly Gly Arg Gly Gly
        195                 200                 205

Gly Arg Gly Gly Gly Arg Gly Gly Gly Arg Gly Gly Gly Gly
    210                 215                 220

Arg Gly Gly Gly Arg Gly Gly Gly Arg Gly Gly Gly Arg
225                 230                 235                 240

Gly Gly Gly Gly Arg Gly Gly Gly Arg Gly Gly Gly Arg Gly
            245                 250                 255

Gly Gly Gly Arg Gly Gly Gly Arg Gly Gly Gly Arg Gly Gly
        260                 265                 270

Gly Gly Arg Gly Gly Gly Arg Gly Gly Gly Arg Gly Gly Gly
    275                 280                 285

Gly Arg Gly Gly Gly Arg Gly Gly Gly Arg Gly Gly Gly Gly
    290                 295                 300

Arg Gly Gly Gly Gly Arg Gly Gly Gly Arg Gly Gly Gly Arg
305                 310                 315                 320

Gly Gly Gly Gly Arg Gly Gly Gly Arg Gly Gly Gly Arg Gly
            325                 330                 335

Gly Gly Gly Arg Gly Gly Gly Arg Gly Gly Gly Arg Gly Gly
        340                 345                 350

Gly Gly Arg Gly Gly Gly Gly Arg Gly Gly Gly Arg Gly Gly Gly
    355                 360                 365

Gly Arg Gly Gly Gly Gly Arg
    370                 375

<210> SEQ ID NO 33
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 'Glu Ala Ala
      Ala Lys' repeating units

<400> SEQUENCE: 33

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Glu
                85                  90                  95

Ala Ala Ala Lys Glu Ala Ala Ala Lys Glu Ala Ala Ala Lys Glu Ala
            100                 105                 110

Ala Ala Lys Glu Ala Ala Ala Lys Glu Ala Ala Ala Lys Glu Ala Ala
        115                 120                 125
```

Ala Lys Glu Ala Ala Ala Lys Glu Ala Ala Ala Lys Glu Ala Ala Ala
    130                 135                 140

Lys Glu Ala Ala Ala Lys Glu Ala Ala Ala Lys Glu Ala Ala Ala Lys
145                 150                 155                 160

Glu Ala Ala Ala Lys Glu Ala Ala Ala Lys Glu Ala Ala Ala Lys Glu
                165                 170                 175

Ala Ala Ala Lys Glu Ala Ala Ala Lys Glu Ala Ala Ala Lys Glu Ala
            180                 185                 190

Ala Ala Lys Glu Ala Ala Ala Lys Glu Ala Ala Ala Lys Glu Ala Ala
        195                 200                 205

Ala Lys Glu Ala Ala Ala Lys Glu Ala Ala Ala Lys Glu Ala Ala Ala
    210                 215                 220

Lys Glu Ala Ala Ala Lys Glu Ala Ala Ala Lys Glu Ala Ala Ala Lys
225                 230                 235                 240

Glu Ala Ala Ala Lys Glu Ala Ala Ala Lys Glu Ala Ala Ala Lys Glu
                245                 250                 255

Ala Ala Ala Lys Glu Ala Ala Ala Lys Glu Ala Ala Ala Lys Glu Ala
            260                 265                 270

Ala Ala Lys Glu Ala Ala Ala Lys Glu Ala Ala Ala Lys Glu Ala Ala
        275                 280                 285

Ala Lys Glu Ala Ala Ala Lys Glu Ala Ala Ala Lys Glu Ala Ala Ala
    290                 295                 300

Lys Glu Ala Ala Ala Lys Glu Ala Ala Ala Lys Glu Ala Ala Ala Lys
305                 310                 315                 320

Glu Ala Ala Ala Lys Glu Ala Ala Ala Lys Glu Ala Ala Ala Lys Glu
                325                 330                 335

Ala Ala Ala Lys Glu Ala Ala Ala Lys Glu Ala Ala Ala Lys Glu Ala
            340                 345                 350

Ala Ala Lys Glu Ala Ala Ala Lys Glu Ala Ala Ala Lys Glu Ala Ala
        355                 360                 365

Ala Lys Glu Ala Ala Ala Lys
    370                 375

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ala Ala Ala Lys Glu Ala Ala Ala Lys Glu Ala Ala Ala Lys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Ala Ala Ala Lys Glu Ala Ala Ala Lys Glu Ala Ala Ala Lys Glu
1               5                   10                  15

Ala Ala Ala Lys
            20

```
<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25
```

POLYSPECIFICITY REAGENTS, METHODS FOR THEIR PREPARATION AND USE

CROSS REFERENCE TO RELATED APPLICATIONS

The present application is a divisional of U.S. application Ser. No. 14/787,760, filed on Oct. 28, 2015, which is the National Stage of International Application No. PCT/US14/35958, filed Apr. 29, 2014, which claims the benefit of U.S. Provisional Patent Application No. 61/817,072 filed Apr. 29, 2013, the entire contents of all of which are incorporated herein by reference.

SEQUENCE LISTING

In accordance with 37 CFR § 1.52(e)(5), the present specification makes reference to a Sequence Listing (submitted electronically as a .txt file named "2009186-0162_SL.txt"). The .txt file was generated on Mar. 9, 2017, and is 142,493 bytes in size. The entire contents of the Sequence Listing are herein incorporated by reference.

FIELD OF THE INVENTION

The present invention relates, inter alia, to polyspecificity reagents, methods of making the same, and methods of using the same in, inter alia, the selection, screening, enrichment, and identification of non-polyspecific, and thus developable, polypeptides.

BACKGROUND OF THE INVENTION

All references cited herein, including patents, patent applications, and non-patent publications referenced throughout are hereby expressly incorporated by reference in their entirety for all purposes.

Biologics, such as antibodies and antibody-based molecules, represent attractive candidates as diagnostic tools and therapeutics (see, e.g., Reichert J. M., mAbs, Vol. 5(1), pp. 1-4 (2013)). To date more than 30 therapeutic monoclonal antibodies have been approved for and successfully applied in diverse indication areas including cancer, organ transplantation, autoimmune and inflammatory disorders, infectious disease, and cardiovascular disease.

However, although many candidate clinical and therapeutic antibodies have been found in early discovery efforts which display exquisite selectivity and high potency towards numerous targets of interest, a large proportion of these antibodies have nonetheless subsequently been discovered through downstream development and clinical efficacy activities to suffer from undesirable characteristics such as: promiscuity of binding, polyspecific binding (also termed herein and throughout, "polyspecificity"), off-target binding, nonspecific binding; poor expression levels or profiles in eukaryotic host cells, such as mammalian host cells and yeast cells; poor chemical and physical properties, such as poor stability during storage (e.g., poor/low "shelf-life" stability), poor (low) solubility, poor (high) viscosity, propensity to aggregate, and the like; and poor clinical and biophysical profiles, such as poor pharmacokinetic profiles, poor pharmacodynamic profiles, fast or poor in vivo clearance rates, short circulation half-life, and the like; thereby requiring the termination of further therapeutic development of such candidate antibodies. Additionally, it has been observed that antibodies derived from display technologies represent a historical minority of all clinical and marketed antibodies, a trend which is believed by many to be due, at least in part, to promiscuity of binding, poor PK profiles, and poor CMC characteristics—liabilities which are further postulated to be largely due to a lack of suitable means and methods by which undevelopable antibodies may be detected and/or counter-selected against when screening for antibodies using display technologies (see, e.g., Meninger 2012; http://www.proteins-congress.com/wordpress/wp-content/uploads/2012/01/Trends-in-Therapeutic-Monoclonal-Antibody-Discovery-Technology.pdf).

The art has developed certain techniques and assays to assess many of the aforementioned developability characteristics for discovered antibodies in the context of downstream development activities ("post-discovery antibodies"), such as CIC, SIC, BVP-ELISA, TMA, and other assays; however, such assays are typically not amenable to their incorporation into high-throughput early polypeptide and antibody discovery platforms, such as antibody display platforms. Furthermore, assessment of these attributes typically requires milligram to gram quantities of protein, thus often imposing a de facto limitation on the number of leads that can be pragmatically considered for development, and consequently reducing the likelihood of program success. Consequently, significant resources are often expended attempting to fix poorly behaving lead candidates with few backups available in later stages of development.

In recognition of this bottleneck, considerable efforts have been made to develop assays with lower material requirements and to bring developability assessments further upstream in the development process (Esfandiary et al., 2013; Sathish et al., 2013). A number of such assays are directed at predicting antibody solubility and aggregation behavior of identified, lead candidates. Self-interaction chromatography (SIC) and cross-interaction chromatography (CIC) are column based, low-to-medium throughput assays that correlate with and thus predict antibody solubility at relatively low concentration (Ahamed et al., 2005; Jacobs et al., 2010; Spencer et al., 2012). A longer retention time on such SIC or CIC columns suggests interaction with antibodies coupled to the column, and is correlated to poor solubility (Jacobs et al., 2010). Sule and co-workers reported a medium throughput gold nanoparticle assay to predict solubility at very low concentration and further broadened the assay scope to be compatible with complex cell culture media (Sule et al., 2011, 2013).

As mentioned above, polyspecificity is a highly undesirable property that has been linked to poor antibody pharmacokinetics (Wu et al., 2007; Hötzel et al., 2012). Certain polyspecificity assays have been reported in the art to serve as medium-throughput substitutes for broad panel tissue immunohistochemistry. Wardemann and colleagues have reported an enzyme-linked immunosorbent assay (ELISA) method using LPS, Insulin, dsDNA, and ssDNA to study polyreactivity in natural antibody repertoires over the course of B-cell maturation (Wardemann et al., 2003). Protein biochips in which a diverse set of proteins are spotted onto an array for high-throughput ELISAs are another type of screening tool. A chip with ~400 different human proteins from Protagen (Dortmund, Germany) has been reported to compare favorably with IHC staining analysis (Lueking et al., 2008), as well as a measure of off-target binding of clinically approved TNF-alpha inhibitors (Feyen et al., 2008). More recently, Frese et al. reported on a 384-well assay that measures polyreactivity to 32 test proteins, termed Protein Panel Profiling or 3P (Frese et al., 2013). Using this assay, the authors showed that FDA-approved therapeutic antibodies show a highly specific profile to the 32 test proteins and apply it to screen candidates from a phage selection process. These particular polyreactivity profiling assays have not yet been correlated with downstream development issues such as solubility, expression, and stability. A recent advance in this area was reported by Hötzel et al., in which a baculovirus particle (BVP) ELISA was shown to predict faster antibody non-target mediated clearance in vivo, while traditional biophysical properties such as Size Exclusion Chromatography retention time, Hydrophobic Interaction Chromatography elution time, Fv charge, and pI did not (Hötzel, et al., 2012).

Accordingly, there is a need in the art for reagents and methods which may be easily generated and implemented into current high-throughput display methodologies which, inter alia, provide for upstream detection and/or counter-selection against non-developable polypeptides, such as antibodies, that are predisposed to suffer from poor developability. There is also a need in the art for reagents and methods with which current libraries may be enriched for developable antibodies by detecting non-developable antibodies in the library and either discarding them or avoiding their inclusion as selected antibodies when performing selections.

SUMMARY OF THE INVENTION

The invention provides, inter alia, the polyspecific reagents (PSR) that may be employed, inter alia, selecting for, screening for, assessing, predicting, ranking, scoring, and correlating developability of one or more polypeptides from amongst a plurality of polypeptides. The herein and throughout disclosed PSRs comprise a mixture of biomolecules that may also be employed in methods for generating enriched pluralities of developable polypeptides from a non-enriched plurality of polypeptides. The herein and throughout disclosed PSRs comprise a mixture of biomolecules may also be employed in counter-selecting against one or more polyspecific polypeptides from a plurality of polypeptides, wherein the polyspecific polypeptide is detected by virtue of its interaction with the PSR, thereby affording the ability to select polypeptides from the plurality that do not interact with the PSR.

In certain embodiments, the invention provides methods of counter-selecting against at least one polyspecific polypeptide from a plurality of polypeptides, the method comprising:

(a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting from the reagent-plurality mixture of step (b) at least one polyspecific polypeptide that interacts with the polyspecificity reagent, thereby detecting at least one polyspecific polypeptide; and (d) selecting at least one polypeptide from the plurality that is not detected in step (c), thereby counter-selecting against the at least one polyspecific polypeptide from the plurality of polypeptides. In certain embodiments, such methods further comprise determining that the at least one polypeptide selected in step (d) binds to at least one test binding partner. In other embodiments, such methods further comprise: (A) performing at least one of steps (b), (c), and (d) by employing flow cytometry; (B) performing at least one of steps (b), (c), and (d) by employing magnetic-activated cell sorting; (C) performing all of steps (b), (c), and (d) by employing flow cytometry; (D) performing all of steps (b), (c), and (d) by employing magnetic-activated cell sorting; or (E) combinations of (A) and (B).

In other embodiments, the invention provides methods of selecting at least one polypeptide from amongst a plurality of polypeptides that specifically interacts with at least one test binding partner, the method comprising: (a) providing the plurality of polypeptides; (b) providing the at least one test binding partner; (c) contacting the plurality of step (a) with the at least one test binding partner of step (b) and a polyspecificity reagent, wherein the polyspecificity reagent comprises a mixture of biomolecules, thereby producing a reagent-plurality mixture; and (d) selecting from the reagent-plurality mixture of step (c) at least one polypeptide that interacts with the at least one test binding partner. In certain embodiments, the at least one polypeptide selected in step (d) does not significantly interact with the polyspecificity reagent.

In some embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In other embodiments, the invention provides methods of generating an enriched plurality of developable polypeptides from a non-enriched plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting from the reagent-plurality mixture of step (b) one or more polyspecific polypeptides from among the plurality of polypeptides that interacts with the polyspecificity reagent; and (d) separating from the non-enriched plurality of polypeptides the one or more polyspecific polypeptides detected in step (c), thereby generating the enriched collection of developable polypeptides. In certain embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In still other embodiments, the invention provides methods of selecting or screening for at least one polypeptide with enhanced developability from amongst a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting from the reagent-plurality mixture of step (b) at least one polypeptide that does not significantly interact with the polyspecificity reagent, thereby detecting at least one developable test polypeptide; and (d) selecting the at least one polypeptide detected in step (d) wherein the at least one polypeptide detected in step (c) and selected in step (d) comprises a polypeptide that has been selected for or screened for enhanced developability relative to members of the plurality that are not detected in step (c) and selected in step (d). In certain embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In other embodiments, the invention provides methods of predicting enhanced developability of at least one polypeptide from amongst a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; and (c) detecting from the reagent-plurality mixture of step (b) at least one polypeptide that does not significantly interact with the polyspecificity reagent, thereby identifying at least one developable polypeptide; wherein the at least one developable polypeptide detected in step (c) is thereby assessed or predicted to possess enhanced developability based on the lack of significant interaction with the polyspecificity reagent relative to members of the plurality that are not identified in step (c).

In certain embodiments, such methods further comprise: (A) performing at least one of steps (a), (b), and (c) by employing flow cytometry; (B) performing at least one of steps (a), (b), and (c), by employing magnetic-activated cell sorting; (C) performing all of steps (a), (b), and (c), by employing flow cytometry; (D) performing all of steps (a), (b), and (c), by employing magnetic-activated cell sorting; or (E) combinations of (A) and (B).

In other embodiments, the invention provides methods of ranking developability of polypeptides in a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting the relative degree of interaction between polypeptides of the plurality and the polyspecificity reagent; and (d) ranking the polypeptides detected in step (c) that are observed to possess a lower degree of interaction with the polyspecificity reagent as possessing enhanced developability, and ranking the polypeptides detected in step (c) that are observed to possess a higher degree of interaction with the polyspecificity reagent as possessing decreased developability. In certain embodiments, such methods further comprise: (A) performing at least one of steps (a), (b), and (c) by employing flow cytometry; (B) performing at least one of steps (a), (b), and (c), by employing magnetic-activated cell sorting; (C) performing all of steps (a), (b), and (c), by employing flow cytometry; (D) performing all of steps (a), (b), and (c), by employing magnetic-activated cell sorting; or (E) combinations of (A) and (B).

In certain embodiments, the invention provides methods of assigning a developability score polypeptides in a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting the relative degree of interaction between polypeptides of the plurality and the polyspecificity reagent; and (d) assigning to the polypeptides detected in step (c) that are observed to possess a lower degree of interaction with the polyspecificity reagent a higher developability score and assigning to the polypeptides detected in step (c) that are observed to possess a higher degree of interaction with the polyspecificity reagent a lower developability score. In certain embodiments, such methods further comprise: (A) performing at least one of steps (a), (b), (c) and (d) by employing flow cytometry; (B) performing at least one of steps (a), (b), (c) and (d) by employing magnetic-activated cell sorting; (C) performing all of steps (a), (b), (c) and (d) by employing flow cytometry; (D) performing all of steps (a), (b), (c) and (d) by employing magnetic-activated cell sorting; or (E) combinations of (A) and (B).

In certain embodiments, the invention provides methods of correlating developability of one or more polypeptides of a plurality of polypeptides with a degree of interaction with a polyspecificity reagent, the method comprising: (a) providing the plurality of polypeptides; (b) contacting the plurality of step (a) with the polyspecificity reagent, wherein the polyspecificity reagent comprises a mixture of biomolecules, thereby producing a reagent-plurality mixture; (c) detecting the degree of interaction between each polypeptide in the plurality of polypeptides with the polyspecificity reagent; and (d) determining the relative degree of interaction between the one or more polypeptides and the polyspecificity reagent, wherein a lower degree of interaction with the polyspecificity reagent correlates with enhanced developability and wherein a higher degree of interaction with the polyspecificity reagent correlates with decreased developability. In certain embodiments, such methods further comprise: (A) performing at least one of steps (a), (b), (c) and (d) by employing flow cytometry; (B) performing at least one of steps (a), (b), (c) and (d) by employing magnetic-activated cell sorting; (C) performing all of steps (a), (b), (c) and (d) by employing flow cytometry; (D) performing all of steps (a), (b), (c) and (d) by employing magnetic-activated cell sorting; or (E) combinations of (A) and (B).

In certain embodiments, the invention provides methods of assessing, screening for, predicting, or identifying, or correlating developability of at least one polypeptide that interacts with a binding partner, the method comprising: (a) providing the at least one polypeptide; (b) contacting the at least one polypeptide of step (a) with a polyspecificity reagent, wherein the polyspecificity reagent comprises a mixture of biomolecules, thereby producing a reagent-polypeptide mixture; (c) determining a degree of interaction between the at least one polypeptide and the polyspecificity reagent, wherein a lower degree of interaction indicates an enhanced developability of the at least one polypeptide and wherein a higher degree of interaction with the polyspecificity reagent indicates a decreased developability of the at least one polypeptide. In certain embodiments, such methods further comprise: (A) performing at least one of steps (a), (b), and (c) by employing flow cytometry; (B) performing at least one of steps (a), (b), and (c), by employing magnetic-activated cell sorting; (C) performing all of steps (a), (b), and (c), by employing flow cytometry; (D) performing all of steps (a), (b), and (c), by employing magnetic-activated cell sorting; or (E) combinations of (A) and (B).

In certain embodiments, the invention provides methods of counter-selecting against at least one polyspecific polypeptide in a library comprising a plurality of polypeptides, wherein said plurality comprises the at least one polyspecific polypeptide and at least one non-polyspecific polypeptide, the method comprising: (a) providing the library comprising a plurality of polypeptides; (b) contacting the library of step (a) with a polyspecificity reagent, wherein the polyspecificity reagent comprises a mixture of biomolecules, thereby generating a reagent-composition mixture; (c) detecting from the reagent-library mixture of step (b) at least one polyspecific polypeptide that interacts with the polyspecificity reagent; and (d) selecting at least one non-polyspecific polypeptide from the library that is not detected in step (c), thereby counter-selecting against the at least one polyspecific polypeptide from the at least one non-polyspecific polypeptide in the library. In certain embodiments, such methods further comprise: determining that the at least one non-polyspecific polypeptide selected in step (d) binds to at least one test binding partner. In certain embodiments, such methods further comprise: (A) performing at least one of steps (b), (c), and (d) by employing flow cytometry; (B) performing at least one of steps (b), (c), and (d) by employing magnetic-activated cell sorting; (C) performing all of steps (b), (c), and (d) by employing flow cytometry; (D) performing all of steps (b), (c), and (d) by employing magnetic-activated cell sorting; or (E) combinations of (A) and (B).

In certain embodiments, the invention provides methods of selecting at least one non-polyspecific polypeptide that interacts with at least one test binding partner from a library comprising a plurality of polypeptides, wherein said plurality comprises the at least one polyspecific polypeptide and at least one non-polyspecific polypeptide, the method comprising: (a) providing the library comprising a plurality of polypeptides; (b) providing the at least one test binding partner; (c) contacting the library of step (a) with the at least one test binding partner of step (b) and a polyspecificity reagent, wherein the polyspecificity reagent comprises a mixture of biomolecules, thereby producing a reagent-library mixture; and (d) selecting from the reagent-plurality mixture of step (c) at least one non-polyspecific polypeptide that interacts with the at least one test binding partner. In certain embodiments of such methods, the at least one non-polyspecific polypeptide selected in step (d) does not significantly interact with the polyspecificity reagent. In certain embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In certain embodiments, the invention provides methods of generating an enriched plurality of developable polypeptides from a non-enriched library of polypeptides, wherein the library of polypeptides comprises at least one polyspecific polypeptide and at least one non-polyspecific polypeptide, the method comprising: (a) providing the library of polypeptides;

(b) contacting the library of step (a) with a polyspecificity reagent, wherein the polyspecificity reagent comprises a mixture of biomolecules, thereby producing a reagent-library mixture;

(c) detecting from the reagent-plurality mixture of step (b) one or more polyspecific polypeptides from among the library of polypeptides that interacts with the polyspecificity reagent; and (d) separating from the non-enriched library of polypeptides the one or more polyspecific polypeptides detected in step (c), thereby generating the enriched plurality of developable polypeptides. In certain embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In certain embodiments, the invention provides methods of selecting or screening for at least one polypeptide with enhanced developability from amongst a library of polypeptides, wherein the library of polypeptides comprises at least one polyspecific polypeptide and at least one non-polyspecific polypeptide, the method comprising: (a) providing the library of polypeptides; (b) contacting the library of step (a) with a polyspecificity reagent, wherein the polyspecificity reagent comprises a mixture of biomolecules, thereby producing a reagent-library mixture; (c) detecting from the reagent-library mixture of step (b) at least one polypeptide that does not significantly interact with the polyspecificity reagent, thereby detecting at least one non-polyspecific polypeptide; and (d) selecting the at least one non-polyspecific polypeptide detected in step (c) wherein the at least one non-polyspecific polypeptide detected in step (c) and selected in step (d) comprises a polypeptide that has been selected for or screened for enhanced developability relative to members of the plurality that are not detected in step (c) and selected in step (d). In certain embodiments, such methods further comprise: (A) performing at least one of steps (a), (b), (c), and (d) by employing flow cytometry; (B) performing at least one of steps (a), (b), (c), and (d) by employing magnetic-activated cell sorting; (C) performing all of steps (a), (b), (c), and (d) by employing flow cytometry; (D) performing all of steps (a), (b), (c), and (d) by employing magnetic-activated cell sorting; or (E) combinations of (A) and (B).

In certain embodiments, the invention provides methods of predicting enhanced developability of at least one polypeptide from amongst a library of polypeptides, wherein the library of polypeptides comprises at least one polyspecific polypeptide and at least one non-polyspecific polypeptide, the method comprising: (a) providing the library of polypeptides; (b) contacting the library of step (a) with a polyspecificity reagent, wherein the polyspecificity reagent comprises a mixture of biomolecules, thereby producing a reagent-library mixture; and (c) detecting from the reagent-library mixture of step (b) at least one polypeptide that does not significantly interact with the polyspecificity reagent, thereby identifying at least one developable polypeptide; wherein the at least one developable polypeptide detected in step (c) is thereby assessed or predicted to possess enhanced developability based on the lack of significant interaction with the polyspecificity reagent relative to polypeptides of the library that are not identified in step (c). In certain embodiments, such methods further comprise: (A) performing at least one of steps (a), (b), and (c) by employing flow cytometry; (B) performing at least one of steps (a), (b), and (c), by employing magnetic-activated cell sorting; (C) performing all of steps (a), (b), and (c), by employing flow cytometry; (D) performing all of steps (a), (b), and (c), by employing magnetic-activated cell sorting; or (E) combinations of (A) and (B).

In certain embodiments, the invention provides methods of ranking developability of polypeptides in a library of polypeptides, wherein the library of polypeptides comprises at least one polyspecific polypeptide and at least one non-polyspecific polypeptide, the method comprising: (a) providing the library of polypeptides; (b) contacting the library of step (a) with a polyspecificity reagent, wherein the polyspecificity reagent comprises a mixture of biomolecules, thereby producing a reagent-library mixture; (c) detecting the relative degree of interaction between polypeptides of the library and the polyspecificity reagent; and (d) ranking the polypeptides detected in step (c) that are observed to possess a lower degree of interaction with the polyspecificity reagent as possessing enhanced developability, and ranking the polypeptides detected in step (c) that are observed to possess a higher degree of interaction with the polyspecificity reagent as possessing decreased developability. In certain embodiments, such methods further comprise: (A) performing at least one of steps (a), (b), and (c) by employing flow cytometry; (B) performing at least one of steps (a), (b), and (c), by employing magnetic-activated cell sorting; (C) performing all of steps (a), (b), and (c), by employing flow cytometry; (D) performing all of steps (a), (b), and (c), by employing magnetic-activated cell sorting; or (E) combinations of (A) and (B).

In certain embodiments, the invention provides methods of assigning a developability score to polypeptides in a library of polypeptides, wherein the library of polypeptides comprises at least one polyspecific polypeptide and at least one non-polyspecific polypeptide, the method comprising: (a) providing the library of polypeptides; (b) contacting the library of step (a) with a polyspecificity reagent, wherein the polyspecificity reagent comprises a mixture of biomolecules, thereby producing a reagent-library mixture; (c) detecting the relative degree of interaction between polypeptides of the library and the polyspecificity reagent; and (d) assigning to the polypeptides detected in step (c) that are observed to possess a lower degree of interaction with the polyspecificity reagent a higher developability score and assigning to the polypeptides detected in step (c) that are observed to possess a higher degree of interaction with the polyspecificity reagent a lower developability score. In certain embodiments, such methods further comprise: (A) performing at least one of steps (a), (b), (c) and (d) by employing flow cytometry; (B) performing at least one of steps (a), (b), (c) and (d) by employing magnetic-activated cell sorting; (C) performing all of steps (a), (b), (c) and (d) by employing flow cytometry; (D) performing all of steps (a), (b), (c) and (d) by employing magnetic-activated cell sorting; or (E) combinations of (A) and (B).

In certain embodiments, the invention provides methods of correlating developability of one or more polypeptides of a library of polypeptides, wherein the library of polypeptides comprises at least one polyspecific polypeptide and at least one non-polyspecific polypeptide, with a degree of interaction with a polyspecificity reagent, the method comprising: (a) providing the library of polypeptides; (b) contacting the library of step (a) with the polyspecificity reagent, wherein the polyspecificity reagent comprises a mixture of biomolecules, thereby producing a reagent-library mixture; (c) detecting the degree of interaction between each polypeptide in the library of polypeptides with the polyspecificity reagent; and (d) determining the relative degree of interaction between the one or more polypeptides and the polyspecificity reagent, wherein a lower degree of interaction with the polyspecificity reagent correlates with enhanced developability and wherein a higher degree of interaction with the polyspecificity reagent correlates with decreased developability. In certain embodiments, such methods further comprise: (A) performing at least one of steps (a), (b), (c) and (d) by employing flow cytometry; (B) performing at least one of steps (a), (b), (c) and (d) by employing magnetic-activated cell sorting; (C) performing all of steps (a), (b), (c) and (d) by employing flow cytometry; (D) performing all of steps (a), (b), (c) and (d) by employing magnetic-activated cell sorting; or (E) combinations of (A) and (B).

In still other embodiments, the methods disclosed herein and throughout may further comprise contacting either: the plurality of polypeptides; the reagent-plurality mixture; or both the plurality of polypeptides and the reagent-plurality mixture; with at least one test binding partner.

In other embodiments, the plurality of polypeptides comprises a library of polypeptides.

In some embodiments of the methods disclosed herein and throughout, the polyspecificity reagent comprises a composition selected from the group consisting of: (a) a soluble cellular fraction; (b) a membrane cellular fraction; (c) a bodily fluid fraction; (d) a serum fraction; (e) a plasma fraction; (f) a cocktail comprising partially purified biomolecules; (g) a collection of virus or virus-derived particles; and (h) a combination of one or more of (a) through (g).

In some embodiments of the methods disclosed herein and throughout, the polyspecificity reagent comprises a composition selected from the group consisting of: (a) a soluble cellular fraction; (b) a membrane cellular fraction; (c) a bodily fluid fraction; (d) a serum fraction; (e) a plasma fraction; (f) a cocktail comprising partially purified biomolecules; (g) a combination of one or more of (a) through (f).

In some embodiments of the methods disclosed herein and throughout, the polyspecificity reagent comprises a cellular soluble fraction that is obtained from a collection of cells in culture.

In some embodiments of the methods disclosed herein and throughout, the polyspecificity reagent comprises a cellular soluble fraction that is obtained from a collection of mammalian cells in culture.

In some embodiments of the methods disclosed herein and throughout, the polyspecificity reagent comprises a cellular soluble fraction that is obtained from a collection of insect cells in culture.

In some embodiments of the methods disclosed herein and throughout, the polyspecificity reagent comprises a cellular membrane fraction that is obtained from a collection of cells in culture.

In some embodiments of the methods disclosed herein and throughout, polyspecificity reagent comprises a cellular membrane fraction that is obtained from a collection of mammalian cells in culture.

In some embodiments of the methods disclosed herein and throughout, the polyspecificity reagent comprises a cellular membrane fraction that is obtained from a collection of insect cells in culture.

In some embodiments of the methods disclosed herein and throughout, the polyspecificity reagent comprises a solubilized cellular membrane fraction.

In some embodiments of the methods disclosed herein and throughout, the polyspecificity reagent comprises a solubilized cellular membrane fraction that is obtained from a collection of mammalian cells in culture.

In some embodiments of the methods disclosed herein and throughout, the polyspecificity reagent comprises a solubilized cellular membrane fraction that is obtained from a collection of insect cells in culture.

In some embodiments of the methods disclosed herein and throughout, the polyspecificity reagent comprises a collection of virus or virus-derived particles selected from the group consisting of baculovirus; adenovirus; lentivirus; rhinovirus; coronavirus; cucumber mosaic virus; cytomegalovirus; respiratory syncytial virus; influenza virus; rotavirus; herpes virus; and virus particles derived from one or more such viruses In some embodiments of the methods disclosed herein and throughout, the polyspecificity reagent comprises at least one detergent.

In some embodiments of the methods disclosed herein and throughout, the polyspecificity reagent comprises at least one detergent selected from the group consisting of beta-mercaptoethanol (B-ME), (Cyclohexyl-beta-D-maltoside (Cymal-6), Sodium Cholate, Polyoxyethylene(23) lauryl ether (Brij35), Decyl Maltose Neopentyl Glycol (DM-NG), n-Dodecyl β-D-maltoside (DDM), n-octyl-β-D-glucoside (OG), and 3-[(3-Cholamidopropyl) dimethylammonio]-1-propanesulfonate (CHAPS).

In some embodiments of the methods disclosed herein and throughout, the plurality of polypeptides comprises at least: from about $1\times10^4$ unique polypeptides to about $1\times10^{18}$ unique polypeptides; $1\times10^4$ unique polypeptides to about $1\times10^{17}$ unique polypeptides; $1\times10^4$ unique polypeptides to about $1\times10^{16}$ unique polypeptides; $1\times10^4$ unique polypeptides to about $1\times10^{15}$ unique polypeptides; $1\times10^4$ unique polypeptides to about $1\times10^{14}$ unique polypeptides; $1\times10^4$ unique polypeptides to about $1\times10^{13}$ unique polypeptides; $1\times10^4$ unique polypeptides to about $1\times10^{12}$ unique polypeptides; $1\times10^4$ unique polypeptides to about $1\times10^{11}$ unique polypeptides; $1\times10^4$ unique polypeptides to about $1\times10^{10}$ unique polypeptides; $1\times10^4$ unique polypeptides to about $1\times10^9$ unique polypeptides; $1\times10^4$ unique polypeptides to about $1\times10^8$ unique polypeptides; $1\times10^4$ unique polypeptides to about $1\times10^7$ unique polypeptides; $1\times10^5$ unique polypeptides to about $1\times10^{18}$ unique polypeptides; $1\times10^6$ unique polypeptides to about $1\times10^{18}$ unique polypeptides; $1\times10^7$ unique polypeptides to about $1\times10^{18}$ unique polypeptides; $1\times10^8$ unique polypeptides to about $1\times10^{18}$ unique polypeptides; $1\times10^9$ unique polypeptides to about $1\times10^{18}$ unique polypeptides; $1\times10^{10}$ unique polypeptides to about $1\times10^{18}$ unique polypeptides; $1\times10^{11}$ unique polypeptides to about $1\times10^{18}$ unique polypeptides; $1\times10^{12}$ unique polypeptides to about $1\times10^{18}$ unique polypeptides; $1\times10^5$ unique polypeptides to about $1\times10^{18}$ unique polypeptides; $1\times10^6$ unique polypeptides to about $1\times10^{17}$ unique polypeptides; $1\times10^7$ unique polypeptides to about $1\times10^{16}$ unique polypeptides; $1\times10^8$ unique polypeptides to about $1\times10^{15}$ unique polypeptides; $1\times10^9$ unique polypeptides to about $1\times10^{14}$ unique polypeptides; or $1\times10^{10}$ unique polypeptides to about $1\times10^{13}$ unique polypeptides.

In some embodiments of the methods disclosed herein and throughout, the plurality of polypeptides is collectively encoded by a plurality of polynucleotides.

In some embodiments of the methods disclosed herein and throughout, the plurality of polynucleotides comprises a library of polynucleotides.

In some embodiments of the methods disclosed herein and throughout, the plurality of polynucleotides comprises at least: from about $1\times10^4$ unique polynucleotides to about $1\times10^{18}$ unique polynucleotides; $1\times10^4$ unique polynucleotides to about $1\times10^{17}$ unique polynucleotides; $1\times10^4$ unique polynucleotides to about $1\times10^{16}$ unique polynucleotides; $1\times10^4$ unique polynucleotides to about $1\times10^{15}$ unique polynucleotides; $1\times10^4$ unique polynucleotides to about $1\times10^{14}$ unique polynucleotides; $1\times10^4$ unique polynucleotides to about $1\times10^{13}$ unique polynucleotides; $1\times10^4$ unique polynucleotides to about $1\times10^{12}$ unique polynucleotides; $1\times10^4$ unique polynucleotides to about $1\times10^{11}$ unique polynucleotides; $1\times10^4$ unique polynucleotides to about $1\times10^{10}$ unique polynucleotides; $1\times10^4$ unique polynucleotides to about $1\times10^9$ unique polynucleotides; $1\times10^4$ unique polynucleotides to about $1\times10^8$ unique polynucleotides; $1\times10^4$ unique polynucleotides to about $1\times10^7$ unique polynucleotides; $1\times10^5$ unique polynucleotides to about $1\times10^{18}$ unique polynucleotides; $1\times10^6$ unique polynucleotides to about $1\times10^{18}$ unique polynucleotides; $1\times10^7$ unique polynucleotides to about $1\times10^{18}$ unique polynucleotides; $1\times10^8$ unique polynucleotides to about $1\times10^{18}$ unique polynucleotides; $1\times10^9$ unique polynucleotides to about $1\times10^{18}$ unique polynucleotides; $1\times10^{10}$ unique polynucleotides to about $1\times10^{18}$ unique polynucleotides; $1\times10^{11}$ unique polynucleotides to about $1\times10^{18}$ unique polynucleotides; $1\times10^{12}$ unique polynucleotides to about $1\times10^{18}$ unique polynucleotides; $1\times10^5$ unique polynucleotides to about $1\times10^{18}$ unique polynucleotides; $1\times10^6$ unique polynucleotides to about $1\times10^{17}$ unique polynucleotides; $1\times10^7$ unique polynucleotides to about $1\times10^{16}$ unique polynucleotides; $1\times10^8$ unique polynucleotides to about $1\times10^{15}$ unique polynucleotides; $1\times10^9$ unique polynucleotides to about $1\times10^{14}$ unique polynucleotides; or $1\times10^{10}$ unique polynucleotides to about $1\times10^{13}$ unique polynucleotides.

In some embodiments of the methods disclosed herein and throughout, each polypeptide of the plurality of polypeptides is encoded by a polynucleotide that is a component of a vector.

In some embodiments of the methods disclosed herein and throughout, each polynucleotide is introduced into one or more of the host cells.

In some embodiments of the methods disclosed herein and throughout, the plurality of polynucleotides is introduced a plurality of host cells.

In some embodiments of the methods disclosed herein and throughout, the plurality of host cells comprises a plurality of vectors collectively harboring the one or more polynucleotides collectively encoding the plurality of polypeptides.

In some embodiments of the methods disclosed herein and throughout, the plurality of polypeptides is expressed by one or more host cells.

In some embodiments of the methods disclosed herein and throughout, the plurality of polypeptides is collectively expressed by a plurality of host cells.

In some embodiments of the methods disclosed herein and throughout, the plurality of polypeptides comprises a naïve discovery polypeptide library.

In some embodiments of the methods disclosed herein and throughout, the plurality of polynucleotides comprises a naïve discovery polynucleotide library.

In some embodiments of the methods disclosed herein and throughout, the host cells comprise a naïve discovery host cell library.

In some embodiments of the methods disclosed herein and throughout, the plurality of polypeptides comprises an optimization polypeptide library.

In some embodiments of the methods disclosed herein and throughout, the plurality of polynucleotides comprises an optimization polynucleotide library.

In some embodiments of the methods disclosed herein and throughout, the host cells comprise an optimization host cell library.

In some embodiments of the methods disclosed herein and throughout, the polypeptides comprise antibodies or antibody fragments.

In some embodiments of the methods disclosed herein and throughout, the polypeptides comprise antibodies or antibody fragments, wherein the antibodies or antibody fragments comprise at least one Fc region.

In some embodiments of the methods disclosed herein and throughout, the polypeptides comprise antibodies or antibody fragments, wherein the antibodies or antibody fragments comprise at least one Fc region and at least one antigen binding region.

In some embodiments of the methods disclosed herein and throughout, the polypeptides comprise antibodies or antibody fragments, wherein the antibodies or antibody fragments comprise full-length IgGs.

In some embodiments of the methods disclosed herein and throughout, the polypeptides comprise multispecific antibodies or antibody fragments.

In some embodiments of the methods disclosed herein and throughout, the polypeptides comprise human or humanized antibodies or antibody fragments.

In some embodiments of the methods disclosed herein and throughout, the host cells are eukaryotic cells.

In some embodiments of the methods disclosed herein and throughout, the host cells are yeast cells.

In some embodiments of the methods disclosed herein and throughout, the host cells provide genotype-phenotype linkage.

In some embodiments of the methods disclosed herein and throughout, the plurality of host cells collectively comprise a genotype-phenotype library.

In some embodiments of the methods disclosed herein and throughout, the invention provides polyspecificity reagents comprising a composition selected from the group consisting of: (a) a soluble cellular fraction; (b) a membrane cellular fraction; (c) a bodily fluid fraction; (d) a serum fraction; (e) a plasma fraction; (f) a cocktail comprising partially purified biomolecules; (g) a collection of virus or virus-derived particles; and (h) a combination of one or more of (a) through (f). In certain embodiments, the polyspecificity reagents comprise at least one detergent.

In certain embodiments, the polyspecificity reagents comprise at least one yeast-compatible detergent. In certain embodiments, the polyspecificity reagents comprise at least one detergent selected from the group consisting of: beta-mercaptoethanol (B-ME), (Cyclohexyl-beta-D-maltoside (Cymal-6), Sodium Cholate, Polyoxyethylene(23)lauryl ether (Brij35), Decyl Maltose Neopentyl Glycol (DM-NG), n-Dodecyl β-D-maltoside (DDM), n-octyl-β-D-glucoside (OG), and 3[(3-Cholamidopropyl)dimethylammonio]-1-propanesulfonate (CHAPS).

In some embodiments of the methods disclosed herein and throughout, a test binding partner is not added to the polyspecificity reagent.

In some embodiments of the methods disclosed herein and throughout the polyspecificity reagent is essentially devoid of a test binding partner.

In some embodiments of the methods disclosed herein and throughout, such methods further comprise performing one or more of the following: cross interaction chromatography (CIC); self-interaction chromatography (SIC); dynamic light scattering (DLS) spectrophotometry; size exclusion chromatography (SEC); circular dichroism (CD); quasi-elastic light scattering; photon correlation spectroscopy; whole cell binding; tissue micro array methodologies; BVP ELISA assays; and differential scanning calorimetry.

In certain embodiments, the invention provides polyspecificity reagents as disclosed herein and throughout for use in the methods disclosed herein and throughout.

BRIEF DESCRIPTION OF THE FIGURES

FIG. 3 depicts comparison sets of antibodies that were used to generate CIC profiles as described in the EXAMPLES.

DETAILED DESCRIPTION OF THE INVENTION

Figure 1:
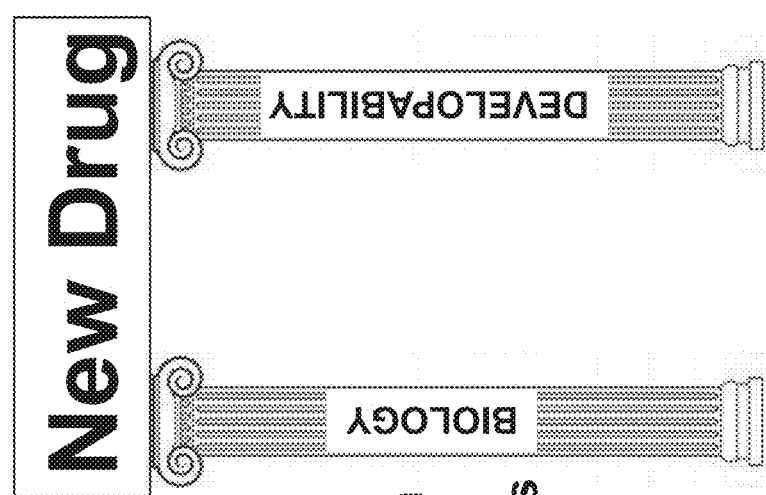
FIG. 1 provides a schematic representation of the importance of both biology and developability of new drug candidates. Exemplary indicia of both desirable biology characteristics and developability characteristics are depicted.
Figure 2:
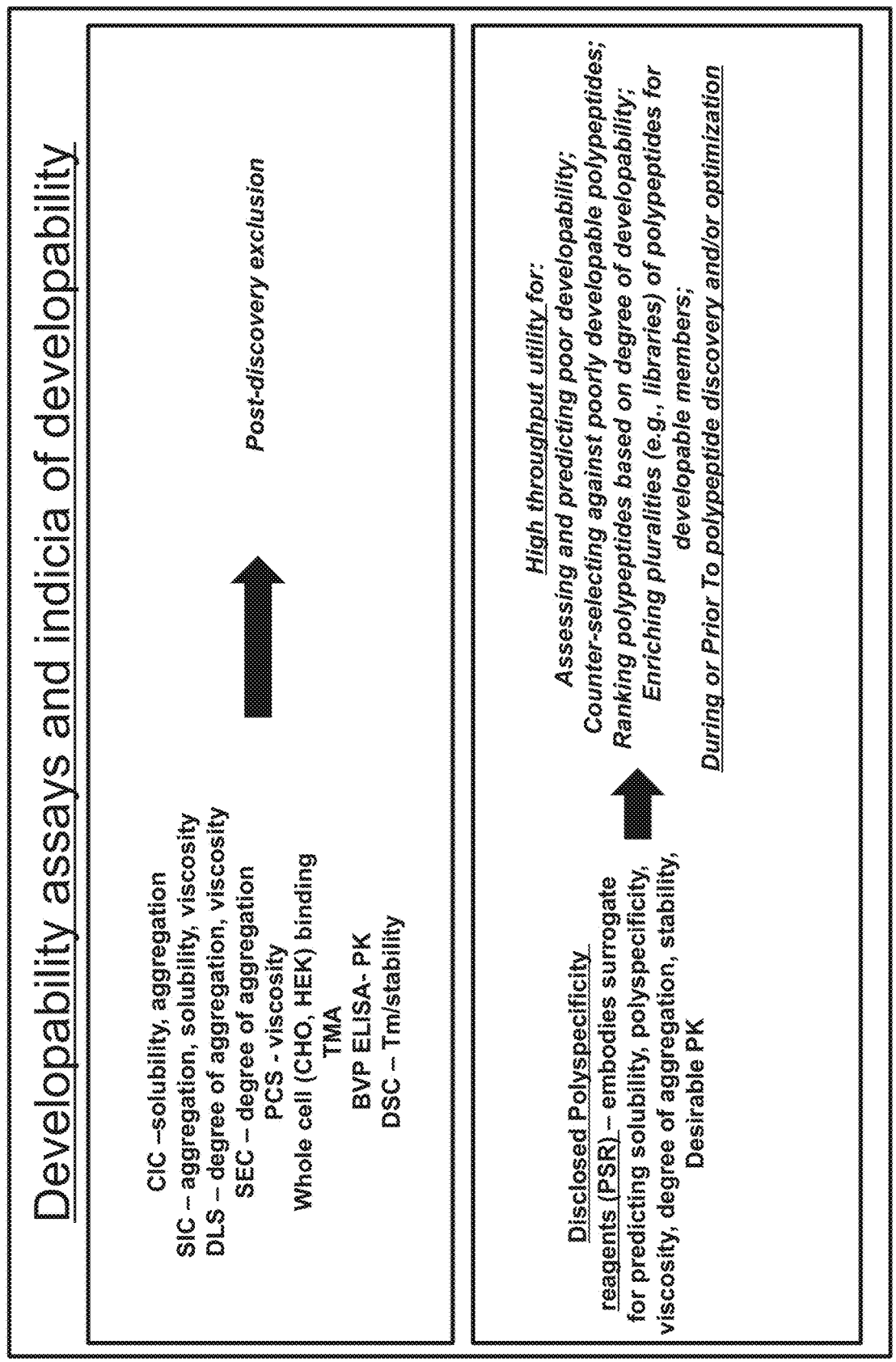
FIG. 2 provides a depiction of exemplary assays that may be employed in assessing developability of polypeptides. Also provided are exemplary indicia of developability which may be interrogated using the depicted methodologies. Upper boxed area; developability methodologies that have employed in post-discovery exclusion processes, and indicia for ascertaining developability. Lower boxed area, exemplary predictive attributes polyspecificity reagents (PSR) disclosed herein and throughout. Also provided are corresponding exemplary utilities of the PSR for, for example: assessing and predicting poor developability of polypeptides; counter-selecting against polyspecific (and thus, poorly developable) antibodies from amongst a plurality of polypeptides; ranking polypeptides based on degree of developability; enriching pluralities (e.g., libraries) of polypeptides for developable members in the plurality; during and/or prior to polypeptide discovery and/or optimization activities. CIC, cross interaction chromatography; SIC, self-interaction chromatography; DLS, dynamic light scattering; SEC, size exclusion chromatography; PCS, photon correlation spectroscopy; TMA, tissue microarray; BVP-ELISA, baculovirus particle—enzyme-linked immunosorbent assay; DSC, differential scanning calorimetry; PK, pharmacokinetics; Tm, melting temperature.

Polyspecific Reagents and Methods of Making them

The present invention provides, inter alia, the surprising discovery that polyspecific reagents (PSR) may be employed, inter alia, selecting for, assessing, predicting, ranking, scoring, and correlating developability of one or more polypeptides from amongst a plurality of polypeptides. The herein and throughout disclosed PSRs comprise a mixture of biomolecule which, when contacted with a plurality of polypeptides to generate a plurality-PSR mixture, may also be employed in methods for, for example: counter-selecting against one or more polyspecific polypeptides from a plurality of polypeptides; selecting at least one polypeptide from amongst a plurality of polypeptides that specifically interact with at least one test binding partner; generating enriched pluralities of developable polypeptides from a non-enriched plurality of polypeptides; selecting or screening for at least one polypeptide with enhanced developability from amongst a plurality of polypeptides; ranking developability of polypeptides in a plurality of polypeptides; assigning developability scores for polypeptides in a plurality of polypeptides; correlating developability of one or more polypeptides of a plurality of polypeptides with a degree of interaction with a PCR; assessing, screening for, predicting, identifying, or correlating developability of at least one polypeptide that interacts with a binding partner; and other methods as disclosed and claimed herein and throughout; wherein the polyspecific polypeptide is detected by virtue of its interaction with the PSR, thereby affording the ability to select polypeptides from the plurality that do not interact with the PSR.

A "mixture of biomolecules" refers to a complex, heterogeneous mixture of a number of biomolecules of different classes, and biochemical and biophysical properties. Examples of biomolecules that are included in the inventive mixtures of biomolecules include: lipids, carbohydrates, lipoproteins, glycolipids, glycoproteins, nucleic acids (both DNA and RNA), lipid rafts containing cell surface and/or transmembrane proteins, peptides, polypeptides, ribosomes and the like. Without being bound by any theory, it is believe that the surprising utility of the herein and throughout disclosed PSRs is derived, at least in part, from the overall biochemical, biophysical, structural, and/or topological milieu provided by such mixtures which, when contacted with a plurality of diverse polypeptides, are believed to non-specifically interact with certain polypeptides, herein referred to as "polyspecific polypeptides" within the plurality. These interactions are believed to not represent a specific interaction between such polypeptides and a presumptive cognate ligand or binding partner—such as those interactions observed for in antibody-cognate antigen interactions, receptor-cognate ligand interactions, and the like—within the mixture of biomolecules; rather such interactions are likely driven by non-specific ionic, electrostatic, hydrophobic or other such interactions between certain non-specific folds or topologies within the PSRs and certain polypeptides within the reagent-contacted plurality that which are predisposed to such non-specific interactions, such as polypeptides with relatively greater regions of hydrophobicity, hydrophilicity, or have regions that are misfolded or are otherwise improperly folded. Furthermore, the mixture of biomolecules, and the PSRs that are generated therewith, are not employed as sources of antigen of interest for use in antigen-positive (e.g., affinity) selections. Rather, the herein and throughout disclosed and claimed mixtures of biomolecules and PSRs generated therewith are employed as reagents for counter-selecting against polyspecificity, polyspecific antibodies, poor developability, and the like in accordance with the methods disclosed and claimed herein and throughout.

In additional to the foregoing, a "polyspecific polypeptide" refers to a polypeptide that has a propensity to significantly interact non-specifically with one or more components of a polyspecificity reagent, such as a complex mixture of biomolecules, as described above and throughout. Exemplary such complex mixtures of biomolecules may also comprise, for example, SMPs or SCPs as described in the Examples and throughout. Such polyspecific polypeptides, while displaying this propensity, may nonetheless also display specificity towards a test binding partner of interest when tested for the ability to bind to such a test binding partner, over other binding potential partners.

The one or more components of such a mixture of biomolecules include, for example: phospholipids; carbohydrate; proteins; peptides; glycoproteins; nucleic acids; either cytoplasmic proteins or cell surface, transmembrane, or otherwise membrane-associated proteins; crude cell extracts; fractionated or partially purified components of cell extracts; and any other partially or completely purified biomolecule; and combinations of subsets or all of such partially or completely purified biomolecules. Exemplary such mixtures of biomolecules also may include: DNA; RNA; serum protein; plasma protein; extracellular matrix protein; ribosomes; hormones; peptides; polypeptides; albumin; human serum albumin; lipids; glycolipids; carbohydrates; phospholipids; lipid rafts; proteases; protease inhibitors; DNAses; DNAse inhibitors; RNAses; and RNAse inhibitors.

Accordingly, disclosed PSRs comprise a mixture of biomolecules that may be obtained from any of a number of sources of such biomolecules and such mixtures of biomolecules. In some embodiments, the mixture of biomolecules is obtained from a collection of eukaryotic cells that have been fractionated such that a soluble fraction and a membrane fraction may be prepared. Any of a number of methodologies for preparing such soluble and membrane fractions of the eukaryotic may be employed in order to generate the inventive PSRs for use in the methods disclosed herein and throughout, such as by mechanical lysis, hypotonic solution-mediated lysis, detergent-mediated lysis, and other methods available in the art, as well as combinations of such lysis methods and conditions. In some embodiments, the PSRs comprise a membrane fraction prepared from eukaryotic cells. In some embodiments, the PSRs comprise a detergent solubilized membrane protein fraction (SMP) prepared from eukaryotic cells, wherein the detergent solubilized membrane protein fraction comprises at least one detergent. In other embodiments, the PSRs comprise a soluble cytosolic fraction (SCP) obtained from eukaryotic cells. Optionally, such SCPs fractions further comprise at least one detergent. Any means for effecting lysis of cells, and recovery of soluble cytosolic fractions and membrane fractions, each either in the presence or absence of one or more detergents, are available in the art and may be employed in preparing polyspecificity reagents, such as SCPs and SMPs, in accordance with the disclosed and claimed inventions. Exemplary means and methods for preparing, polyspecificity reagents amenable for use according to the disclosed and claimed inventions, such as e.g., SMPs and SCPs, include those disclosed in the following: Cho et al., *Protein Eng Des Sel*, Vol. 23(7), pages 567-577 (2010); US 20090203538; Tillotson et al., *Protein Eng Des Sel*, Vol. 26(2), pages 101-112 (2013); Hötzel et al., *Protein Eng Des Sel*, Vol. 24(9), pages 679-689 (2011); and Barret et al., *J Chromatogr A*, Vol. 1281, pages 135-141 (2013).

Figure 7:
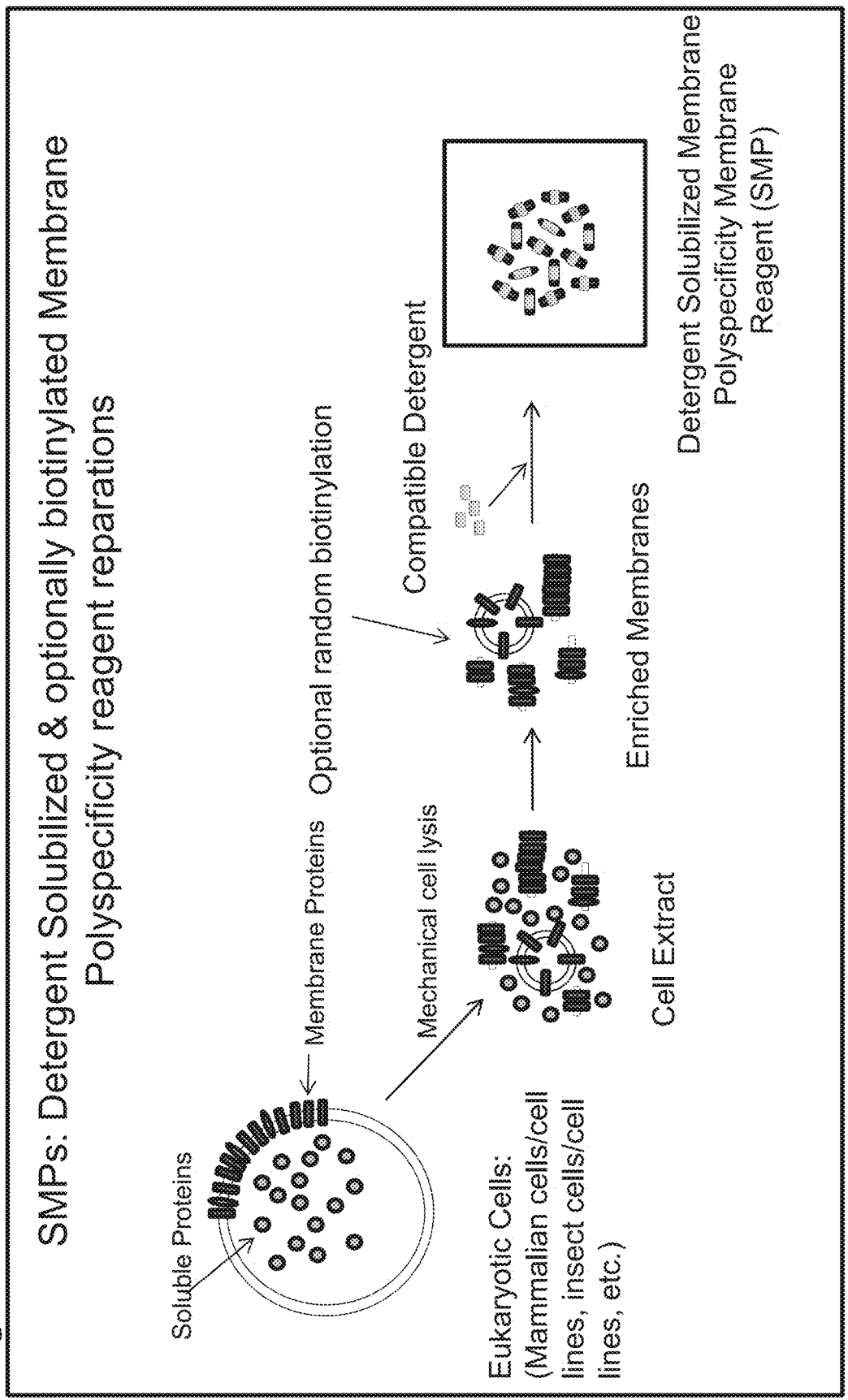
FIG. 7 depicts a graphic representation of an exemplary method for generating an exemplary PSR, a detergent solubilized membrane polyspecificity reagent (SMP), as disclosed herein and throughout.
Figure 8:
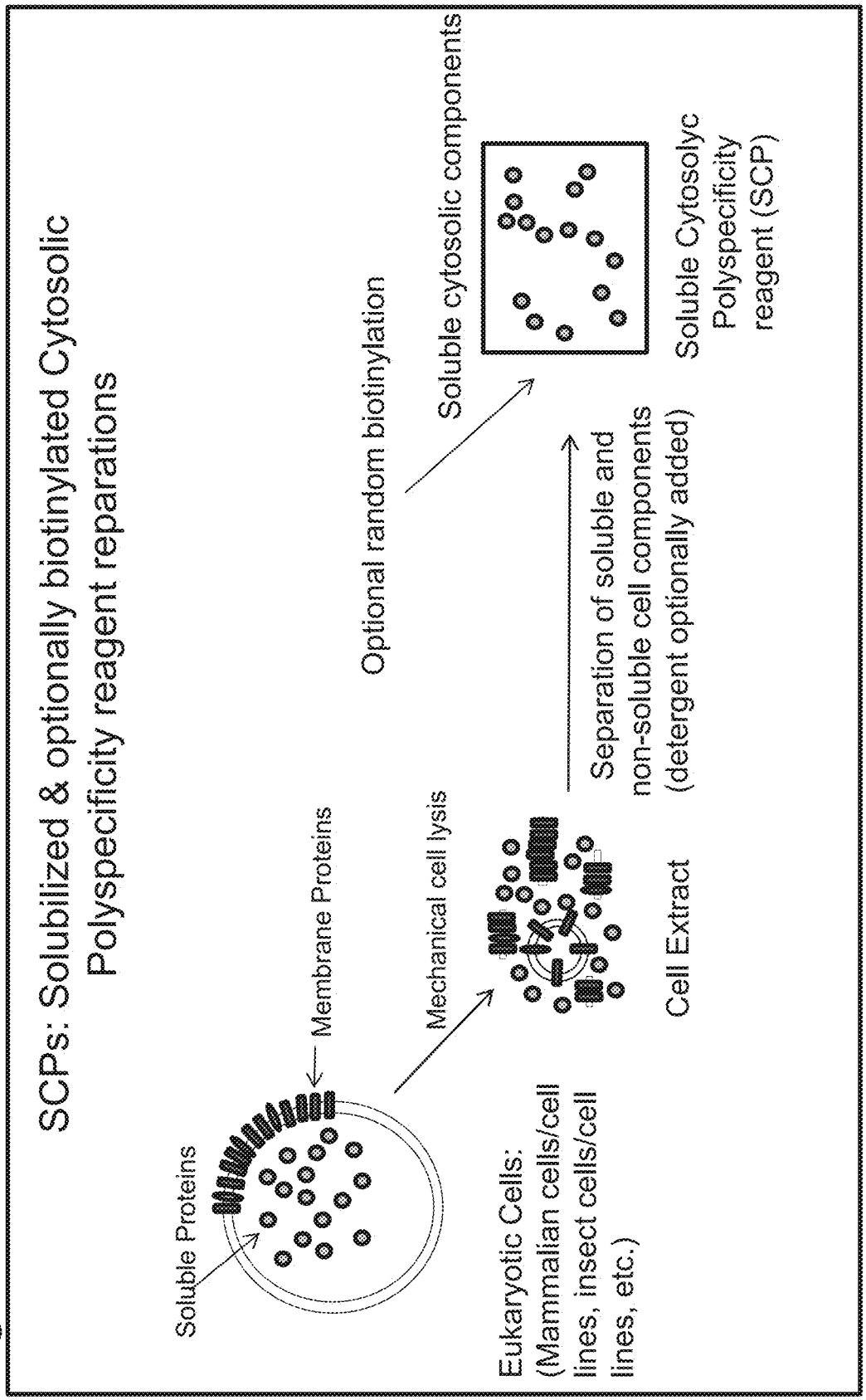
FIG. 8 depicts a graphic representation of an exemplary method for generating an exemplary PSR, a soluble cytoplasmic polyspecificity reagent (SCP), as disclosed herein and throughout.
Figure 9:
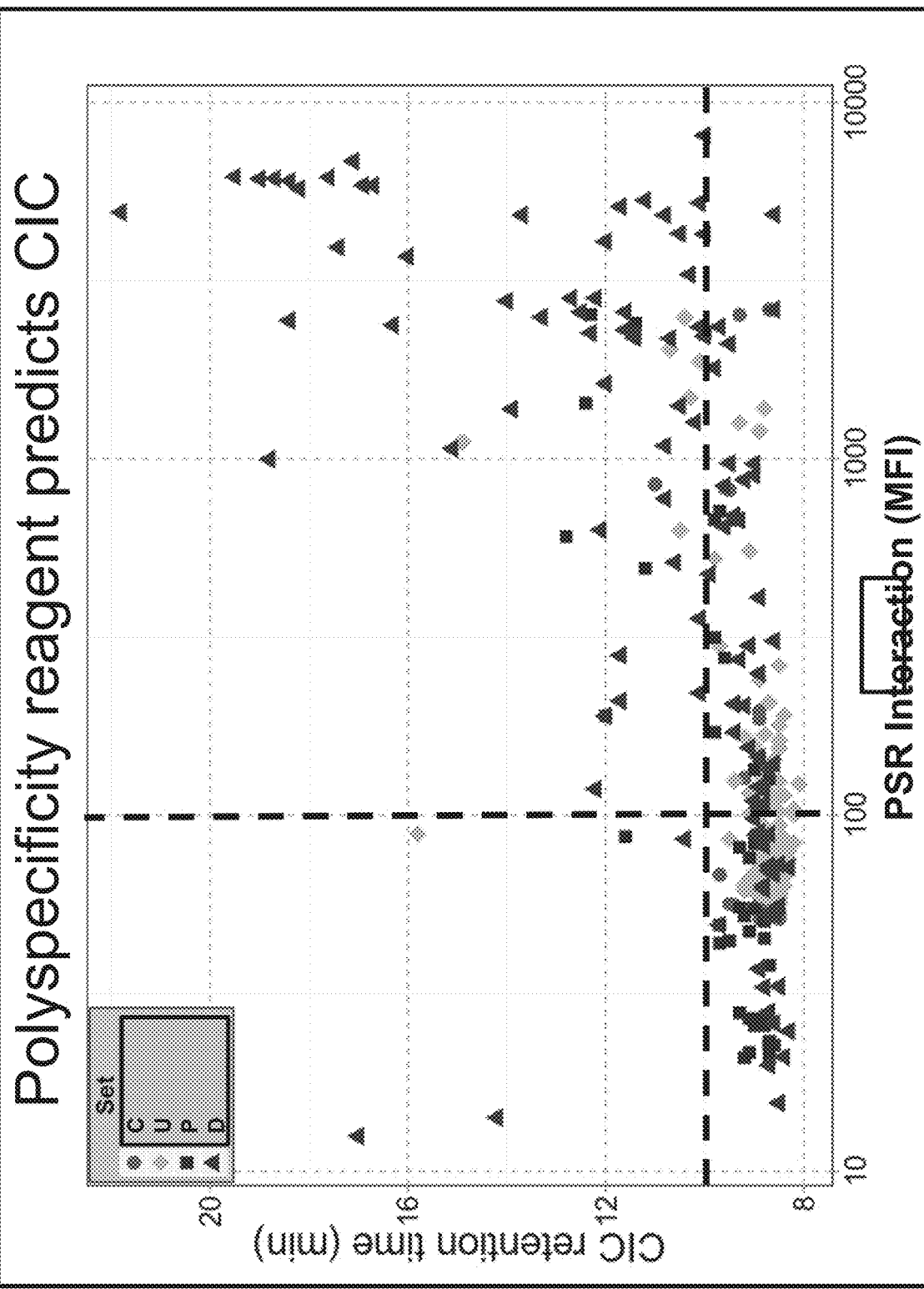
FIG. 9 provides a graph plotting CIC retention times (y-axis) as a function of the degree of PSR interaction expressed as mean florescence intensity (MFI) for the C, U, P, and D sets of antibodies as described in the EXAMPLES and depicted in FIG. 3.

Exemplary methods for preparing SMPs and SCPs are provided in the Examples and depicted in FIGS. 7 and 8, respectively.

In certain embodiments, the SMPs and/or SCPs are prepared from mammalian cells. Exemplary such mammalian cells include, e.g.: primary mammalian cells; immortalized mammalian cell lines; transformed mammalian cell lines; CHO cells; CHO-S cells; HEK 293 cells; HEK 293T cells; HeLa cells; A431 cells; Saos cells; NIH cells; NIH 3T3 cells; Caco-2 cells; HepG2 cells; Hep3B cells; COS cells; U2O3 cells; Jurkat T cells; BHK cells; PER C.6, Sp2/0, NS0 cells; variants or progeny thereof; combinations of subsets or all of such sources; and any other cell line available in the art. In certain embodiments, such mammalian cells are placed in culture and propagated for a period of time by methods available in the art prior to harvesting and preparation of SMPs and/or SCPs for use in the disclosed methods.

In other embodiments the SMPs and/or SCPs are prepared from insect cells. Exemplary such insect cells include, e.g.: Sf9 cells Sf21 cells; Sf21/Sf9 cells; Trichplusia ni BTi-Tn5b1-4 cells; variants or progeny thereof; combinations of subsets or all of such sources; and any other cell line available in the art In some embodiments, PSRs which may be generated and employed in the disclosed methods may comprise a mixture of biomolecules derived from sources such as: bodily fluids; animal serum; human serum; animal plasma; human plasma; animal extracellular matrix; human extracellular matrix; animal semen; human semen; virus or virus-derived particles; combinations of subsets or all of such sources; and/or any other mixture of biomolecules that may be derived from biological sources available in the art. Such sources of mixtures of biomolecules may be prepared and fractionated, when desired, as described above.

In embodiments in which the PSRs comprise virus or virus-derived particles, such virus or virus-derived particles may comprise baculovirus; adenovirus; lentivirus; rhinovirus; coronavirus; cucumber mosaic virus; cytomegalovirus; respiratory syncytial virus; influenza virus; rotavirus; herpes virus; combinations of subsets or all of such viruses; and/or virus-derived particles generated from one or more of such viruses.

In further embodiments, PSRs which may be generated and employed in the disclosed methods may comprise a cocktail of partially purified biomolecules. "A cocktail of partially purified biomolecules" refers to a mixture of biomolecules that is prepare by mixing, in vitro, partially purified components such as partially or completely purified: DNA; RNA; serum protein; plasma protein; extracellular matrix protein; ribosomes; hormones; peptides; polypeptides; albumin; human serum albumin; lipids; glycolipids; carbohydrates; phospholipids; lipid rafts; proteases; protease inhibitors; DNAses; DNAse inhibitors; RNAses; RNAse inhibitors; crude cell extracts; fractionated or partially purified components of cell extracts; and any other partially or completely purified biomolecule; and combinations of subsets or all of such partially or completely purified biomolecules.

When one or more detergents are employed in the generation of the disclosed PSRs, such detergents may be selected from those detergents that are compatible with host cells that express the plurality of polypeptides which are to be contacted with the PSRs in accordance with the disclosed methods. "Compatible with host cells" means that host cells that are contacted with the one or more detergents that are to be employed in generating the PSRs, such as SMPs, generally remain viable. "Remain viable" means that, in the context of a plurality of host cells employed in accordance with the disclosed methods, at least approximately 50 percent of the plurality of host cells remain alive when contacted with the PSR comprising the one or more detergent for a sufficient period of time so as to practice the disclosed and claimed methods. Applicants have discovered, inter alia, that, for example: beta-mercaptoethanol (B-ME); (Cyclohexyl-beta-D-maltoside (Cymal-6); Sodium Cholate, Polyoxyethylene$_{(23)}$ lauryl ether (Brij35); Decyl Maltose Neopentyl Glycol (DM-NG); n-Dodecyl β-D-maltoside (DDM), n-octyl-β-D-glucoside (OG); 3-[(3-Cholamidopropyl)dimethylammonio]-1-propanesulfonate (CHAPS); and combinations of subsets and/or all of such detergents are compatible with yeast host cells (e.g., are yeast-compatible) and, as such, may be employed in accordance with the disclosed and claim methods.

Methods Comprising the Use Polyspecific Reagents

As mentioned above, Applicants have discovered, inter alia, that the disclosed polyspecific reagents (PSR) may be employed, inter alia, selecting for, assessing, predicting, ranking, scoring, and correlating developability of one or more polypeptides from amongst a plurality of polypeptides. Such methods advantageously provide methods of detecting, selecting, and/or identifying polypeptides of interest which possess enhanced developability and developability characteristics in a high-throughput manner, in the early discovery processes. This is distinguished from, and highly advantageous over, current methods of assessing developability of candidate therapeutic polypeptides, which require that the candidate therapeutic polypeptide is selected prior to performing such developability assessments. Accordingly, the methods disclosed and claimed herein and throughout provide, inter alia, the advantage of distinguishing from among a plurality of polypeptides those possessing enhanced developability from those polypeptides possessing decreased developability, so that polypeptides possessing enhanced developability may be preferentially selected in the early discovery processes with high confidence that such polypeptides will remain attractive as clinical and therapeutic drug candidates as downstream development activities (e.g., formulation and other CMC development, clinical trials, and the like) are initiated and executed.

Accordingly, Applicants have disclosed and claimed herein and throughout exemplary embodiments of methods in which the disclosed and claimed PSRs may be employed. It is to be understood that, as such embodiments are herein and throughout disclosed and claimed sequentially, as must naturally be the case, it is nonetheless expressly disclosed and claimed that any and all such embodiments may be employed as combinations of subsets of such embodiments. Furthermore all descriptions of the meanings of various terms and phrases found in the disclosed and claimed methods, all numbers and all ranges of numbers, and species disclosed as being embraced by disclosed genuses are hereby expressly disclosed and claimed for all combinations of subsets of such methods.

In accordance with the disclosed methods, "developability" refers to the extent to which one or more polypeptides in a plurality of polypeptides possess desirable characteristics, such as, e.g.: desirable expression, for example, in mammalian cells; solubility; viscosity; aggregation; chemical and/or physical stability; desirable "shelf-life"; melting temperature; pharmacokinetic profiles; circulation half-life; and clearance characteristics. Such characteristics may serve as indicia, independently, as combinations of sub-sets of such indicia, or in totality, for the likelihood that such one or more polypeptides may be successfully developed as a therapeutic candidate, and ultimately an approved drug. Accordingly, as understood in the art, generally, polypeptides with desirable developability characteristics possess, e.g., relatively high solubility, relatively low viscosity, relatively low propensity for aggregation, relatively high chemical stability, relatively high physical stability, relatively long "shelf life", relatively high melting temperature, relatively long circulation half-life, relatively long clearance time, and the like. Polypeptides with undesirable developability characteristics possess, e.g., relatively low solubility, relatively high viscosity, relatively high propensity for aggregation, relatively poor chemical stability, relatively poor physical stability, relatively short "shelf life", relatively low melting temperature, relatively short circulation half-life, relatively short clearance time, and the like.

Methods and assays which may be employed to ascertain the degree to which polypeptides possess such desirable (or undesirable, as the case may be) developability characteristics are available in the art, and include, for example: cross interaction chromatography (CIC); self-interaction chromatography (SIC); dynamic light scattering; size exclusion chromatography (SEC), dynamic light scattering (DLS) spectroscopy; photon correlation spectroscopy; quasi-elastic light scattering, circular dichroism (CD), viscosity measurements; whole cell binding; tissue micro array methodologies; BVP ELISA assays; differential scanning calorimetry; and the like (see, e.g., He et al., *J. Pharm. Sci.*, Vol. 100(4), pp. 1330-1340 (2011); Wagner et al., *Pharm. Develop. & Technol* (posted online 2012; http://informahealthcare.com/doi/abs/10.3109/10837450.2011.649851); Hotzel et al., *mAbs*, Vol. 4(6), pages 753-7601 (2012); Weiqiang et al., *J. Pharm. Sci.*, Vol. 101(5), pp. 1701-1720 (2012); Banks et al., *J. Pharm. Sci.*, Vol. 101(8), pp. 2720-2732 (2012); Lie et al., *J. Pharm. Sci.*, Vol. 94(9), pp. 1928-1948 (2005); and Payne et al., *Biopolymers*, Vol. 85(5), pp. 527-533 (2006)).

Furthermore, in the context of the disclosed and claimed methods, libraries, or polypeptides selected or identified as possessing enhanced developability are referred to as "developable" polypeptides. Polypeptides that are detected in accordance with the disclosed and claimed methods as possessing decreased developability are so detected by virtue of their interaction with the disclosed and claimed PSRs, and as such are referred to as "polyspecific" polypeptides. Such polyspecific polypeptides are further referred to as relatively "undevelopable" or relatively "non-developable" polypeptides.

Any means for detecting an interaction between one or more polypeptides and a moiety with which the one or more polypeptide interacts may be employed in accordance with the disclosed and claimed methods. Exemplary such means include, e.g.: flow cytometry; magnetic-activated cell sorting (MAGS); florescence assisted cell sorting (FACS); immunohistochemistry; column and/or affinity chromatography or separations; sedimentation methodologies (e.g., centrifugation); immunoprecipitation; two-hybrid assays, such as mammalian two-hybrid assays and yeast two-hybrid assays; florescence resonance energy transfer (FRET) assays; affinity chromatography; and the like. In certain embodiments detecting such an interaction comprises employing magnetic-activated cell sorting (MAGS); florescence assisted cell sorting (FACS); and/or combinations of magnetic-activated cell sorting (MAGS) and florescence assisted cell sorting (FACS).

Reagents which may be employed in any of the detecting means mentioned above, or in any other detecting means in the art, include, for example: fluorophores; biotin and biotinylation radioisotopes; affinity peptide tags (e.g., His tags, myc tags, FLAG tags, and the like); which may be conjugated to, linked to, or otherwise associated with (such as by either a covalent or a non-covalent linkage or bond) to a polypeptide, antibody, and/or a test binding partner (e.g., an antigen), Accordingly, Applicants have discovered that that the disclosed PSRs may be employed in methods for, for example: counter-selecting against at least one polyspecific polypeptide from a plurality of polypeptides, the method comprising: (a) providing the plurality of polypeptides;

(b) contacting the plurality of step (a) with a polyspecificity reagent, wherein the polyspecificity reagent comprises a mixture of biomolecules, thereby producing a reagent-plurality mixture;

(c) detecting from the reagent-plurality mixture of step (b) at least one polyspecific polypeptide that interacts with the polyspecificity reagent, thereby detecting at least one polyspecific polypeptide; and (d) selecting at least one polypeptide from the plurality that is not detected in step (c), thereby counter-selecting against the at least one polyspecific polypeptide from the plurality of polypeptides. In certain embodiments, the methods further comprise determining that the at least one polypeptide selected in step (d) binds to at least one test binder.

Figure 17:
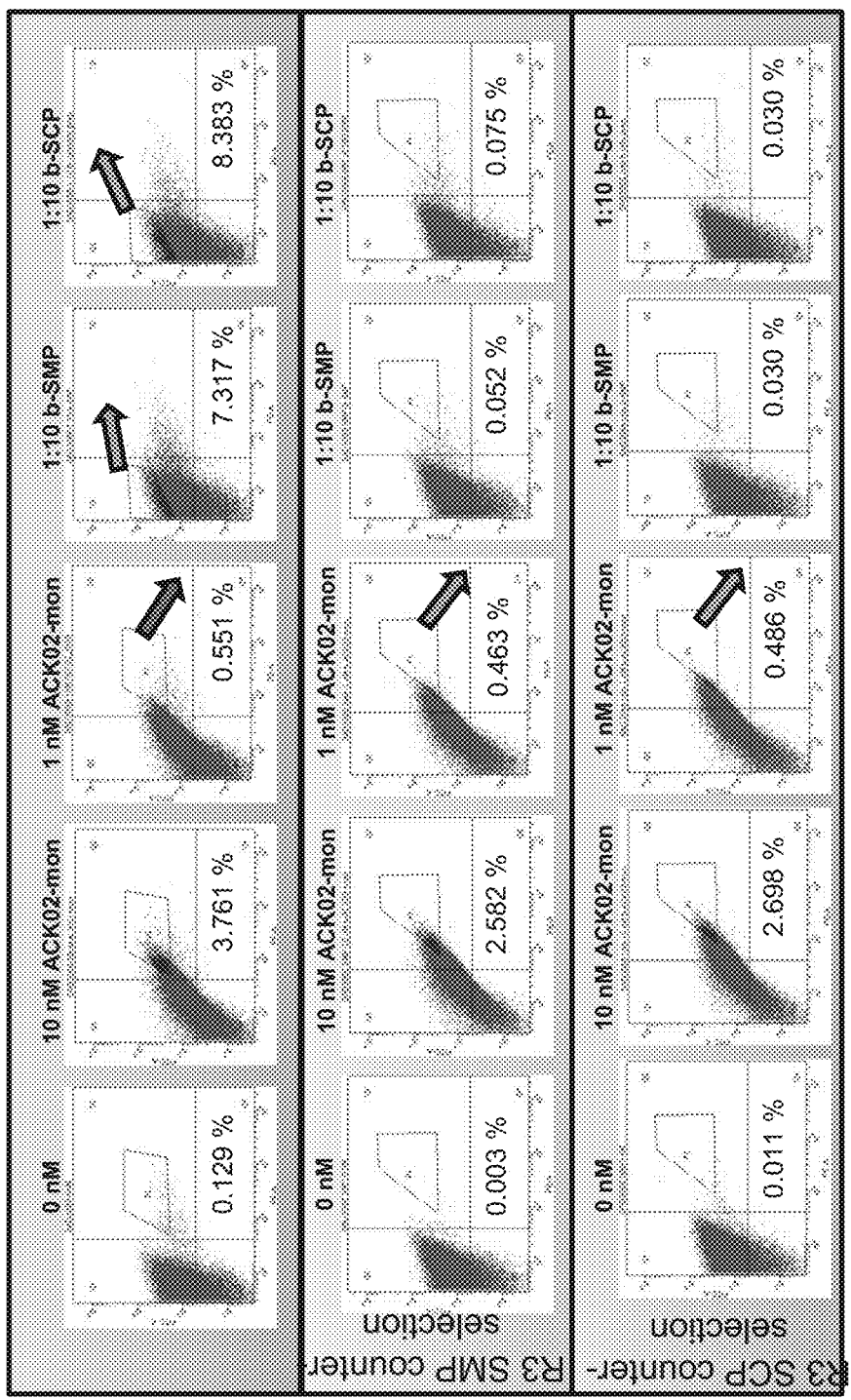
FIG. 17 depicts the FACS results of the R3 round for library 1 as depicted in FIG. 15 and as described in Example 4.
Figure 18:
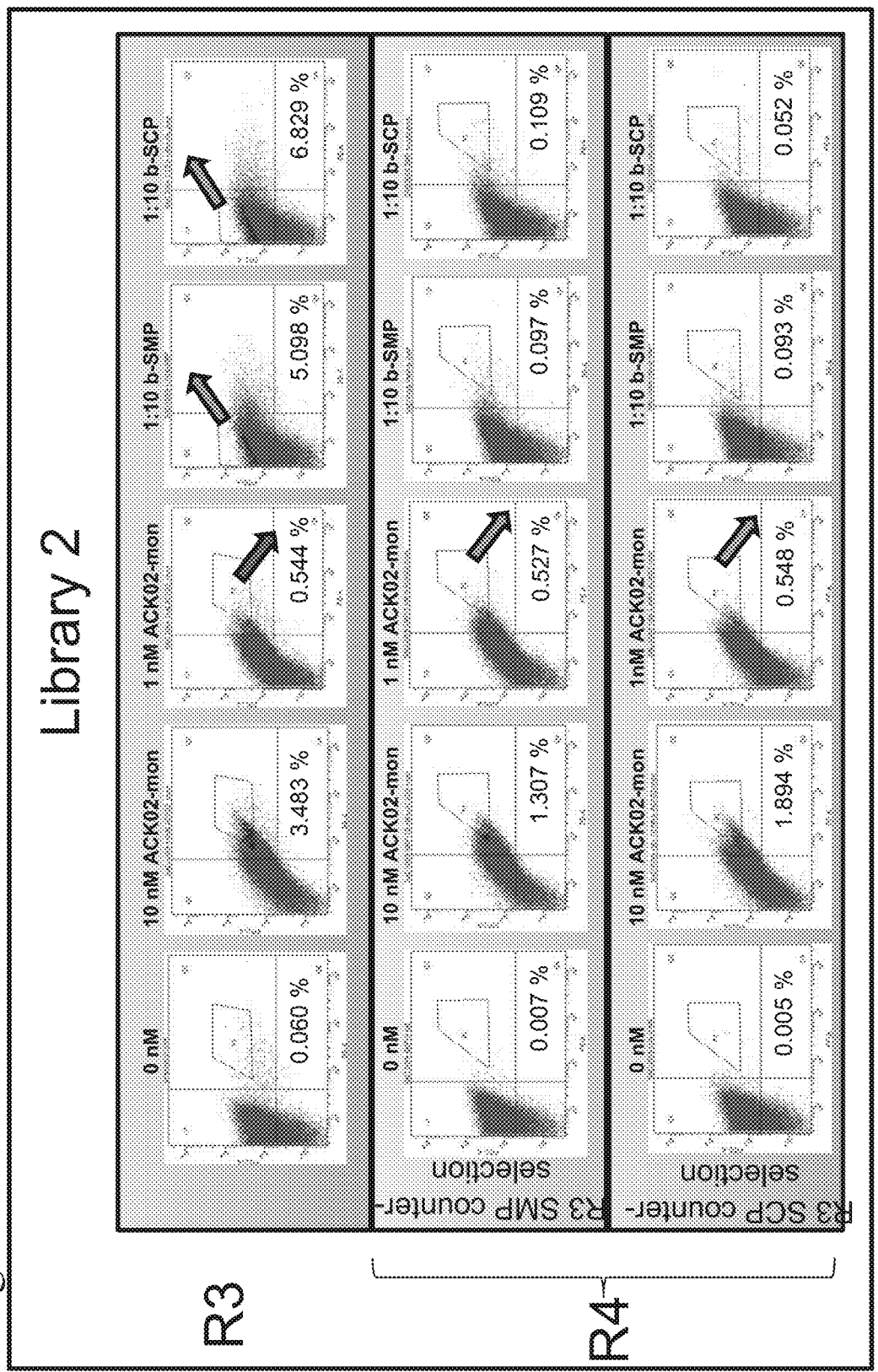
FIG. 18 depicts the FACS results of the R3 round for library 2 as depicted in FIG. 15 and as described in Example 4.
Figure 19:
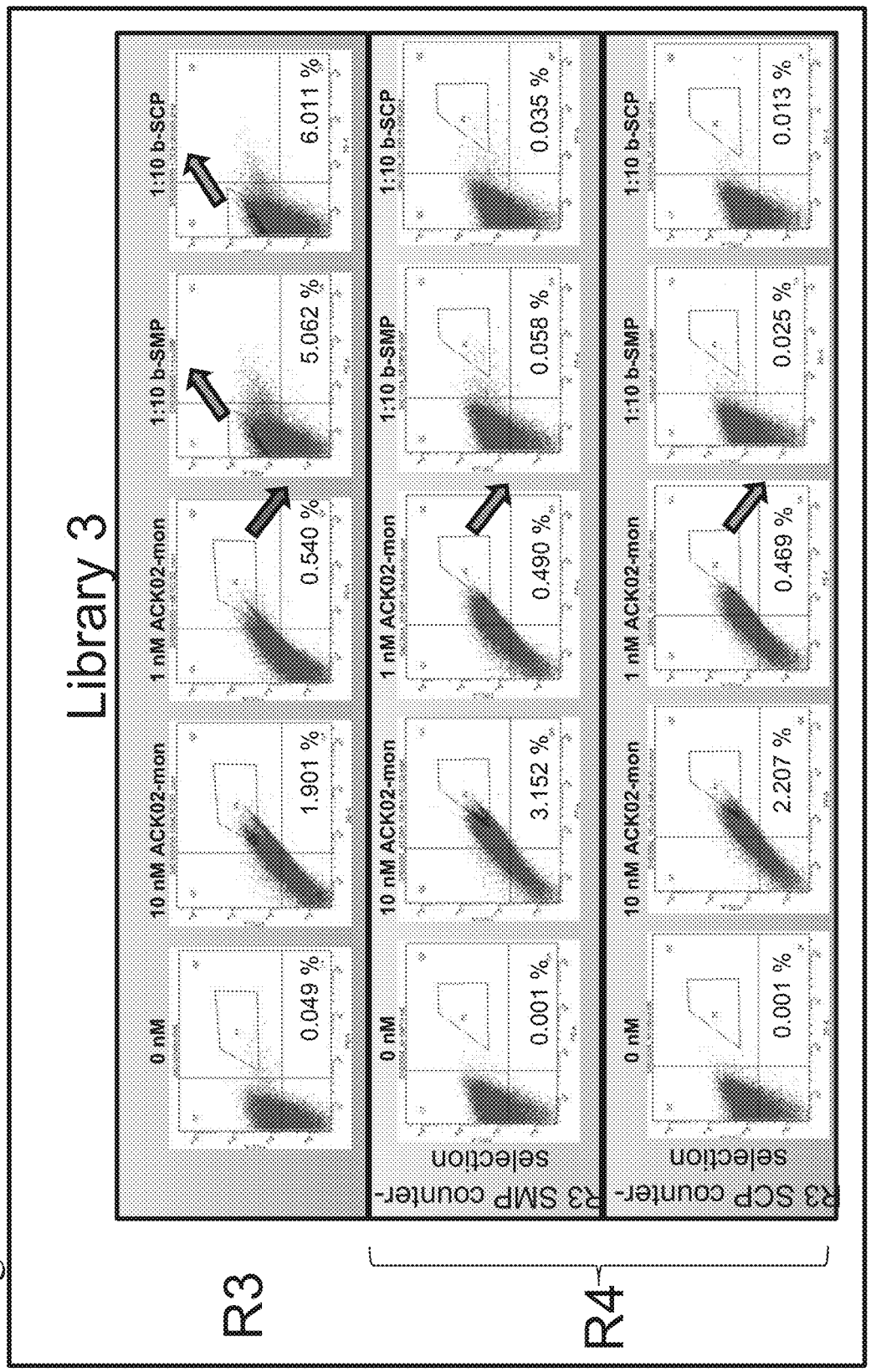
FIG. 19 depicts the FACS results of the R3 round for library 3 as depicted in FIG. 15 and as described in Example 4.

"Counter-selecting against" in the context of the disclosed and claimed methods refers to detecting at least one polypeptide from a plurality of polypeptides that interacts with a PSR, such as an SMP or an SCP, but selecting at least one polypeptide that does not so-interact with the PSR (such as an SMP or an SCP). Such counter-selecting may be performed in accordance with the disclosed and claimed methods by, for example, selecting in a FACS experiment those polypeptides, or host cells expressing and displaying those polypeptides, that are scored by the FACS equipment as not significantly interacting with the a PSR in the plurality-reagent mixture. As will be understood by the artisan, such polypeptides are identified as not significantly interacting with the PSR by observing a FACS graph as depicted in, for example, FIGS. 13, 17, 18, and 19, and selecting such polypeptides (or host cells expressing and displaying such polypeptides) by choosing to selection gate that resides in upper left quadrant of the FACS graph, as indicated in, for example, FIGS. 13, 17, 18, and 19 (see, for example, FIG. 13, extreme lower left hand graph and gate in upper left hand quadrant; FIGS. 17, 18 and 19: top row, last two fight-hand graphs and gates in upper left-hand quadrants of such).

A "test binder" or "test binding partner", used interchangeably throughout, refers to a binding moiety of interest that is tested for the ability of such binder to significantly interact with one or more polypeptides from or in a plurality of polypeptides. Exemplary test binders include, for example: an antigen; an epitope of an antigen; a small molecule; a drug; a peptide; a whole cell expressing an antigen of interest on its surface cell surface; a glycoprotein; a moiety comprising a carbohydrate; a moiety comprising a lipid; and the like. In certain embodiments, the test binder comprises an antigen selected from the group consisting of: a cell surface protein; a transmembrane protein; a solubilized membrane protein; a polypeptide ligand; a hormone; a neurohormone; a neurotransmitter; a neuromodulator; and one or more epitopes of such antigens.

The ability of a test binding partner to "significantly interact" refers to the ability of the test binder to specifically bind to one or more polypeptides from or in a plurality of polypeptides. A test binding partner that "significantly binds" to such one or more polypeptides from or in a plurality of polypeptides such that the dissociation constant ($K_D$) associated with such binding is selected from the group consisting of: from about 100 uM to about 0.01 pM; from about 100 uM to about 0.1 pM; from about 100 uM to about 1 pM; from about 1 uM to about 10 pM; from about 1 uM to about 100 pM; from about 1 uM to about 1 nM; from about 1 uM to about 10 nM; from about 1 uM to about 100 nM; from about 1 uM to about 200 nM; from about 1 uM to about 300 nM; from about 1 uM to about 400 nM; from about 1 uM to about 500 uM; and combinations of such ranges of dissociation constants.

It is to be understood that, whereas the disclosed methods are amenable to the presence of a test binding partner, such methods, may nonetheless be practiced without the presence of such a test binding partner. For instance, methods of: counter-selecting against one or more polyspecific polypeptides from a plurality of polypeptides; generating enriched pluralities of developable polypeptides from a non-enriched plurality of polypeptides; selecting or screening for at least one polypeptide with enhanced developability from amongst a plurality of polypeptides; ranking developability of polypeptides in a plurality of polypeptides; assigning developability scores for polypeptides in a plurality of polypeptides; correlating developability of one or more polypeptides of a plurality of polypeptides with a degree of interaction with a PCR; assessing, screening for, predicting, identifying, or correlating developability of at least one polypeptide; and other similar methods as disclosed and claimed herein and throughout; may be practiced in the absence of a test binding partner.

Indeed, as the artisan will understand, one advantage of the reagents and methods disclosed throughout comprise the ability to counter-select or otherwise bias a plurality of polypeptides, such as a library of polypeptides, against, or away from, polypeptides within the plurality or library that have decreased developability prior to, and in the absence of, any test binding partner. Similarly, the reagents and methods disclosed throughout comprise the ability to enrich or otherwise bias a plurality of polypeptides, such as a library of polypeptides, within the plurality or library that have enhanced developability prior to, and in the absence of, any test binding partner. Accordingly, the disclosed methods provide the generation of pluralities, such as libraries, from which there is a greater likelihood of obtaining or identifying a greater number of developable members form such plurality or library, in a manner that is agnostic as to the nature of any particular test binding partner of interest.

A "plurality of polypeptides" refers to two or more different polypeptides present in a sample of polypeptides. Such a sample comprises a solution in which the plurality of polypeptides resides. Accordingly, such a plurality of polypeptides may comprise, for example: two different polypeptides; three different polypeptides; four different polypeptides; five different polypeptides; 10 different polypeptides, 20 different polypeptides; 30 different polypeptides; 40 different polypeptides; 50 different polypeptides; 100 different polypeptides; 200 different polypeptides; 300 different polypeptides; 400 different polypeptides; 500 different polypeptides; 600 different polypeptides; 700 different polypeptides; 800 different polypeptides; 900 different polypeptides; 1,000 different polypeptides; 2,000 different polypeptides; 5,000 different polypeptides; 10,000 different polypeptides; 20,000 different polypeptides; 50,000 different polypeptides; 100,000 different polypeptides; 200,000 different polypeptides; 500,000 different polypeptides; 1,000,000 different polypeptides; 2,000,000 different polypeptides; 3,000,000 different polypeptides; 5,000,000 different polypeptides; 10,000,000 different polypeptides; 20,000,000 different polypeptides; 50,000,000 different polypeptides; 100,000,000 different polypeptides; 200,000,000 different polypeptides; 300,000,000 different polypeptides; 400,000,000 different polypeptides; 500,000,000 different polypeptides; 600,000,000 different polypeptides; 700,000,000 different polypeptides; 800,000,000 different polypeptides; 900,000,000 different polypeptides; 1 billion 200,000,000 different polypeptides; 10 billion different polypeptides; 20 billion different polypeptides; 30 billion different polypeptides; 40 billion different polypeptides; 50 billion different polypeptides; 60 billion different polypeptides; 70 billion different polypeptides; 80 billion different polypeptides; 90 billion different polypeptides; 100 billion different polypeptides; 200 billion different polypeptides; 300 billion different polypeptides; 400 billion different polypeptides; 500 billion different polypeptides; 600 billion different polypeptides; 700 billion different polypeptides; 800 billion different polypeptides; 900 billion different polypeptides; 1 trillion different polypeptides; 20 trillion different polypeptides; 30 trillion different polypeptides; 40 trillion different polypeptides; 50 trillion different polypeptides; 60 trillion different polypeptides; 70 trillion different polypeptides; 80 trillion different polypeptides; 90 trillion different polypeptides; 100 trillion different polypeptides; 200 trillion different polypeptides; 300 trillion different polypeptides; 400 trillion different polypeptides; 500 trillion different polypeptides; 600 trillion different polypeptides; 700 trillion different polypeptides; 800 trillion different polypeptides; 900 trillion different polypeptides; more than 900 trillion different polypeptides; 1,000,000,000,000,000 different polypeptides; 10,000,000,000,000,000 different polypeptides; 100,000,000,000,000,000 different polypeptides; all numbers and ranges in between such; or any and all combinations and sums of such. In all of the above, it is understood that one or more of each such different polypeptide may be represented more than once in the plurality. In some embodiments, the plurality of polypeptides is collectively encoded by a plurality of polynucleotides. In certain embodiments, such a plurality of polynucleotides comprises a library of polynucleotides.

Herein and throughout, it is understood that the term, "different" may also be referred to as "unique", and that the terms "different" and "unique" may be used interchangeably.

A "plurality-reagent mixture" refers to a composition comprising a plurality comprising more than one different polypeptide and a PSR, or more than one host cell and a PSR, wherein each host cell expresses a different polypeptide. Such plurality-reagent mixtures are generating by contact the plurality with the PSR in one container or vessel. However, subsequent to the generation of the plurality-reagent mixture, the mixture may be aliquoted into two or more aliquots, wherein each aliquot is contained in a separate container or vessel, is contained in a single container or vessel. In some embodiments the plurality-reagent mixture comprises yeast host cells, such as *Saccharomyces Cerevisiae* host cells, that have been contacted with the PSR. In certain embodiments the plurality-reagent mixture comprises a plurality that has been admixed with a PSR that comprises SMP. In other embodiments, the plurality-reagent mixture comprises a plurality that has been admixed with a PSR that comprises SCP. In other embodiments, the plurality-reagent mixture comprises a plurality that has been admixed with a PSR comprising on or more of the following, or combinations thereof: a soluble cellular fraction; a membrane cellular fraction; a bodily fluid fraction; a serum fraction; a plasma fraction; a cocktail comprising partially purified biomolecules; a collection of virus or virus-derived particles; DNA; RNA; serum protein; plasma protein; extracellular matrix protein; ribosomes; hormones; peptides; polypeptides; albumin; human serum albumin; lipids; glycolipids; carbohydrates; phospholipids; lipid rafts; proteases; protease inhibitors; DNAses; DNAse inhibitors; RNAses; RNAse inhibitors; crude cell extracts; fractionated or partially purified components of cell extracts.

In other embodiments, the plurality of polynucleotides is collectively incorporated into a plurality of vectors. In other embodiments, the plurality of vectors comprises a library of vectors.

In certain other embodiments, the plurality of polypeptides is expressed by a plurality of host cells. "Host cells" or "a host cell" refers to a cell, or a plurality of cells, into which has been introduced one or more heterologous polynucleotides which encode one or more polypeptides. In certain embodiments, the plurality of host cells comprises a plurality of yeast host cells. In certain embodiments the plurality of host cells comprises *Pichia* cells. In certain embodiments, the plurality of host cells comprises *Saccharomyces cerevisiae* cells. In certain embodiments, the plurality of host cells comprises a plurality of mammalian cells. In certain embodiments, such mammalian host cells may comprise, e.g., human, mouse, rat, hamster, or primate cells. Suitable cells also include known cells or cell lines, including but not limited to Jurkat T cells, NIH3T3, CHO, BHK, COS, HEK293, PER C.6, HeLa, Sp2/0, NS0 cells, and variants or progeny thereof, or the like. In certain embodiments, the plurality of host cells comprises a plurality of insect cells. In certain embodiments, such insect host cells may comprise, e.g., Sf21 cells, Sf9 cells, Sf21/Sf9 cells, *Trichoplusia ni* cells, Bti-Tn5b1-4 cells, and variants or progeny thereof, or the like.

In certain embodiments, the host cells provide for genotype-phenotype linkage. "genotype-phenotype linkage" refers to the ability of such host cells to express a polynucleotide that has been introduced into said host cell, thereby generating an encoded polypeptide, which polypeptide is physically associated with the surface of the host cell that produced it, and remains physically associated with the surface of the host cell for a time sufficient for the disclosed and claimed methods to be performed. Accordingly, the genotype of the selected host cell—which includes the nucleic acid sequence of the polynucleotide which encodes the expressed polypeptide—and the phenotype of the selected host cell—which includes the expressed polypeptide that is physically associated with the host cell surface and which is encoded by the polynucleotide that was introduced into the host cell—are both retained with high fidelity and may be ascertained by the artisan. Accordingly, when one or more host cells, such as yeast host cells, from a plurality of host cells, is selected as a result of detecting a polypeptide that is physically associated with the host cell surface and that specifically interacts with a test binder, both the amino acid sequence of the polypeptide and the nucleic acid of the polynucleotide that encoded the polypeptide may be obtained from the selected host cell. In certain embodiments, genotype-phenotype linkage is ascertained by magnetic-activated cell sorting; flow cytometry, such as FACS; and/or combinations of the two, as disclosed and claimed herein and throughout.

As is understood in the art, any of a number of reagents and methods for "detecting" a polypeptide in accordance with the disclosed methods. Exemplary such detecting reagents include, for example: fluorophores, radioisotopes, biotin and biotinylation, and the like.

Accordingly, in certain embodiments, such a plurality of host cells comprises a genotype-phenotype linkage library of host cells. In certain embodiments, the genotype-phenotype linkage library comprise yeast host cells. In some embodiments, the genotype-phenotype linkage library comprises *Saccharomyces cerevisiae* host cells. In some embodiments the genotype-phenotype linkage library comprises *Pichia* host cells. Exemplary host cells that provide genotype-phenotype linkage and host cell genotype-phenotype libraries are published in, for example: WO2007130520; Weaver-Feldhaus et al, FEBS Letters, Vol. 564, pp. 24-34 (2004); Mazor et al., Nature Biotech, Vol. 25(5), pp. 563-565 (2007); U.S. Pat. No. 6,696,251; Boder et al., Nature Biotech, Vol. 17, pp. 553-557 (1997); WO2008118476; U.S. Pat. No. 8,067,339; WO2012009568; WO2009036379; WO2010105256; and the like.

In some embodiments, a plurality of polypeptides comprises a library of such polypeptides. Exemplary polypeptides, polynucleotides, vectors, host cells, and yeast host cells, and libraries comprising such which may be employed in accordance with the disclosed and claimed methods include those disclosed in the following: WO2009036379; WO2010105256; WO2012009568; Knappik et al, J. Mol. Biol., Vol. 296, pp. 57-86 (2000); EP 1438400; EP 1558741; EP 0682710; EP 1578903; EP 0682710; EP1026239; EP 1716233; EP1268801; EP873398; EP 1056883; EP 1056883; EP 2454376; EP 2263089; U.S. Ser. No. 13/161,445; U.S. Ser. No. 13/250,520; U.S. Ser. No. 11/642,593; U.S. Ser. No. 11/864,525; U.S. Ser. No. 11/040,159: U.S. Ser. No. 13/139,332; U.S. Ser. No. 12/625,337; U.S. Pat. No. 8,067,339; U.S. Ser. No. 12/240,541; U.S. Ser. No. 12/056,264; U.S. Ser. No. 11/317,680; WO2009000006; WO2008118476; Weaver-Feldhaus et al, FEBS Letters, Vol. 564, pp. 24-34 (2004); Mazor et al., Nature Biotech, Vol. 25(5), pp. 563-565 (2007); U.S. Pat. No. 6,696,251; Boder et al., Nature Biotech, Vol. 17, pp. 553-557 (1997); WO2007130520; Hu et al., J. Biol. Chem., Vol. 284(24), pp. 16389-16376 (2009); and the like.

In certain embodiments, methods are provided for selecting at least one polypeptide from amongst a plurality of polypeptides that specifically interacts with at least one test binding partner, the methods comprising: (a) providing the plurality of polypeptides; (b) providing the at least one test binding partner; (c) contacting the plurality of step (a) with the at least one test binding partner of step (b) and a polyspecificity reagent, wherein the polyspecificity reagent comprises a mixture of biomolecules, thereby producing a reagent-plurality mixture; and (d) selecting from the reagent-plurality mixture of step (c) at least one polypeptide that interacts with the at least one test binding partner. In certain embodiments the at least one polypeptide that is selected in step (d) does not significantly interact with the polyspecificity reagent.

In certain embodiments, methods are provided of generating an enriched plurality of developable polypeptides from a non-enriched plurality of polypeptides, the methods comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting from the reagent-plurality mixture of step (b) one or more polyspecific polypeptides from among the plurality of polypeptides that interacts with the polyspecificity reagent; and (d) separating from the non-enriched plurality of polypeptides the one or more polyspecific polypeptides detected in step (c), thereby generating the enriched collection of developable polypeptides.

An "enriched plurality of developable polypeptides" refers to a plurality of polypeptides that is obtained by detecting and removing one or more polyspecific polypeptides from the plurality, thus increasing the proportion of developable polypeptides in the enriched plurality in accordance with the disclosed and claimed methods. Accordingly, "non-enriched plurality of polypeptides" refers to the plurality of polypeptides prior to detection and removal of the one or more polyspecific polypeptide.

In certain embodiments, methods are provided for selecting or screening for at least one polypeptide with enhanced developability from amongst a plurality of polypeptides, the methods comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting from the reagent-plurality mixture of step (b) at least one polypeptide that does not significantly interact with the polyspecificity reagent, thereby detecting at least one developable test polypeptide; and (d) selecting the at least one polypeptide detected in step (d); wherein the at least one polypeptide detected in step (c) and selected in step (d) comprises a polypeptide that has been selected for or screened for enhanced developability relative to members of the plurality that are not detected in step (c) and selected in step (d).

A polypeptide with "enhanced developability" refers to a polypeptide that possesses desirable solubility, viscosity, stability, aggregation, pharmacokinetic, circulation half-life, and/or clearance characteristics or profiles as evidenced by a lack of significant interaction with a PSR, optionally relative to such characteristics of profiles observed in a reference polypeptide. As disclosed and claimed herein and throughout, for example, in the Examples, Applicants have demonstrated that a polypeptide that does not significantly interact with the disclosed PSR (such as an SMP or an SCP), optionally relative to the amount or degree of PSR interaction observed for a reference polypeptide, may be predicted to possess enhanced developability. Accordingly, use of the disclosed PSRs in assessing polyspecificity of polypeptides in accordance with the disclosed and claimed methods serves as a predictive tool for selecting or screening for polypeptides with enhanced developability from amongst a plurality of polypeptides.

In certain embodiments, a polypeptide may be identified or otherwise determined to possess enhanced developability by virtue of, for example, an assessment of any one or more of the forgoing characteristics or profiles of the polypeptide relative to such an assessment made for another polypeptide, such as a reference polypeptide. Accordingly, in certain embodiments, developability of a polypeptide may be assessed and compared with the developability of a reference polypeptide.

A polypeptide with "decreased developability" refers to a polypeptide that possesses undesirable solubility, viscosity, stability, aggregation, pharmacokinetic, circulation half-life, and/or clearance characteristics or profiles as evidenced by a significant interaction with a PSR, optionally relative to such characteristics of profiles observed in a reference polypeptide. As disclosed and claimed herein and throughout, for example, in the Examples, Applicants have demonstrated that a polypeptide that significantly interacts with the disclosed PSR (such as an SMP or an SCP), optionally relative to the amount or degree of PSR interaction observed for a reference polypeptide, may be predicted to possess decreased developability. Accordingly, use of the disclosed PSRs in assessing polyspecificity of polypeptides in accordance with the disclosed and claimed methods serves as a predictive tool for counter-selecting against, or selecting or screening away from, polypeptides with decreased developability from amongst a plurality of polypeptides.

In certain embodiments, a polypeptide may be identified or otherwise determined to possess decreased developability by virtue of, for example, an assessment of any one or more of the forgoing characteristics or profiles of the polypeptide relative to such an assessment made for another polypeptide, such as a reference polypeptide. Accordingly, in certain embodiments, developability of a polypeptide may be assessed and compared with the developability of a reference polypeptide.

Accordingly, in certain embodiments, methods are provided for predicting enhanced developability of at least one polypeptide from amongst a plurality of polypeptides, the methods comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; and (c) detecting from the reagent-plurality mixture of step (b) at least one polypeptide that does not significantly interact with the polyspecificity reagent, thereby identifying at least one developable polypeptide; wherein the at least one developable polypeptide detected in step (c) is thereby assessed or predicted to possess enhanced developability based on the lack of significant interaction with the polyspecificity reagent relative to members of the plurality that are not identified in step (c).

In certain embodiments, methods are for ranking developability of polypeptides in a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting the relative degree of interaction between polypeptides of the plurality and the polyspecificity reagent; and (d) ranking the polypeptides detected in step (c) that are observed to possess a lower degree of interaction with the polyspecificity reagent as possessing enhanced developability, and ranking the polypeptides detected in step (c) that are observed to possess a higher degree of interaction with the polyspecificity reagent as possessing decreased developability.

"Ranking developability" refers to categorizing or triaging, in ascending or descending order, the detected degree of interaction of polypeptides from a plurality of polypeptides with the PSR. The degree of interaction may be assessed by any number of means available in the art that provides an output value that correlates with a strength or affinity of a polypeptide for a moiety to which it is bound. Exemplary such means include flow cytometry means, such as FACS; ELISA; quantitative immunoaffinity assays or immunoprecipitation assays; mammalian two hybrid or yeast two-hybrid assays, and the like. In the context of FACS, as demonstrated in the Examples, a degree of interaction between polypeptides in the plurality and the PSR may be ascertained by generating a mean florescence intensity (MFI) for each polypeptide-PSR interaction that is detected, and then ordering the MFI in either ascending or descending order, thereby ranking the polypeptides in the plurality according to the relative degree of interaction between each detected polypeptide and the PSR. Such a ranking provides for a ranking of polypeptides of the plurality such that those polypeptides possessing enhanced developability are readily ascertained, as are those polypeptides possessing decreased developability. In certain embodiments, an MFI of 500 or less is demonstrative of a polypeptides possessing enhanced developability. In certain embodiments, an MFI of 400 or less is demonstrative of a polypeptides possessing enhanced developability. In certain embodiments, an MFI of 300 or less is demonstrative of a polypeptide possessing enhanced developability. In certain embodiments, an MFI of 200 or less is demonstrative of a polypeptide possessing enhanced developability. In certain embodiments, an MFI of 100 or less is demonstrative of a polypeptide possessing enhanced developability. In certain embodiments, an MFI of 1000 or more is demonstrative of polypeptide possessing decreased developability. In certain embodiments, an MFI of 900 or more is demonstrative of polypeptide possessing decreased developability. In certain embodiments, an MFI of 800 or more is demonstrative of polypeptide possessing decreased developability. In certain embodiments, an MFI of 700 or more is demonstrative of polypeptide possessing decreased developability. In certain embodiments, an MFI of 600 or less is demonstrative of a polypeptide possessing decreased developability.

Accordingly, in certain embodiments are provided methods for assigning a developability score polypeptides in a plurality of polypeptides, the method comprising: (a) providing the plurality of polypeptides; (b) contacting the plurality of step (a) with a polyspecificity reagent, wherein the polyspecificity reagent comprises a mixture of biomolecules, thereby producing a reagent-plurality mixture; (c) detecting the relative degree of interaction between polypeptides of the plurality and the polyspecificity reagent; and (d) assigning to the polypeptides detected in step (c) that are observed to possess a lower degree of interaction with the polyspecificity reagent a higher developability score and assigning to the polypeptides detected in step (c) that are observed to possess a higher degree of interaction with the polyspecificity reagent a lower developability score. The developability score may be generated according to any of the methodologies described above and in the Examples and Figures. For example, MFI may be employed to generate and assign developability scores.

Accordingly, in certain embodiments are provided methods for correlating developability of one or more polypeptides of a plurality of polypeptides with a degree of interaction with a polyspecificity reagent, the method comprising: (a) providing the plurality of polypeptides; (b) contacting the plurality of step (a) with the polyspecificity reagent, wherein the polyspecificity reagent comprises a mixture of biomolecules, thereby producing a reagent-plurality mixture; (c) detecting the degree of interaction between each polypeptide in the plurality of polypeptides with the polyspecificity reagent; and (d) determining the relative degree of interaction between the one or more polypeptides and the polyspecificity reagent, wherein a lower degree of interaction with the polyspecificity reagent correlates with enhanced developability and wherein a higher degree of interaction with the polyspecificity reagent correlates with decreased developability.

In other embodiments are provided methods for assessing, screening for, predicting, or identifying, or correlating developability of at least one polypeptide that interacts with a binding partner, the method comprising: (a) providing the at least one polypeptide; (b) contacting the at least one polypeptide of step (a) with a polyspecificity reagent, wherein the polyspecificity reagent comprises a mixture of biomolecules, thereby producing a reagent-polypeptide mixture; (c) determining a degree of interaction between the at least one polypeptide and the polyspecificity reagent, wherein a lower degree of interaction indicates an enhanced developability of the at least one polypeptide and wherein a higher degree of interaction with the polyspecificity reagent indicates a decreased developability of the at least one polypeptide. In certain of these embodiments, the PSR does not comprise a collection virus or virus-derived particles.

In each of the methods disclosed and claimed herein and throughout, each method may further comprise (A) performing at least one of the disclosed steps by employing flow cytometry;

(B) performing at least one of the disclosed steps by employing magnetic-activated cell sorting;

(C) performing all of the disclosed steps by employing by employing flow cytometry; (D) performing all of the disclosed steps by employing magnetic-activated cell sorting; or (E) combinations of (A) and (B).

In each of the methods disclosed and claimed herein and throughout, each method may method further comprise contacting either: the plurality of polypeptides; the reagent-plurality mixture; or both the plurality of polypeptides and the reagent-plurality mixture; with at least one test binding partner.

As will be understood by the artisan, whereas the disclosed methods certainly allow for the ability to detect the reagent-plurality mixture using methods known in the art, such detection is not required in order to perform the disclosed methods.

In certain embodiments, the plurality of polypeptides and/or the plurality of polynucleotides are collectively expressed by a plurality of host cells. In certain embodiments, the plurality of polypeptides are collectively physically associated with the cell surface of a plurality host cells, such that a given polypeptide that is expressed in the plurality is physically associated with the host cell that expressed the given polypeptide and that harbored a polynucleotide that encoded the given polypeptide. In certain embodiments such host cells afford genotype-phenotype linkage. In certain embodiments such a plurality of host cells comprise a genotype-phenotype library.

In certain embodiments the plurality of polypeptides comprises antibodies or antibody fragments. In certain embodiments the plurality of polynucleotides collectively encode a plurality of antibodies or antibody fragments. In certain embodiments the plurality of antibodies or antibody fragments, or polynucleotides encoding the same, comprise a library of such antibodies or antibody fragments, or polynucleotides encoding the same. In certain embodiments, the antibodies comprise multispecific antibodies or multispecific antibody fragments.

As would be understood by those of ordinary skill in the art, the term "antibody" is used herein in the broadest sense and specifically encompasses at least monoclonal antibodies, polyclonal antibodies, multi-specific antibodies (e.g., bispecific antibodies) as disclosed in, for example, International PCT application No. PCT/US13/76711; WO2011028952; US20110054151; WO9509917A1; U.S. Pat. Nos. 5,731,168; 5,807,706; 5,821,333; 7,183,076; 7,642,228; 7,695,936; 7,951,917; 8,216,805; and the like; chimeric antibodies; humanized antibodies, such as disclosed in, for example, human antibodies, antibody fragments, and derivatives thereof, as U.S. Pat. Nos. 7,566,771B1; 7,244,615B2; 7,678,371B2; 8,349,324B2; 7,087,409B2; 5,869,619A; 5,821,123A; 7,022,500B1; 5,693,761A; 5,530,101A; WO2011056864A1; WO2004072266A2; WO2006055778A2; U.S. Pat. No. 7,981,843B2; WO2005069970; WO2010135558; WO2011084255A2; U.S. Pat. Nos. 6,881,557 B2; 7,709,226 B2; and the like.

An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. An "antibody" also refers to an immunoglobulin molecule, a fragment of an immunoglobulin molecule, or a derivative thereof, which has the ability to specifically bind to an antigen, which may be, for example: a protein; a polypeptide; peptide; a hormone; a cytokine; a chemokine; a growth factor; a neurotransmitter; a carbohydrate-containing biological molecule; a lipid or fatty acid-containing biological molecule; or other biological molecule; via an epitope present on such antigen.

Antibodies (used interchangeably with "immunoglobulins, or "immunoglobulin molecules") can be monomeric, dimeric, trimeric, tetrameric, pentameric, etc., and comprise a class of structurally related proteins consisting of two pairs of polypeptide chains: one pair of light chains (LC) and one pair of heavy chains (HC), all of which are inter-connected by disulfide bonds. The structure of immunoglobulins has been well characterized. See for instance Fundamental Immunology Ch. 7 (Paul, W., ed., 2nd ed. Raven Press, N.Y. (1989)).

Traditional natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable region.

Each of the light and heavy chains is made up of two distinct regions, referred to as the variable and constant regions. The IgG heavy chain is composed of four immunoglobulin domains linked from N- to C-terminus in the order VH-CH1-CH2-CH3, referring to the "variable heavy domain" (also referred to as a "heavy chain variable domain", used interchangeably throughout), heavy chain constant domain 1, heavy chain constant domain 2, and heavy chain constant domain 3 respectively (also referred to as VH-Cγ1-Cγ2-Cγ3, referring to the variable heavy domain, constant gamma 1 domain, constant gamma 2 domain, and constant gamma 3 domain respectively). The IgG light chain is composed of two immunoglobulin domains linked from N- to C-terminus in the order VL-CL, referring to the "variable light domain" (also referred to as a "light chain variable domain", used interchangeably throughout) and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light chain and one heavy chain, each light chain comprising a VL and a CL, and each heavy chain comprising a VH, CH1, a CH2, and a CH3. In some mammals, for example in camels and llamas, IgG antibodies may consist of only two heavy chains, each heavy chain comprising a variable domain attached to the Fc region.

The heavy chain constant region typically is comprised of three domains, CH1, CH2, and CH3, and the CH1 and CH2 domains are connected by a hinge region. Each light chain typically is comprised of a light chain variable domain (abbreviated herein as "$V_L$" or "VL") and a light chain constant domain. The $V_H$ and $V_L$ domains may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4. Typically, the numbering of amino acid residues in this region is performed by the method described in Kabat (see, e.g., Kabat et al, in "Sequences of Proteins of Immunological Interest," $5^{th}$ Edition, U.S. Department of Health and Human Services, 1992). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "variable", "variable domain", or "variable region" each interchangeably refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al, Nature, 1989, 342: 877; Martin and Thornton, J. Mol. Biol, 1996, 263: 800. Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al, in "Sequences of Proteins of Immunological Interest," $5^{th}$ Edition, U.S. Department of Health and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

By "Fc" or "Fc region", as used herein is meant the polypeptide comprising the constant region of an antibody excluding the first constant region immunoglobulin domain. Thus "Fc region" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Accordingly, and without departing from the above, "Fc region" may also be defined as comprising a "CH2 domain or a variant thereof" and a "CH3 domain or a variant thereof". Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

A variable light chain (VL) and corresponding variable heavy domain (VH) comprise a binding domain, also referred to interchangeably throughout as an "antigen binding site" that interacts with an antigen. Thus, a "first variable light domain" and a "first variable heavy domain" together form a "first antigen binding site". Similarly, in the case of multispecific antibodies a "second variable light domain" and a "second variable heavy domain" of such multispecific antibodies together form a "second antigen binding site". A "third variable light domain" and a "third variable heavy domain" of such multispecific antibodies together form a "third antigen binding site", and so on.

The antigen binding sites for use in accordance with the invention, including the VHs, VLs, and/or CDRs that comprise such, may be obtained or derived from any source of such, as will be understood by the artisan. Accordingly, such antigen binding sites, VHs, VLs, and/or CDRs may be obtained or derived from hybridoma cells that express antibodies against a target recognized by such; from B cells from immunized donors, which express antibodies against a target recognized by such; from B-cells that have been stimulated to express antibodies against a target recognized by such; and or from identification of antibodies or antibody fragments that have been identified by screening a library comprising a plurality of polynucleotides or polypeptides for antigen binding antibodies (or antigen binding fragments thereof). With regard to the design, preparation, display, and implementation of such libraries for use in identifying and obtaining antigen binding sites for use in accordance with the invention, see, e.g., WO 2009/036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

Any one or more of the antigen binding sites, VHs, VLs, or CDRs, and combinations thereof, of antibodies, including multispecific antibodies and antibody fragments antibodies or multispecific antibodies, may comprise sequences from a variety of species. In some embodiments, such antigen binding sites, VHs, VLs, or CDRs, and combinations thereof may be obtained from a nonhuman source, including but not limited to mice, rats, rabbits, camels, llamas, and monkeys. In some embodiments, the scaffold and/or framework regions can be a mixture from different species. As such, an antibody of antibody fragment in accordance with the invention may comprise a chimeric antibody and/or a humanized antibody.

In general, both "chimeric antibodies" and "humanized antibodies" refer to antibodies in which regions from more than one species have been combined. For example, "chimeric antibodies" traditionally comprise variable region(s) from a mouse or other nonhuman species and the constant region(s) from a human.

Further, "humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, one, some, or all of which are encoded by nucleic acids originating in a non-human organism, are grafted into the framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (see, e.g., U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein). In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004.

Accordingly, any one or more of the antigen binding sites, or one or more VHs, VLs, CDRs, or combinations thereof, which comprise the antibodies, multispecific antibodies, and/or fragments thereof, may be derived from a non-human species and/or result from humanization of a non-human antibody or antibody fragment. Such VHs, VLs, and/or CDRs obtained or derived from non-human species, when included in antibodies, multispecific antibodies, and/or antibody fragments thereof, are referred to as "humanized" such regions and/or domains.

All such antibodies, including full length antibodies, such as IgGs, multispecific antibodies, antibody fragments, multispecific antibody fragments, humanized antibodies, humanized multispecific antibodies, humanized antibody fragments, humanized multispecific antibody fragments, and the like are herein and throughout collectively referred to as "antibodies". Accordingly, it is to be understood that all disclosure pertaining to "antibodies" also expressly discloses including full length antibodies, such as IgGs, multispecific antibodies, antibody fragments, multispecific antibody fragments, humanized antibodies, humanized multispecific antibodies, humanized antibody fragments, humanized multispecific antibody fragments, and the like.

Antibodies optionally comprise first and second polypeptides that each comprise a hinge region, wherein each hinge region comprises at least one thiol group that is capable of participating in an intermolecular disulfide bond such that the first and the second polypeptide are covalently linked as a result of formation of the disulfide bond. As is understood in the art, chemical modification may be introduced into (or onto) certain residues within such hinge regions which effect the introduction of such thiol groups for disulfide bond formation. Alternatively, the thiol groups may be provided by a cysteine residue that is present within the hinge region. Such cysteines may be provided by native hinge polypeptide sequence, or may be introduced by mutagenesis into nucleic acid encoding the hinge region. As used herein, a "hinge" or a "hinge region" antibodies may comprise or constitute a "linker moiety".

In certain embodiments, antibodies comprise one or more linkers or linker moieties. Such linkers or linker moieties may comprise a peptidic linker moiety or a non-peptidic linker moiety. The terms "linker" and "linker moiety" and the like, means a divalent species (-L-) covalently bonded in turn to a polypeptide having a valency available for bonding and to an amino acid that comprises the antibodies, which amino acid has a valency available for bonding. The available bonding site may conveniently comprise a side chain of an amino acid (e.g., a lysine, cysteine, or aspartic acid side chain, and homologs thereof). In some embodiments, the available bonding site in antibody is the side chain of a lysine or a cysteine residue. In some embodiments, the available bonding site in the antibody is the N-terminal amine of a polypeptide comprising the antibody. In some embodiments, the available bonding site in the antibody is the C-terminal carboxyl of a polypeptide comprising the antibody. In some embodiments, the available bonding site in the antibody is a backbone atom (e.g., a c-alpha carbon atom) of a polypeptide comprising the antibody.

Preferably, a linker moiety is employed to covalently attach a VH or a VL to the C-terminus of a CH3 domain of an antibody. A linker moiety may also be employed to covalently attach a first VH or a first VL to a second VH or a second VL, respectively. A linker moiety may also be employed to covalently attach a first VH or a first VL to a second VL or a second VH, respectively. A linker moiety may also be employed to covalently attach a VH of a single chain antigen binding site, such as an scFv, to the VL of such a single chain antigen binding site, and vice versa. A linker moiety may also be employed to attach the VH or the VL of such a single chain antigen binding site, such as an scFv, to a C-terminus of a CH3 domain or variant thereof. A linker moiety may also be employed to attach a VH to the N-terminus of a CL domain or to the N-terminus of a CH2. A linker moiety may also be employed to attach a VL to the N-terminus of a CL domain or to the N-terminus of a CH2 domain. As will be appreciated, combinations and/or multiples of the foregoing may be employed in order to prepare any of the antibodies, such that a plurality of antigen binding sites may be included in such antibodies, optionally with a multiple of specificities. Accordingly, an antibody may be generated by employing one or more linkers to covalently attach one, two, three, four, five, six, seven, or more VLs, VHs, and/or single chain antigen binding sites, such as scFvs to the first polypeptide, the second polypeptide, a VH, or a VL attached to the first polypeptide or the second polypeptide, and the like, so as to generate an antibody having bi-, tri-, tetra-, pent-, hexa-, hepta-, or octa-valency, and so on, and/or bi-, tri-, tetra-, pent-, hexa-, hepta-, or octa-specificity, and so on.

Accordingly, in certain embodiments, the multivalent antibody comprises a first VL that is covalently attached to the CH3 domain, or variant thereof, of the first heavy chain of the antibody via a linker moiety, forming the second antigen binding site. In additional embodiments, antibody comprises a first VH that is covalently attached to the CH3 domain, or variant thereof, of the Fc region of the antibody via a linker moiety, thereby forming the second antigen binding site.

In further embodiments, the antibody comprises a third antigen binding site, wherein the third antigen binding site is covalently attached via a linker moiety to either the first VL or the first VH. In still further embodiments, the third antigen binding site comprises a single chain antigen binding site, such single chain variable region (scFv), wherein the scFv comprises a second VL that is covalently attached to a second VH via a linker moiety or wherein the second VL is covalently attached to the second VH via a linker moiety.

In further embodiments, the antibodies further comprise additional binding sites, such as a fourth antigen binding site, a fifth antigen binding site, a sixth antigen binding site, and so on, wherein one or more of which may comprise a single chain antigen binding site, such as an scFv, which are attached via linker moieties to the other VLs and/or VHs of the multivalent antibody.

In certain embodiments the linker moieties comprise amino acids that are selected from glycine, alanine, proline, asparagine, glutamine, lysine, aspartate, and glutamate. In a further embodiment the linker moiety is made up of a majority of amino acids that are sterically unhindered, such as glycine, alanine and/or serine. In certain embodiments the linker moiety is comprises a sequence selected from the group [Gly-Ser]$_n$ (SEQ ID NO: 1); [Gly-Gly-Ser]$_n$ (SEQ ID NO: 2); [Gly-Gly-Gly-Ser]$_n$ (SEQ ID NO: 3); [Gly-Gly-Gly-Gly-Ser]$_n$ (SEQ ID NO: 4); [Gly-Gly-Gly-Gly-Ser-Gly-Gly-Gly-Gly]$_n$ (SEQ ID NO: 5); [Gly-Gly-Gly-Gly-Ser-Gly-Gly-Gly-Gly-Ser-Gly-Gly-Gly-Gly]$_n$ (SEQ ID NO: 6); [Gly-Gly-Gly-Gly-Ser Gly-Gly-Gly-Gly-Ser-Gly-Gly-Gly-Gly-Ser-Gly-Gly-Gly-Gly]$_n$ (SEQ ID NO: 7); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 8); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 9); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 10); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Such linkers may comprise: an acidic linker, a basic linker, and a structural motif, or combinations thereof; a polyglycine, a polyalanine, poly(Gly-Ala), or poly(Gly-Ser); (Gly)3, (Gly)4 (SEQ ID NO: 11), or (Gly)5 (SEQ ID NO: 12); (Gly)$_3$Lys(Gly)$_4$ (SEQ ID NO: 13), (Gly)$_3$AsnGlySer(Gly)$_2$ (SEQ ID NO: 14), (Gly)$_3$Cys(Gly)$_4$ (SEQ ID NO: 15), or GlyProAsnGlyGly (SEQ ID NO: 16), [Gly-Ser]$_n$ (SEQ ID NO: 1), [Gly-Gly-Ser]$_n$ (SEQ ID NO: 2), [Gly-Gly-Gly-Ser]$_n$ (SEQ ID NO: 3), [Gly-Gly-Gly-Gly-Ser]$_n$ (SEQ ID NO: 4), [Gly-Gly-Gly-Gly-Ser-Gly-Gly-Gly-Gly]$_n$ (SEQ ID NO: 5), [Gly-Gly-Gly-Gly-Ser-Gly-Gly-Gly-Gly-Ser-Gly-Gly-Gly-Gly]$_n$ (SEQ ID NO: 6), [Gly-Gly-Gly-Gly-Ser Gly-Gly-Gly-Gly-Ser-Gly-Gly-Gly-Gly-Ser-Gly-Gly-Gly-Gly]$_n$ (SEQ ID NO: 7); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 8); [Gly-Gly-Gly-Gly-Ser-Gly-Gly-Gly-Gly-Ser-Gly-Gly-Gly-Gly-Ser-Gly-Gly-Gly-Gly-Ser-Gly-Gly- Gly-Gly-Gly]$_n$ (SEQ ID NO: 9); or [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 10); [Gly-Glu]$_n$ (SEQ ID NO: 17), [Gly-Gly-Glu]$_n$ (SEQ ID NO: 18), [Gly-Gly-Gly-Glu]$_n$ (SEQ ID NO: 19), [Gly-Gly-Gly-Gly-Glu]$_n$ (SEQ ID NO: 20), [Gly-Asp]$_n$ (SEQ ID NO: 21); [Gly-Gly-Asp]$_n$ (SEQ ID NO: 22), [Gly-Gly-Gly-Asp]$_n$ (SEQ ID NO: 23), [Gly-Gly-Gly-Gly-Asp]$_n$ (SEQ ID NO: 24); where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

In certain embodiments, charged linker moieties are employed. Such charges linker moieties may contain a significant number of acidic residues (e.g., Asp, Glu, and the like), or may contain a significant number of basis residues (e.g., Lys, Arg, and the like), such that the linker moiety has a pi lower than 7 or greater than 7, respectively. As understood by the artisan, and all other things being equal, the greater the relative amount of acidic or basic residues in a given linker moiety, the lower or higher, respectively, the pI of the linker moiety will be. Such linker moieties may impart advantages to the multivalent antibodies, such as improving solubility and/or stability characteristics of such polypeptides at a particular pH, such as a physiological pH (e.g., between H 7.2 and pH 7.6, inclusive), or a pH of a pharmaceutical composition comprising such antibodies, as well as allowing for optimization of characteristics such as rotational and translational flexibility of the domains and/or regions of the antibody that are attached via the linker moiety. Such characteristics may advantageously be optimized and tailored for any given antibody by the artisan.

For example, an "acidic linker" is a linker moiety that has a pi of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker moiety that has a pi of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group consisting of [Gly-Glu]$_n$ (SEQ ID NO: 17); [Gly-Gly-Glu]$_n$ (SEQ ID NO: 18); [Gly-Gly-Gly-Glu]$_n$ (SEQ ID NO: 19); [Gly-Gly-Gly-Gly-Glu]$_n$ (SEQ ID NO: 20); [Gly-Asp]$_n$ (SEQ ID NO: 21); [Gly-Gly-Asp]$_n$ (SEQ ID NO: 22); [Gly-Gly-Gly-Asp]$_n$ (SEQ ID NO: 23); [Gly-Gly-Gly-Gly-Asp]$_n$ (SEQ ID NO: 24); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75. In certain embodiments, a basic linker will contain a sequence that is selected from the group consisting of [Gly-Lys]$_n$ (SEQ ID NO: 25); [Gly-Gly-Lys]$_n$ (SEQ ID NO: 26); [Gly-Gly-Gly-Lys]$_n$ (SEQ ID NO: 27); [Gly-Gly-Gly-Gly-Lys]$_n$ (SEQ ID NO: 28); [Gly-Arg]$_n$ (SEQ ID NO: 29); [Gly-Gly-Arg]$_n$ (SEQ ID NO: 30); [Gly-Gly-Gly-Arg]$_n$ (SEQ ID NO: 31); [Gly-Gly-Gly-Gly-Arg]$_n$ (SEQ ID NO: 32); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Additionally, linker moieties may be employed which possess certain structural motifs or characteristics, such as an alpha helix. For example, such a linker moiety may contain a sequence that is selected from the group consisting of [Glu-Ala-Ala-Ala-Lys]$_n$ (SEQ ID NO: 33), where n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75: for example, [Glu-Ala-Ala-Ala-Lys]$_3$ (SEQ ID NO: 34), [Glu-Ala-Ala-Ala-Lys]$_4$ (SEQ ID NO: 35), or [Glu-Ala-Ala-Ala-Lys]$_5$ (SEQ ID NO: 36), and so on.

In still further embodiments each linker moiety employed in an antibody independently comprises: polyglycine, polyalanine, poly(Gly-Ala), or poly(Gly-Ser), (Gly)$_3$, (Gly)$_4$ (SEQ ID NO: 11), and (Gly)$_5$ (SEQ ID NO: 12), (Gly)$_3$Lys(Gly)$_4$ (SEQ ID NO: 13), (Gly)$_3$AsnGlySer(Gly)$_2$ (SEQ ID NO: 14), (Gly)$_3$Cys(Gly)$_4$ (SEQ ID NO: 15), and Gly-ProAsnGlyGly (SEQ ID NO: 16), a combination of Gly and Ala, a combination of Gly and Ser, a combination of, Gly and Glu, a combination of Gly and Asp, a combination of Gly and Lys, or combinations thereof.

In certain embodiments, the antibodies comprise, for example, a CH2 domain variant and/or a CH3 domain variant, wherein such variants each independently comprise at least one different amino acid substitution such that a heterodimeric domain pair is generated such that heterodimerization of the first and second polypeptides of the antibodies favored over homodimerization.

With regard to a "variant" of a domain or region of an antibody as used herein throughout, such a variant refers a polypeptide sequence that comprises such a domain or region, and that differs from that of a parent polypeptide sequence by virtue of at least one amino acid modification. The parent polypeptide sequence may be a naturally occurring or wild-type (WT) polypeptide sequence, or may be a modified version of a WT sequence. Preferably, the variant has at least one amino acid modification compared to the parent polypeptide, region, or domain, e.g. from about one to about ten amino acid modifications, and preferably from about one to about five amino acid modifications compared to the parent. The variant polypeptide sequence herein will preferably possess at least about 80% homology with a parent sequence, and most preferably at least about 90% homology, more preferably at least about 95% homology.

By "parent polypeptide", "parent polypeptide sequence", "parent protein", "precursor polypeptide", or "precursor protein" as used herein is meant an unmodified polypeptide or polypeptide sequence that is subsequently modified to generate a variant polypeptide or polypeptide sequence. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it.

By "Fc polypeptide variant" or "variant Fc polypeptide" as used herein is meant an Fc polypeptide that differs from a parent Fc polypeptide by virtue of at least one amino acid modification. By "Fc variant antibody" or "antibody Fc variant" as used herein is meant an antibody that differs from a parent antibody by virtue of at least one amino acid modification in the Fc region.

By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

Interaction between heterodimeric pairs of antibodies comprising such heterodimeric pairs may be promoted at the heterodimeric pair interface by the formation of protuberance-into-cavity complementary regions at such interfaces; the formation of non-naturally occurring disulfide bonds at such interfaces; leucine zipper at such interfaces; hydrophobic regions at such interfaces; and/or hydrophilic regions at such interfaces. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. Non-naturally occurring disulfide bonds are constructed by replacing on the first polypeptide a naturally occurring amino acid with a free thiol-containing residue, such as cysteine, such that the free thiol interacts with another free thiol-containing residue on the second polypeptide such that a disulfide bond is formed between the first and second polypeptides Exemplary heterodimerization pairs and methods for making such in accordance with the present invention are available in the art, and are disclosed, for example, in US 2011/0054151; US 2007/0098712; and the like.

In certain embodiments, the heterodimeric pairs are contained within the Fc region of the antibodies. Fc regions that contain such heterodimeric pairs are referred to as "heterodimeric Fc regions"

Accordingly, in certain embodiments, the antibodies comprise a CH2 and/or a CH3 domain variant, wherein either: a) the CH2 domain variant and the CH3 domain variant each independently comprises a at least one protuberance in either the CH2 domain or the CH3 domain of the first polypeptide and at least one corresponding cavity in the CH2 domain or the CH3 domain of the second; or the CH2 domain variant and the CH3 domain variant each independently comprises at least one cavity in either the CH2 domain or the CH3 domain of the first polypeptide and at least one corresponding protuberance in the CH2 domain or the CH3 domain of the second polypeptide. In certain other embodiments, the antibodies comprise a CH2 and/or a CH3 domain variant, wherein either: a) the CH2 domain variant and the CH3 domain variant each independently comprises at least one substituted negatively-charged amino acid in either the CH2 domain or the CH3 domain of the first polypeptide and at least one corresponding positively-charged amino acid in either the CH2 domain or the CH3 domain of the second polypeptide; or b) the CH2 domain variant and the CH3 domain variant each independently comprises at least one substituted positively-charged amino acid in either the CH2 domain or the CH3 domain of the first polypeptide and at least one corresponding substituted negatively-charged substituted amino acid in either the CH2 domain or the CH3 domain of the second polypeptide.

With regard to Fc function in "natural" antibodies (i.e., those antibodies generated in vivo via native biological antibody synthesis by native B-cells), the Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65). The FcγRs bind the IgG Fc region with different affinities. The extracellular domains of FcγRIIIa and FcγRIIIb are 96% identical; however FcγRIIIb does not have an intracellular signaling domain. Furthermore, whereas FcγRT, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge.

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-76). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A particular feature of the Fc region of "natural" antibodies is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins.

In some embodiments, the antibodies comprise an Fc variant. An Fc variant comprises one or more amino acid modifications relative to a parent Fc polypeptide, wherein the amino acid modification(s) provide one or more optimized properties. Fc variants further comprise either a CH2 domain variant, a CH3 domain variant, or both a CH2 domain variant and a CH3 domain variant. By "modification" herein is meant an alteration in the physical, chemical, or sequence properties of a protein, polypeptide, antibody, or immunoglobulin. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution Y349T refers to a variant polypeptide, in this case a constant heavy chain variant, in which the tyrosine at position 349 is replaced with threonine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

An Fc variant disclosed herein differs in amino acid sequence from its parent by virtue of at least one amino acid modification. The antibodies may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein also include glycoform modifications. Modifications may be made genetically using molecular biology, or may be made enzymatically or chemically.

Fc variants disclosed herein are defined according to the amino acid modifications that compose them. Thus, for example, the substitution Y349T refers to a variant polypeptide, in this case a constant heavy chain variant, in which the tyrosine at position 349 is replaced with threonine. Likewise, Y349T/T394F defines an Fc variant with the substitutions Y349T and T394F relative to the parent Fc polypeptide. The identity of the WT amino acid may be unspecified, in which case the aforementioned variant is referred to as 349T/394F. It is noted that the order in which substitutions are provided is arbitrary, that is to say that, for example, 349T/394F is the same Fc variant as 394F/349T. Unless otherwise noted, constant region and Fc positions discussed herein are numbered according to the EU index or EU numbering scheme (Kabat et al., 1991, Sequences of Proteins of Immunological Interest, 5th Ed., United States Public Health Service, National Institutes of Health, Bethesda). The EU index or EU index as in Kabat or EU numbering scheme refers to the numbering of the EU antibody (Edelman et al., 1969, Proc Natl Acad Sci USA 63:78-85).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgD, IgM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

Fc variants that comprise or are CH3 domain variants as described above may comprise at least one substitution at a position in a CH3 domain selected from the group consisting of 349, 351, 354, 356, 357, 364, 366, 368, 370, 392, 394, 395, 396, 397, 399, 401, 405, 407, 409, 411, and 439, wherein numbering is according to the EU index as in Kabat. In a preferred embodiment, CH3 domain variants comprise at least one CH3 domain substitution per heavy chain selected from the group consisting of 349A, 349C, 349E, 349I, 349K, 349S, 349T, 349W, 351 E, 351K, 354C, 356K, 357K, 364C, 364D, 364E, 364F, 364G, 364H, 364R, 364T, 364Y, 366D, 366K, 366S, 366W, 366Y, 368A, 368E, 368K, 368S, 370C, 370D, 370E, 370G, 370R, 370S, 370V, 392D, 392E, 394F, 394S, 394W, 394Y, 395T, 395V, 396T, 397E, 397S, 397T, 399K, 401 K, 405A, 405S, 407T, 407V, 409D, 409E, 411 D, 411 E, 411K, and 439D. Each of these variants can be used individually or in any combination for each heavy chain Fc region. As will be appreciated by those in the art, each heavy chain can comprise different numbers of substitutions. For example, both heavy chains that make up the Fc region may comprise a single substitution, one chain may comprise a single substitution and the other two substitutions, both can contain two substitutions (although each chain will contain different substitutions), etc.

In some embodiments, the CH2 and/or CH3 domain variants are made in combinations, that is, two or more variants per heavy chain Fc domain, selected from the group outlined above.

Other CH2 and/or CH3 domain variants that favor heterodimerization that may be employed in the design and preparation of antibodies are provided in, for example, Ridgeway et al., 1996, Protein Engineering 9[7]:617-621; U.S. Pat. No. 5,731,168; Xie et al., 2005, J Immunol Methods 296:95-101; Davis et al., 2010, Protein Engineering, Design & Selection 23[4]:195-202; Gunasekaran et al., 2010, J Biol Chem 285[25]:1937-19646; and PCT/US2009/000071).

The Fc variants disclosed herein may be optimized for improved or reduced binding to Fc receptors or Fc ligands. By "Fc receptor" or "Fc ligand" as used herein is meant a molecule, preferably a polypeptide, from any organism that binds to the Fc region of an antibody to form an Fc-ligand complex. Fc ligands include but are not limited to FcγRs, (as described above, including but not limited to FcγRIIIa, FcγRIIa, FcγRIIb, FcγRI and FcRn), C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs. Fc ligands may include undiscovered molecules that bind Fc.

Antibodies may be designed to optimize properties, including but are not limited to enhanced or reduced affinity for an Fc receptor. By "greater affinity" or "improved affinity" or "enhanced affinity" or "better affinity" than a parent Fc polypeptide, as used herein, is meant that an Fc variant binds to an Fc receptor with a significantly higher equilibrium constant of association (KA or $K_a$) or lower equilibrium constant of dissociation (KD or $K_d$) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower KA or higher KD than the parent Fc polypeptide. Greater or reduced affinity can also be defined relative to an absolute level of affinity.

In one embodiment, particularly useful Fc modifications for the present invention are variants that reduce or ablate binding to one or more FcγRs and/or complement proteins, thereby reducing or ablating Fc-mediated effector functions such as ADCC, ADCP, and CDC. Such variants are also referred to herein as "knockout variants" or "KO variants". Variants that reduce binding to FcγRs and complement are useful for reducing unwanted interactions mediated by the Fc region and for tuning the selectivity of the antibodies. Preferred knockout variants are described in U.S. Ser. No. 11/981,606, filed Oct. 31, 2007, entitled "Fc Variants with Optimized Properties". Preferred modifications include but are not limited substitutions, insertions, and deletions at positions 234, 235, 236, 237, 267, 269, 325, and 328, wherein numbering is according to the EU index. Preferred substitutions include but are not limited to 234G, 235G, 236R, 237K, 267R, 269R, 325L, and 328R, wherein numbering is according to the EU index. A preferred variant comprises 236R/328R. Variants may be used in the context of any IgG isotype or IgG isotype Fc region, including but not limited to human IgG1, IgG2, IgG3, and/or IgG4 and combinations thereof. Preferred IgG Fc regions for reducing FcγR and complement binding and reducing Fc-mediated effector functions are IgG2 and IgG4 Fc regions. Hybrid isotypes may also be useful, for example hybrid IgG1/IgG2 isotypes as described in US 2006-0134105. Other modifications for reducing FcγR and complement interactions include but are not limited to substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Fc modifications that improve binding to FcγRs and/or complement are also amenable to incorporation in the design and preparation of antibodies. Such Fc variants may enhance Fc-mediated effector functions such as ADCC, ADCP, and/or CDC. Preferred modifications for improving FcγR and complement binding are described in, e.g., U.S. Pat. No. 8,188,231 and US 2006-0235208. Preferred modifications comprise a substitution at a position selected from the group consisting of 236, 239, 268, 324, and 332, wherein numbering is according to the EU index. Preferred substitutions include but are not limited to 236A, 239D, 239E, 268D, 267E, 268E, 268F, 324T, 332D, and 332E. Preferred variants include but are not limited to 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, ibid.

As disclosed throughout, polynucleotides, which may be used interchangeably with "nucleic acids", may be prepared which encode polypeptides, including antibodies, and that may then be cloned into host cells, such as yeast cells or mammalian cells, expressed and assayed, in accordance with the disclosed and claimed methods. Thus, nucleic acids, and particularly DNA, may be made that encode each protein sequence. These practices are carried out using well-known procedures. For example, a variety of methods that may find use in generating such polynucleotides are described in Molecular Cloning-A Laboratory Manual, 3rd Ed. (Maniatis, Cold Spring Harbor Laboratory Press, New York, 2001), and Current Protocols in Molecular Biology (John Wiley & Sons). There are a variety of techniques that may be used to efficiently generate DNA encoding polypeptides, such as antibodies. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode polypeptides, such as antibodies.

Polypeptides, such as antibodies, may be produced by culturing a host cell transformed with nucleic acid, e.g., expression vectors containing nucleic acid encoding the polypeptides, such as antibodies, under the appropriate conditions to induce or cause expression of the polypeptides. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast cells, and plant cells. For example, a variety of cell lines that are useful in expressing and displaying polypeptides, such as antibodies, in accordance with the disclosed and claimed methods are described in the ATCC® cell line catalog, available from the American Type Culture Collection.

In certain embodiments, the polypeptides, such as antibodies are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In alternate embodiments, polypeptides, such as antibodies, are produced in insect cells (e.g. Sf21/Sf9, Trichoplusia ni Bti-Tn5b1-4) or yeast cells (e.g. S. cerevisiae, Pichia, etc.).

The nucleic acids that encode the polynucleotides, which may be antibodies, may be incorporated into one or more expression vectors, as appropriate, in order to express the encoded polypeptides. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which are useful for harboring polynucleotides that encode polypeptides, such as antibodies include but are not limited to those which enable protein expression in mammalian cells, bacteria, insect cells, yeast cells, and in vitro systems. As is known in the art, a variety of expression vectors are available, commercially or otherwise, that are useful expressing and displaying polypeptides, such as antibodies.

Expression vectors typically comprise a protein or polypeptide to be expressed, which is operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the polypeptide, which may be an antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

As disclosed throughout, the disclosed and claimed methods may comprise selecting one or more polypeptides, which may be antibodies, which, inter alia, bind to at least one binding partner. Such binding partners may comprise antigens.

Virtually any antigen may be targeted by the antibodies in accordance with the disclosed and claimed methods, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin MA, Activin RIA ALK-2, Activin RIB ALK-4, Activin RITA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Ax1, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bpl, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (FLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular FLAP-like alkaline phosphatase, TfR, TGF, TGF-alpha, TGF-beta, TGF-beta Pan Specific, TGF-beta RI (ALK-5), TGF-beta RII, TGF-beta RII, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1Apo-2, DR4), TNFRSF10B (TRAIL R2DRS, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2TNFRH2), TNFRST23 (DcTRAIL R1TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

Additional exemplary antigens that may serve as test binding partners to be targeted by antibodies include but are not limited to: CD20, CD19, Her2, EGFR, EpCAM, c-MET, CD3, FcγRIIIa (CD16), FcγRIIa (CD32a), FcγRIIb (CD32b), FcγRI (CD64), Toll-like receptors (TLRs) such as TLR4 and TLR9, cytokines such as IL-2, IL-5, IL-13, IL-12, IL-23, and TNFα, cytokine receptors such as IL-2R, chemokines, chemokine receptors, growth factors such as VEGF and HGF, and the like.

Monoclonal antibody therapy has emerged as an important therapeutic modality for cancer (Weiner et al., 2010, Nature Reviews Immunology 10:317-327; Reichert et al., 2005, Nature Biotechnology 23[9]:1073-1078). For anticancer treatment it may be desirable to target one antigen (antigen-1) whose expression is restricted to the cancerous cells while co-targeting a second antigen (antigen-2) that mediates some immunological killing activity. For other treatments it may be beneficial to co-target two antigens, for example two angiogenic factors or two growth factors that are each known to play some role in proliferation of the tumor. Exemplary co-targets for oncology which may serve as test binding partners in accordance with the disclosed and claimed methods include but are not limited to: HGF and VEGF, IGF-1R and VEGF, Her2 and VEGF, CD19 and CD3, CD20 and CD3, Her2 and CD3, CD19 and FcγRIIIa, CD20 and FcγRIIIa, Her2 and FcγRIIIa. An antibody may be capable of binding VEGF and phosphatidylserine; VEGF and ErbB3; VEGF and PLGF; VEGF and ROBO4; VEGF and BSG2; VEGF and CDCP1; VEGF and ANPEP; VEGF and c-MET; HER-2 and ERB3; HER-2 and BSG2; HER-2 and CDCP1; HER-2 and ANPEP; EGFR and CD64; EGFR and BSG2; EGFR and CDCP1; EGFR and ANPEP; IGF1R and PDGFR; IGF1R and VEGF; IGF1R and CD20; CD20 and CD74; CD20 and CD30; CD20 and DR4; CD20 and VEGFR2; CD20 and CD52; CD20 and CD4; HGF and c-MET; HGF and NRP1; HGF and phosphatidylserine; ErbB3 and IGF1R; ErbB3 and IGF1,2; c-Met and Her-2; c-Met and NRP1; c-Met and IGF1R; IGF1,2 and PDGFR; IGF1,2 and CD20; IGF1,2 and IGF1R; IGF2 and EGFR; IGF2 and HER2; IGF2 and CD20; IGF2 and VEGF; IGF2 and IGF1R; IGF1 and IGF2; PDGFRa and VEGFR2; PDGFRa and PLGF; PDGFRa and VEGF; PDGFRa and c-Met; PDGFRa and EGFR; PDGFRb and VEGFR2; PDGFRb and c-Met; PDGFRb and EGFR; RON and c-Met; RON and MTSP1; RON and MSP; RON and CDCP1; VGFR1 and PLGF; VGFR1 and RON; VGFR1 and EGFR; VEGFR2 and PLGF; VEGFR2 and NRP1; VEGFR2 and RON; VEGFR2 and DLL4; VEGFR2 and EGFR; VEGFR2 and ROBO4; VEGFR2 and CD55; LPA and S1 P; EPHB2 and RON; CTLA4 and VEGF; CD3 and EPCAM; CD40 and IL6; CD40 and IGF; CD40 and CD56; CD40 and CD70; CD40 and VEGFR1; CD40 and DR5; CD40 and DR4; CD40 and APRIL; CD40 and BCMA; CD40 and RANKL; CD28 and MAPG; CD80 and CD40; CD80 and CD30; CD80 and CD33; CD80 and CD74; CD80 and CD2; CD80 and CD3; CD80 and CD19; CD80 and CD4; CD80 and CD52; CD80 and VEGF; CD80 and DR5; CD80 and VEGFR2; CD22 and CD20; CD22 and CD80; CD22 and CD40; CD22 and CD23; CD22 and CD33; CD22 and CD74; CD22 and CD19; CD22 and DR5; CD22 and DR4; CD22 and VEGF; CD22 and CD52; CD30 and CD20; CD30 and CD22; CD30 and CD23; CD30 and CD40; CD30 and VEGF; CD30 and CD74; CD30 and CD19; CD30 and DR5; CD30 and DR4; CD30 and VEGFR2; CD30 and CD52; CD30 and CD4; CD138 and RANKL; CD33 and FTL3; CD33 and VEGF; CD33 and VEGFR2; CD33 and CD44; CD33 and DR4; CD33 and DR5; DR4 and CD137; DR4 and IGF1,2; DR4 and IGF1R; DR4 and DR5; DR5 and CD40; DR5 and CD137; DR5 and CD20; DR5 and EGFR; DR5 and IGF1,2; DR5 and IGFR, DR5 and HER-2, and EGFR and DLL4. Other target combinations include one or more members of the EGF/erb-2/erb-3 family.

Other targets (one or more) involved in oncological diseases that may serve as test binding partners may be selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, FGF10, FGF18, FGF2, FGF4, FGF7, IGF1R, IL2, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFBIII, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR113, NR2F6, NR4A3, ESR1, ESR2, NR0B1, NR0B2, NR1D2, NR1H2, NR1H4, NR112, NR2C1, NR2C2, NR2E1, NR2E3, NR2F1, NR2F2, NR3C1, NR3C2, NR4A1, NR4A2, NR5A1, NR5A2, NR6 μl, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH2O, CDH7, CDH9, CDH1, CDH10, CDH13, CDH18, CDH19, CDH2O, CDH7, CDH8, CDH9, ROBO2, CD44, ILK, ITGA1, APC, CD164, COL6A1, MTSS1, PAP, TGFBIII, AGR2, AIG1, AKAP1, AKAP2, CANT1, CAVI, CDH12, CLDN3, CLN3, CYB5, CYC1, DAB21P, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33 μl, SLC43 μl, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDCI, STAB 1, VEGF, VEGFC, ANGPTL3, BA11, COL4A3, IL8, LAMA5, NRP1, NRP2, STAB 1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL1A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p161NK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (GF), NGFR, NME1 (M23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, 1D2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-111), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94), RON, c-Met, CD64, DLL4, PLGF, CTLA4, phophatidylserine, ROBO4, CD80, CD22, CD40, CD23, CD28, CD80, CD55, CD38, CD70, CD74, CD30, CD138, CD56, CD33, CD2, CD137, DR4, DRS, RANKL, VEGFR2, PDGFR, VEGFR1, MTSP1, MSP, EPHB2, EPHA1, EPHA2, EpCAM, PGE2, NKG2D, LPA, SIP, APRIL, BCMA, MAPG, FLT3, PDGFR alpha, PDGFR beta, ROR1, PSMA, PSCA, SCD1, and CD59.

Monoclonal antibody therapy has become an important therapeutic modality for treating autoimmune and inflammatory disorders (Chan & Carter, 2010, Nature Reviews Immunology 10:301-316; Reichert et al., 2005, Nature Biotechnology 23[9]:1073-1078). Many proteins have been implicated in general autoimmune and inflammatory responses, and thus may be targeted by antibodies. Autoimmune and inflammatory targets which may serve as test binding partners in accordance with the disclosed and claimed methods include: C5, CCL1 (I-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (1P-10), CXCL11 (1-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF$_1$, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL12RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144).

Exemplary co-targets for autoimmune and inflammatory disorders include but are not limited to IL-1 and TNFalpha, IL-6 and TNFalpha, IL-6 and IL-1, IgE and IL-13, IL-1 and IL-13, IL-4 and IL-13, IL-5 and IL-13, IL-9 and IL-13, CD19 and FcγRIIb, and CD79 and FcγRIIb.

Antibodies with specificity for the following pairs of targets to treat inflammatory disease may also serve as test binding partners in accordance with the disclosed and claimed methods: TNF and IL-17A; TNF and RANKL; TNF and VEGF; TNF and SOST; TNF and DKK; TNF and alphaVbeta3; TNF and NGF; TNF and IL-23p19; TNF and IL-6; TNF and SOST; TNF and IL-6R; TNF and CD-20; IgE and IL-13; IL-13 and IL23p19; IgE and IL-4; IgE and IL-9; IgE and IL-9; IgE and IL-13; IL-13 and IL-9; IL-13 and IL-4; IL-13 and IL-9; IL-13 and IL-9; IL-13 and IL-4; IL-13 and IL-23p19; IL-13 and IL-9; IL-6R and VEGF; IL-6R and IL-17A; IL-6R and RANKL; IL-17A and IL-1 beta; IL-1 beta and RANKL; IL-1beta and VEGF; RANKL and CD-20; IL-1alpha and IL-1 beta; IL-1 alpha and IL-1beta.

Pairs of targets that may serve as test binding partners in accordance with the disclosed and claimed methods also include: IL-13 and IL-1 beta, implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-13; IL-13 and LHR agonist; IL-13 and CL25; IL-13 and SPRR2a; IL-13 and SPRR2b; and IL-13 and ADAMS. Additional targets that may serve as test binding partners in accordance with the disclosed and claimed methods, which are involved in asthma, may be selected from the group consisting of CSF1 (MCSF), CSF2 (GM-CSF), CSF3 (GCSF), FGF2, IFNA1, IFNB1, IFNG, histamine and histamine receptors, IL1A, IL1 B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCLi, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCLi, CCR2, CCR3, CCR4, CCR5, CCR6, CCR7, CCR8, CX3CR1, GPR2, XCR1, FOS, GATA3, JAK1, JAK3, STATE, TBX21, TGFB1, TNF, TNFSF6, YY1, CYSLTR1, FCER1A, FCER2, LTB4R, TB4R2, LTBR, and Chitinase.

Pairs of targets involved in rheumatoid arthritis (RA) may be co-targeted by the invention, including but not limited to TNF and IL-18; TNF and IL-12; TNF and IL-23; TNF and 1L-1beta; TNF and MIF; TNF and IL-17; and TNF and IL-15.

Antigens that may serve as test binding partners in accordance with the disclosed and claimed methods also include and which are implicated in systemic lupus erythematosus (SLE) include: CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGSI, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, ILIR2, ITGA2, ITGA3, MS4A1, ST6GALI, CDIC, CHSTIO, HLA-A, HLA-DRA, and NT5E; CTLA4, B7.1, B7.2, BlyS, BAFF, C5, IL-4, IL-6, IL-10, IFN-α, and TNF-α.

Ahamed T., Ottens M., van Dedem G. W., van der Wielen L. A., *J. Chromatog. A.*, 2005; 1089:111-124.

Blaise L., Wehnert A., Steukers M. P., van den Beucken T., Hoogenboom H. R., Hufton S. E., *Gene,* 2004; 342:211-218.

Boder E. T., Wittrup K. D. *Nat., Biotechnol.,* 1997; 15:553-557.

Carter P. J., *Nat. Rev. Immunol.,* 2006; 6:343-357.

Cho Y. K., Shusta E. V., *PEDS,* 2010; 23:567-577.

Esfandiary R., Hayes D. B., Parupudi A., Casas-Finet J., Bai S., Samra H. S., Shah A. U., Sathish H. A., *J. Pharm. Sci.,* 2013; 102:62-72.

Feyen O., Lueking A., Kowald A., Stephan C., Meyer H. E., Gobel U., Niehues T., *Anal. Bioanal. Chem.,* 2008; 391: 1713-1720.

Frese K., Eisenmann M., Ostendorp R., Brocks B., Pabst S., *mAbs,* 2013; 5:1-9.

He F., Hogan S., Latypov R. F., Narhi L. O., Razinkov V. I., *J. Pharm. Sci.,* 2010; 99:1707-1720.

He F., Woods C. E., Becker G. W., Narhi L. O., Razinkov V. I., *J. Pharm. Sci.,* 2011; 100:5126-5141.

Hoogenboom H. R., *Nat. Biotechnol.,* 2005; 23:1105-1116.

Horlick R. A., Macomber J. L., Bowers P. M., Neben T. Y., Tomlinson G. L., Krapf I. P., Dalton J. L., Verdino P., King D. J., *J. Biol. Chem.,* 2013; 288:19861-19869.

Hötzel I., Theil F.-P., Bernstein L. J., et al., *MAbs,* 2012; 4:753-760.

Jacobs S. A., Wu S. J., Feng Y., Bethea D., O'Neil K. T., *Pharm. Res.,* 2010; 27:65-71.

Kontermann R., Dubel S. Antibody Engineering 2010. Springer Protocols.

Kuroda K., Ueda M., *Biotechnol. Lett.,* 2011; 33:1-9.

Lauer T. M., Agrawal N. J., Chennamsetty N., Egodage K., Helk B., Trout B. L., *J. Pharm. Sci.,* 2012; 101:102-115.

Lueking A., Beator J., Patz E., Mullner S., Mehes G., Amersdorfer P., *BioTechniques,* 2008; 45:Pi-Pv.

Miller B. R., Demarest S. J., Lugovskoy A., et al., *PEDS,* 2010; 23:549-557.

Mouquet H., Nussenzweig M. C., *Cell. Mol. Life Sci.,* 2012; 69:1435-1445.

Notkins A. L., *Trends Immunol.,* 2004; 25:174-179.

Poetz O., Ostendorp R., Brocks B., Schwenk J. M., Stoll D., Joos T. O., Templin M. F., *Proteomics,* 2005; 5:2402-2411.

Rakestraw J. A., Aird D., Aha P. M., Baynes B. M., Lipovsek D., *PEDS,* 2011; 24:525-530.

Reichert J. M., *mAbs,* 2013; 5:1-4.

Sathish H., Angell N., Lowe D., Shah A., Bishop S. Biophys., *Life Sci.,* 2013; 4:127-146.

Sazinsky S. L., Ott R. G., Silver N. W., Tidor B., Ravetch J. V., Wittrup K. D., *Proc. Natl Acad. Sci., USA* 2008; 105:20167-20172.

Spencer S., Bethea D., Raju T. S., Giles-Komar J., Feng Y., *mAbs,* 2012; 4:319-325.

Sule S. V., Dickinson C. D., Lu J., Chow C. K., Tessier P. M., *Mol. Pharm.,* 2013; 10:1322-1331.

Sule S. V., Sukumar M., Weiss W. F. t., Marcelino-Cruz A. M., Sample T., Tessier P. M., *Biophys.* 2011; 101:1749-1757.

Tasumi S., Velikovsky C. A., Xu G., Gai S. A., Wittrup K. D., Flajnik M. F., Mariuzza R. A., Pancer Z., *Proc. Natl. Acad. Sci., USA* 2009; 106:12891-12896.

Tiller T., Tsuiji M., Yurasov S., Velinzon K., Nussenzweig M. C., Wardemann H., *Immunity,* 2007; 26:205-213.

Tillotson B. J., Cho Y. K., Shusta E. V. *PEDS* 2013; 60:27-37.

Wang F., Sen S., Zhang Y., Ahmad I., Zhu X., Wilson I. A., Smider V. V., Magliery T. J., Schultz P. G., *Proc. Natl. Acad. Sci. USA,* 2013; 110:4261-4266.

Wardemann H., Yurasov S., Schaefer A., Young J. W., Meffre E., Nussenzweig M. C., *Science,* 2003; 301:1374-1377.

Wu H., Pfarr D. S., Johnson S., Brewah Y. A., Woods R. M., Patel N. K., White W. I., Young J. F., Kiener P. A., *J. Mol. Biol.,* 2007; 368:652-665.

Wu S. J., Luo J., O'Neil K. T., et al., *PEDS,* 2010; 23:643-651.

Zhou Z. H., Tzioufas A. G., Notkins A. L., *J. Autoimmun.,* 2007; 29:219-228.

Zweig M. H., Campbell G., *Clin. Chem.,* 1993; 39:561-577.

EXAMPLES

Example 1

Materials and Methods

Polyspecificity Reagent Preparation

Approximately one billion mammalian cells (CHO-S cells or HEK293 cells) or insect cells (Sf9 cells) at approximately $10^6$-$10^7$ cells/mL were each independently transferred from a tissue culture environment into 4×250 mL conical tubes, pelleted at 550×g for 3 min, and each batch of cells (CHO-S, HEK293, and Sf9 cells) were each independently processed and the polyspecificity reagents prepared therefrom were used as described below.

All steps described below were performed at 4 degrees Celsius (° C.) or on ice with ice-cold buffers.

Cells were washed with 100 mL of PBSF (1×PBS+1 mg/mL BSA) and combined into one conical tube. After removing supernatant, the cell pellet was resuspended in 30 mL Buffer B (50 mM HEPES, 0.15 M NaCl, 2 mM CaCl2, 5 mM KCl, 5 mM MgCl2, 10% Glycerol, pH 7.2) and pelleted at 550×g for 3 min. Buffer B supernatant was decanted, and the cells resuspended in 3× pellet volume of Buffer B plus 2.5× protease inhibitor (Roche, complete, EDTA free). Protease inhibitors were included in Buffer B for all subsequent steps.

Cells were homogenized four times with 30-second pulses (Polyton homogenizer, PT1200E) and the supernatant collected after pelleting the homogenized mixture at 2100×g for 5 minutes. The supernatant was cleared with an additional centrifugation step and transferred to a 45 mL Oak Ridge high-speed centrifuge tube (Nalgene). The membrane fraction was pelleted at 40,000×g for one hour at 4° C. Supernatant was collected and set aside as Soluble Cytoplasmic Polyspecific reagent (SCP). The pellet was rinsed with 1 mL Buffer B and the supernatant discarded. The pellet was then transferred into a Dounce homogenizer with 3 mL of Buffer B and resuspended by moving the pestle slowly up and down for 30-35 strokes. The enriched membrane fraction (EMF) was then moved into a new collection tube, and the pestle rinsed to collect all potential EMF components. The protein concentration of the purified EMF and SCPs was determined using standard protein quantification kits (e.g., the Dc-protein assay kit (BioRad)).

The EMF was then transferred into Solubilization Buffer (50 mM HEPES, 0.15 M NaCl, 2 mM CaCl2, 5 mM KCl, 5 mM MgCl2, 1% n-Dodecyl-b-D-Maltopyranoside (DDM), lx protease inhibitor, pH 7.2) to a final concentration of 1 mg/mL in order to solubilize the EMF. The mixture was then rotated overnight at 4° C. followed by centrifugation in an Oak Ridge tube at 40,000×g for 1 hour. The supernatant was collected into a new tube, and represented the unbiotinylated soluble membrane polyspecific reagent (SMP). The protein concentration was quantified as mentioned above for EMF and SCP protein determination.

Biotinylated SMP and SCP Preparation

A NHS-LC-Biotin stock solution was prepared according to manufacturer's protocol (Pierce, Thermo Fisher). Approximately 20 µL of biotin reagent was added for every 1 mg of SMP or SCP sample and incubated at 4° C. for 3 hours with gentle agitation. For EMF sample, the volume was adjusted to 25 mL with Buffer B and transferred to Oak Ridge centrifuge tube. The biotinylated EMF (b-EMF) was then pelleted at 40,000×g for 1 hour. The pellet was then rinsed two times with 3 mL of Buffer C (Buffer B without the glycerol) without disturbing the pellet. Residual solution was removed and the pellet resuspended with the Dounce homogenizer, as described previously, with 3 mL of Buffer C. The resuspended pellet now represents b-EMF and can be solubilized as described above to make b-SMPs.

For SCPs, the biotinylated SCP sample (biotinylated as described above for SMPs), aliquots of no more than ten milligrams of each biotinylated SCP (b-SCP) sample was placed in 15 mL Buffer C and transferred to an Amicon centrifuge filter (15 mL capacity, 30 kDa-cut off). Additional filters were used in order to process the entirety of each b-SCP sample. Each b-SCP-aliquot was then centrifuged at 3600×g until volume is <500 uL for approximately 30-40 minutes in order to remove excess biotin. Each b-SCP aliquot was then washed two times by the addition of 15 mL Buffer C each time. After the final wash, the b-SCP aliquots were combined and total protein quantified. The b-SCPs were then diluted to 1 mg/mL and all preps stored at −80 C until needed for experimental use.

Both biotinylated and non-biotinylated SMPs and SCPs were employed in different selections.

PSR Binding Assay

Approximately $2\times10^6$ IgG-presenting yeast host cells were into transferred into a 96-well assay plate and centrifuged at 3000×g for 3 minutes to remove supernatant. The pellet was resuspended in 50 µL of freshly prepared 1:10 dilution of stock b-SMPs orb-SCPs and incubated on ice for 20 minutes. Cells were washed twice with 200 µL of cold PBSF, resuspended in 50 µL of secondary labeling mix (Extravidin-R-PE, anti-human LC-FITC, and propidium iodide (PI)), and incubated on ice for 20 minutes followed by 2 washes with 200 uL cold PB SF. Cells were then resuspended in 100 µL of ice-cold PB SF, and the plate run on FACSCanto (BD Biosciences) using an HTS sample injector. Flow cytometry data was analyzed for mean fluorescence intensity in the R-PE channel and normalized to proper controls in order to assess non-specific binding. In general, less than 200 mean florescence intensity (MFI) units was considered low non-specificity, 200 to 1000 MFI was considered medium specificity, and >1000 MFI was considered high non-specificity.

Magnetic-Activated Cell Sorting (MACS)

In various Examples described below, host cells were optionally first selected for antigen binding by incubation with streptavidin-conjugated magnetic beads for magnetic-activated cell sorting (MACS), to which biotinylated antigen was bound. Those host cells expressing IgG, which were associated with the cell surface of the host cell harboring the IgG-encoding polynucleotide and which bound to the antigen, were then collected.

PSR Counter-Selection on Diverse IgG Population

A plurality of yeast host cells harboring a plurality of IgG-encoding vectors (approximately $2\times10^7$ different IgGs-encoding vectors) were transferred into a 1.5 mL centrifuge tube and centrifuged at 3000×g for 3 minutes to remove supernatant. The pellet was then resuspended in 200 uL of freshly prepared 1:10 dilution of stock b-SMPs or b-SCPs prepared as described above and incubated on ice for 20 minutes. The yeast cells were then washed twice with 1 mL of cold PBSF and the cell pellet resuspended in 200 uL of secondary labeling mix (Extravidin-R-PE, anti-human LC-FITC, and propidium iodide (PI)). The cells were then incubated on ice for 20 minutes followed by two washes with 1 mL cold PB SF. The cells were then resuspended in 200 uL of ice-cold PBSF and the sample run on FACSAria II (BD Biosciences) using an HTS sample injector. Approximately 100,000 PI-negative yeast events were recorded. The data was used to sort PI-negative (viable), LC-FITC-positive (IgG-presenting), and EA-R-PE negative (polyspecificity reagent-negative) populations. A control yeast sample without polyspecificity reagent added was also run to determine positive and negative delineations. Yeast cells were sorted directly into growth media and either propagated to saturation for additional enrichment sorting or plated on agar plates for obtaining yeast IgG isolates.

Cross Interaction Chromatography (CIC) Assay

Cross-interaction chromatography assays were performed generally as described in the literature (see, e.g., Spencer et al., *MAbs*, Vol. 4(3), pp. 319-325 (2012); Jacobs et al., *Pharm. Research*, Vol. 27(1), pp. 65-71 (2010)). Briefly, A CIC column was prepared by coupling human polyclonal IgG (Sigma I 4506), placed in coupling buffer (0.1M NaHCO3, 0.2M NaCl, pH8.2) to 10 mg/ml, onto a HiTrap NETS-activated resin (GE Healthcare #17-0716-01) followed by passivation with ethanolamine. A blank column was prepared similarly except ethanolamine passivation was performed with no prior IgG coupling. The columns were then connected to an HPLC and run at 0.1 mL per min until baseline was flat. A sample of IgG or Fab at 0.5-1 mg/mL in PBS or HBS was then injected (10 uL). Peak retention times on the column were monitored by A280 nM detector and compared to reference IgGs run on same column to determine level of sample IgG cross-interaction. Typical non-interacting IgG elutes from the column between 8.5 and 9.0 minutes.

Baculovirus Particle Assay

Baculovirus particles (BVP) were prepared by adding 900 uL of stock particles to 900 uL of sodium carbonate buffer (1:2), although this ratio can differ by particle preparation as desired.

Baculovirus particles were incubated on ELISA plates (Nunc-polysorp 80040LE-0903) by adding 50 ul of 1:1 BVP stock: 50 mM sodium carbonate (pH 9.6) per well and placed at 4 degrees C. for 16-24 hours. The next day, unbound BVPs were aspirated from the wells. One hundred ul of PBS with 0.5% BSA was added for 60 min at RT (22-25 C). After 60 min of incubation, the blocking buffer was aspirated, and the wells washed three times with 100 ul of PBS at RT (22-25 C). Fifty ul of respective primary antibodies (i.e. test antibodies) diluted to 1 uM in PBS with 0.5% BSA were then added to the wells and then incubated for 60 min at RT (22-25 C). After 60 min incubation, the test antibodies were aspirated and the wells washed six times in 100 ul of PBS at RT (22-25 C). Fifty ul of anti-Human-IgG-HRP (prepared in PBS) was then added to each well incubated for 60 min at RT (22-25 C). After 60 min incubation, the anti-Human-IgG-HRP was aspirated from the wells, and the wells washed six times in 100 ul of PBS at RT (22-25 C). Fifty ul of TMB substrate was then added to each well and incubated for 10-15 min. The reactions were then stopped by adding 50 ul of 2 M sulfuric acid to each well. Absorbance was then read at 450 nm.

Affinity Assessment of IgGs

Fifty ug/mL Her2-Fc in HBS was loaded onto AHQ sensors (ForteBio) offline for 1 hour. The sensors were then loaded onto a ForteBio RED384 instrument and equilibrated in PBSF prior to dipping into 200 nM Fab samples with association monitoring for 5 minutes. The sensors were then transfer back to PBSF buffer for monitoring dissociation kinetics. Data was then fit to a 1:1 binding model using the ForteBio analysis software to extract kinetic binding parameters.

Cell Staining Assays

Purified IgGs were normalized to 100 nM in PB SF. BT-474 cells were propagated using standard cell culturing techniques. Cells were harvested and $1\times10^5$ cells were aliquoted into a 96-well FACs canto plate. The cells were washed two times with 200 uL PBSF with subsequent centrifugation at 500×g for 3 mins. One hundred uL of 100 nM IgG were incubated with cells on ice for 30 minutes. The cells were then washed two times as before, and incubated with 100 uL of anti-human R-PE secondary reagent for 15 minutes on ice. The cells were then washed an additional two times and resuspended in 100 uL for reading on the FACSCanto (BD Biosciences) using an HTS sample injector.

Example 2

Assessment of CIC Profiles of Clinical Antibodies

A set of clinical antibodies, with examples that are currently in clinical development as well as examples that are currently marketed as therapeutics, was obtained and evaluated by cross interaction chromatography (CIC) using methods generally provided in the art, and briefly outlined above.

Figure 4:
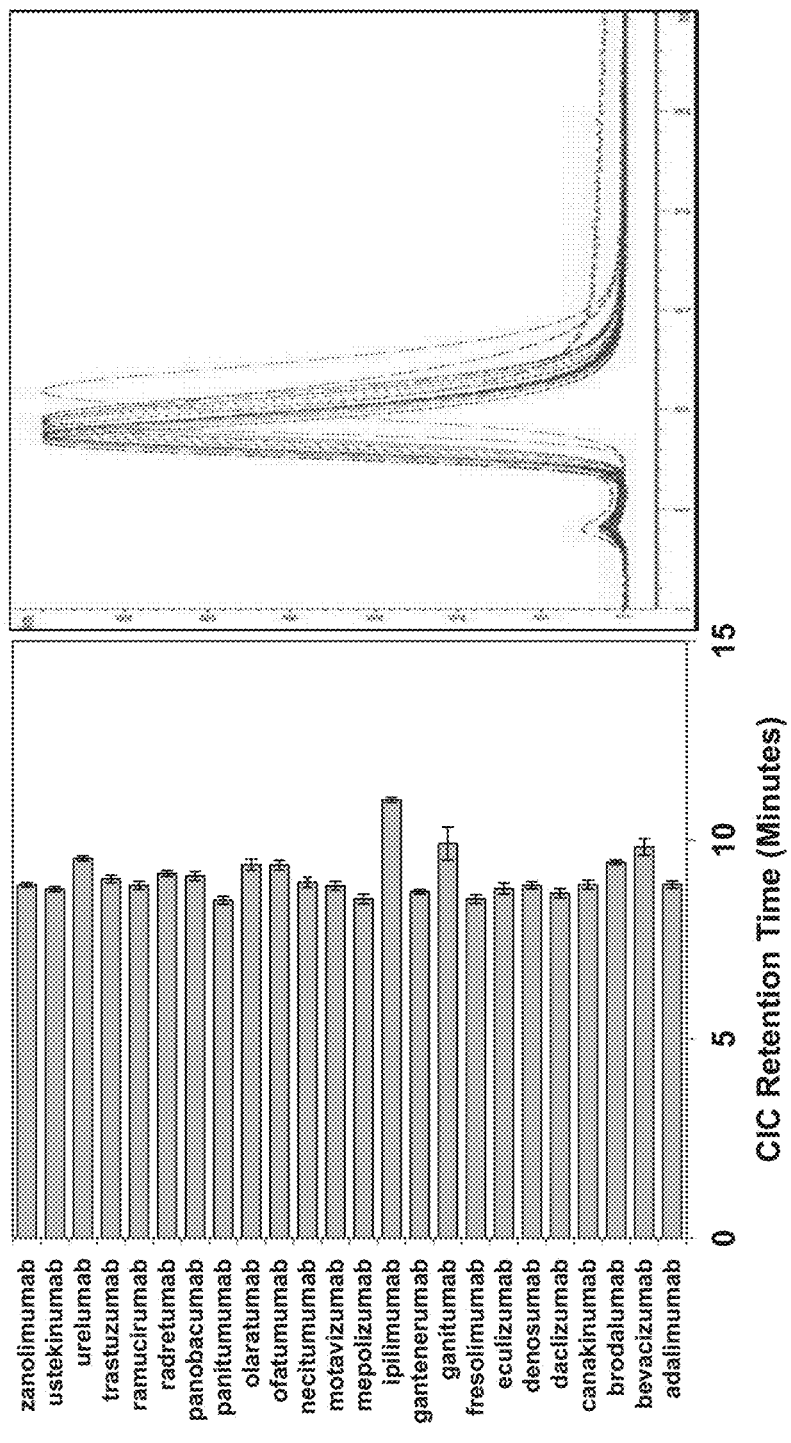
FIG. 4 depicts CIC profiles obtained for the indicated clinical antibodies.

The results, indicated in FIG. 4, demonstrate that each member of the set of clinical antibodies possess an attractive CIC profile, with retention times ranging from approximately 8 minutes to no greater than approximately 11 minutes. As attractive CIC profiles are considered indicative of developable antibodies, these results indicate that CIC retention times and profiles approximately within this range is predictive of enhanced developability of polypeptides, such as antibodies.

Comparison of CIC Profiles from Clinical Antibodies and Antibodies from Display Libraries The same set of 24 clinical antibodies (designated as C in FIGS. 3, 5, 6, 9, and 11) was again subjected to CIC, as well as the following:

158 antibodies randomly chosen from a yeast host cell genotype-phenotype library, which was not interrogated with any antigen and which expresses approximately $1\times10^{10}$ full-length IgGs (designated as U in FIGS. 3, 5,6, 9, and 11); and 48 preferred antibodies selected from the same yeast host cell genotype-phenotype library from which the U antibodies were obtained, but which were previously selected via antigen-positive selections based on solely on high affinity and selectivity towards antigen (i.e., not counter-selected against polyspecific antibodies) and considered "good antigen-binders" (designated as P in FIGS. 3, 5,6, 9, and 11).

Figure 5:
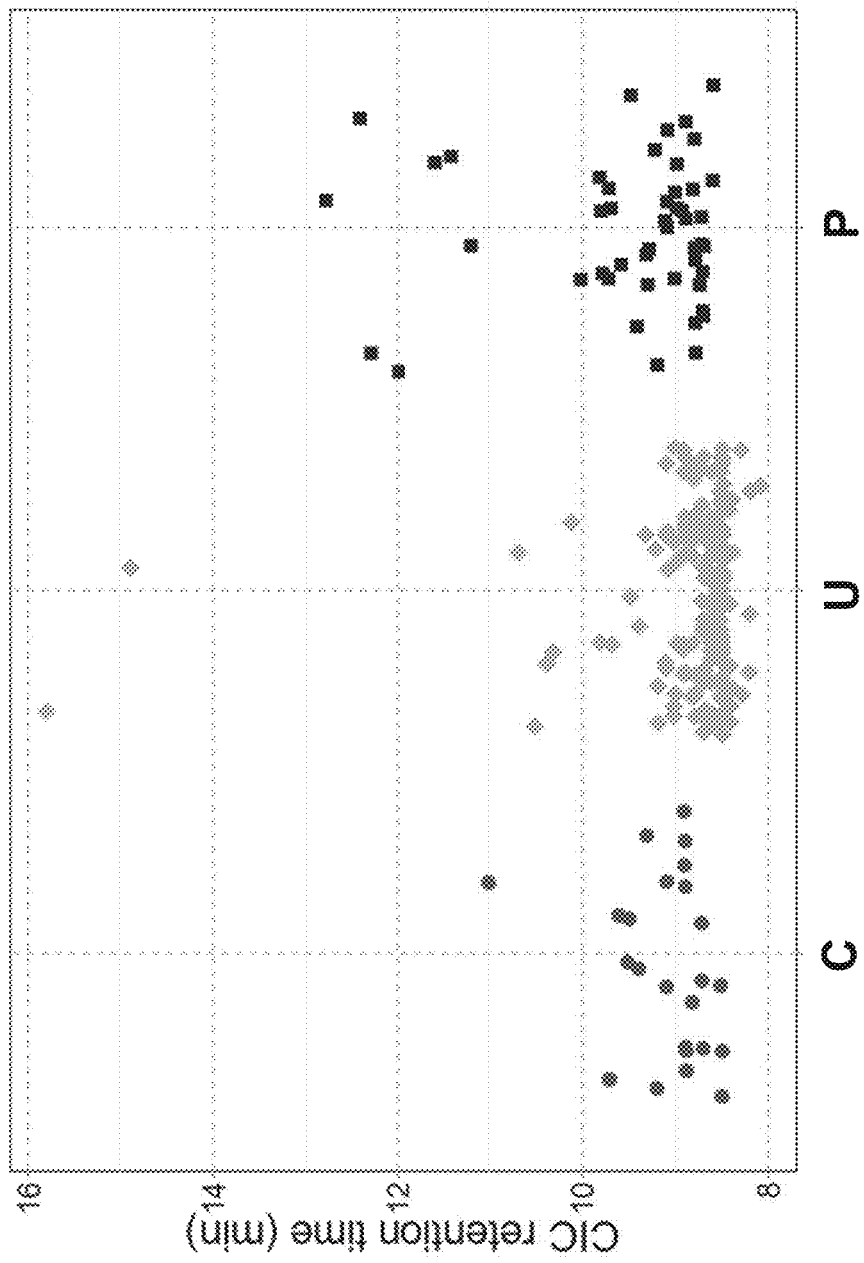
FIG. 5 provides a plot of CIC retention times obtained from a CIC assay of the C, U, and P sets of antibodies as described in the EXAMPLES and depicted in FIG. 3.

The results, depicted in FIG. 5, demonstrate that whereas the majority of both U and P antibodies displayed CIC profiles and retention times that were similar to those obtained for C antibodies, and are thus predicted to have enhanced developability, a minority of both the U and the C antibodies displayed longer retention times and are thus predicted to have decreased developability. With regard to the P antibodies, the relative proportion of antibodies having unattractive CIC retention times, and hence predicted to have decreased developability was increase relative to the proportion of antibodies predicted to have decreased developability in the U subset. These results indicated that, positive selections based on affinity towards antigen alone (i.e., not counter-selected against polyspecific antibodies) have a propensity to also select for polyspecificity, as indicated by the increased proportion of so-selected antibodies displaying unattractive CIC retention times and profiles.

In a separate experiment, CIC profiles were obtained for a subsequent preparation of the C, U, and P, sets of antibodies in addition to a set of 116 un-preferred antibodies selected from the same yeast host cell genotype-phenotype library from which the U and P antibodies were obtained (designated as D in FIGS. 3, 5,6, 9, and 11). This D set of antibodies were selected via antigen-positive selections similar to the P antibodies (i.e., not counter-selected against polyspecific antibodies); however, this set of antibodies displayed sub-optimal (i.e., low) affinity toward antigen and considered "poor binders".

Figure 6:
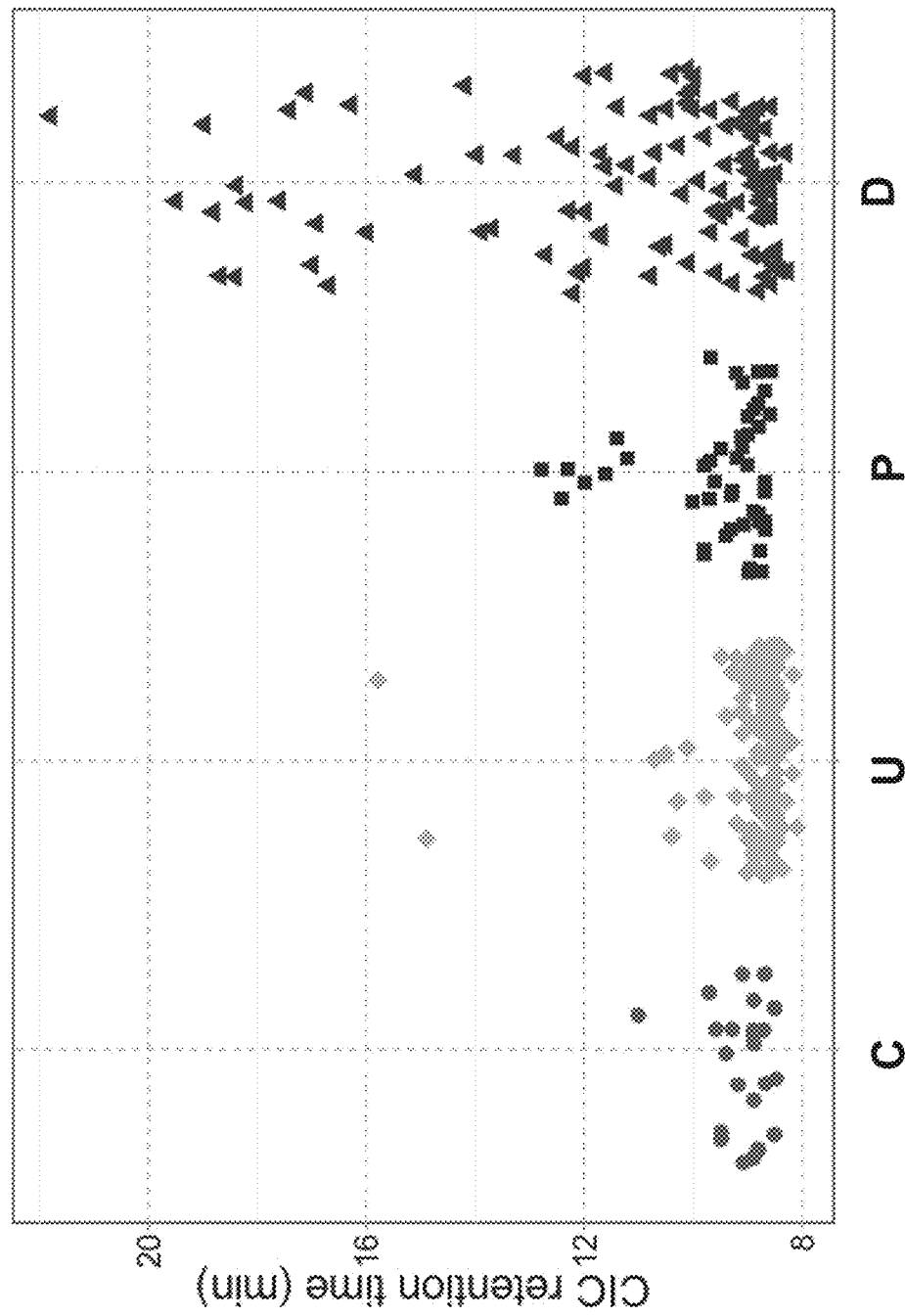
FIG. 6 provides a plot of CIC retention times obtained from a CIC assay of the C, U, P, and D sets of antibodies as described in the EXAMPLES and depicted in FIG. 3.

The results, depicted in FIG. 6, demonstrate that a large proportion (approximately half) of the D set of antibodies were found to display unattractive CIC profiles and retention times, and thus were predicted to have decreased developability.

Correlation Between PSR Interaction of Antibodies and CIC Retention Time and Profile In order to assess whether CIC retention time observed for antibodies may correlate with polyspecificity as demonstrated by interaction with the disclosed and claimed PSRs, additional preparations of each of the C, U, P, and D, antibodies were subjected to CIC. Additionally, a sample of each preparation was contacted with a PSR (SMP) prepared as described above and as schematically depicted in FIG. 7, and antibodies within the SMP-antibody mixture that interacted the SMP were detected by employing FACS as described above. Mean florescence intensity (MFI) was recorded for each detected interaction, and each detected antibody was ranked based on the relative degree of interaction, expressed as MFI, of each polypeptide detected as interacting with the SMP. The MFI scores for each of the antibodies was plotted against the CIC retention time for each of the antibodies, as indicated in the FIG. 9.

The results indicate that those antibodies that were detected as having a relatively high degree of interaction with the PSR (SMP) also displayed unattractive CIC profiles and retention times. Thus, the antibodies that had relatively high MFI scores and deemed to be polyspecific antibodies, defined in this experiment as MFI scores above approximately 500 correlated with unattractive CIC profiles and retention times, and were thus predicted to have decreased developability. Those antibodies that had relatively moderate MFI scores and deemed to be moderately polyspecific antibodies, defined in this experiment as MFI scores within the range of above 200 and below 500, correlated with CIC profiles and retention times of intermediate attractiveness and were thus predicted to have moderate developability. In contrast, the antibodies that had relatively low MFI scores and deemed to not be polyspecific antibodies, defined in this experiment as MFI scores above below 200, correlated with attractive CIC profiles and retention and were thus predicted to have enhanced developability. Furthermore, the results demonstrate that the degree of interaction of polypeptides, such as antibodies, from or in a plurality of polypeptides with PSR correlates with and predicts CIC profile and retention time. Accordingly, the degree of interaction of polypeptides, such as antibodies, with PSR correlates with and predicts developability.

Receiver operating characteristic (ROC) analysis was then performed in accordance with standard statistical and computational procedures (see, e.g., Surujballi et al., *Clinical and Diagnostic Lab. Immunol.*, Vol. 8(1), pp. 40-43 (2001) in order to assess the extent to which polyspecificity of polypeptides, such as antibodies, as demonstrated by the degree of interaction with PSR, constitutes a sensitive and specific predictor of CIC retention time and profile, and hence degree of developability.

Figure 10:
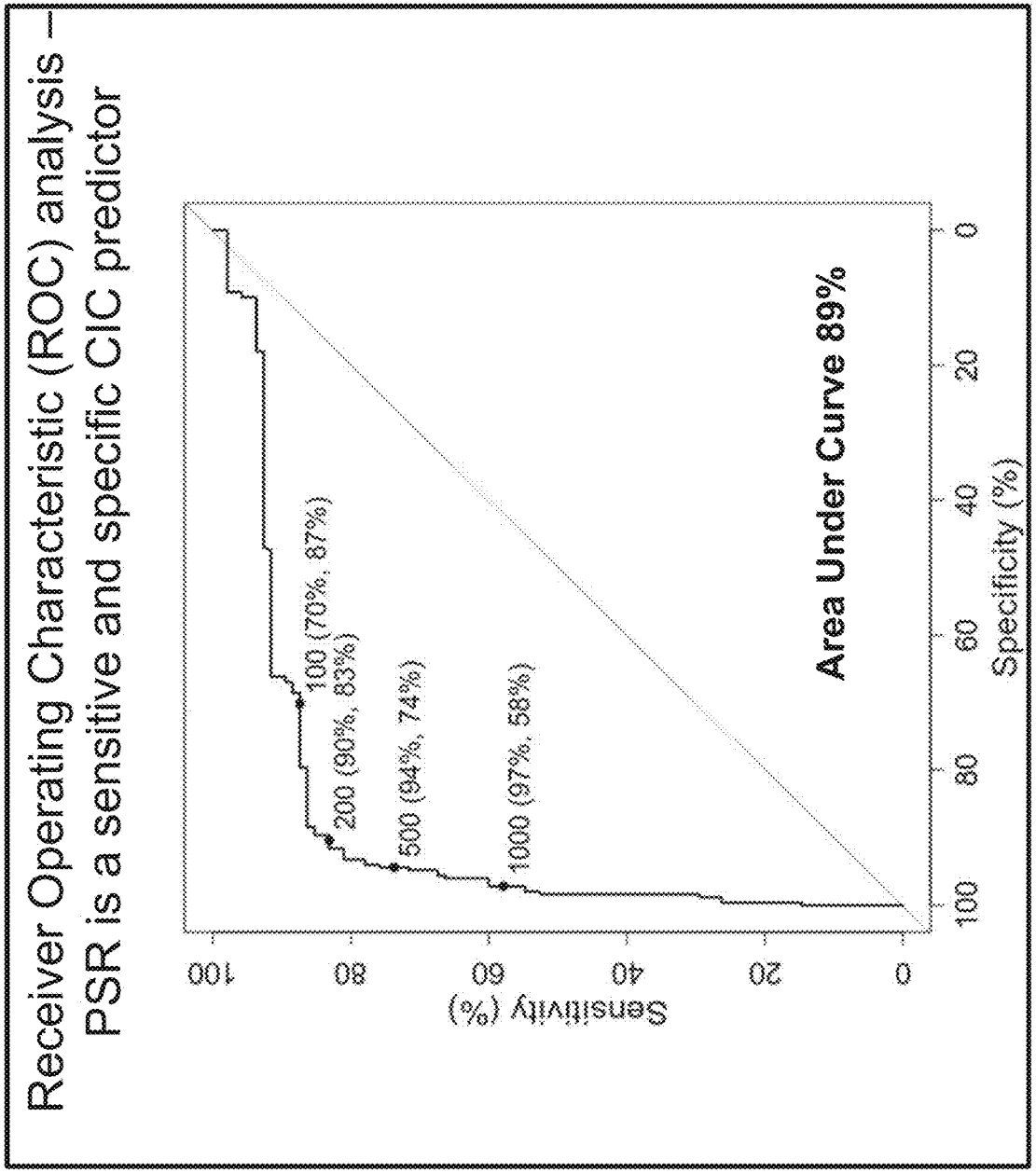
FIG. 10 provides a graphical representation of a receiver operating characteristic analysis of the capability of the herein and throughout disclosed PSRs to predict CIC profiles of polypeptides.

The results, depicted in FIG. 10, demonstrate that polyspecificity of polypeptides, such as antibodies as ascertained by the degree of interaction between PCR and polypeptides, is a specific and sensitive predictor of CIC retention time and profile, and thus a predictor of developability. For example, MFI scores within the range of greater than 200 to less than 500 are deemed to constitute acceptable predictors of such; MFI scores below 200 are deemed to constitute highly acceptable and desired predictors of such.

Correlation of PSR Interaction and BVP-ELISA Readout

Figure 11:
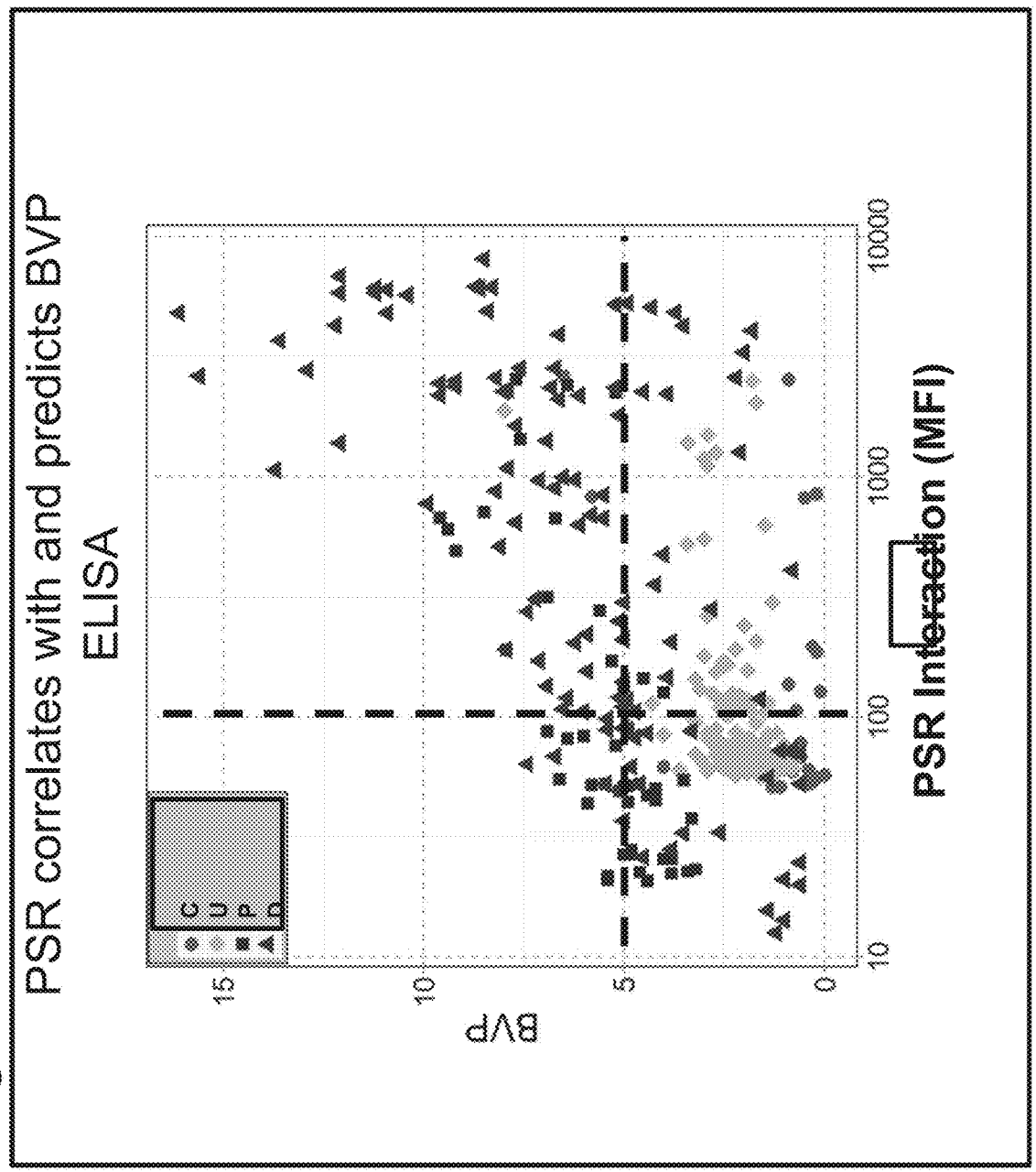
FIG. 11 provides a graph plotting BVP-ELISA readouts (y-axis) as a function of the degree of PSR interaction expressed as mean florescence intensity (MFI) for the C, U, P, and D sets of antibodies as described in the EXAMPLES and depicted in FIG. 3.

A Baculovirus-ELISA assay has been developed in order to assess and predict circulation clearance rates of post-discovery antibodies (see, e.g., Sotzel et al, mABS, Vol. 4(6), pp. 753-760 (2012). In order to determine whether PSR interaction of antibodies correlates with and predicts BVP-ELISA readout, samples of the C, U, P, and D sets of antibodies described above were prepared and subjected to the BVP-ELISA as described above. Samples of the C, U, P, and D sets of antibodies were also contacted with PSR (SMP) and MFI scores obtained. MFI scores for each antibody was ranked and plotted against the BVP-ELISA readout for each antibody, as depicted in FIG. 11.

The results demonstrate that the degree of PSR interaction of antibodies correlates with and thus predicts, BVP-ELISA readout. Accordingly, the relative degree of interaction of antibodies, which provides a relative degree of polyspecificity of antibodies, correlates with relative degree of developability of antibodies.

Example 3

Assessment of PSR Interaction in Polypeptide Library Selections

In order to determine whether polypeptides selected from a plurality of polypeptides, such as a library of polypeptides, possess detectible PSR interaction (and hence, polyspecificity), FACS-based analysis of PSR polyspecificity of antibodies selected from a plurality of antibodies expressed by a yeast host cell genotype-phenotype library was performed, wherein the selected antibodies had been first selected based solely on affinity towards a test binding partner (i.e., an antigen of interest) in the absence of a PSR. Host yeast cells from the yeast host cell genotype-phenotype library that expressed the selected antibodies were propagated to sufficient cell number, contacted with a PSR (SMP), thereby generating a plurality-PSR reagent mixture. The plurality-PSR reagent mixture was then subjected to FACS in order to detect polyspecific polypeptides with the plurality-PSR reagent mixture that significantly interacted with the PSR. The results, depicted in the left hand window of FIG. 12, demonstrate that many polypeptides that were first selected based on antigen affinity (i.e., antigen-positive selection) alone, were polyspecific as determined by a significant degree of interaction of such polyspecific polypeptides with the PSR.

Figure 12:
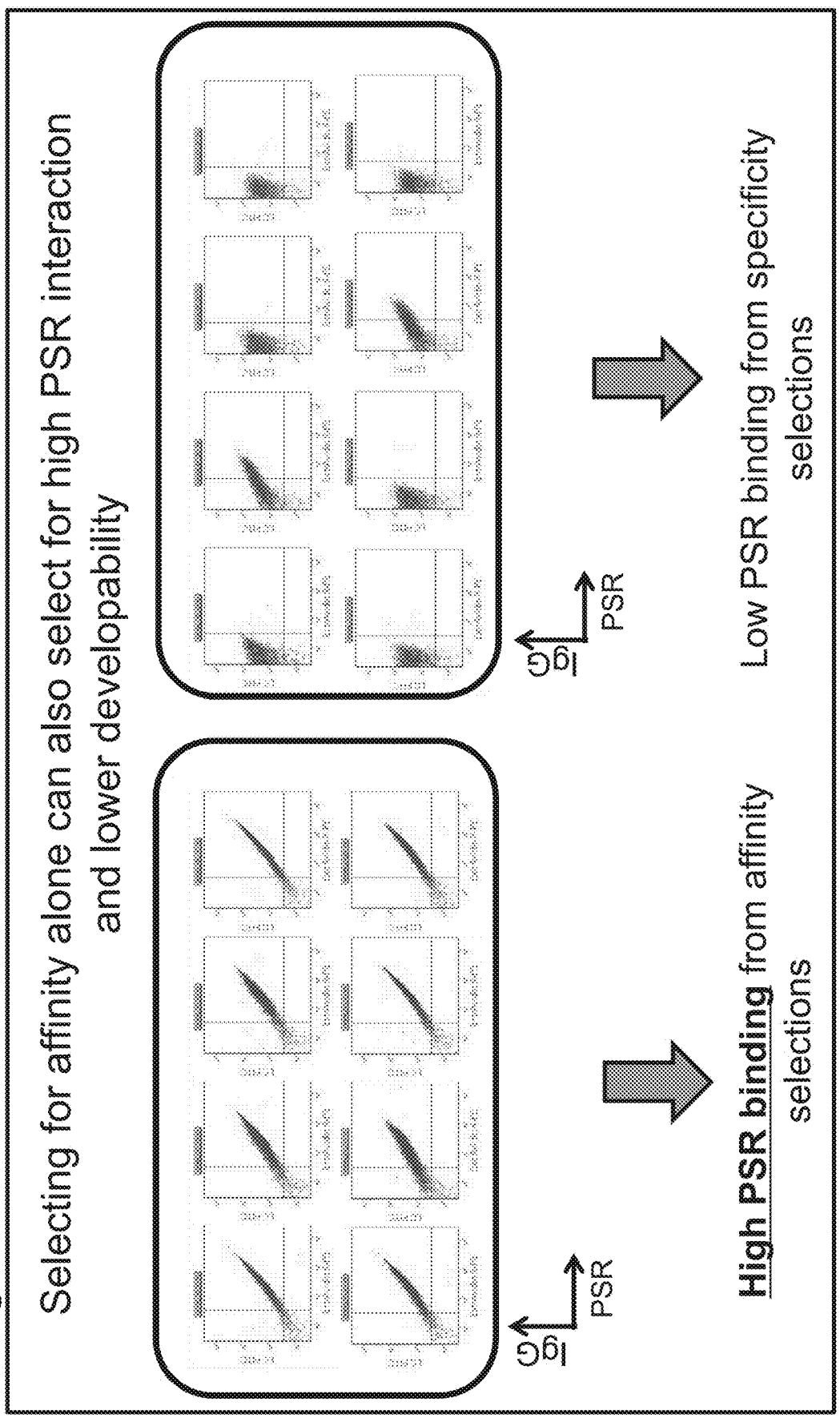
FIG. 12 provides the results of: FACS-based analysis of PSR polyspecificity of polypeptides selected from a plurality of polypeptides expressed by a yeast host cell genotype-phenotype library, wherein the selected polypeptides had been first selected based on affinity towards a test binding in the absence of a PSR (left window); and FACS-based analysis of polypeptides selected from a plurality of polypeptides expressed by a yeast host cell genotype-phenotype library which was counter-selected against polyspecific polypeptides by contacting the plurality with a PSR (SMP).

In contrast, as depicted in the right hand window of FIG. 12, when a plurality of antibodies expressed by a yeast host cell genotype-phenotype library was contacted with the PSR and counter-selected against detected polyspecific polypeptides in accordance with the methods disclosed and claimed herein and throughout, polypeptides from the plurality that do not significantly interact with the PSR were detected and selected. Accordingly, contacting a plurality of polypeptides, such as antibodies, with a PSR allows for selection of developable antibodies from a plurality comprising developable and polyspecific polypeptides. Additionally, contacting a plurality of polypeptides, such as antibodies, with a PSR allows for generating an enriched plurality of developable polypeptides from a non-enriched plurality of polypeptides.

Figure 13:
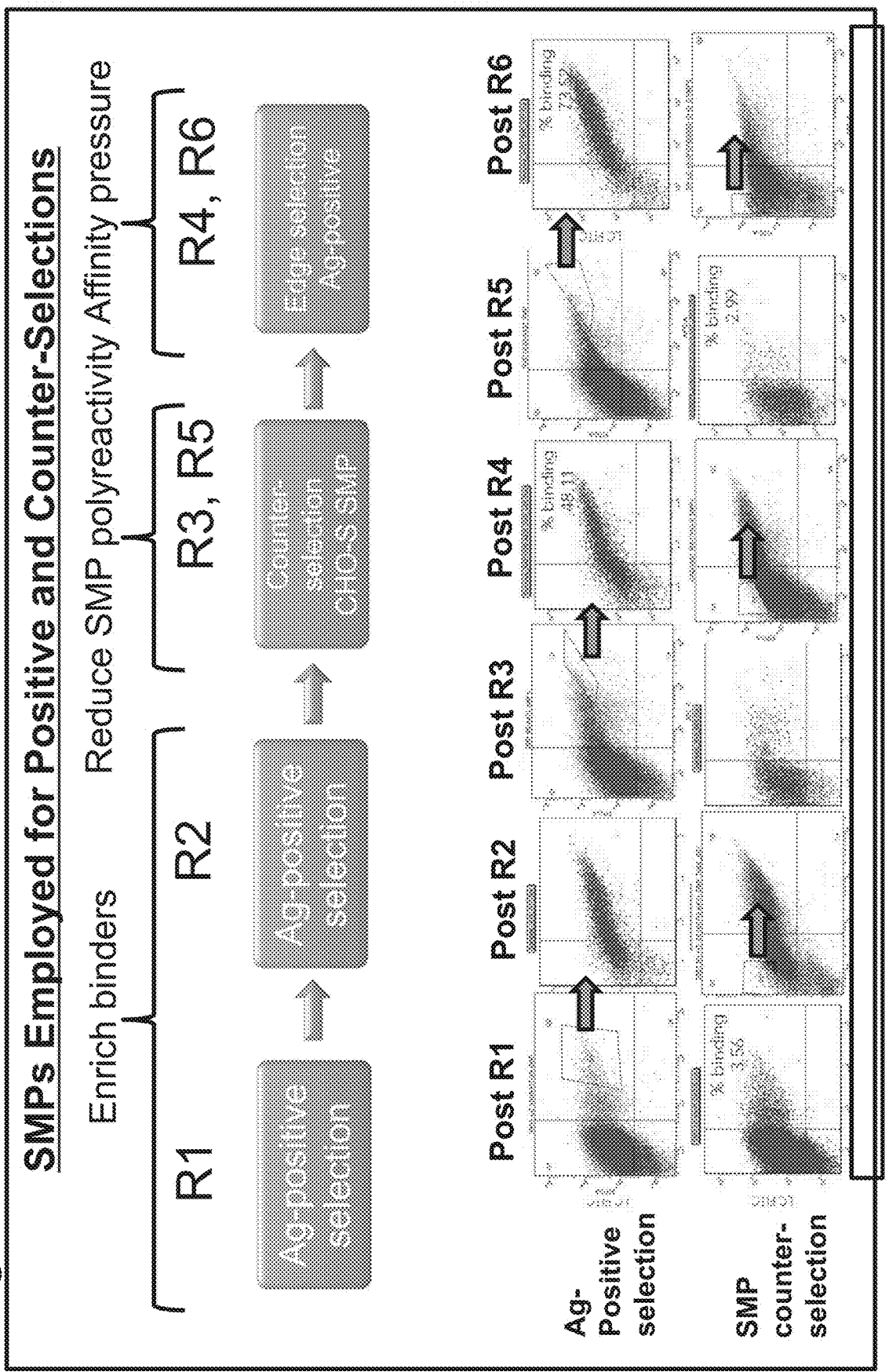
FIG. 13 provides an exemplary scheme for employing a method of alternating antigen-positive selection and PSR (SMP) counter-selection rounds in order to counter-select against polyspecific antibodies. FACS-based plots which provide the results of each selection and counter-selection round are provided.

Assessment of Selection of Polypeptides from Polypeptide Display Libraries Using Alternating Rounds of Positive-Antigen (Affinity) Selections and Counter-Selections In order to determine whether employing methods of alternating rounds of positive-antigen (affinity) selections and PSR counter-selections provide for an affinity maturation methodology that yields developable polypeptides with improved affinity, the selection scheme outlined in the top portion of FIG. 13 was employed using a plurality of antibodies expressed by a yeast host cell genotype-phenotype library. As indicated, two rounds (R1 and R2) of positive antigen (affinity) selections using FACS were performed, followed by a round three (R3) counter-selection, which counter-selection was performed by contacting the plurality host cells selected in R2 with a PSR (SMP), thereby generating a plurality-PSR reagent mixture. Polyspecific polypeptides detected in this plurality-PSR reagent mixture were counter-selected against in R3, thereby generating an enriched plurality of developable antibodies. The yeast cells expressing the developable antibodies were subjected to another round of antigen-positive selection (R4), then another round of counter-selection (R5), then another round or antigen positive selection (affinity) (R6). Post-round FACS plots of the pluralities of polypeptides/yeast host cells expressing and displaying them are provided at the bottom portion of FIG. 13. Arrow in each plot indicates the plurality, encompassed by the indicated selection gate that was subjected to each subsequent selection (or counter-selection) round.

The results indicate that such alternating rounds of antigen-positive (affinity) and counter-selection against polyspecific antibodies provides methods of selecting developable polypeptides while affinity maturing the developable population. In such methods, use of the alternating counter-selection rounds provides for the continual counter-selection against those affinity-matured polypeptides in the plurality that also have detectable polyspecificity. Accordingly, the methods also provide methods of generating enriched for developable antibodies from pluralities of polypeptides obtained from previous affinity maturation (antigen-positive) rounds, which pluralities comprise both developable and polyspecific polypeptides.

Figure 14:
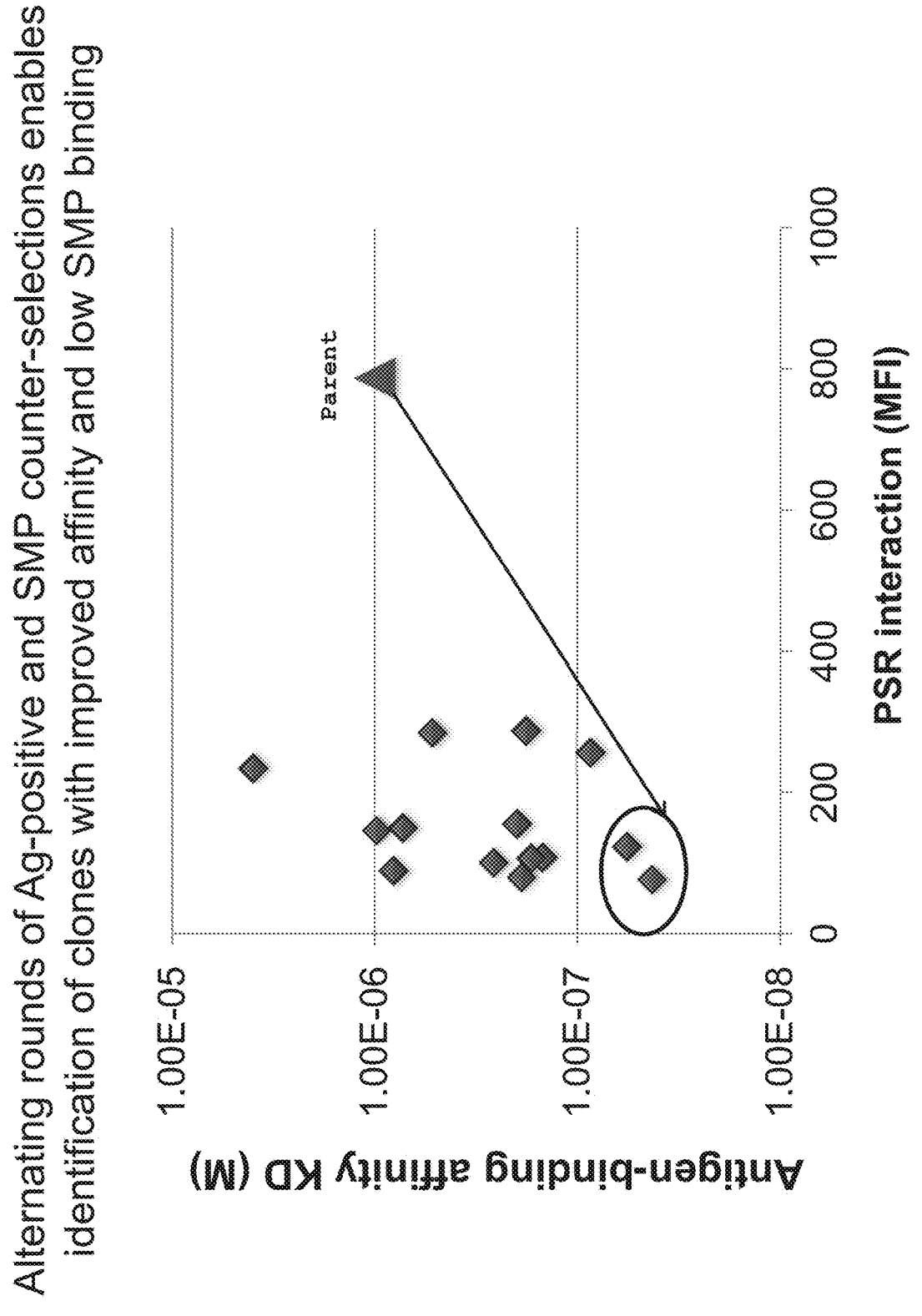
FIG. 14 depicts improved affinity and low PSR (SMP) polyspecificity achieved by performing the alternating rounds of antigen-positive selections and SMP counter-selections depicted in FIG. 13.

The improvement in affinity observed for the developable antibodies detected and selected by performing the experiment above is depicted in FIG. 14. As indicated, the parent polypeptide, the sequence of which was variegated, thereby generating a library of polypeptides (and yeast host cells expressing and displaying them), and developable antibodies detected and selected from the library in the experiment exhibited improved binding affinity to the test binder (antigen), while also exhibiting enhanced developability.

Example 4

Figure 15:
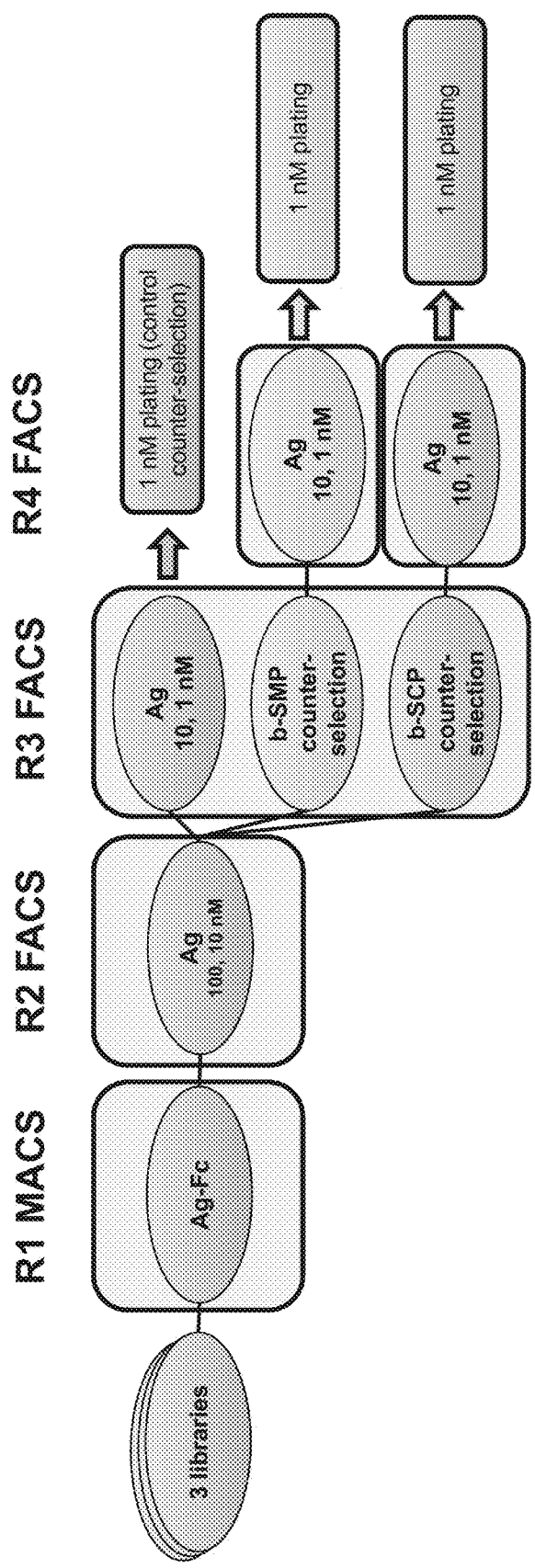
FIG. 15 provides an outline of the selection scheme employed in Example 4.
Figure 16:
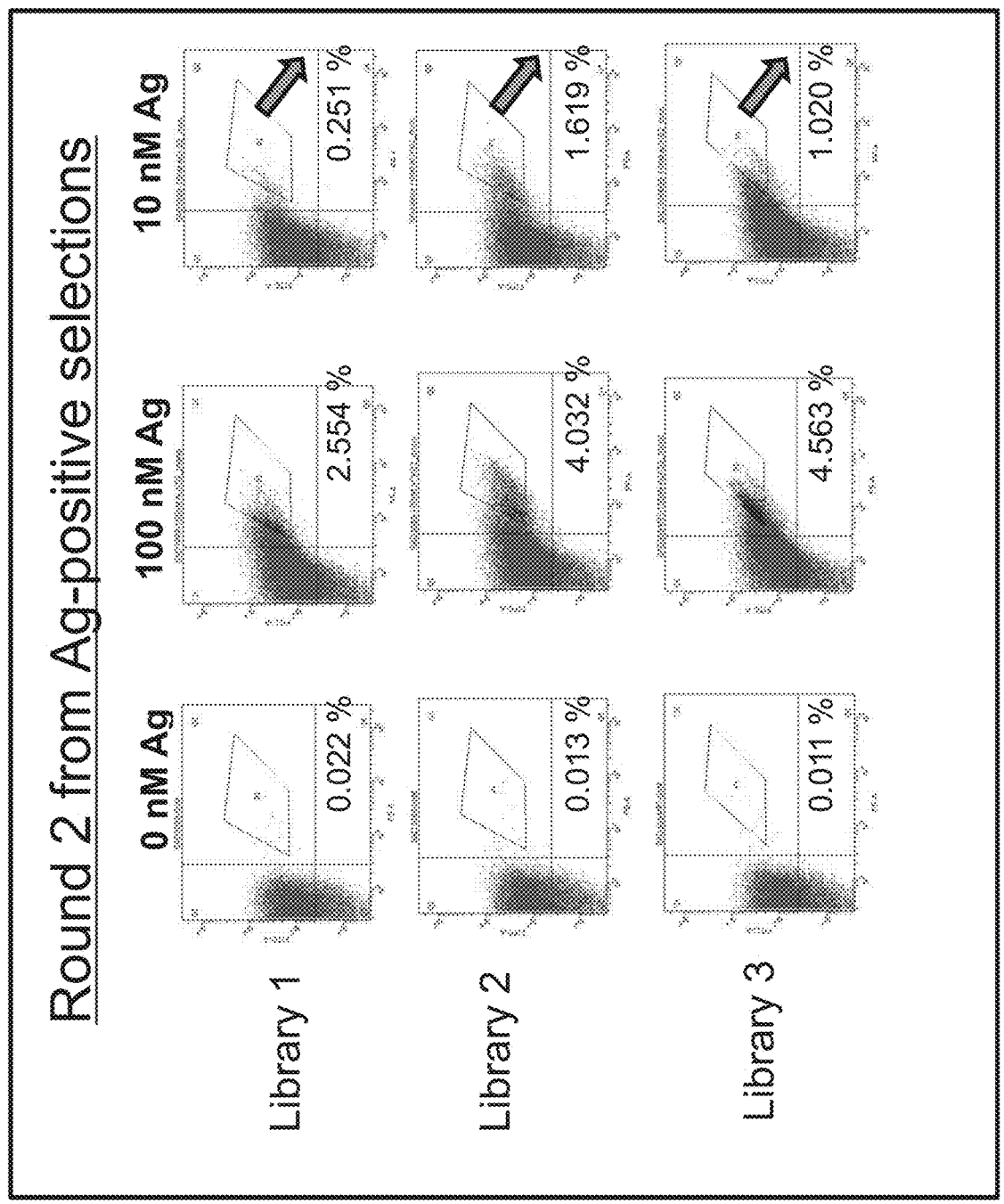
FIG. 16 depicts FACS plots of the antigen-positive selections performed in R2 as depicted in FIG. 15 and as described in Example 4.

Comparison of Counter-Selections Employing SMPs Versus Counter-Selections Employing SCPs Both SMPs and SCPs prepared as described above were next evaluated and compared for the ability to counter-select against polyspecific antibodies (IgGs) from a plurality of antibodies expressed by yeast host cell genotype-phenotype libraries. As depicted in FIG. 15, each of three different genotype-phenotype host cell libraries were subjected to four consecutive rounds of selections (R1 through R4). R1 was performed using magnetic activated cell sorting (MACS) of each genotype-phenotype library, which were each contacted with antigen (a mammalian cell surface protein) that was conjugated to the magnetic beads. Cells from each library which bound to the beads via expressed IgG were collected and then subjected to flow cytometry (florescence-activated cell sorting (FACS)) in the presence of zero (secondary only as negative control), 10, or 100 nM antigen (Schematized in FIG. 15; results depicted in FIG. 16), and antigen-binding populations from each library in the 10 nM antigen condition were collected for further selections. As depicted in the top row of each of FIGS. 17, 18, and 19, selections were performed for antigen-positive populations that interacted with 1 nM antigen from each of the three libraries, and then plated. Yeast host cells collected in R2 were subjected to a either Ag-positive selections or counter-selections in (R3) in the presence of either a 1:10 dilution of stock b-SMP or a 1:10 dilution of stock b-SCP as indicated in FIGS. 17, 18, and 19 (Top row of each Figure, see gating in next-to-last and last FACS plots on the right, respectively, in each Figure, indicating counter-selections against polyspecific antibodies). In order to confirm that the counter-selected cell populations maintained binding affinity for the antigen while possessing minimal PSR polyspecificity, the counter-selected populations were recovered (denoted by ascending arrows), grown up, and divided into five aliquots for the R4 selection. Each of the five aliquots from each counter-selection (b-SMP and b-SCP), were then contacted with one of the following: 0 nM antigen, 1 antigen, 10 nM antigen, a 1:10 dilution of stock SMP, or a 1:10 dilution of stock SCP, as indicated in FIGS. 17, 18, and 19 middle and bottom rows.

The results demonstrate that including the counter-selection against either p-SMP or b-SCP resulted in selections of yeast cells expressing IgGs that specifically interacted with the antigen with an affinity of no lower than 1 nM, and did not significantly interact with the tested b-PSR. Thus, both SMPs and SCPs may be employed as PSRs in selections for counter-selecting against polyspecific polypeptides that possess a lower degree of developability. This also allows for the enrichment for polypeptides in a plurality of polypeptides (and host cells harboring polynucleotides that encode for the polypeptides), such as antibodies, that possess a higher degree of developability.

Figure 20:
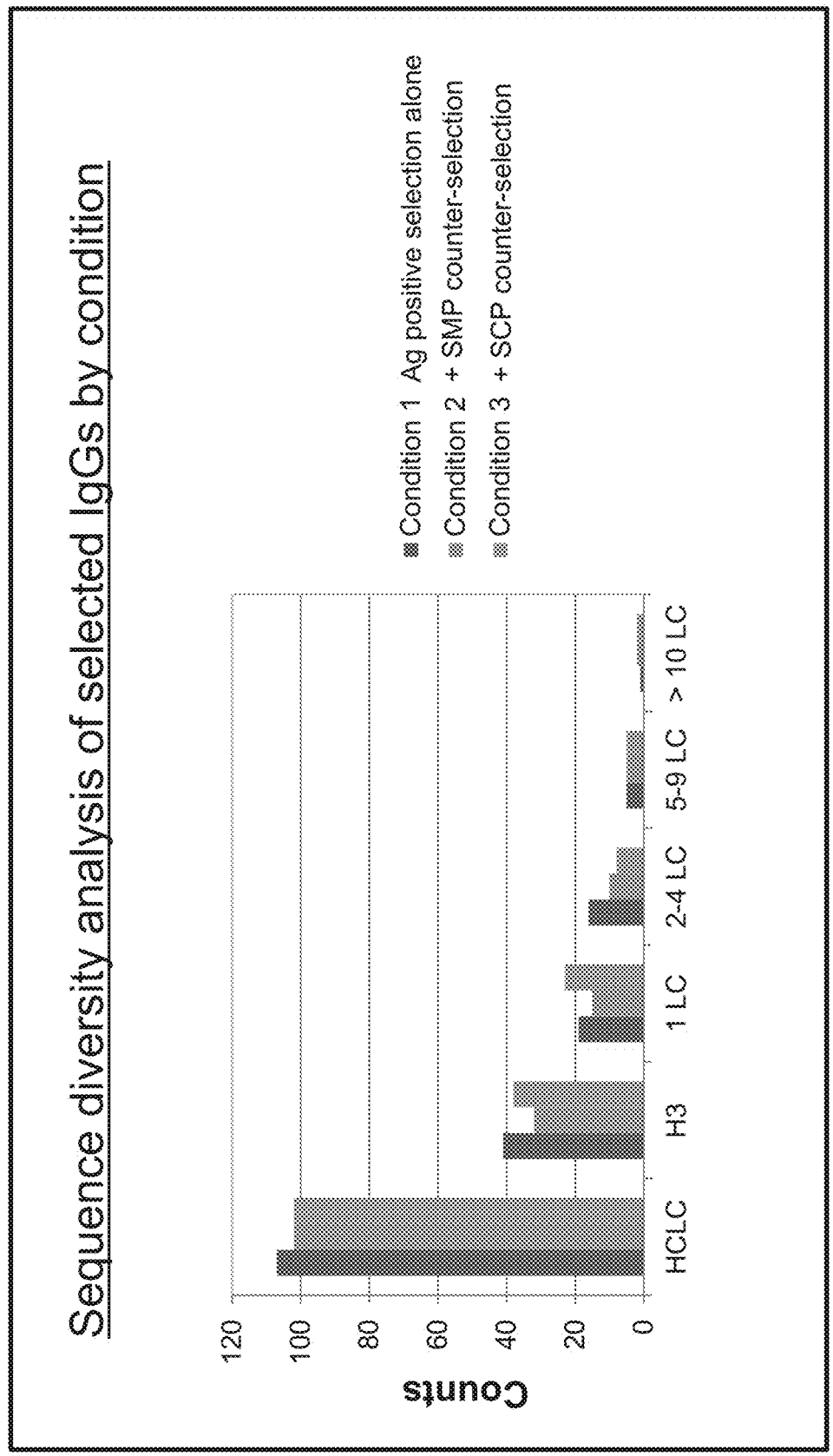
FIG. 20 depicts the amino acid sequence diversity of antibodies selected as described in Example 4.

FIG. 20 provides a depiction of the sequence diversity observed in the plurality of developable polypeptides that were selected in experiment depicted in FIGS. 17 through 19. The results indicate that both methods employing either SMP or SCP counter-selection yield pluralities of developable antibodies that collectively display sequence diversity that is comparable to the sequence diversity obtained when positive antigen (affinity) selections are performed alone (with no counter-selections). Accordingly, there is no appreciable loss of sequence diversity in selected pluralities of antibodies from display libraries when counter-selections are employed in concert with antigen-positive (affinity) selections.

Figure 21:
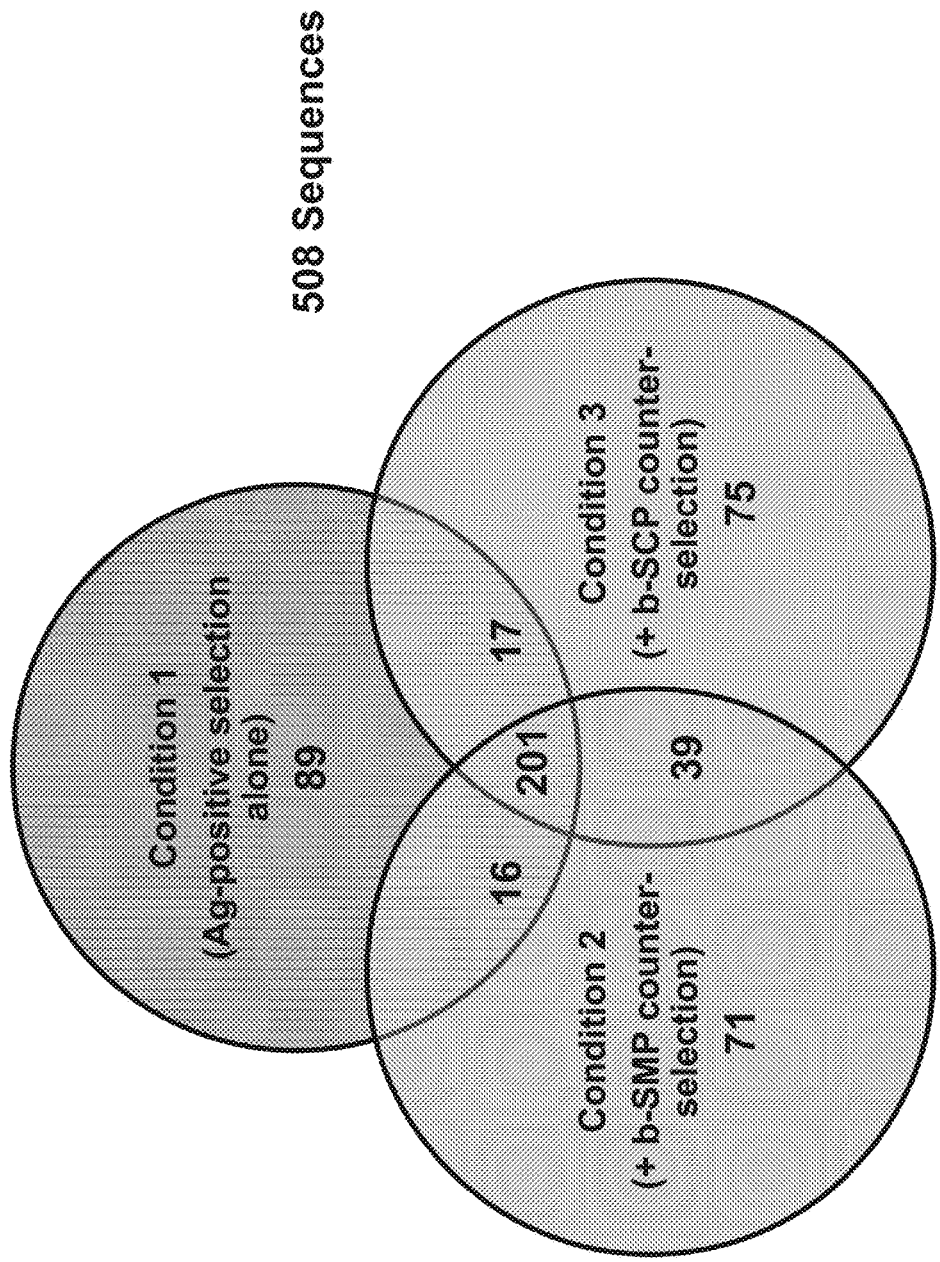
FIG. 21 provides a Venn diagram depicting unique and common antibody sequences selected in each condition as tested and described in Example 4.
Figure 22:
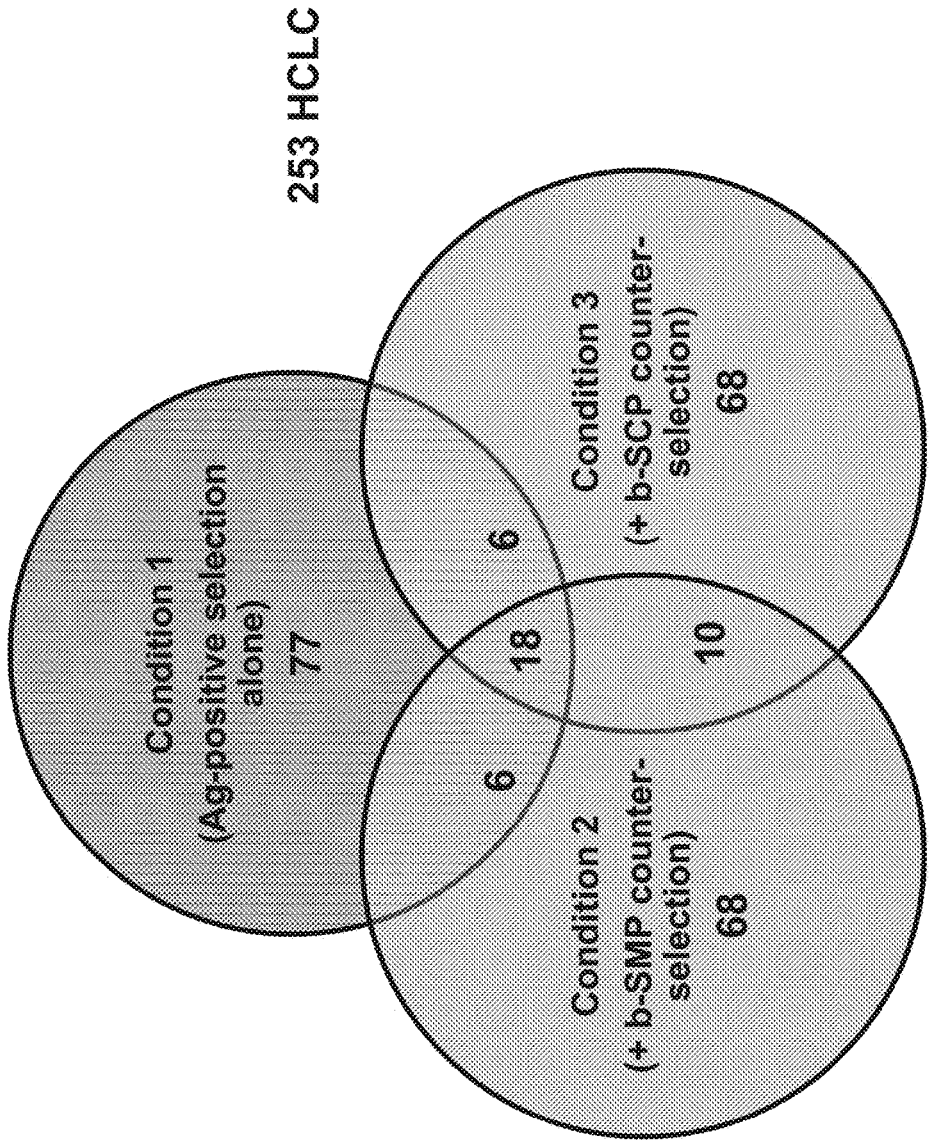
FIG. 22 provides a Venn diagram depicting unique and common antibody HCLC (heavy chain and light chain) sequences selected in each condition as tested and described in Example 4.
Figure 23:
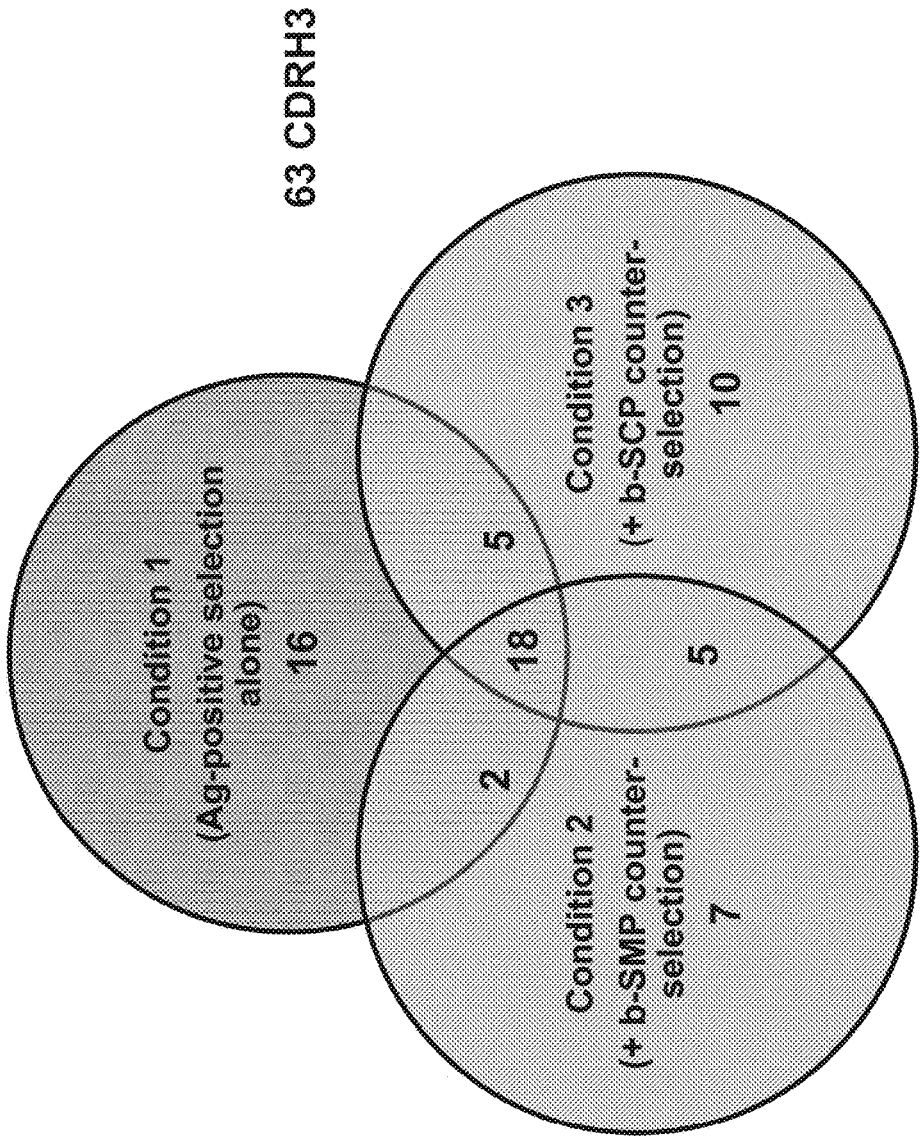
FIG. 23 provides a Venn diagram depicting unique and common antibody CDRH3 (heavy chain and light chain) sequences selected in each condition as tested and described in Example 4.

FIGS. 21 through 23 proved Venn diagrams which depict the amount of unique antibody sequences selected in each condition (no counter-selection, SMP counter-selection, and SCP counter-selection). The results indicate that whereas some sequences selected were common to all or subsets of the three different selection conditions, a large number of sequence selected in each selection condition were unique to each condition.

Figure 24:
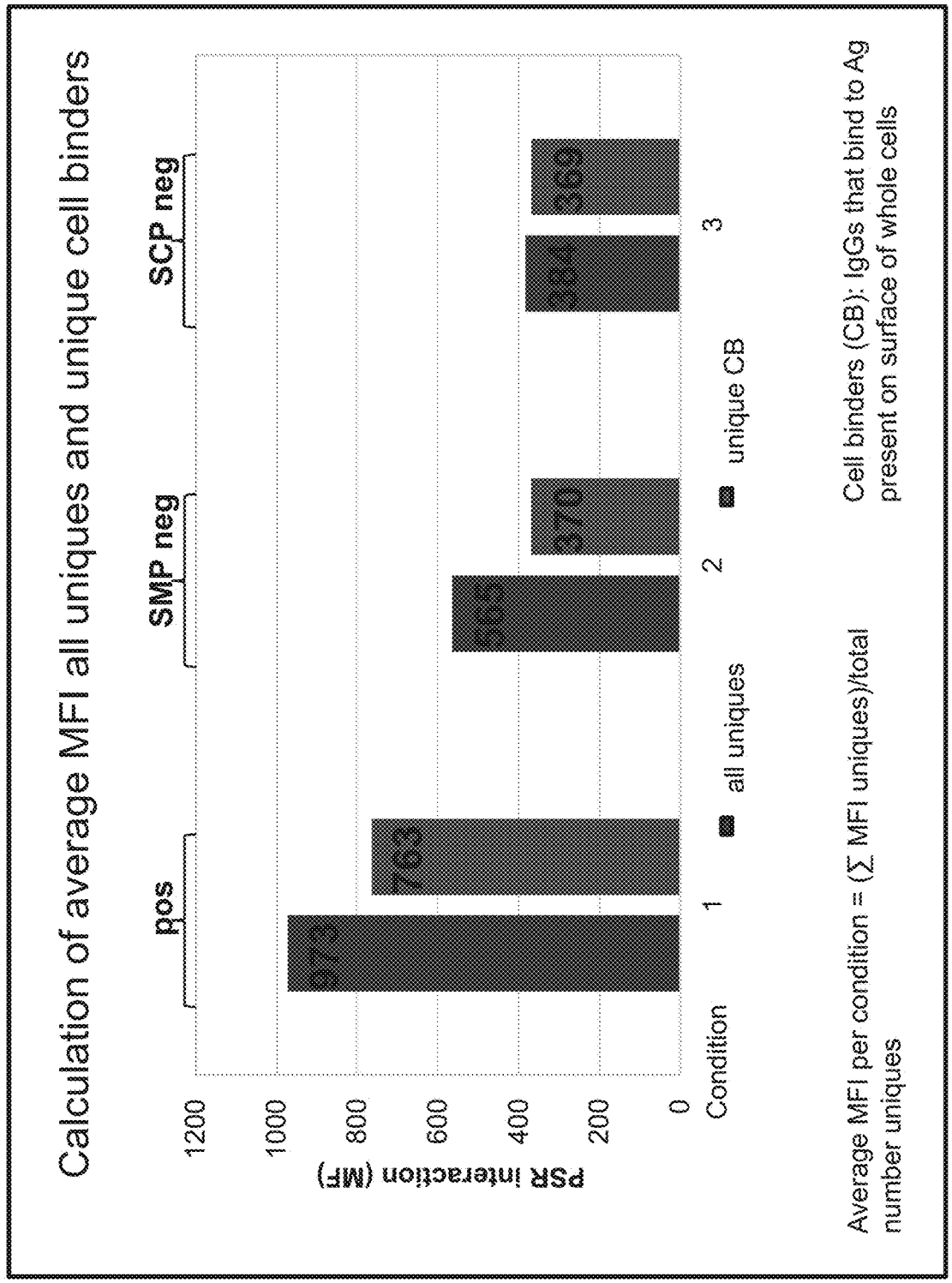
FIG. 24 provides average PSR interaction (MFI) data for antibodies selected in each condition as tested and described in Example 4.
Figure 25:
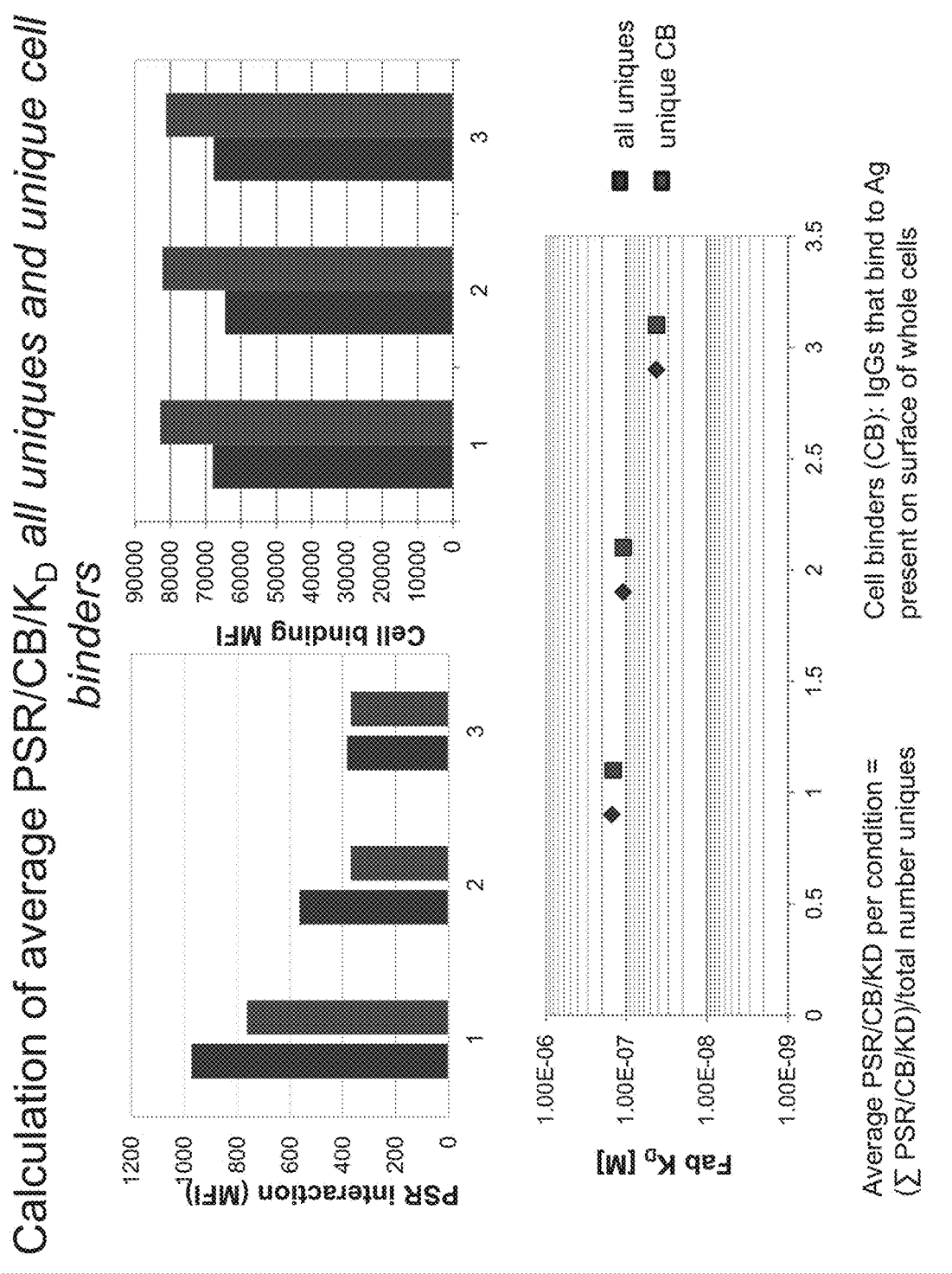
FIG. 25 provides average PSR interaction (MFI), whole cell binding (MFI), and affinity (KD) data for antibodies selected in each condition as tested and described in Example 4.

FIGS. 24 and 25 collectively depict: the average SMP scores (MFI) of each unique antibody (unique based on amino acid sequence) selected in each condition; average whole cell binding (MFI) to a cell line expressing the test binding partner (cell surface antigen) on the cell surface as a positive control for native antigen binding in the context of whole cells, and average affinity as expressed by average dissociation constant (Molar $K_D$). The results indicate that both SMP and SCP counter-selection conditions yielded average MFI that was significantly lower than that observed in the antigen-positive (affinity) alone selections, demonstrating that both SMPs and SCPs may be employed in methods for selecting developable antibodies, antibodies with enhanced developability, generating enriched pluralities of developable antibodies from non-enriched pluralities of antibodies, correlating, assessing, and predicting developability of antibodies from or in a plurality of antibodies, and the like.

Figure 26:
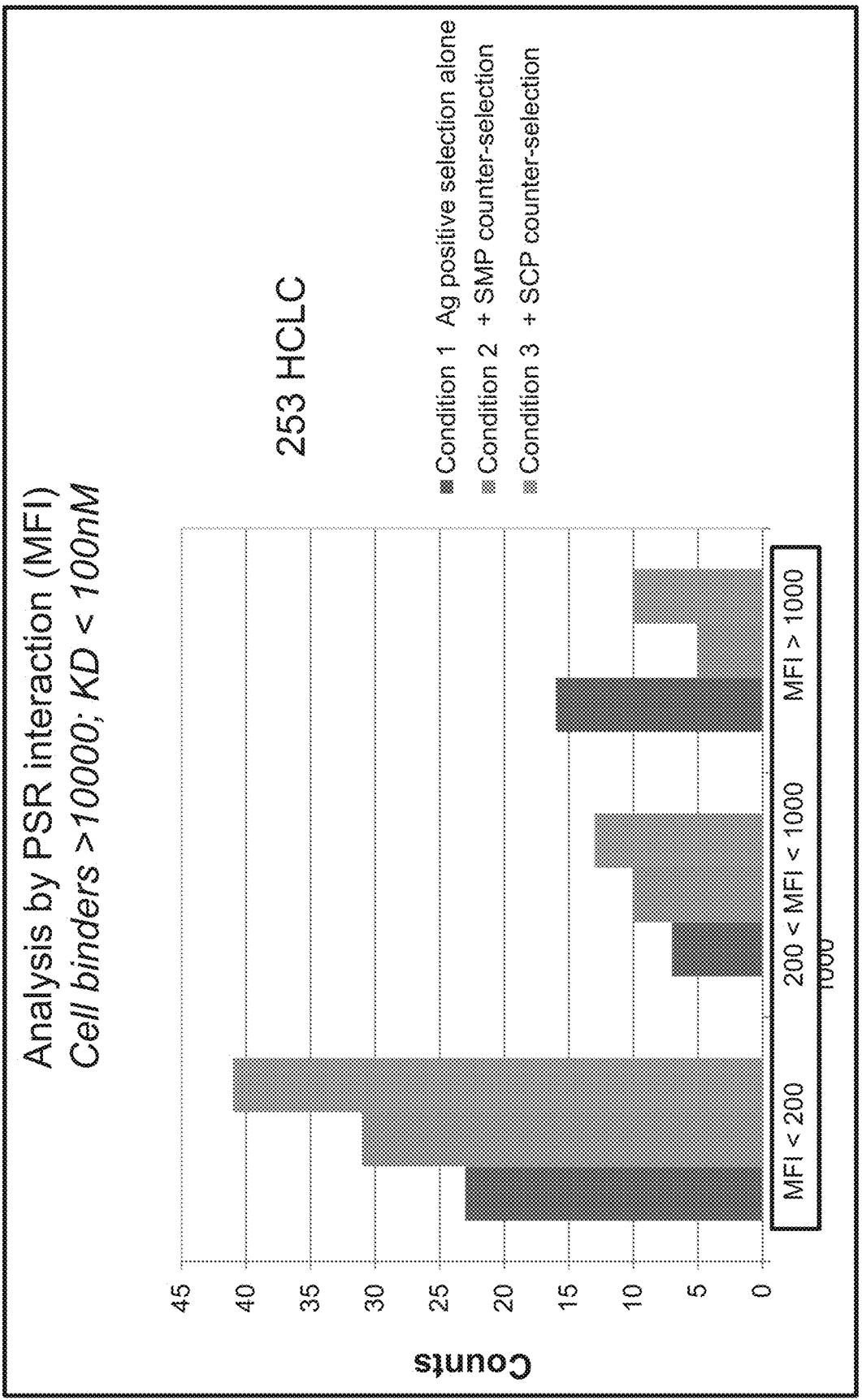
FIG. 26 provides PSR interaction (WI) data for antibodies selected in each condition as tested and described in Example 4.
Figure 27:
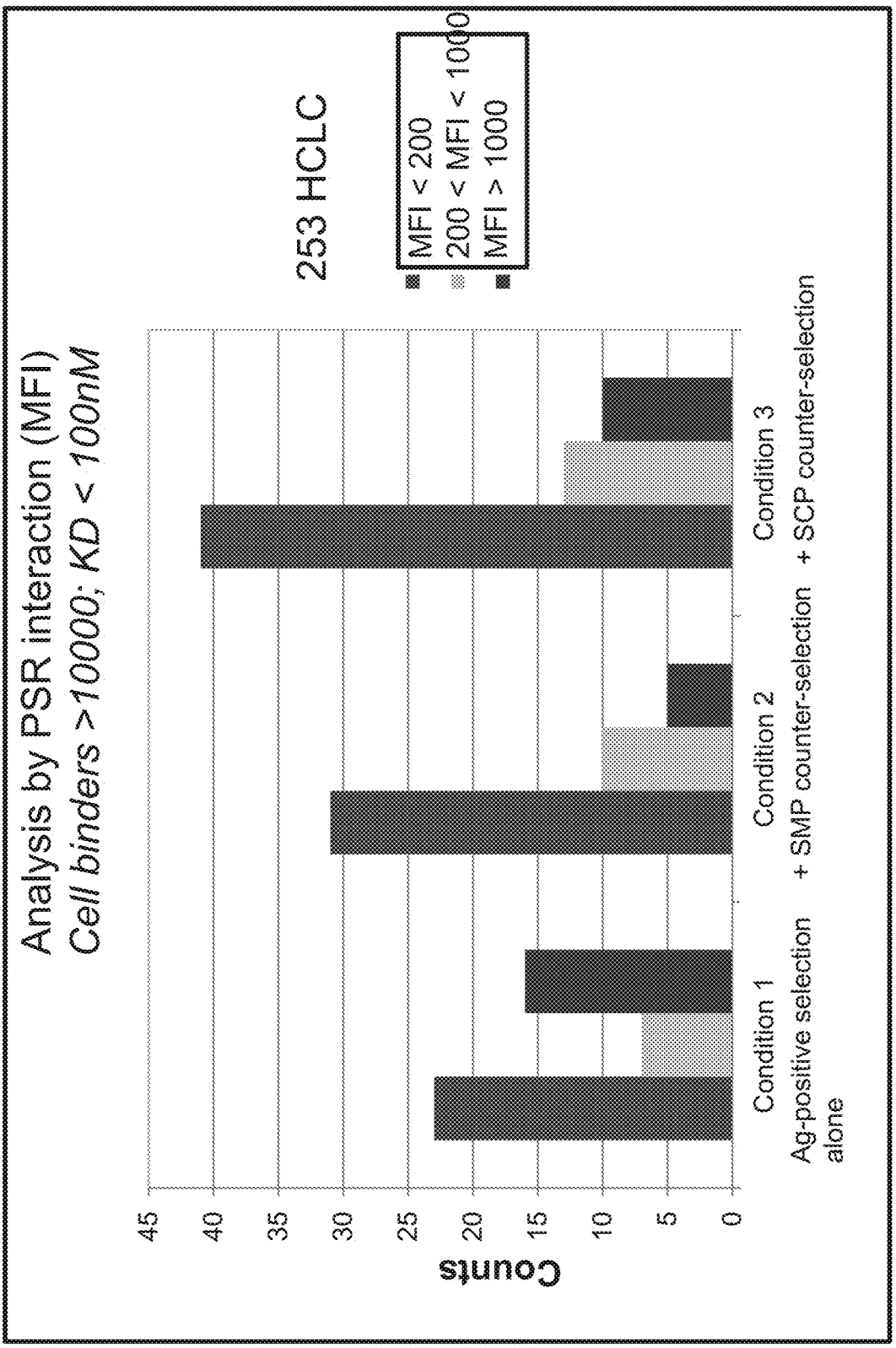
FIG. 27 provides PSR interaction (WI) data for antibodies selected in each condition as tested and described in Example 4.

FIGS. 26 and 27 depict the score and ranking of antibodies selected in each of the three conditions. The results indicate that both SMP and SCP counter-selections yielded significantly more antibodies with observed MFI of less than 200 relative to selections employing antigen-positive selections alone. The results also indicate that both SMP and SCP counter-selection conditions yielded significantly fewer antibodies displaying PSR interaction (MFI) greater than 1000 relative to the number of such antibodies yielded in the antigen-positive selection alone condition.

Figure 28:
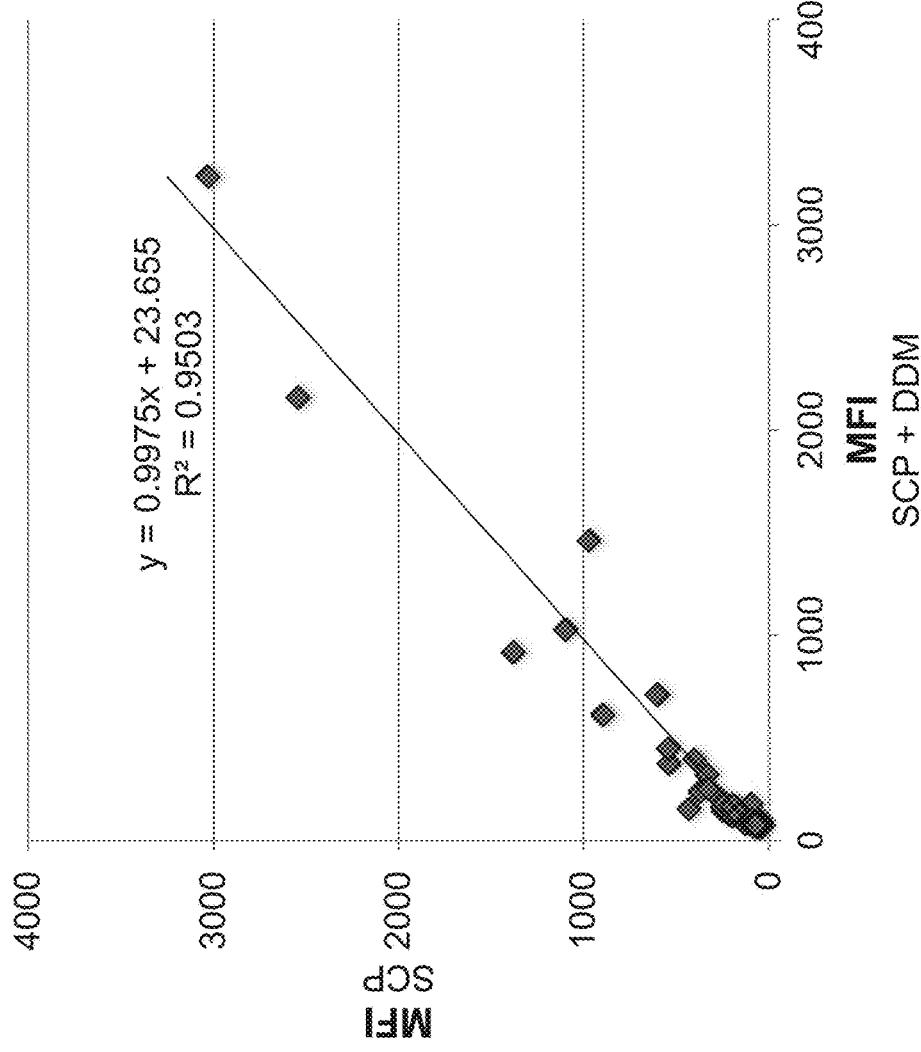
FIG. 28 provides a plot of WI determined for antibodies selected using condition 2 versus condition and 3 as tested and described in Example 4.
Figure 29:
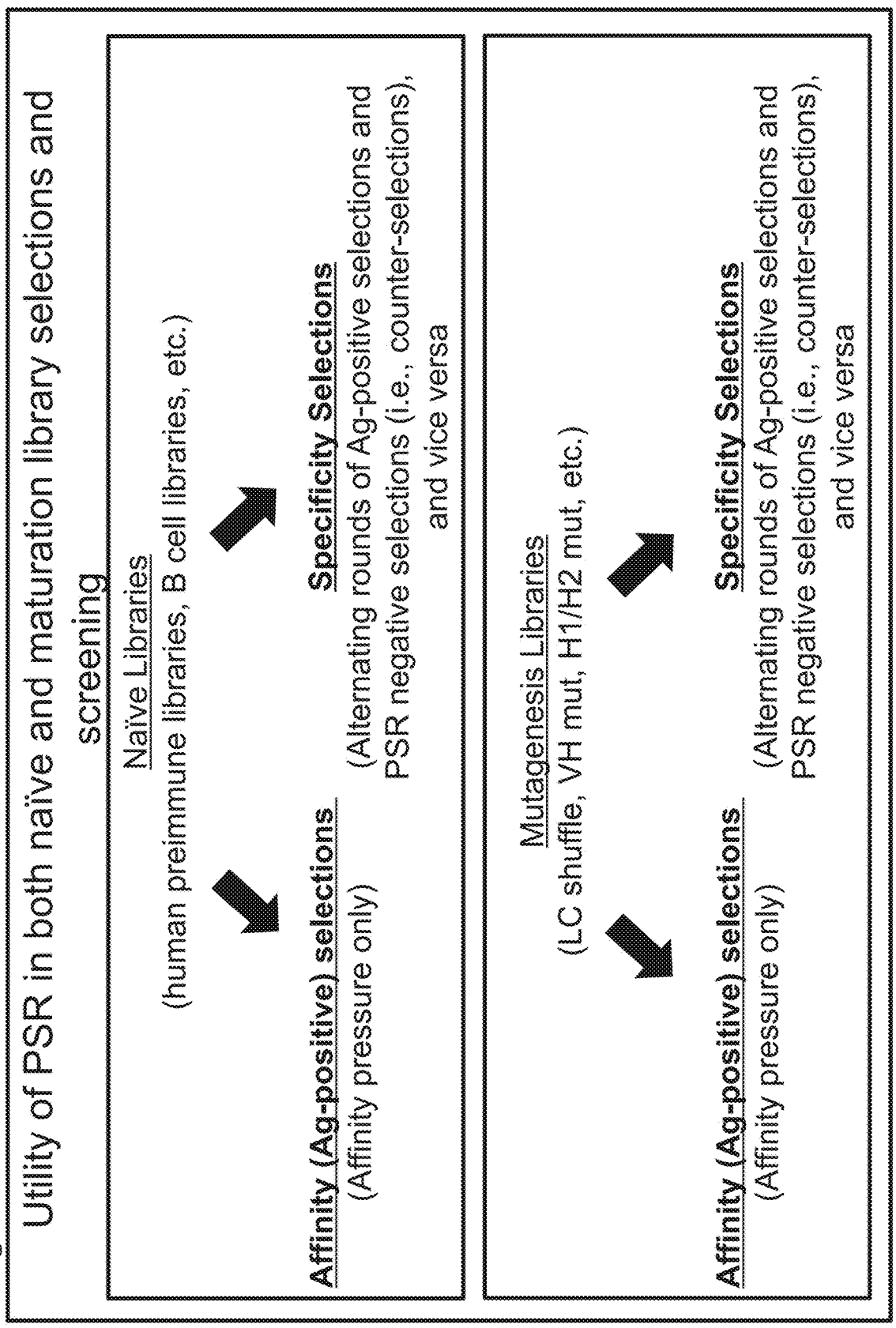
FIG. 29 illustrated exemplary utilities in employing the use of PSRs in exemplary library screening processes.
Figure 30:
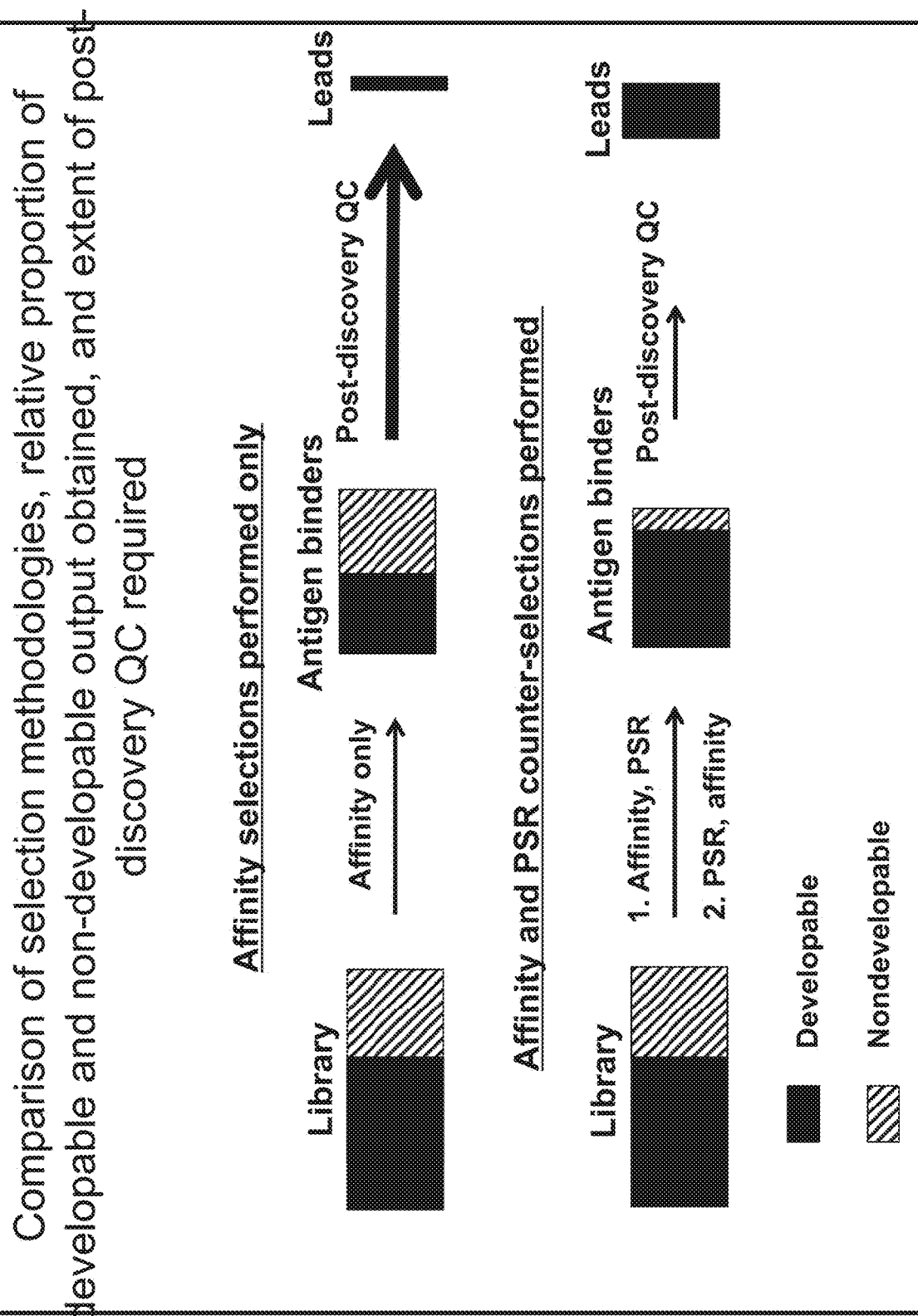
FIG. 30 provides a graphic representation of library selection methodologies that employ PSR counter-selections and those that do not, and the relative proportion of developable and non-developable output obtained and the extent of post-discovery QC required in each scenario.

FIG. 28 demonstrates that both SMPs (+detergent) and SCPs (without detergent) yielded antibodies with PSR MFI values of largely similar magnitude ($R^2=0.9503$). Accordingly, the absence of detergent in SCP preparations does not result in a significant decrease in the ability of such SCPs to detectably interact with polyreactive polypeptides.

In order to further assess the extent to which the nature and/or source of a polyspecificity reagent (e.g., cell type, presence/absence of detergent, etc.) impacts the utility of such polyspecificity reagent in accordance with the methods disclosed throughout, three different biotinylated PSRs were prepared as described above: a CHO cell-derived SMP preparation containing detergent (DDM); an Sf9 cell-derived SMP preparation containing detergent (DDM); and an Sf9 cell-derived SCP preparation with no detergent. Seventeen exemplary antibodies selected from a library described in, for example WO 20100105256 and WO 2012009568) and previously characterized as having low, medium and high binding to CHO cell derived SMPs, were tested in a PSR interaction assay as described above.

Figure 31:
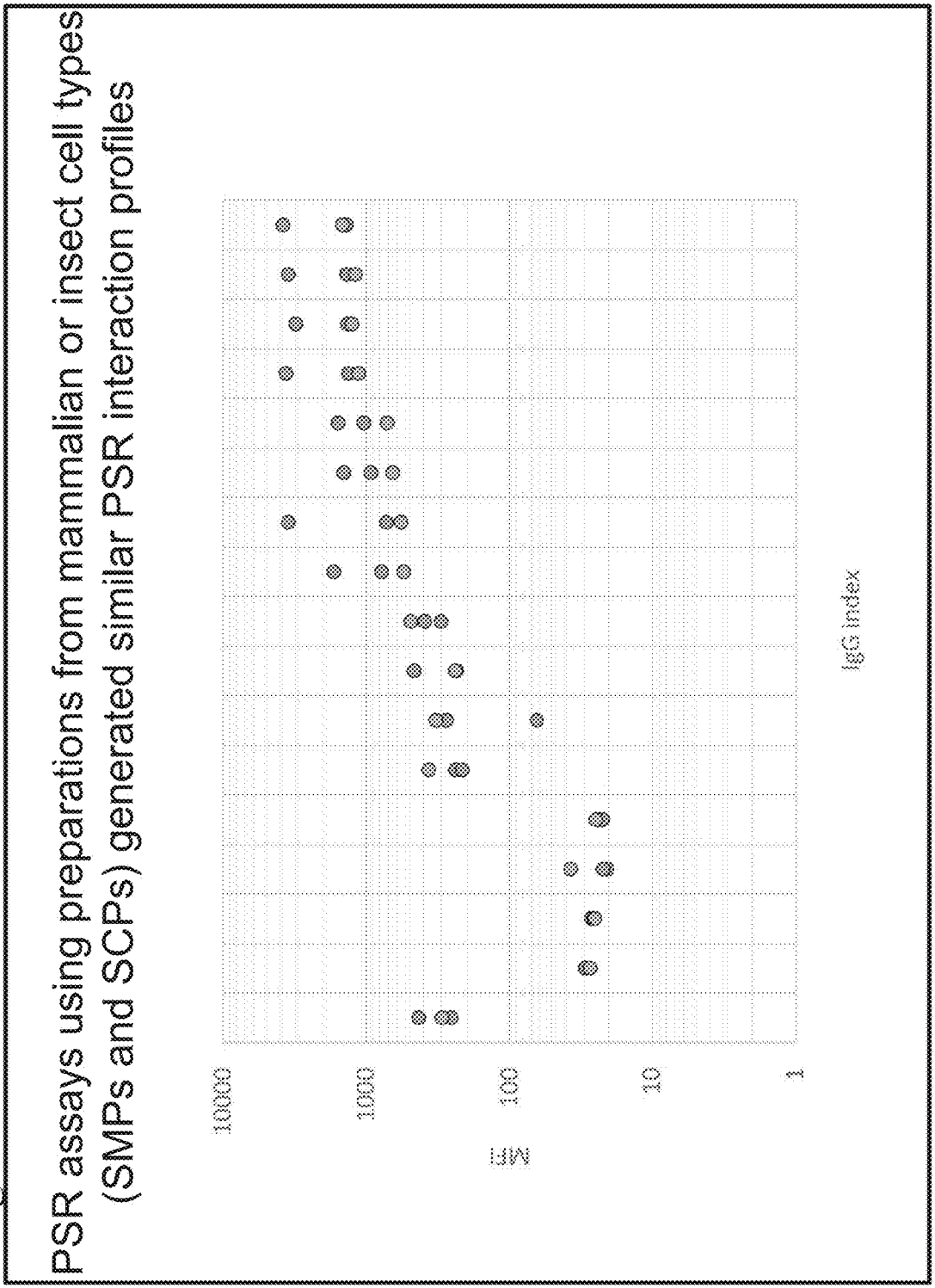
FIG. 31 provides the results of PSR interaction assays conducted using seventeen exemplary antibodies selected from a library described in, for example WO 20100105256 and WO 2012009568) and previously characterized as having low, medium and high binding to CHO cell derived SMPs, were tested against the following three different cell lysate preparations: biotinylated soluble membrane proteins (SMP) derived from CHO cells (depicted with blue circles); biotinylated soluble membrane proteins (SMP) derived from insect Sf9 cells (depicted with orange circles); and biotinylated soluble cytosolic proteins (SCP) from insect Sf9 cells (depicted with grey circles).

The results, depicted in FIG. 31, demonstrate that there is good correlation in the PSR assay readout (e.g., ability to identify or predict developable and non-developable antibodies, etc.) between biotinylated SMPs (with detergent) and a biotinylated SCPs (with no detergent), indicating that although addition of detergent may be important in the preparation of certain PSRs, the presence of detergent itself has limited influence on the assayed polyspecificity. Thus, PSRs without the presence of detergent (such as, e.g., SCPs) may be employed, particularly when employing detergent-sensitive polypeptide (such as, e.g., antibody) display host cells or organisms. Similarly, SMP preps from divergent cell types (mammalian CHO cells and insect Sf9 cells) demonstrate correlated polyspecificity profiles.

The results of Example 4, inter alia, collectively demonstrate that both SMPs and SCPs may be employed in accordance with the methods disclosed and claimed herein and throughout. Collectively, these results demonstrate that the relative insensitivity of the PSR assay to detergent, cell fraction, and cell type suggests the following: the PSR interaction largely involves a generic interaction, as opposed to a specific off-target interaction; and the disclosed polyspecificity reagents and methods of using them are widely applicable to multiple selection or display systems.

Ahamed T., Ottens M., van Dedem G. W., van der Wielen L. A., *J. Chromatog. A.,* 2005; 1089:111-124.

Blaise L., Wehnert A., Steukers M. P., van den Beucken T., Hoogenboom H. R., Hufton S. E., *Gene,* 2004; 342:211-218.

Boder E. T., Wittrup K. D. Nat., *Biotechnol.,* 1997; 15:553-557.

Carter P. J., *Nat. Rev. Immunol.,* 2006; 6:343-357.

Cho Y. K., Shusta E. V., *PEDS,* 2010; 23:567-577.

Esfandiary R., Hayes D. B., Parupudi A., Casas-Finet J., Bai S., Samra H. S., Shah A. U., Sathish H. A., *J. Pharm. Sci.,* 2013; 102:62-72.

Feyen O., Lueking A., Kowald A., Stephan C., Meyer H. E., Gobel U., Niehues T., *Anal. Bioanal. Chem.,* 2008; 391:1713-1720.

Frese K., Eisenmann M., Ostendorp R., Brocks B., Pabst S., *mAbs,* 2013; 5:1-9.

He F., Hogan S., Latypov R. F., Narhi L. O., Razinkov V. I., *J. Pharm. Sci.,* 2010; 99:1707-1720.

He F., Woods C. E., Becker G. W., Narhi L. O., Razinkov V. I., *J. Pharm. Sci.,* 2011; 100:5126-5141.

Hoogenboom H. R., *Nat. Biotechnol.,* 2005; 23:1105-1116.

Horlick R. A., Macomber J. L., Bowers P. M., Neben T. Y., Tomlinson G. L., Krapf I. P., Dalton J. L., Verdino P., King D. J., *J. Biol. Chem.,* 2013; 288:19861-19869.

Hötzel I., Theil F.-P., Bernstein L. J., et al., *MAbs,* 2012; 4:753-760.

Jacobs S. A., Wu S. J., Feng Y., Bethea D., O'Neil K. T., *Pharm. Res.,* 2010; 27:65-71.

Kontermann R., Dubel S. Antibody Engineering 2010. Springer Protocols.

Kuroda K., Ueda M., *Biotechnol. Lett.,* 2011; 33:1-9.

Lauer T. M., Agrawal N. J., Chennamsetty N., Egodage K., Helk B., Trout B. L., *J. Pharm. Sci.,* 2012; 101:102-115.

Lueking A., Beator J., Patz E., Mullner S., Mehes G., Amersdorfer P., *BioTechniques,* 2008; 45:Pi-Pv.

Miller B. R., Demarest S. J., Lugovskoy A., et al., *PEDS,* 2010; 23:549-557.

Mouquet H., Nussenzweig M. C., *Cell. Mol. Life Sci.,* 2012; 69:1435-1445.

Notkins A. L., *Trends Immunol.,* 2004; 25:174-179.

Poetz O., Ostendorp R., Brocks B., Schwenk J. M., Stoll D., Joos T. O., Templin M. F., *Proteomics,* 2005; 5:2402-2411.

Rakestraw J. A., Aird D., Aha P. M., Baynes B. M., Lipovsek D., *PEDS,* 2011; 24:525-530.

Reichert J. M., *mAbs,* 2013; 5:1-4.

Sathish H., Angell N., Lowe D., Shah A., Bishop S. Biophys., *Life Sci.,* 2013; 4:127-146.

Sazinsky S. L., Ott R. G., Silver N. W., Tidor B., Ravetch J. V., Wittrup K. D., *Proc. Natl Acad. Sci., USA* 2008; 105:20167-20172.

Spencer S., Bethea D., Raju T. S., Giles-Komar J., Feng Y., *mAbs,* 2012; 4:319-325.

Sule S. V., Dickinson C. D., Lu J., Chow C. K., Tessier P. M., *Mol. Pharm.,* 2013; 10:1322-1331.

Sule S. V., Sukumar M., Weiss W. F. t., Marcelino-Cruz A. M., Sample T., Tessier P. M., *Biophys. J.,* 2011; 101:1749-1757.

Tasumi S., Velikovsky C. A., Xu G., Gai S. A., Wittrup K. D., Flajnik M. F., Mariuzza R. A., Pancer Z., *Proc. Natl. Acad. Sci., USA* 2009; 106:12891-12896.

Tiller T., Tsuiji M., Yurasov S., Velinzon K., Nussenzweig M. C., Wardemann H., *Immunity,* 2007; 26:205-213.

Tillotson B. J., Cho Y. K., Shusta E. V. *PEDS* 2013; 60:27-37.

Wang F., Sen S., Zhang Y., Ahmad I., Zhu X., Wilson I. A., Smider V. V., Magliery T. J., Schultz P. G., *Proc. Natl. Acad. Sci. USA,* 2013; 110:4261-4266.

Wardemann H., Yurasov S., Schaefer A., Young J. W., Meffre E., Nussenzweig M. C., *Science,* 2003; 301:1374-1377.

Wu H., Pfarr D. S., Johnson S., Brewah Y. A., Woods R. M., Patel N. K., White W. I., Young J. F., Kiener P. A., *J. Mol. Biol.,* 2007; 368:652-665.

Wu S. J., Luo J., O'Neil K. T., et al., *PEDS,* 2010; 23:643-651.

Zhou Z. H., Tzioufas A. G., Notkins A. L., *J. Autoimmun.,* 2007; 29:219-228.

Zweig M. H., Campbell G., *Clin. Chem.,* 1993; 39:561-577.

Additional exemplary, non-limiting embodiments of the invention are set forth below:

Embodiment 1

A method of counter-selecting against at least one polyspecific polypeptide from a plurality of polypeptides, the method comprising:
(a) providing the plurality of polypeptides;
(b) contacting the plurality of step (a) with a poly specificity reagent, wherein the polyspecificity reagent comprises a mixture of biomolecules, thereby producing a reagent-plurality mixture;
(c) detecting from the reagent-plurality mixture of step (b) at least one polyspecific polypeptide that interacts with the polyspecificity reagent, thereby detecting at least one polyspecific polypeptide; and
(d) selecting at least one polypeptide from the plurality that is not detected in step (c), thereby counter-selecting against the at least one polyspecific polypeptide from the plurality of polypeptides.

Embodiment 2

The method of embodiment 1, wherein the counter-selecting further comprises determining that the at least one polypeptide selected in step (d) binds to at least one test binding partner.

Embodiment 3

The method of embodiment 1 or embodiment 2, wherein the method further comprises:
(A) performing at least one of steps (b), (c), and (d) by employing flow cytometry;
(B) performing at least one of steps (b), (c), and (d) by employing magnetic-activated cell sorting;
(C) performing all of steps (b), (c), and (d) by employing flow cytometry;
(D) performing all of steps (b), (c), and (d) by employing magnetic-activated cell sorting; or
(E) combinations of (A) and (B).

Embodiment 4

A method of selecting at least one polypeptide from amongst a plurality of polypeptides that specifically interacts with at least one test binding partner, the method comprising:
(a) providing the plurality of polypeptides;
(b) providing the at least one test binding partner;
(c) contacting the plurality of step (a) with the at least one test binding partner of step (b) and a polyspecificity reagent, wherein the polyspecificity reagent comprises a mixture of biomolecules, thereby producing a reagent-plurality mixture; and
(d) selecting from the reagent-plurality mixture of step (c) at least one polypeptide that interacts with the at least one test binding partner.

Embodiment 5

The method of embodiment 4, wherein the at least one polypeptide selected in step (d) does not significantly interact with the polyspecificity reagent.

Embodiment 6

The method of embodiment 4 or embodiment 5, wherein the method further comprises:
(A) performing at least one of steps (a), (b), (c), and (d) by employing flow cytometry;
(B) performing at least one of steps (a), (b), (c), and (d) by employing magnetic-activated cell sorting;
(C) performing all of steps (a), (b), (c), and (d) by employing flow cytometry;
(D) performing all of steps (a), (b), (c), and (d) by employing magnetic-activated cell sorting; or
(E) combinations of (A) and (B).

Embodiment 7

A method of generating an enriched plurality of developable polypeptides from a non-enriched plurality of polypeptides, the method comprising:
(a) providing the plurality of polypeptides;
(b) contacting the plurality of step (a) with a polyspecificity reagent, wherein the polyspecificity reagent comprises a mixture of biomolecules, thereby producing a reagent-plurality mixture;
(c) detecting from the reagent-plurality mixture of step (b) one or more polyspecific polypeptides from among the plurality of polypeptides that interacts with the polyspecificity reagent; and
(d) separating from the non-enriched plurality of polypeptides the one or more polyspecific polypeptides detected in step (c), thereby generating the enriched collection of developable polypeptides.

Embodiment 8

The method of embodiment 7, wherein the method further comprises:
(A) performing at least one of steps (a), (b), (c), and (d) by employing flow cytometry;
(B) performing at least one of steps (a), (b), (c), and (d) by employing magnetic-activated cell sorting;
(C) performing all of steps (a), (b), (c), and (d) by employing flow cytometry;
(D) performing all of steps (a), (b), (c), and (d) by employing magnetic-activated cell sorting; or
(E) combinations of (A) and (B).

Embodiment 9

A method of selecting or screening for at least one polypeptide with enhanced developability from amongst a plurality of polypeptides, the method comprising:

(a) providing the plurality of polypeptides;
(b) contacting the plurality of step (a) with a polyspecificity reagent, wherein the polyspecificity reagent comprises a mixture of biomolecules, thereby producing a reagent-plurality mixture;
(c) detecting from the reagent-plurality mixture of step (b) at least one polypeptide that does not significantly interact with the polyspecificity reagent, thereby detecting at least one developable test polypeptide; and
(d) selecting the at least one polypeptide detected in step (c)

wherein the at least one polypeptide detected in step (c) and selected in step (d) comprises a polypeptide that has been selected for or screened for enhanced developability relative to members of the plurality that are not detected in step (c) and selected in step (d).

Embodiment 10

The method of embodiment 9, wherein the method further comprises:
(A) performing at least one of steps (a), (b), (c), and (d) by employing flow cytometry;
(B) performing at least one of steps (a), (b), (c), and (d) by employing magnetic-activated cell sorting;
(C) performing all of steps (a), (b), (c), and (d) by employing flow cytometry;
(D) performing all of steps (a), (b), (c), and (d) by employing magnetic-activated cell sorting; or
(E) combinations of (A) and (B).

Embodiment 11

A method of predicting enhanced developability of at least one polypeptide from amongst a plurality of polypeptides, the method comprising:
(a) providing the plurality of polypeptides;
(b) contacting the plurality of step (a) with a polyspecificity reagent, wherein the polyspecificity reagent comprises a mixture of biomolecules, thereby producing a reagent-plurality mixture; and
(c) detecting from the reagent-plurality mixture of step (b) at least one polypeptide that does not significantly interact with the polyspecificity reagent, thereby identifying at least one developable polypeptide;

wherein the at least one developable polypeptide detected in step (c) is thereby assessed or predicted to possess enhanced developability based on the lack of significant interaction with the polyspecificity reagent relative to members of the plurality that are not identified in step (c).

Embodiment 12

The method of embodiment 11, wherein the method further comprises:
(A) performing at least one of steps (a), (b), and (c) by employing flow cytometry;
(B) performing at least one of steps (a), (b), and (c), by employing magnetic-activated cell sorting;
(C) performing all of steps (a), (b), and (c), by employing flow cytometry;
(D) performing all of steps (a), (b), and (c), by employing magnetic-activated cell sorting; or
(E) combinations of (A) and (B).

Embodiment 13

A method of ranking developability of polypeptides in a plurality of polypeptides, the method comprising:
(a) providing the plurality of polypeptides;
(b) contacting the plurality of step (a) with a polyspecificity reagent, wherein the polyspecificity reagent comprises a mixture of biomolecules, thereby producing a reagent-plurality mixture;
(c) detecting the relative degree of interaction between polypeptides of the plurality and the polyspecificity reagent; and
(d) ranking the polypeptides detected in step (c) that are observed to possess a lower degree of interaction with the polyspecificity reagent as possessing enhanced developability, and ranking the polypeptides detected in step (c) that are observed to possess a higher degree of interaction with the polyspecificity reagent as possessing decreased developability.

Embodiment 14

The method of embodiment 13, wherein the method further comprises:
(A) performing at least one of steps (a), (b), and (c) by employing flow cytometry;
(B) performing at least one of steps (a), (b), and (c), by employing magnetic-activated cell sorting;
(C) performing all of steps (a), (b), and (c), by employing flow cytometry;
(D) performing all of steps (a), (b), and (c), by employing magnetic-activated cell sorting; or
(E) combinations of (A) and (B).

Embodiment 15

A method of assigning a developability score polypeptides in a plurality of polypeptides, the method comprising:
(a) providing the plurality of polypeptides;
(b) contacting the plurality of step (a) with a polyspecificity reagent, wherein the polyspecificity reagent comprises a mixture of biomolecules, thereby producing a reagent-plurality mixture;
(c) detecting the relative degree of interaction between polypeptides of the plurality and the polyspecificity reagent; and
(d) assigning to the polypeptides detected in step (c) that are observed to possess a lower degree of interaction with the polyspecificity reagent a higher developability score and assigning to the polypeptides detected in step (c) that are observed to possess a higher degree of interaction with the polyspecificity reagent a lower developability score.

Embodiment 16

The method of embodiment 15, wherein the method further comprises:
(A) performing at least one of steps (a), (b), (c) and (d) by employing flow cytometry;
(B) performing at least one of steps (a), (b), (c) and (d) by employing magnetic-activated cell sorting;
(C) performing all of steps (a), (b), (c) and (d) by employing flow cytometry;
(D) performing all of steps (a), (b), (c) and (d) by employing magnetic-activated cell sorting; or
(E) combinations of (A) and (B).

Embodiment 17

A method of correlating developability of one or more polypeptides of a plurality of polypeptides with a degree of interaction with a polyspecificity reagent, the method comprising:

(a) providing the plurality of polypeptides;
(b) contacting the plurality of step (a) with the polyspecificity reagent, wherein the polyspecificity reagent comprises a mixture of biomolecules, thereby producing a reagent-plurality mixture;
(c) detecting the degree of interaction between each polypeptide in the plurality of polypeptides with the polyspecificity reagent; and
(d) determining the relative degree of interaction between the one or more polypeptides and the polyspecificity reagent, wherein a lower degree of interaction with the polyspecificity reagent correlates with enhanced developability and wherein a higher degree of interaction with the polyspecificity reagent correlates with decreased developability.

Embodiment 18

The method of embodiment 17, wherein the method further comprises:
(A) performing at least one of steps (a), (b), (c) and (d) by employing flow cytometry;
(B) performing at least one of steps (a), (b), (c) and (d) by employing magnetic-activated cell sorting;
(C) performing all of steps (a), (b), (c) and (d) by employing flow cytometry;
(D) performing all of steps (a), (b), (c) and (d) by employing magnetic-activated cell sorting; or
(E) combinations of (A) and (B).

Embodiment 19

A method of assessing, screening for, predicting, or identifying, or correlating developability of at least one polypeptide that interacts with a binding partner, the method comprising:
(a) providing the at least one polypeptide;
(b) contacting the at least one polypeptide of step (a) with a polyspecificity reagent, wherein the polyspecificity reagent comprises a mixture of biomolecules, thereby producing a reagent-polypeptide mixture;
(c) determining a degree of interaction between the at least one polypeptide and the polyspecificity reagent, wherein a lower degree of interaction indicates an enhanced developability of the at least one polypeptide and wherein a higher degree of interaction with the polyspecificity reagent indicates a decreased developability of the at least one polypeptide.

Embodiment 20

The method of embodiment 19, wherein the method further comprises:
(A) performing at least one of steps (a), (b), and (c) by employing flow cytometry;
(B) performing at least one of steps (a), (b), and (c), by employing magnetic-activated cell sorting;
(C) performing all of steps (a), (b), and (c), by employing flow cytometry;
(D) performing all of steps (a), (b), and (c), by employing magnetic-activated cell sorting; or
(E) combinations of (A) and (B).

Embodiment 21

The method of any one of embodiments 1, 3, and 7 through 20, the method further comprising contacting either:
the plurality of polypeptides;
the reagent-plurality mixture; or
both the plurality of polypeptides and the reagent-plurality mixture;
with at least one test binding partner.

Embodiment 22

The method of any one of embodiments 1 through 21, wherein the plurality of polypeptides comprises a library of polypeptides.

Embodiment 23

The method of any one of embodiments 1 through 22, wherein the polyspecificity reagent comprises a composition selected from the group consisting of:
(a) a soluble cellular fraction;
(b) a membrane cellular fraction;
(c) a bodily fluid fraction;
(d) a serum fraction;
(e) a plasma fraction;
(f) a cocktail comprising partially purified biomolecules;
(g) a collection of virus or virus-derived particles; and
(h) a combination of one or more of (a) through (g).

Embodiment 24

The method of any one of embodiments 1 through 23, wherein the polyspecificity reagent comprises a composition selected from the group consisting of:
(a) a soluble cellular fraction;
(b) a membrane cellular fraction;
(c) a bodily fluid fraction;
(d) a serum fraction;
(e) a plasma fraction;
(f) a cocktail comprising partially purified biomolecules;
(g) a combination of one or more of (a) through (f).

Embodiment 25

The method of any one of embodiments 1 through 24, wherein the polyspecificity reagent comprises a cellular soluble fraction that is obtained from a collection of cells in culture.

Embodiment 26

The method of any one of embodiments 1 through 25, wherein the polyspecificity reagent comprises a cellular soluble fraction that is obtained from a collection of mammalian cells in culture.

Embodiment 27

The method of any one of embodiments 1 through 25, wherein the polyspecificity reagent comprises a cellular soluble fraction that is obtained from a collection of insect cells in culture.

Embodiment 28

The method of any one of embodiments 1 through 24, wherein the polyspecificity reagent comprises a cellular membrane fraction that is obtained from a collection of cells in culture.

Embodiment 29

The method of any one of embodiments 1 through 25, wherein the polyspecificity reagent comprises a cellular membrane fraction that is obtained from a collection of mammalian cells in culture.

Embodiment 30

The method of any one of embodiments 1 through 25, wherein the polyspecificity reagent comprises a cellular membrane fraction that is obtained from a collection of insect cells in culture.

Embodiment 31

The method of any one of embodiments 1 through 24 and embodiments 28 through 30, wherein the polyspecificity reagent comprises a solubilized cellular membrane fraction.

Embodiment 32

The method of any one of embodiments 1 through 24, embodiment 28, embodiment 29, and embodiment 31, wherein the polyspecificity reagent comprises a solubilized cellular membrane fraction that is obtained from a collection of mammalian cells in culture.

Embodiment 33

The method of any one of embodiments 1 through 24, embodiment 28, embodiment 30, and embodiment 31, wherein the polyspecificity reagent comprises a solubilized cellular membrane fraction that is obtained from a collection of insect cells in culture.

Embodiment 34

The method of any one of embodiments 1 through 24, wherein the polyspecificity reagent comprises a collection of virus or virus-derived particles selected from the group consisting of baculovirus; adenovirus; lentivirus; rhinovirus; coronavirus; cucumber mosaic virus; cytomegalovirus; respiratory syncytial virus; influenza virus; rotavirus; herpes virus; and virus particles derived from one or more such viruses.

Embodiment 35

The method of any one of embodiments 1 through 34, wherein the polyspecificity reagent comprises at least one detergent.

Embodiment 36

The method of any one of embodiments 1 through 35, wherein the polyspecificity reagent comprises at least one detergent selected from the group consisting of beta-mercaptoethanol (B-ME), (Cyclohexyl-beta-D-maltoside (Cymal-6), Sodium Cholate, Polyoxyethylene$_{(23)}$ lauryl ether (Brij35), Decyl Maltose Neopentyl Glycol (DM-NG), n-Dodecyl β-D-maltoside (DDM), n-octyl-β-D-glucoside (OG), and 3-[(3-Cholamidopropyl)dimethylammonio]-1-propanesulfonate (CHAPS).

Embodiment 37

The method of any one of embodiments 1 through 36, wherein the plurality of polypeptides comprises at least: from about $1\times10^4$ unique polypeptides to about $1\times10^{18}$ unique polypeptides; $1\times10^4$ unique polypeptides to about $1\times10^{17}$ unique polypeptides; $1\times10^4$ unique polypeptides to about $1\times10^{16}$ unique polypeptides; $1\times10^4$ unique polypeptides to about $1\times10^{15}$ unique polypeptides; $1\times10^4$ unique polypeptides to about $1\times10^{14}$ unique polypeptides; $1\times10^4$ unique polypeptides to about $1\times10^{13}$ unique polypeptides; $1\times10^4$ unique polypeptides to about $1\times10^{12}$ unique polypeptides; $1\times10^4$ unique polypeptides to about $1\times10^{11}$ unique polypeptides; $1\times10^4$ unique polypeptides to about $1\times10^{10}$ unique polypeptides; $1\times10^4$ unique polypeptides to about $1\times10^{9}$ unique polypeptides; $1\times10^4$ unique polypeptides to about $1\times10^{8}$ unique polypeptides; $1\times10^4$ unique polypeptides to about $1\times10^{7}$ unique polypeptides; $1\times10^5$ unique polypeptides to about $1\times10^{18}$ unique polypeptides; $1\times10^6$ unique polypeptides to about $1\times10^{18}$ unique polypeptides; $1\times10^7$ unique polypeptides to about $1\times10^{18}$ unique polypeptides; $1\times10^8$ unique polypeptides to about $1\times10^{18}$ unique polypeptides; $1\times10^9$ unique polypeptides to about $1\times10^{18}$ unique polypeptides; $1\times10^{10}$ unique polypeptides to about $1\times10^{18}$ unique polypeptides; $1\times10^{11}$ unique polypeptides to about $1\times10^{18}$ unique polypeptides; $1\times10^{12}$ unique polypeptides to about $1\times10^{18}$ unique polypeptides; $1\times10^5$ unique polypeptides to about $1\times10^{18}$ unique polypeptides; $1\times10^6$ unique polypeptides to about $1\times10^{17}$ unique polypeptides; $1\times10^7$ unique polypeptides to about $1\times10^{16}$ unique polypeptides; $1\times10^8$ unique polypeptides to about $1\times10^{15}$ unique polypeptides; $1\times10^9$ unique polypeptides to about $1\times10^{14}$ unique polypeptides; or $1\times10^{10}$ unique polypeptides to about $1\times10^{13}$ unique polypeptides.

Embodiment 38

The method of any one of embodiments 1 through 37, wherein the plurality of polypeptides is collectively encoded by a plurality of polynucleotides.

Embodiment 39

The method of embodiment 38, wherein the plurality of polynucleotides comprises a library of polynucleotides.

Embodiment 40

The method of any one of embodiments 1 through 39, wherein the plurality of polynucleotides comprises at least: from about $1\times10^4$ unique polynucleotides to about $1\times10^{18}$ unique polynucleotides; $1\times10^4$ unique polynucleotides to about $1\times10^{17}$ unique polynucleotides; $1\times10^4$ unique polynucleotides to about $1\times10^{16}$ unique polynucleotides; $1\times10^4$ unique polynucleotides to about $1\times10^{15}$ unique polynucleotides; $1\times10^4$ unique polynucleotides to about $1\times10^{14}$ unique polynucleotides; $1\times10^4$ unique polynucleotides to about $1\times10^{13}$ unique polynucleotides; $1\times10^4$ unique polynucleotides to about $1\times10^{12}$ unique polynucleotides; $1\times10^4$ unique polynucleotides to about $1\times10^{11}$ unique polynucleotides; $1\times10^4$ unique polynucleotides to about $1\times10^{10}$ unique polynucleotides; $1\times10^4$ unique polynucleotides to about $1\times10^{9}$ unique polynucleotides; $1\times10^4$ unique polynucleotides to about $1\times10^{8}$ unique polynucleotides; $1\times10^4$ unique polynucleotides to about $1\times10^{7}$ unique polynucleotides; $1\times10^5$ unique polynucleotides to about $1\times10^{18}$ unique polynucleotides; $1\times10^6$ unique polynucleotides to about $1\times10^{18}$ unique polynucleotides; $1\times10^7$ unique polynucleotides to about $1\times10^{18}$ unique polynucleotides; $1\times10^8$ unique polynucleotides to about $1\times10^{18}$ unique polynucleotides; $1\times10^9$ unique polynucleotides to about $1\times10^{18}$ unique polynucleotides; $1\times10^{10}$ unique polynucleotides to about $1\times10^{18}$ unique polynucleotides; $1\times10^{11}$ unique polynucleotides to about $1\times10^{18}$ unique polynucleotides; $1\times10^{12}$ unique polynucleotides to about $1\times10^{18}$ unique polynucleotides; $1\times10^{5}$ unique polynucleotides to about $1\times10^{18}$ unique polynucleotides; $1\times10^{6}$ unique polynucleotides to about $1\times10^{17}$ unique polynucleotides; $1\times10^{7}$ unique polynucleotides to about $1\times10^{16}$ unique polynucleotides; $1\times10^{8}$ unique polynucleotides to about $1\times10^{15}$ unique polynucleotides; $1\times10^{9}$ unique polynucleotides to about $1\times10^{14}$ unique polynucleotides; or $1\times10^{10}$ unique polynucleotides to about $1\times10^{13}$ unique polynucleotides.

Embodiment 41

The method of any one of embodiments 1 through 40, wherein each polypeptide of the plurality of polypeptides is encoded by a polynucleotide that is a component of a vector.

Embodiment 42

The method of any one of embodiments 38 through 41, wherein each polynucleotide is introduced into one or more of the host cells.

Embodiment 43

The method of any one of embodiments 38 through 42, wherein the plurality of polynucleotides is introduced a plurality of host cells.

Embodiment 44

The method of embodiment 42 or embodiment 43, wherein the plurality of host cells comprises a plurality of vectors collectively harboring the one or more polynucleotides collectively encoding the plurality of polypeptides.

Embodiment 45

The method of any one of embodiments 1 through 44, wherein the plurality of polypeptides is expressed by one or more host cells.

Embodiment 46

The method of any one of embodiments 1 through 45, wherein the plurality of polypeptides is collectively expressed by a plurality of host cells.

Embodiment 47

The method of any one of embodiments 1 through 46, wherein the plurality of polypeptides comprises a naïve discovery polypeptide library.

Embodiment 48

The method of any one of embodiments 38 through 44, wherein the plurality of polynucleotides comprises a naïve discovery polynucleotide library.

Embodiment 49

The method of any one of embodiments 42 through 46, wherein the host cells comprise a naïve discovery host cell library.

Embodiment 50

The method of any one of embodiments 1 through 46, wherein the plurality of polypeptides comprises an optimization polypeptide library.

Embodiment 51

The method of any one of embodiments 38 through 44, wherein the plurality of polynucleotides comprises an optimization polynucleotide library.

Embodiment 52

The method of any one of embodiments 42 through 46, wherein the host cells comprise an optimization host cell library.

Embodiment 53

The method of any one of embodiments 1 through 52, wherein the polypeptides comprise antibodies or antibody fragments.

Embodiment 54

The method of any one of embodiments 1 through 53, wherein the polypeptides comprise antibodies or antibody fragments, wherein the antibodies or antibody fragments comprise at least one Fc region.

Embodiment 55

The method of any one of embodiments 1 through 54, wherein the polypeptides comprise antibodies or antibody fragments, wherein the antibodies or antibody fragments comprise at least one Fc region and at least one antigen binding region.

Embodiment 56

The method of any one of embodiments 1 through 55, wherein the polypeptides comprise antibodies or antibody fragments, wherein the antibodies or antibody fragments comprise full-length IgGs.

Embodiment 57

The method of any one of embodiments 1 through 56, wherein the polypeptides comprise multispecific antibodies or antibody fragments.

Embodiment 58

The method of any one of embodiments 1 through 57, wherein the polypeptides comprise human or humanized antibodies or antibody fragments.

Embodiment 59

The method of any one of embodiments 42 through 46, 49, and 52, wherein the host cells are eukaryotic cells.

Embodiment 60

The method of any one of embodiments 42 through 46, 49, 52, and 59, wherein the host cells are yeast cells.

Embodiment 61

The method of any one of embodiments 42 through 46, 49, 52, 59, and 60, wherein the host cells provide genotype-phenotype linkage.

Embodiment 62

The method of any one of embodiments 42 through 46, 49, 52, 59, 60, and 61, wherein the plurality of host cells collectively comprise a genotype-phenotype library.

Embodiment

A method of counter-selecting against at least one polyspecific polypeptide in a library comprising a plurality of polypeptides, wherein said plurality comprises the at least one polyspecific polypeptide and at least one non-polyspecific polypeptide, the method comprising:
- (e) providing the library comprising a plurality of polypeptides;
- (f) contacting the library of step (a) with a polyspecificity reagent, wherein the polyspecificity reagent comprises a mixture of biomolecules, thereby generating a reagent-composition mixture;
- (g) detecting from the reagent-library mixture of step (b) at least one polyspecific polypeptide that interacts with the polyspecificity reagent; and
- (h) selecting at least one non-polyspecific polypeptide from the library that is not detected in step (c), thereby counter-selecting against the at least one polyspecific polypeptide from the at least one non-polyspecific polypeptide in the library.

Embodiment 64

The method of embodiment 63, wherein the counter-selecting further comprises determining that the at least one non-polyspecific polypeptide selected in step (d) binds to at least one test binding partner.

Embodiment 65

The method of embodiment 63 or embodiment 64, wherein the method further comprises:
- (A) performing at least one of steps (b), (c), and (d) by employing flow cytometry;
- (B) performing at least one of steps (b), (c), and (d) by employing magnetic-activated cell sorting;
- (C) performing all of steps (b), (c), and (d) by employing flow cytometry;
- (D) performing all of steps (b), (c), and (d) by employing magnetic-activated cell sorting; or
- (E) combinations of (A) and (B).

Embodiment 66

A method of selecting at least one non-polyspecific polypeptide that interacts with at least one test binding partner from a library comprising a plurality of polypeptides, wherein said plurality comprises the at least one polyspecific polypeptide and at least one non-polyspecific polypeptide, the method comprising:
- (a) providing the library comprising a plurality of polypeptides;
- (b) providing the at least one test binding partner;
- (c) contacting the library of step (a) with the at least one test binding partner of step (b) and a polyspecificity reagent, wherein the polyspecificity reagent comprises a mixture of biomolecules, thereby producing a reagent-library mixture; and
- (d) selecting from the reagent-plurality mixture of step (c) at least one non-polyspecific polypeptide that interacts with the at least one test binding partner.

Embodiment 67

The method of embodiment 66, wherein the at least one non-polyspecific polypeptide selected in step (d) does not significantly interact with the polyspecificity reagent.

Embodiment 68

The method of embodiment 66 or embodiment 67, wherein the method further comprises:
- (A) performing at least one of steps (a), (b), (c), and (d) by employing flow cytometry;
- (B) performing at least one of steps (a), (b), (c), and (d) by employing magnetic-activated cell sorting;
- (C) performing all of steps (a), (b), (c), and (d) by employing flow cytometry;
- (D) performing all of steps (a), (b), (c), and (d) by employing magnetic-activated cell sorting; or
- (E) combinations of (A) and (B).

Embodiment 68

A method of generating an enriched plurality of developable polypeptides from a non-enriched library of polypeptides, wherein the library of polypeptides comprises at least one polyspecific polypeptide and at least one non-polyspecific polypeptide, the method comprising:
- (a) providing the library of polypeptides;
- (b) contacting the library of step (a) with a polyspecificity reagent, wherein the polyspecificity reagent comprises a mixture of biomolecules, thereby producing a reagent-library mixture;
- (c) detecting from the reagent-plurality mixture of step (b) one or more polyspecific polypeptides from among the library of polypeptides that interacts with the polyspecificity reagent; and
- (d) separating from the non-enriched library of polypeptides the one or more polyspecific polypeptides detected in step (c), thereby generating the enriched plurality of developable polypeptides.

Embodiment 69

The method of embodiment 68, wherein the method further comprises:
- (A) performing at least one of steps (a), (b), (c), and (d) by employing flow cytometry;
- (B) performing at least one of steps (a), (b), (c), and (d) by employing magnetic-activated cell sorting;
- (C) performing all of steps (a), (b), (c), and (d) by employing flow cytometry;
- (D) performing all of steps (a), (b), (c), and (d) by employing magnetic-activated cell sorting; or
- (E) combinations of (A) and (B).

Embodiment 70

A method of selecting or screening for at least one polypeptide with enhanced developability from amongst a library of polypeptides, wherein the library of polypeptides comprises at least one polyspecific polypeptide and at least one non-polyspecific polypeptide, the method comprising:
(a) providing the library of polypeptides;
(b) contacting the library of step (a) with a polyspecificity reagent, wherein the polyspecificity reagent comprises a mixture of biomolecules, thereby producing a reagent-library mixture;
(c) detecting from the reagent-library mixture of step (b) at least one polypeptide that does not significantly interact with the polyspecificity reagent, thereby detecting at least one non-polyspecific polypeptide; and
(d) selecting the at least one non-polyspecific polypeptide detected in step (c)
wherein the at least one non-polyspecific polypeptide detected in step (c) and selected in step (d) comprises a polypeptide that has been selected for or screened for enhanced developability relative to members of the plurality that are not detected in step (c) and selected in step (d).

Embodiment 71

The method of embodiment 70, wherein the method further comprises:
(A) performing at least one of steps (a), (b), (c), and (d) by employing flow cytometry;
(B) performing at least one of steps (a), (b), (c), and (d) by employing magnetic-activated cell sorting;
(C) performing all of steps (a), (b), (c), and (d) by employing flow cytometry;
(D) performing all of steps (a), (b), (c), and (d) by employing magnetic-activated cell sorting; or
(E) combinations of (A) and (B).

Embodiment 72

A method of predicting enhanced developability of at least one polypeptide from amongst a library of polypeptides, wherein the library of polypeptides comprises at least one polyspecific polypeptide and at least one non-polyspecific polypeptide, the method comprising:
(a) providing the library of polypeptides;
(b) contacting the library of step (a) with a polyspecificity reagent, wherein the polyspecificity reagent comprises a mixture of biomolecules, thereby producing a reagent-library mixture; and
(c) detecting from the reagent-library mixture of step (b) at least one polypeptide that does not significantly interact with the polyspecificity reagent, thereby identifying at least one developable polypeptide;
wherein the at least one developable polypeptide detected in step (c) is thereby assessed or predicted to possess enhanced developability based on the lack of significant interaction with the polyspecificity reagent relative to polypeptides of the library that are not identified in step (c).

Embodiment 73

The method of embodiment 72, wherein the method further comprises:
(A) performing at least one of steps (a), (b), and (c) by employing flow cytometry;
(B) performing at least one of steps (a), (b), and (c), by employing magnetic-activated cell sorting;
(C) performing all of steps (a), (b), and (c), by employing flow cytometry;
(D) performing all of steps (a), (b), and (c), by employing magnetic-activated cell sorting; or
(E) combinations of (A) and (B).

Embodiment 74

A method of ranking developability of polypeptides in a library of polypeptides, wherein the library of polypeptides comprises at least one polyspecific polypeptide and at least one non-polyspecific polypeptide, the method comprising:
(a) providing the library of polypeptides;
(b) contacting the library of step (a) with a polyspecificity reagent, wherein the polyspecificity reagent comprises a mixture of biomolecules, thereby producing a reagent-library mixture;
(c) detecting the relative degree of interaction between polypeptides of the library and the polyspecificity reagent; and
(d) ranking the polypeptides detected in step (c) that are observed to possess a lower degree of interaction with the polyspecificity reagent as possessing enhanced developability, and ranking the polypeptides detected in step (c) that are observed to possess a higher degree of interaction with the polyspecificity reagent as possessing decreased developability.

Embodiment 75

The method of embodiment 74, wherein the method further comprises:
(A) performing at least one of steps (a), (b), and (c) by employing flow cytometry;
(B) performing at least one of steps (a), (b), and (c), by employing magnetic-activated cell sorting;
(C) performing all of steps (a), (b), and (c), by employing flow cytometry;
(D) performing all of steps (a), (b), and (c), by employing magnetic-activated cell sorting; or
(E) combinations of (A) and (B).

Embodiment 76

A method of assigning a developability score to polypeptides in a library of polypeptides, wherein the library of polypeptides comprises at least one polyspecific polypeptide and at least one non-polyspecific polypeptide, the method comprising:
(a) providing the library of polypeptides;
(b) contacting the library of step (a) with a polyspecificity reagent, wherein the polyspecificity reagent comprises a mixture of biomolecules, thereby producing a reagent-library mixture;
(c) detecting the relative degree of interaction between polypeptides of the library and the polyspecificity reagent; and
(d) assigning to the polypeptides detected in step (c) that are observed to possess a lower degree of interaction with the polyspecificity reagent a higher developability score and assigning to the polypeptides detected in step (c) that are observed to possess a higher degree of interaction with the polyspecificity reagent a lower developability score.

Embodiment 77

The method of embodiment 76, wherein the method further comprises:

(A) performing at least one of steps (a), (b), (c) and (d) by employing flow cytometry;
(B) performing at least one of steps (a), (b), (c) and (d) by employing magnetic-activated cell sorting;
(C) performing all of steps (a), (b), (c) and (d) by employing flow cytometry;
(D) performing all of steps (a), (b), (c) and (d) by employing magnetic-activated cell sorting; or
(E) combinations of (A) and (B).

Embodiment 78

A method of correlating developability of one or more polypeptides of a library of polypeptides, wherein the library of polypeptides comprises at least one polyspecific polypeptide and at least one non-polyspecific polypeptide, with a degree of interaction with a polyspecificity reagent, the method comprising:
(a) providing the library of polypeptides;
(b) contacting the library of step (a) with the polyspecificity reagent, wherein the polyspecificity reagent comprises a mixture of biomolecules, thereby producing a reagent-library mixture;
(c) detecting the degree of interaction between each polypeptide in the library of polypeptides with the polyspecificity reagent; and
(d) determining the relative degree of interaction between the one or more polypeptides and the polyspecificity reagent, wherein a lower degree of interaction with the polyspecificity reagent correlates with enhanced developability and wherein a higher degree of interaction with the polyspecificity reagent correlates with decreased developability.

Embodiment 79

The method of embodiment 78, wherein the method further comprises:
(A) performing at least one of steps (a), (b), (c) and (d) by employing flow cytometry;
(B) performing at least one of steps (a), (b), (c) and (d) by employing magnetic-activated cell sorting;
(C) performing all of steps (a), (b), (c) and (d) by employing flow cytometry;
(D) performing all of steps (a), (b), (c) and (d) by employing magnetic-activated cell sorting; or
(E) combinations of (A) and (B).

Embodiment 80

The method of any one of embodiments 63, 65, and 69 through 79, the method further comprising contacting either:
the library of polypeptides;
the reagent-library mixture; or
both the library of polypeptides and the reagent-library mixture;
with at least one test binding partner.

Embodiment 81

The method of any one of embodiments 63 through 80, wherein the polyspecificity reagent comprises a composition selected from the group consisting of:
(a) a soluble cellular fraction;
(b) a membrane cellular fraction;
(c) a bodily fluid fraction;
(d) a serum fraction;
(e) a plasma fraction;
(f) a cocktail comprising partially purified biomolecules;
(g) a collection of virus or virus-derived particles; and
(h) a combination of one or more of (a) through (g).

Embodiment 82

The method of any one of embodiments 63 through 81, wherein the polyspecificity reagent comprises a composition selected from the group consisting of:
(a) a soluble cellular fraction;
(b) a membrane cellular fraction;
(c) a bodily fluid fraction;
(d) a serum fraction;
(e) a plasma fraction;
(f) a cocktail comprising partially purified biomolecules; and
(g) a combination of one or more of (a) through (f).

Embodiment 83

The method of any one of embodiments 63 through 82, wherein the polyspecificity reagent comprises a cellular soluble fraction that is obtained from a collection of cells in culture.

Embodiment 84

The method of any one of embodiments 63 through 83, wherein the polyspecificity reagent comprises a cellular soluble fraction that is obtained from a collection of mammalian cells in culture.

Embodiment 85

The method of any one of embodiments 63 through 83, wherein the polyspecificity reagent comprises a cellular soluble fraction that is obtained from a collection of insect cells in culture.

Embodiment 86

The method of any one of embodiments 63 through 82, wherein the polyspecificity reagent comprises a cellular membrane fraction that is obtained from a collection of cells in culture.

Embodiment 87

The method of any one of embodiments 63 through 82 and 86, wherein the polyspecificity reagent comprises a cellular membrane fraction that is obtained from a collection of mammalian cells in culture.

Embodiment 88

The method of any one of embodiments 63 through 82 and 86, wherein the polyspecificity reagent comprises a cellular membrane fraction that is obtained from a collection of insect cells in culture.

Embodiment 89

The method of any one of embodiments 63 through 82 and embodiments 86 through 88, wherein the polyspecificity reagent comprises a solubilized cellular membrane fraction.

Embodiment 90

The method of any one of embodiments 63 through 82, embodiment 86, embodiment 87, and embodiment 89, wherein the polyspecificity reagent comprises a solubilized cellular membrane fraction that is obtained from a collection of mammalian cells in culture.

Embodiment 91

The method of any one of embodiments 63 through 82, embodiment 86, embodiment 88, and embodiment 89, wherein the polyspecificity reagent comprises a solubilized cellular membrane fraction that is obtained from a collection of insect cells in culture.

Embodiment 92

The method of any one of embodiments 63 through 81, wherein the polyspecificity reagent comprises a collection of virus or virus-derived particles selected from the group consisting of baculovirus; adenovirus; lentivirus; rhinovirus; coronavirus; cucumber mosaic virus; cytomegalovirus; respiratory syncytial virus; influenza virus; rotavirus; herpes virus; and virus particles derived from one or more such viruses

Embodiment 93

The method of any one of embodiments 63 through 92, wherein the polyspecificity reagent comprises at least one detergent.

Embodiment 94

The method of any one of embodiments 63 through 93, wherein the polyspecificity reagent comprises at least one detergent selected from the group consisting of beta-mercaptoethanol (B-ME), (Cyclohexyl-beta-D-maltoside (Cymal-6), Sodium Cholate, Polyoxyethylene$_{(23)}$ lauryl ether (Brij35), Decyl Maltose Neopentyl Glycol (DM-NG), n-Dodecyl β-D-maltoside (DDM), n-octyl-β-D-glucoside (OG), and 3-[(3-Cholamidopropyl)dimethylammonio]-1-propanesulfonate (CHAPS).

Embodiment 95

The method of any one of embodiments 63 through 94, wherein the library of polypeptides comprises at least: from about $1\times10^4$ unique polypeptides to about $1\times10^{18}$ unique polypeptides; $1\times10^4$ unique polypeptides to about $1\times10^{17}$ unique polypeptides; $1\times10^4$ unique polypeptides to about $1\times10^{16}$ unique polypeptides; $1\times10^4$ unique polypeptides to about $1\times10^{15}$ unique polypeptides; $1\times10^4$ unique polypeptides to about $1\times10^{14}$ unique polypeptides; $1\times10^4$ unique polypeptides to about $1\times10^{13}$ unique polypeptides; $1\times10^4$ unique polypeptides to about $1\times10^{12}$ unique polypeptides; $1\times10^4$ unique polypeptides to about $1\times10^{11}$ unique polypeptides; $1\times10^4$ unique polypeptides to about $1\times10^{10}$ unique polypeptides; $1\times10^4$ unique polypeptides to about $1\times10^9$ unique polypeptides; $1\times10^4$ unique polypeptides to about $1\times10^8$ unique polypeptides; $1\times10^4$ unique polypeptides to about $1\times10^7$ unique polypeptides; $1\times10^5$ unique polypeptides to about $1\times10^{18}$ unique polypeptides; $1\times10^6$ unique polypeptides to about $1\times10^{18}$ unique polypeptides; $1\times10^7$ unique polypeptides to about $1\times10^{18}$ unique polypeptides; $1\times10^8$ unique polypeptides to about $1\times10^{18}$ unique polypeptides; $1\times10^9$ unique polypeptides to about $1\times10^{18}$ unique polypeptides; $1\times10^{10}$ unique polypeptides to about $1\times10^{18}$ unique polypeptides; $1\times10^{11}$ unique polypeptides to about $1\times10^{18}$ unique polypeptides; $1\times10^{12}$ unique polypeptides to about $1\times10^{18}$ unique polypeptides; $1\times10^5$ unique polypeptides to about $1\times10^{18}$ unique polypeptides; $1\times10^6$ unique polypeptides to about $1\times10^{17}$ unique polypeptides; $1\times10^7$ unique polypeptides to about $1\times10^{16}$ unique polypeptides; $1\times10^8$ unique polypeptides to about $1\times10^{15}$ unique polypeptides; $1\times10^9$ unique polypeptides to about $1\times10^{14}$ unique polypeptides; or $1\times10^{10}$ unique polypeptides to about $1\times10^{13}$ unique polypeptides.

Embodiment 96

The method of any one of embodiments 63 through 95, wherein the library of polypeptides is collectively encoded by a plurality of polynucleotides.

Embodiment 97

The method of embodiment 96, wherein the plurality of polynucleotides comprises a library of polynucleotides.

Embodiment 98

The method of any one of embodiments 63 through 97, wherein the plurality of polynucleotides comprises at least: from about $1\times10^4$ unique polynucleotides to about $1\times10^{18}$ unique polynucleotides; $1\times10^4$ unique polynucleotides to about $1\times10^{17}$ unique polynucleotides; $1\times10^4$ unique polynucleotides to about $1\times10^{16}$ unique polynucleotides; $1\times10^4$ unique polynucleotides to about $1\times10^{15}$ unique polynucleotides; $1\times10^4$ unique polynucleotides to about $1\times10^{14}$ unique polynucleotides; $1\times10^4$ unique polynucleotides to about $1\times10^{13}$ unique polynucleotides; $1\times10^4$ unique polynucleotides to about $1\times10^{12}$ unique polynucleotides; $1\times10^4$ unique polynucleotides to about $1\times10^{11}$ unique polynucleotides; $1\times10^4$ unique polynucleotides to about $1\times10^{10}$ unique polynucleotides; $1\times10^4$ unique polynucleotides to about $1\times10^9$ unique polynucleotides; $1\times10^4$ unique polynucleotides to about $1\times10^8$ unique polynucleotides; $1\times10^4$ unique polynucleotides to about $1\times10^7$ unique polynucleotides; $1\times10^5$ unique polynucleotides to about $1\times10^{18}$ unique polynucleotides; $1\times10^6$ unique polynucleotides to about $1\times10^{18}$ unique polynucleotides; $1\times10^7$ unique polynucleotides to about $1\times10^{18}$ unique polynucleotides; $1\times10^8$ unique polynucleotides to about $1\times10^{18}$ unique polynucleotides; $1\times10^9$ unique polynucleotides to about $1\times10^{18}$ unique polynucleotides; $1\times10^{10}$ unique polynucleotides to about $1\times10^{18}$ unique polynucleotides; $1\times10^{11}$ unique polynucleotides to about $1\times10^{18}$ unique polynucleotides; $1\times10^{12}$ unique polynucleotides to about $1\times10^{18}$ unique polynucleotides; $1\times10^5$ unique polynucleotides to about $1\times10^{18}$ unique polynucleotides; $1\times10^6$ unique polynucleotides to about $1\times10^{17}$ unique polynucleotides; $1\times10^7$ unique polynucleotides to about $1\times10^{16}$ unique polynucleotides; $1\times10^8$ unique polynucleotides to about $1\times10^{15}$ unique polynucleotides; $1\times10^9$ unique polynucleotides to about $1\times10^{14}$ unique polynucleotides; or $1\times10^{10}$ unique polynucleotides to about $1\times10^{13}$ unique polynucleotides.

Embodiment 99

The method of any one of embodiments 63 through 98, wherein each polypeptide of the library of polypeptides is encoded by a polynucleotide that is a component of a vector.

Embodiment 100

The method of any one of embodiments 96 through 99, wherein each polynucleotide is introduced into one or more of the host cells.

Embodiment 101

The method of any one of embodiments 96 through 99, wherein the plurality of polynucleotides is collectively introduced a plurality of host cells.

Embodiment 102

The method of embodiment 100 or 101, wherein the plurality of host cells comprises a plurality of vectors collectively harboring the one or more polynucleotides collectively encoding the library of polypeptides.

Embodiment 103

The method of any one of embodiments 63 through 102, wherein the library of polypeptides is expressed by one or more host cells.

Embodiment 104

The method of any one of embodiments 63 through 103, wherein the library of polypeptides is collectively expressed by a plurality of host cells.

Embodiment 105

The method of any one of embodiments 63 through 104, wherein the library of polypeptides comprises a naïve discovery polypeptide library.

Embodiment 106

The method of any one of embodiments 96 through 102 wherein the plurality of polynucleotides comprises a naïve discovery polynucleotide library.

Embodiment 107

The method of any one of embodiments 100 through 104, wherein the host cells comprise a naïve discovery host cell library.

Embodiment 108

The method of any one of embodiments 63 through 104, wherein the library of polypeptides comprises an optimization polypeptide library.

Embodiment 109

The method of any one of embodiments 96 through 102, wherein the library of polynucleotides comprises an optimization polynucleotide library.

Embodiment 110

The method of any one of embodiments 100 through 104, wherein the host cells comprise an optimization host cell library.

Embodiment 111

The method of any one of embodiments 63 through 110, wherein the polypeptides comprise antibodies or antibody fragments.

Embodiment 112

The method of any one of embodiments 63 through 111, wherein the polypeptides comprise antibodies or antibody fragments, wherein the antibodies or antibody fragments comprise at least one Fc region.

Embodiment 113

The method of any one of embodiments 63 through 112, wherein the polypeptides comprise antibodies or antibody fragments, wherein the antibodies or antibody fragments comprise at least one Fc region and at least one antigen binding region.

Embodiment 114

The method of any one of embodiments 1 through 113, wherein the polypeptides comprise antibodies or antibody fragments, wherein the antibodies or antibody fragments comprise full-length IgGs.

Embodiment 115

The method of any one of embodiments 63 through 114, wherein the polypeptides comprise multispecific antibodies or antibody fragments.

Embodiment 116

The method of any one of embodiments 63 through 115, wherein the polypeptides comprise human or humanized antibodies or antibody fragments.

Embodiment 117

The method of any one of embodiments 100 through 104, 107, and 110, wherein the host cells are eukaryotic cells.

Embodiment 118

The method of any one of embodiments 100 through 104, 107, 110, and 117, wherein the host cells are yeast cells.

Embodiment 119

The method of any one of embodiments 100 through 104, 107, 110, 117, and 118, wherein the host cells provide genotype-phenotype linkage.

Embodiment 120

The method of any one of embodiments 100 through 104, 107, 110, and 117 through 119, wherein host cells comprise a genotype-phenotype library.

Embodiment 121

A polyspecificity reagent comprises a composition selected from the group consisting of:
(a) a soluble cellular fraction;
(b) a membrane cellular fraction;

(c) a bodily fluid fraction;
(d) a serum fraction;
(e) a plasma fraction;
(f) a cocktail comprising partially purified biomolecules;
(g) a collection of virus or virus-derived particles; and
(h) a combination of one or more of (a) through (f).

Embodiment 122

The polyspecificity reagent of embodiment 121, wherein the polyspecificity reagent comprises at least one detergent.

Embodiment 123

The polyspecificity reagent of embodiment 121 or embodiment 122, wherein the polyspecificity reagent comprises at least one yeast-compatible detergent.

Embodiment 124

The polyspecificity reagent of embodiment 122 or embodiment 123, wherein the polyspecificity reagent comprises at least one detergent selected from the group consisting of: beta-mercaptoethanol (B-ME), (Cyclohexyl-beta-D-maltoside (Cymal-6), Sodium Cholate, Polyoxyethylene$_{(23)}$lauryl ether (Brij35), Decyl Maltose Neopentyl Glycol (DM-NG), n-Dodecyl β-D-maltoside (DDM), n-octyl-β-D-glucoside (OG), and 3-[(3-Cholamidopropyl)dimethylammonio]-1-propanesulfonate (CHAPS).

Embodiment 125

The polyspecificity reagent of any one of embodiments 121 through 125 for use in any one of the methods of embodiments 1 through 120.

Embodiment 126

The method of any one of embodiments 1 through 121, wherein a test binding partner is not added to the polyspecificity reagent.

Embodiment 127

The method of any one of embodiments 1 through 121 and embodiment 126, wherein the polyspecificity reagent is essentially devoid of a test binding partner.

Embodiment 128

The method of any one of embodiments 1 through 121 and embodiments 126 through 127, wherein the method further comprises performing one or more of the following: cross interaction chromatography (CIC); self-interaction chromatography (SIC); dynamic light scattering (DLS) spectrophotometry; size exclusion chromatography (SEC); circular dichroism (CD); quasi-elastic light scattering; photon correlation spectroscopy; whole cell binding; tissue micro array methodologies; BVP ELISA assays; and differential scanning calorimetry.

Those skilled in the art will recognize, or will ascertain using no more than routine experimentation, many equivalents to the embodiments and methods disclosed and claimed herein and throughout. Such equivalents are encompassed the scope of the claims.

What is claimed is:

1. A method of counter-selecting against at least one polyspecific polypeptide from a plurality of polypeptides, the method comprising:
   (a) providing the plurality of polypeptides;
   (b) contacting the plurality of step (a) with a polyspecificity reagent, wherein the polyspecificity reagent comprises a soluble cellular fraction, thereby producing a reagent-plurality mixture;
   (c) detecting from the reagent-plurality mixture of step (b) at least one polyspecific polypeptide that interacts with the polyspecificity reagent, thereby detecting at least one polyspecific polypeptide; and
   (d) selecting at least one polypeptide from the plurality that is not detected in step (c), thereby counter-selecting against the at least one polyspecific polypeptide from the plurality of polypeptides.

2. The method of claim 1, the method further comprising contacting either:
   the plurality of polypeptides;
   the reagent-plurality mixture; or
   both the plurality of polypeptides and the reagent-plurality mixture;
   with at least one test binding partner.

3. The method of claim 1, wherein the polyspecificity reagent comprises at least one detergent.

4. The method of claim 1, wherein the polyspecificity reagent comprises at least one detergent selected from the group consisting of beta-mercaptoethanol (B-ME), (Cyclohexyl-beta-D-maltoside (Cymal-6), Sodium Cholate, Polyoxyethylene$_{(23)}$ lauryl ether (Brij35), Decyl Maltose Neopentyl Glycol (DM-NG), n-Dodecyl β-D-maltoside (DDM), n-octyl-β-D-glucoside (OG), and 3-[(3-Cholamidopropyl) dimethylammonio]-1-propanesulfonate (CHAPS).

5. The method of claim 1, wherein the polypeptides comprise antibodies, human antibodies, humanized antibodies, full length IgGs, multispecific antibodies, bispecific antibodies, antibody fragments, or combinations thereof.

6. The method of claim 1, wherein the polyspecificity reagent is obtained from a collection of cells in culture.

7. The method of claim 1, wherein the polyspecificity reagent is obtained from:
   (a) a collection of mammalian cells in culture; or
   (b) a collection of insect cells in culture.

8. The method of claim 1, wherein the soluble cellular fraction is prepared in the presence of one or more protease inhibitors.

9. The method of claim 1, wherein the soluble cellular fraction is prepared at 4 degrees Celsius or on ice.

10. The method of claim 1, wherein the polyspecificity reagent is prepared by collecting the supernatant after centrifugation and removal of a mixture comprising an enriched membrane fraction (EMF).

11. The method of claim 1, wherein the polyspecificity reagent comprises a soluble cytoplasmic polyspecific reagent (SCP).

12. The method of claim 5, wherein the polypeptides comprise human antibodies.

13. The method of claim 5, wherein the polypeptides comprise full-length IgGs.

* * * * *